United States Patent
Bernett et al.

(10) Patent No.: US 11,739,145 B2
(45) Date of Patent: Aug. 29, 2023

(54) BISPECIFIC BINDING AGENTS BINDING TO CLDN18.2 AND CD3

(71) Applicants: Astellas Pharma Europe BV, Leiden (NL); Xencor, Inc., Pasadena, CA (US)

(72) Inventors: Matthew Bernett, Monrovia, CA (US); Alex Nisthal, Monrovia, CA (US); Gregory Moore, Monrovia, CA (US)

( * ) Notice: Subject to any disclaimer, the term of this patent is extended or adjusted under 35 U.S.C. 154(b) by 0 days.

(21) Appl. No.: 18/062,465

(22) Filed: Dec. 6, 2022

(65) Prior Publication Data
US 2023/0137677 A1    May 4, 2023

Related U.S. Application Data

(63) Continuation of application No. PCT/EP2022/066299, filed on Jun. 15, 2022.

(51) Int. Cl.
*C07K 16/28* (2006.01)
*A61K 39/00* (2006.01)

(52) U.S. Cl.
CPC .......... *C07K 16/28* (2013.01); *C07K 16/2809* (2013.01); *A61K 2039/505* (2013.01); *C07K 2317/24* (2013.01); *C07K 2317/31* (2013.01); *C07K 2317/33* (2013.01); *C07K 2317/92* (2013.01)

(58) Field of Classification Search
CPC .......... C07K 16/28; C07K 16/2809; C07K 2317/24; C07K 2317/31; A61K 2039/505
See application file for complete search history.

(56) References Cited

FOREIGN PATENT DOCUMENTS

| | | |
|---|---|---|
| CN | 111518214 A | 8/2020 |
| WO | 2016086189 A2 | 6/2016 |
| WO | 2018054484 A1 | 3/2018 |
| WO | 2021237717 A1 | 12/2021 |
| WO | 2020025792 A1 | 2/2022 |

*Primary Examiner* — Aurora M Fontainhas
*Assistant Examiner* — Jennifer A Benavides
(74) *Attorney, Agent, or Firm* — Neal, Gerber & Eisenberg LLP

(57) ABSTRACT

The present invention provides binding agents comprising at least two binding domains, wherein a first binding domain has specificity for CLDN18.2 and a second binding domain has specificity for CD3, and methods of using these binding agents or nucleic acids encoding therefor for treating cancer.

22 Claims, 44 Drawing Sheets
Specification includes a Sequence Listing.

1 + 1 Fab-scFv-Fc

2 + 1 Fab$_2$-scFv-Fc

| Sample | Subset | Count | Concentration (ng/ml) | Test Article | Mean PE-A |
|---|---|---|---|---|---|
| Ramos | live cells | 4671 | 2.38 | XENP24647 | 125 |
| NUGC-4 | live cells | 4627 | 100.00 | XENP24647 | 342 |

| Sample | Subset | Count | Concentration (ng/ml) | Test Article | Mean PE-A |
|---|---|---|---|---|---|
| Ramos | live cells | 4622 | 2.38 | XENP24647 | 138 |
| SNU-601 | live cells | 4600 | 25.00 | XENP24647 | 1673 |

Fig. 23

| XENP | Clone | Antibody | hCLDN18.2 EC50 (nM) | cCLDN18.2 EC50 (nM) | mCLDN18.2 EC50 (nM) |
|---|---|---|---|---|---|
| 24644 | H0L0 | Bivalent | 4 | 3 | 5 |
| 24647 | H0L0 | 2 + 1 | 4 | 1 | 3 |
| 29476 | H1L1 | 2 + 1 | 6 | 2 | 6 |
| 24645 | H0L0 | 1 + 1 | 145 | 108 | 35 |
| 29472 | H1L1 | 1 + 1 | 146 | 142 | 43 |

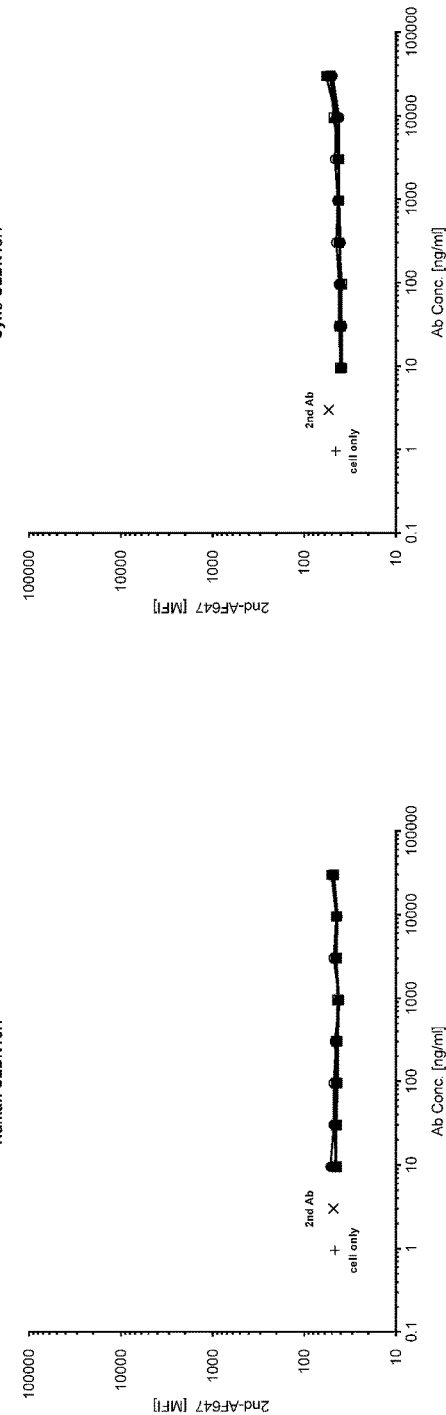
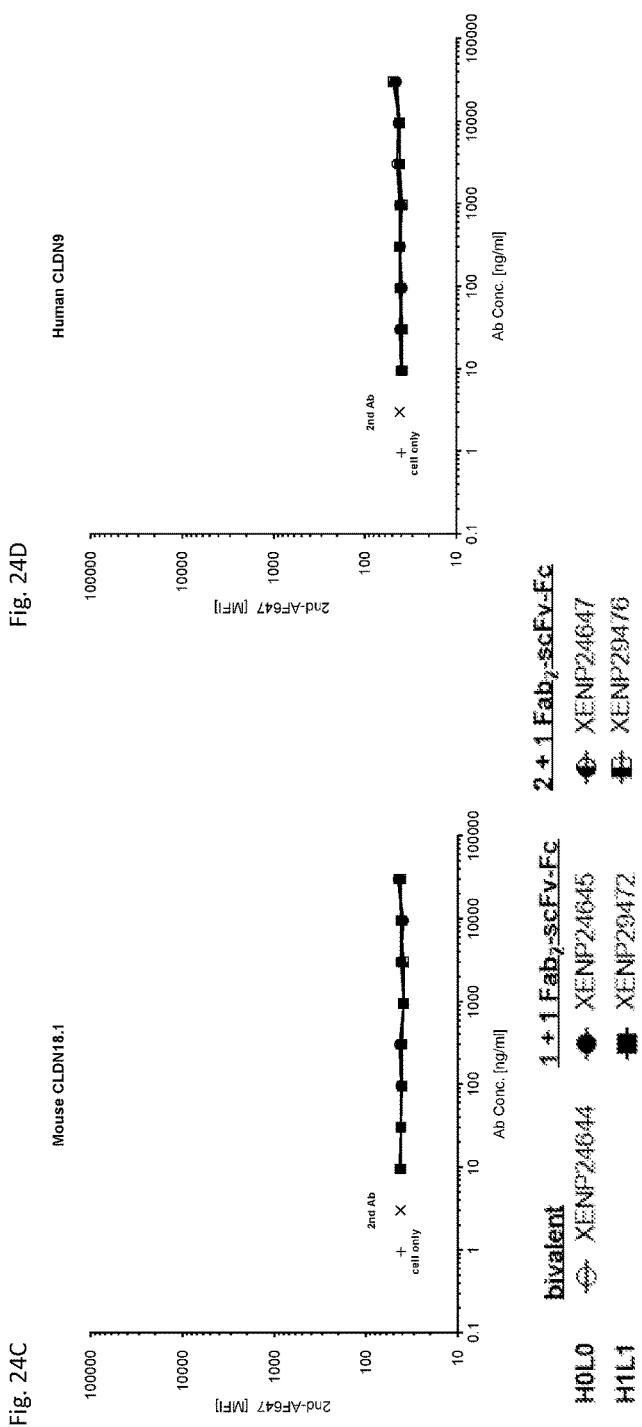
Fig. 24A Human CLDN18.1
Fig. 24B Cyno CLDN18.1
Fig. 24C Mouse CLDN18.1
Fig. 24D Human CLDN9

- ● XENP31726_H1L1; CD3-HighInt#1[VLVH]; 2+1
- ■ XENP32461_H1L1; CD3-HighInt#2[VLVH]; 2+1
- ▲ XENP29478_H1L1; CD3-HighInt#1[VHVL]; 2+1
- ◆ XENP29472_H1L1; CD3-High[VHVL]; 1+1
- ★ CLDN18.2 x CD3 AMG 910
- × Target cells only
- + Target + Effector cells only

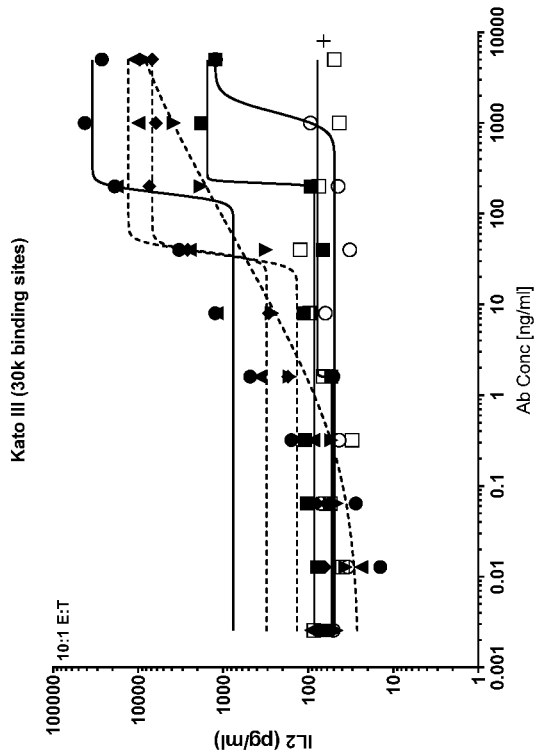
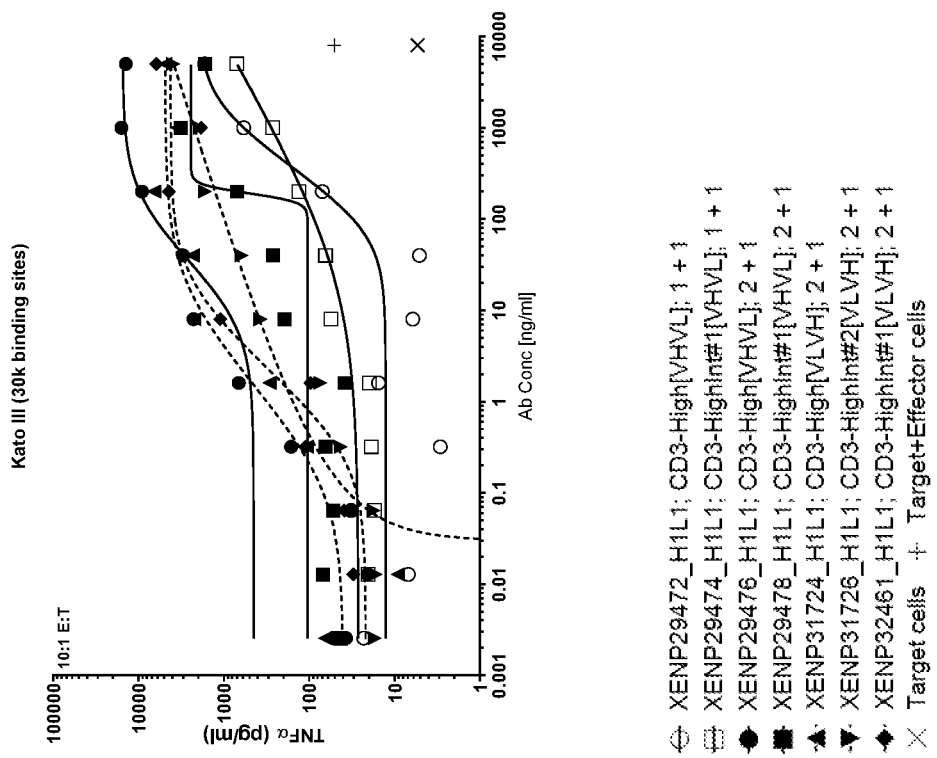
Fig. 33B
Fig. 33A

BISPECIFIC BINDING AGENTS BINDING TO CLDN18.2 AND CD3

CROSS-REFERENCE TO RELATED APPLICATIONS

This application is a continuation of International Application No. PCT/EP2022/066299, filed on Jun. 15, 2022, which claims priority to International Application No. PCT/EP2021/066141, filed on Jun. 15, 2021. The contents of each of the aforementioned applications are incorporated herein by reference in their entireties.

SEQUENCE LISTING

The instant application contains a Sequence Listing which has been submitted in ST.26 XML format via Patent Center and is hereby incorporated by reference in its entirety. Said ST.26 XML copy, created on Dec. 6, 2022, is named "026156-8042 Sequence Listing.xml", and is 136,834 bytes in size.

Cancers of the stomach and the esophagus (gastroesophageal; GE) are among the malignancies with the highest unmet medical need. Gastric cancer is the third leading cause of cancer death worldwide (Prz Gastroenterol. 2019; 14(1): 26-38). The incidence of esophageal cancer has increased in recent decades, coinciding with a shift in histological type and primary tumor location. Adenocarcinoma of the esophagus is now more prevalent than squamous cell carcinoma in the United States and Western Europe, with most tumors located in the distal esophagus. The overall five-year survival rate for GE cancer is 20-25%, despite the aggressiveness of established standard treatment associated with substantial side effects.

The majority of patients presents with locally advanced or metastatic disease and has to be subjected to first-line chemotherapy. Treatment regimens are based on a backbone of platinum and fluoropyrimidine derivatives mostly combined with a third compound (e.g., taxane or anthracyclines). Still, median progression free survival of 5 to 7 months and median overall survival of 9 to 11 months are the best that can be expected.

The lack of a major benefit from the various newer generation combination chemotherapy regimens for these cancers has stimulated research into the use of targeted agents. Recently, for Her2/neu-positive gastroesophageal cancers Trastuzumab has been approved. However, as only ~20% of patients express the target and are eligible for this treatment, the medical need is still high.

The tight junction molecule claudin 18 (CLDN18) is an integral transmembrane protein (tetraspanin) having four membrane spanning hydrophobic regions and two extracellular loops (loop1 embraced by hydrophobic region 1 and hydrophobic region 2; loop2 embraced by hydrophobic regions 3 and 4). CLDN18 exists in two different splice variants, which are described in mouse and in human (Niimi, Mol. Cell. Biol. 21:7380-90, 2001). The splice variants (Genbank accession number: splice variant 1 (CLDN18.1): NP_057453, NM_016369, and splice variant 2 (CLDN18.2): NM_001002026, NP_001002026) have a molecular weight of approximately 27.9/27.72 kD. The splice variants CLDN18.1 and CLDN18.2 differ in the N-terminal portion which comprises the first transmembrane (TM) region and loop1, whereas the primary protein sequence of the C-terminus is identical.

In normal tissues, there is no detectable expression of CLDN18.2 with exception of stomach where CLDN18.2 is expressed exclusively on short-lived differentiated gastric epithelial cells. CLDN18.2 is maintained in the course of malignant transformation and thus frequently displayed on the surface of human gastric cancer cells. Moreover, this pan-tumoral antigen is ectopically activated at significant levels in esophageal, pancreatic and lung adenocarcinomas. The CLDN18.2 protein is also localized in lymph node metastases of gastric cancer adenocarcinomas and in distant metastases especially into the ovary (so-called Krukenberg tumors).

The differential expression of claudins such as CLDN18.2 between cancer and normal cells, their membrane localization and their absence from the vast majority of toxicity relevant normal tissues makes these molecules attractive targets for cancer immunotherapy and the use of antibody-based therapeutics for targeting CLDN18.2 in cancer therapy promises a high level of therapeutic specificity.

The chimeric IgG1 antibody IMAB362 (Zolbetuximab (previously named Claudiximab)) which is directed against CLDN18.2 has been developed by Ganymed Pharmaceuticals AG. IMAB362 recognizes the first extracellular domain (ECD1) of CLDN18.2 with high affinity and specificity. IMAB362 does not bind to any other claudin family member including the closely related splice variant 1 of Claudin 18 (CLDN18.1). IMAB362 shows precise tumor cell specificity and bundles two independent highly potent mechanisms of action. Upon target binding IMAB362 mediates cell killing mainly by ADCC and CDC. Thus, IMAB362 lyses efficiently CLDN18.2-positive cells, including human gastric cancer cell lines in vitro and in vivo. Anti-tumor efficacy of IMAB362 was demonstrated in mice carrying xenografted tumors inoculated with CLDN18.2-positive cancer cell lines.

IgG1 antibodies typically engage the cellular immune system via interaction of the Fc domain with Fc receptors (FcγRs) expressed on various immune cells including natural killer cells which are the main agents of ADCC. However, IgG1 monoclonal antibodies (mAbs) triggering ADCC face several limitations including broad distribution of low affinity Fc receptor variants in the population (up to 80%) as well as in vivo IgG1 modifications reducing the mAb efficacy (Chames et al., (2009) Br J Pharmacol, 157(2):220-233). Therapeutic antibodies also have to compete with the patients IgGs resulting in high doses of mAbs necessary in vivo. Furthermore, therapeutic antibodies may interact with FcγRIIb (an inhibitory FcγR expressed by B cells, macrophages, dendritic cells and neutrophils) resulting in negative signaling that decreases their efficacy.

It has been an object of the invention to provide novel agents and methods for the therapy of cancer diseases.

The solution of the problem underlying the invention is based on the concept of generating a binding agent that comprises at least one binding domain that is specific for CLDN18.2, i.e., cancer cells. The binding agent also comprises a binding domain that is specific for the T cell-specific antigen CD3 allowing to bind to T cells and to pull the T cells into the complex, thus making it possible to target the cytotoxic effect of the T cells to the cancer cells. Formation of this complex can induce signalling in cytotoxic T cells, either on its own or in combination with accessory cells, which leads to the release of cytotoxic mediators.

We report for the first time that binding agents comprising at least one binding domain in the Fab format targeting CLDN18.2 and another binding domain in the scFv format targeting a T cell-specific antigen such as CD3 can induce potent T cell-mediated lysis and are effective in treating tumor diseases.

SUMMARY OF THE INVENTION

The invention generally provides binding agents that bind to CLDN18.2, particularly bispecific binding agents that bind to CLDN18.2 and CD3.

The invention provides a binding agent comprising a binding domain with specificity for CLDN18.2 and a binding domain with specificity for CD3, wherein the binding agent comprises at least three polypeptide chains, wherein a first polypeptide chain comprises a variable region of a heavy chain (VH) derived from an immunoglobulin with specificity for CLDN18.2 (VH(CLDN18.2)), a second polypeptide chain comprises a variable region of a VH derived from an immunoglobulin with specificity for CD3 (VH(CD3)) and a variable region of a light chain (VL) derived from an immunoglobulin with specificity for CD3 (VL(CD3)), and a third polypeptide chain comprises a VL derived from an immunoglobulin with specificity for CLDN18.2 (VL(CLDN18.2)).

In one embodiment, the binding agent of the invention is a bispecific trimeric binding agent.

In one embodiment, the first polypeptide chain comprises a constant region 1 of a heavy chain (CHI1) derived from an immunoglobulin or a functional variant thereof.

In one embodiment, the first and the second polypeptide chains comprise a constant region 2 of a heavy chain (CH2) derived from an immunoglobulin or a functional variant thereof and a constant region 3 of a heavy chain (CH3) derived from an immunoglobulin or a functional variant thereof.

In one embodiment, the third polypeptide chain comprises a constant region of a light chain (CL) derived from an immunoglobulin or a functional variant thereof.

In one embodiment, the VH and the CH1, CH2 and CH3 on the first polypeptide chain are arranged, from N-terminus to C-terminus, in the order VH(CLDN18.2)-CH1-CH2-CH3.

In one embodiment, the VH, the VL, and the CH2 and CH3 on the second polypeptide chain are arranged, from N-terminus to C-terminus, in the order VH(CD3)-VL(CD3)-CH2-CH3, or VL(CD3)-VH(CD3)-CH2-CH3.

In one embodiment, the first polypeptide chain interacts with the second polypeptide chain and with the third polypeptide chain. In one embodiment, the VH(CLDN18.2) and the VL(CLDN18.2) interact to form the binding domain with specificity for CLDN18.2, and the VH(CD3) and the VL(CD3) interact to form the binding domain with specificity for CD3.

In one embodiment, the CH2 on the first polypeptide chain interacts with the CH2 on the second polypeptide chain and/or the CH3 on the first polypeptide chain interacts with the CH3 on the second polypeptide chain. In one embodiment, the CH1 on the first polypeptide chain interacts with the CL on the third polypeptide chain.

In one embodiment, the binding agent of the invention comprises a further binding domain with specificity for CLDN18.2, wherein the second polypeptide chain further comprises a VH(CLDN18.2) and wherein the binding agent comprises a fourth polypeptide chain identical to the third polypeptide chain.

In one embodiment, the binding agent of the invention is a bispecific tetrameric binding agent.

In one embodiment, the second polypeptide chain further comprises a CH1 derived from an immunoglobulin or a functional variant thereof.

In one embodiment, the immunoglobulin is IgG1, preferably human IgG1. In one embodiment, in the binding agent described herein, VH(CLDN18.2) and/or VL(CLDN18.2) are derived from IgG1, VH(CD3) and/or VL(CD3) are derived from IgG1, and/or CH1, CH2, CH3, and/or CL are derived from IgG1, wherein IgG1 preferably is human IgG1.

In one embodiment, the VHs, the VL, and the CH1, CH2 and CH3 on the second polypeptide chain are arranged, from N-terminus to C-terminus, in the order VH(CLDN18.2)-CH1-VH(CD3)-VL(CD3)-CH2-CH3, or VH(CLDN18.2)-CH1-VL(CD3)-VH(CD3)-CH2-CH3.

In one embodiment, the second polypeptide chain interacts with the fourth polypeptide chain.

In one embodiment, the VH(CLDN18.2) on the second polypeptide chain interacts with the VL(CLDN18.2) on the fourth polypeptide chain to form the further binding domain with specificity for CLDN18.2.

In one embodiment, the CH1 on the second polypeptide chain interacts with the CL on the fourth polypeptide chain.

In one embodiment, the VH(CD3) comprises CDR1, CDR2 and CDR3 of an amino acid sequence selected from the group consisting of SEQ ID NO: 54, 58 and 61.

In one embodiment, the VH(CD3) comprises (i) a CDR1 comprising the amino acid sequence TYAMN (SEQ ID NO: 43) or a functional variant thereof, a CDR2 comprising the amino acid sequence RIRSKANNYATYYADSVKG (SEQ ID NO: 50) or a functional variant thereof, and a CDR3 comprising the amino acid sequence HGNFGDSYVSWFAY (SEQ ID NO: 45) or a functional variant thereof, (ii) a CDR1 comprising the amino acid sequence TYAMN (SEQ ID NO: 43) or a functional variant thereof, a CDR2 comprising the amino acid sequence RIRSKYNNYATYYADSVKG (SEQ ID NO: 44) or a functional variant thereof, and a CDR3 comprising the amino acid sequence HGNFGDEYVSWFAY (SEQ ID NO: 51) or a functional variant thereof, or (iii) a CDR1 comprising the amino acid sequence TYAMN (SEQ ID NO: 43) or a functional variant thereof, a CDR2 comprising the amino acid sequence RIRSKYNNYATYYADSVKG (SEQ ID NO: 44) or a functional variant thereof, and a CDR3 comprising the amino acid sequence HGNFGDSYVSWFAY (SEQ ID NO: 45) or a functional variant thereof.

In one embodiment, the VL(CD3) comprises CDR1, CDR2 and CDR3 of SEQ ID NO: 55.

In one embodiment, the VL(CD3) comprises a CDR1 comprising the amino acid sequence GSSTGAVTTSNYAN (SEQ ID NO: 46) or a functional variant thereof, a CDR2 comprising the amino acid sequence GTNKRAP (SEQ ID NO: 47) or a functional variant thereof, and a CDR3 comprising the amino acid sequence ALWYSNHWV (SEQ ID NO: 48) or a functional variant thereof.

In one embodiment, the VH(CLDN18.2) comprises CDR1, CDR2 and CDR3 of SEQ ID NO: 39.

In one embodiment, the VH(CLDN18.2) comprises a CDR1 comprising the amino acid sequence SYWIN (SEQ ID NO: 32) or a functional variant thereof, a CDR2 comprising the amino acid sequence NIYPSDSYTNYNQKFQG (SEQ ID NO: 33) or a functional variant thereof, and a CDR3 comprising the amino acid sequence SWRGNSFDY (SEQ ID NO: 34) or a functional variant thereof.

In one embodiment, the VL(CLDN18.2) comprises CDR1, CDR2 and CDR3 of SEQ ID NO: 42.

In one embodiment, the VL(CLDN18.2) comprises a CDR1 comprising the amino acid sequence KSSQSLLNSGNQKNYLT (SEQ ID NO: 35) or a functional variant thereof, a CDR2 comprising the amino acid sequence WASTRES (SEQ ID NO: 36) or a functional variant thereof, and a CDR3 comprising the amino acid sequence QNDYSYPFT (SEQ ID NO: 37) or a functional variant thereof.

In one embodiment, (i) the VH(CD3) comprises CDR1, CDR2 and CDR3 of SEQ ID NO: 58, the VL(CD3) comprises CDR1, CDR2 and CDR3 of SEQ ID NO: 55, the VH(CLDN18.2) comprises CDR1, CDR2 and CDR3 of SEQ ID NO: 39, and the VL(CLDN18.2) comprises CDR1, CDR2 and CDR3 of SEQ ID NO: 42, (ii) the VH(CD3) comprises CDR1, CDR2 and CDR3 of SEQ ID NO: 61, the VL(CD3) comprises CDR1, CDR2 and CDR3 of SEQ ID NO: 55, the VH(CLDN18.2) comprises CDR1, CDR2 and CDR3 of SEQ ID NO: 39, and the VL(CLDN18.2) comprises CDR1, CDR2 and CDR3 of SEQ ID NO: 42, or (iii) the VH(CD3) comprises CDR1, CDR2 and CDR3 of SEQ ID NO: 54, the VL(CD3) comprises CDR1, CDR2 and CDR3 of SEQ ID NO: 55, the VH(CLDN18.2) comprises CDR1, CDR2 and CDR3 of SEQ ID NO: 39, and the VL(CLDN18.2) comprises CDR1, CDR2 and CDR3 of SEQ ID NO: 42.

In one embodiment, the VH(CD3) comprises or consists of an amino acid sequence represented by SEQ ID NO: 58 or a functional variant thereof, the VL(CD3) comprises or consists of an amino acid sequence represented by SEQ ID NO: 55 or a functional variant thereof, the VH(CLDN18.2) comprises or consists of an amino acid sequence represented by SEQ ID NO: 39 or a functional variant thereof, and/or the VL(CLDN18.2) comprises or consists of an amino acid sequence represented by SEQ ID NO: 42 or a functional variant thereof.

In one embodiment, the VH(CD3) comprises or consists of an amino acid sequence represented by SEQ ID NO: 61 or a functional variant thereof, the VL(CD3) comprises or consists of an amino acid sequence represented by SEQ ID NO: 55 or a functional variant thereof, the VH(CLDN18.2) comprises or consists of an amino acid sequence represented by SEQ ID NO: 39 or a functional variant thereof, and/or the VL(CLDN18.2) comprises or consists of an amino acid sequence represented by SEQ ID NO: 42 or a functional variant thereof.

In one embodiment, the VH(CD3) comprises or consists of an amino acid sequence represented by SEQ ID NO: 54 or a functional variant thereof, the VL(CD3) comprises or consists of an amino acid sequence represented by SEQ ID NO: 55 or a functional variant thereof, the VH(CLDN18.2) comprises or consists of an amino acid sequence represented by SEQ ID NO: 39 or a functional variant thereof, and/or the VL(CLDN18.2) comprises or consists of an amino acid sequence represented by SEQ ID NO: 42 or a functional variant thereof.

In one embodiment, on the first polypeptide chain the CH1 is connected to the CH2 by a peptide linker. In one embodiment, the peptide linker comprises the amino acid sequence EPKSCDKTHTCPPCP (SEQ ID NO: 27) or a functional variant thereof.

In one embodiment, the VH(CD3) or VL(CD3) is connected to the CH2 by a peptide linker. In one embodiment, the VH(CD3) or VL(CD3) is connected to the CH1 by a peptide linker. In one embodiment, the peptide linker comprises the amino acid sequence $(G_4S)_x$ or a functional variant thereof, wherein x is 2, 3, 4, 5 or 6. In one embodiment, the peptide linker comprises the amino acid sequence $(G_4S)_2$ (SEQ ID NO: 26) or a functional variant thereof. In one embodiment, the peptide linker connecting the VH(CD3) or VL(CD3) and the CH2 comprises the amino acid sequence KTHTCPPCP (SEQ ID NO: 21) or a functional variant thereof. In one embodiment, the peptide linker comprises the amino acid sequence $(G_4S)_2$KTHTCPPCP (SEQ ID NO: 23) or a functional variant thereof. In one embodiment, the peptide linker comprises the amino acid sequence EPKSSDKTHTCPPCP (SEQ ID NO: 22) or a functional variant thereof.

In one embodiment, the VH(CD3) and the VL(CD3) are connected to one another by a peptide linker. In one embodiment, the peptide linker comprises the amino acid sequence $(GKPGS)_x$ or a functional variant thereof, wherein x is 2, 3, 4, 5 or 6. In one embodiment, the peptide linker comprises the amino acid sequence $(GKPGS)_4$ (SEQ ID NO: 11) or a functional variant thereof.

In certain embodiments, the CH1, CH2 and/or CH3 domains of the binding agent of the invention comprise one or more amino acid modifications, in particular substitutions and/or deletions, in positions corresponding to positions of human IgG1 according to EU numbering. In one embodiment, the CH1 on the first and/or the second polypeptide chain comprises an amino acid sequence comprising an aspartic acid residue at position 208 according to EU numbering. In one embodiment, the CH1 on the first polypeptide chain comprises an amino acid sequence comprising an aspartic acid residue at position 208 according to EU numbering and the CH1 on the second polypeptide chain comprises an amino acid sequence comprising an asparagine residue at position 208 according to EU numbering.

Furthermore, in certain embodiments, the binding agent of the invention does not substantially, e.g., not detectably, bind to human FcγRI, IIa, IIb, and/or IIIa. In one embodiment, the CH2 on the first and/or the second polypeptide chain comprises an amino acid sequence comprising one or more of the following: a proline residue at position 233, a valine residue at position 234, an alanine residue at position 235, a deletion at position 236, a lysine residue at position 267 and a glutamic acid residue at position 295 according to EU numbering. In one embodiment, the CH2s on the first and the second polypeptide chain comprise an amino acid sequence comprising a proline residue at position 233, a valine residue at position 234, an alanine residue at position 235, a deletion at position 236 and a lysine residue at position 267 according to EU numbering and wherein the CH2 on the first polypeptide chain further comprises a glutamic acid residue at position 295 according to EU numbering and the CH2 on the second polypeptide chain further comprises a glutamine residue at position 295 according to EU numbering.

In one embodiment, the CH3 on the first and/or the second polypeptide chain comprises an amino acid sequence comprising one or more of the following: a glutamine residue at position 357, a lysine residue at position 364, an aspartic acid residue at position 368, a serine residue at position 370, an aspartic acid residue at position 384, a glutamic acid residue at position 418 and an aspartic acid residue at position 421 according to EU numbering. In one embodiment, the CH3 on the first polypeptide chain comprises an amino acid sequence comprising a glutamic acid residue at position 357, a serine residue at position 364, an aspartic acid residue at position 368, a serine residue at position 370, an aspartic acid residue at position 384, a glutamic acid residue at position 418 and an aspartic acid residue at position 421 according to EU numbering and the CH3 on the second polypeptide chain comprises an amino acid sequence comprising a glutamine residue at position 357, a lysine residue at position 364, a leucine residue at position 368, a lysine residue at position 370, an asparagine residue at position 384, a glutamine residue at position 418 and an asparagine residue at position 421 according to EU numbering.

In one embodiment, the first polypeptide chain comprises an amino acid sequence represented by SEQ ID NO: 28 or a functional variant thereof. In one embodiment, the second polypeptide chain comprises an amino acid sequence represented by SEQ ID NO: 30 or a functional variant thereof. In one embodiment, the second polypeptide chain comprises an amino acid sequence represented by SEQ ID NO: 29 or a functional variant thereof. In one embodiment, the third polypeptide chain comprises an amino acid sequence represented by SEQ ID NO: 31 or a functional variant thereof.

In one embodiment, the first polypeptide chain comprises or consists of an amino acid sequence represented by SEQ ID NO: 73 or a functional variant thereof. In one embodiment, the second polypeptide chain comprises or consists of an amino acid sequence selected from the group consisting of SEQ ID NO: 74, 75, 76 and 77 or a functional variant thereof. In one embodiment, the third polypeptide chain comprises or consists of an amino acid sequence represented by SEQ ID NO: 78 or a functional variant thereof.

Preferably, in one embodiment, (i) the first polypeptide chain comprises or consists of an amino acid sequence represented by SEQ ID NO: 73 or a functional variant thereof,
(ii) the second polypeptide chain comprises or consists of an amino acid sequence represented by SEQ ID NO: 75 or a functional variant thereof, and
(iii) the third polypeptide chain comprises or consists of an amino acid sequence represented by SEQ ID NO: 78 or a functional variant thereof.

Preferably, in one embodiment, (i) the first polypeptide chain comprises or consists of an amino acid sequence represented by SEQ ID NO: 73 or a functional variant thereof,
(ii) the second polypeptide chain comprises or consists of an amino acid sequence represented by SEQ ID NO: 74 or a functional variant thereof, and
(iii) the third polypeptide chain comprises or consists of an amino acid sequence represented by SEQ ID NO: 78 or a functional variant thereof.

Preferably, in one embodiment, (i) the first polypeptide chain comprises or consists of an amino acid sequence represented by SEQ ID NO: 73 or a functional variant thereof,
(ii) the second polypeptide chain comprises or consists of an amino acid sequence represented by SEQ ID NO: 76 or a functional variant thereof, and
(iii) the third polypeptide chain comprises or consists of an amino acid sequence represented by SEQ ID NO: 78 or a functional variant thereof.

Preferably, in one embodiment, (i) the first polypeptide chain comprises or consists of an amino acid sequence represented by SEQ ID NO: 73 or a functional variant thereof,
(ii) the second polypeptide chain comprises or consists of an amino acid sequence represented by SEQ ID NO: 77 or a functional variant thereof, and
(iii) the third polypeptide chain comprises or consists of an amino acid sequence represented by SEQ ID NO: 78 or a functional variant thereof.

The invention also provides a binding agent comprising a binding domain with specificity for CLDN18.2 comprising a variable region of a heavy chain (VH) derived from an immunoglobulin with specificity for CLDN18.2 (VH (CLDN18.2)) and a variable region of a light chain (VL) derived from an immunoglobulin with specificity for CLDN18.2 (VL(CLDN18.2)), wherein the VH(CLDN18.2) comprises a CDR1 comprising the amino acid sequence SYWIN (SEQ ID NO: 32) or a functional variant thereof, a CDR2 comprising the amino acid sequence NIYPSDSYTNYNQKFQG (SEQ ID NO: 33) or a functional variant thereof, and a CDR3 comprising the amino acid sequence SWRGNSFDY (SEQ ID NO: 34) or a functional variant thereof, and the VL(CLDN18.2) comprises a CDR1 comprising the amino acid sequence KSSQSLLNSGNQKNYLT (SEQ ID NO: 35) or a functional variant thereof, a CDR2 comprising the amino acid sequence WASTRES (SEQ ID NO: 36) or a functional variant thereof, and a CDR3 comprising the amino acid sequence QNDYSYPFT (SEQ ID NO: 37) or a functional variant thereof. In one embodiment, the binding agent further comprises a binding domain with specificity for CD3. In one embodiment, the binding domain with specificity for CD3 comprises a VH derived from an immunoglobulin with specificity for CD3 (VH (CD3)) and a VL derived from an immunoglobulin with specificity for CD3 (VL(CD3)), wherein the VH(CD3) comprises CDR1, CDR2 and CDR3 of an amino acid sequence selected from the group consisting of SEQ ID NO: 54, 58 and 61, and the VL(CD3) comprises CDR1, CDR2 and CDR3 of SEQ ID NO: 55.

In one embodiment, the functional variant of the amino acid sequence NIYPSDSYTNYNQKFQG (SEQ ID NO: 33) comprises or retains the amino acid residues QG.

In one embodiment, the binding agent is in the format of a full-length antibody or an antibody fragment. In one embodiment, the binding domain with specificity for CLDN18.2 is in the format of a Fab fragment, a Fab' fragment, a F(ab')₂ fragment, an Fv fragment, or an scFv fragment. In one embodiment, the binding domain with specificity for CD3 is in the format of a Fab fragment, a Fab' fragment, a F(ab')₂ fragment, an Fv fragment, or an scFv fragment.

In one embodiment, the binding agent is a bispecific molecule such as a bispecific antibody. In one embodiment, the binding agent is a bispecific single chain antibody. In one embodiment, the binding agent is capable of binding monovalently or bivalently to CLDN18.2. In one embodiment, the binding agent comprises two binding domains with specificity for CLDN18.2. In one embodiment, the binding domain with specificity for CLDN18.2 is in the format of a Fab fragment and the binding domain with specificity for CD3 is in the format of an scFv fragment. In one embodiment, the VH(CLDN18.2) is connected to the VL(CLDN18.2) by a peptide linker and/or the VH(CD3) is connected to the VL(CD3) by a peptide linker such as a peptide linker selected from the group consisting of SEQ ID NO: 2-20.

The invention also provides a binding agent comprising two binding domains with specificity for CLDN18.2 and a binding domain with specificity for CD3, wherein the binding agent comprises at least four polypeptide chains, wherein the first polypeptide chain comprises or consists of an amino acid sequence represented by SEQ ID NO: 73 or a functional variant thereof, the second polypeptide chain comprises or consists of an amino acid sequence represented by SEQ ID NO: 74 or a functional variant thereof, the third polypeptide chain comprises or consists of an amino acid sequence represented by SEQ ID NO: 78 or a functional variant thereof, and the fourth polypeptide chain is identical to the third polypeptide chain. In one embodiment, the polypeptide chains of the binding agent and/or the domains on the polypeptide chains of the binding agent interact with one another as described herein. In one embodiment, the first polypeptide chain interacts with the second polypeptide chain and with the third polypeptide chain, and the second polypeptide chain interacts with the fourth polypeptide chain.

The invention also provides a binding agent comprising a binding domain with specificity for CLDN18.2 and a binding domain with specificity for CD3, wherein the binding agent comprises at least three polypeptide chains, wherein the first polypeptide chain comprises or consists of an amino acid sequence represented by SEQ ID NO: 73 or a functional variant thereof, the second polypeptide chain comprises or consists of an amino acid sequence represented by SEQ ID NO: 75 or a functional variant thereof, and the third polypeptide chain comprises or consists of an amino acid sequence represented by SEQ ID NO: 78 or a functional variant thereof. In one embodiment, the polypeptide chains of the binding agent and/or the domains on the polypeptide chains of the binding agent interact with one another as described herein. In one embodiment, the first polypeptide chain interacts with the second polypeptide chain and with the third polypeptide chain.

The invention also provides a binding agent comprising two binding domains with specificity for CLDN18.2 and a binding domain with specificity for CD3, wherein the binding agent comprises at least four polypeptide chains, wherein the first polypeptide chain comprises or consists of an amino acid sequence represented by SEQ ID NO: 73 or a functional variant thereof, the second polypeptide chain comprises or consists of an amino acid sequence represented by SEQ ID NO: 76 or a functional variant thereof, the third polypeptide chain comprises or consists of an amino acid sequence represented by SEQ ID NO: 78 or a functional variant thereof, and the fourth polypeptide chain is identical to the third polypeptide chain. In one embodiment, the polypeptide chains of the binding agent and/or the domains on the polypeptide chains of the binding agent interact with one another as described herein. In one embodiment, the first polypeptide chain interacts with the second polypeptide chain and with the third polypeptide chain, and the second polypeptide chain interacts with the fourth polypeptide chain.

The invention also provides a binding agent comprising two binding domains with specificity for CLDN18.2 and a binding domain with specificity for CD3, wherein the binding agent comprises at least four polypeptide chains, wherein the first polypeptide chain comprises or consists of an amino acid sequence represented by SEQ ID NO: 73 or a functional variant thereof, the second polypeptide chain comprises or consists of an amino acid sequence represented by SEQ ID NO: 77 or a functional variant thereof, the third polypeptide chain comprises or consists of an amino acid sequence represented by SEQ ID NO: 78 or a functional variant thereof, and the fourth polypeptide chain is identical to the third polypeptide chain. In one embodiment, the polypeptide chains of the binding agent and/or the domains on the polypeptide chains of the binding agent interact with one another as described herein. In one embodiment, the first polypeptide chain interacts with the second polypeptide chain and with the third polypeptide chain, and the second polypeptide chain interacts with the fourth polypeptide chain.

In one embodiment, the VH(CLDN18.2), VL(CLDN18.2), VH(CD3) and/or VL(CD3) are humanized.

In one embodiment, CD3 is expressed on the surface of T cells. In one embodiment, the binding agent of the invention binds to the epsilon chain of CD3. In one embodiment, binding of the binding agent to CD3 on T cells results in proliferation and/or activation of the T cells. In one embodiment, proliferation and/or activation of T cells includes proliferation and/or activation of CD4 and/or CD8 T cells, preferably CD107a+ T cells. In one embodiment, said proliferated and/or activated T cells are capable of degranulation. In one embodiment, said activated T cells release cytotoxic factors, e.g., perforins and granzymes, and initiate cytolysis and/or apoptosis of cancer cells.

In one embodiment, CLDN18.2 is expressed in cancer cells. In one embodiment, CLDN18.2 is expressed on the surface of cancer cells. In one embodiment, the binding agent binds to an extracellular portion of CLDN18.2. In one embodiment, the binding agent induces T cell-mediated cytotoxicity against cancer cells expressing CLDN18.2.

In one embodiment, the cancer cells are from a cancer selected from the group consisting of gastric cancer, esophageal cancer, cancer of the gastroesophageal junction (GEJ), pancreatic cancer, lung cancer such as non-small cell lung cancer (NSCLC), breast cancer, ovarian cancer, colon cancer, rectal cancer, colorectal cancer, hepatic cancer, head-neck cancer, cancer of the gallbladder and the metastasis thereof, a Krukenberg tumor, peritoneal metastasis and/or lymph node metastasis.

In some embodiments, the binding agent of the invention or one or more of the polypeptide chains of the binding agent of the invention comprise or do not comprise secretion signals such as N-terminal secretion signals, in particular immunoglobulin such as IgG secretion signals such as the sequence MGWSCIILFLVATATGVHS and/or comprise or do not comprise tags, in particular C-terminal tags such as His-tags, in particular the sequence Gly-Gly-Ser-(His)$_6$ or (His)$_6$, or a Strep-tag.

In some embodiments, the binding agent of the invention comprises one or more posttranslational modifications. The invention also provides a binding agent which is derived from one or more posttranslational modifications of a binding agent described herein. In one embodiment, the one or more posttranslational modifications are selected from pyroglutamylation at the N-terminus of one or more VH(CLDN18.2), pyroglutamylation at the N-terminus of VH(CD3), deletion of lysine at the C-terminus of the first polypeptide chain and deletion of lysine at the C-terminus of the second polypeptide chain.

The invention also provides a nucleic acid encoding a polypeptide chain of the binding agent of the invention. The invention also provides a nucleic acid encoding the binding agent of the invention. The invention also provides a set of nucleic acids together encoding the binding agent of the invention.

The invention also provides a vector comprising the nucleic acid or the set of nucleic acids of the invention. The invention also provides a set of vectors comprising the set of nucleic acids of the invention. In one embodiment, each nucleic acid of the set of nucleic acids is contained in a vector of the set of vectors. In one embodiment, the vector or the set of vectors is capable of expressing the binding agent.

In one embodiment, a nucleic acid is operably linked to any number of regulatory elements (promoters, origin of replication, selectable markers, ribosomal binding sites, inducers, etc.). The vector can be an expression vector and can be extra-chromosomal or integrating vector. In some embodiments, nucleic acids encoding a polypeptide chain of the binding agent of the invention are each contained within a single expression vector. The nucleic acids can be under control of different or the same promoters. In such embodiments, different vector ratios can be used to drive formation of the binding agent of the invention.

The invention also provides a host cell comprising said nucleic acid, set of nucleic acids, vector or set of vectors. In one embodiment, the host cell is a mammalian cell, preferably selected from the group consisting of CHO cells, BHK cells, HeLa cells, COS cells, HEK293 cells, HEK293 T cells and the like. In one embodiment, the host cell is a bacterial cell, a yeast cell, a fungal cell, a plant cell or an insect cell.

The invention also provides a pharmaceutical composition comprising the binding agent of the invention, the nucleic acid of the invention, the set of nucleic acids of the invention, the vector of the invention, the set of vectors of the invention or the host cell of the invention. In one embodiment, the pharmaceutical composition further comprises a pharmaceutically acceptable carrier and/or excipient.

The invention also provides the binding agent of the invention, the nucleic acid of the invention, the set of nucleic acids of the invention, the vector of the invention, the set of vectors of the invention, the host cell of the invention or the pharmaceutical composition of the invention for use in therapy.

The invention also provides the binding agent of the invention, the nucleic acid of the invention, the set of nucleic acids of the invention, the vector of the invention, the set of vectors of the invention, the host cell of the invention or the pharmaceutical composition of the invention for use in treating or preventing cancer.

The invention also provides a method of treating or preventing cancer comprising administering the binding agent of the invention, the nucleic acid of the invention, the set of nucleic acids of the invention, the vector of the invention, the set of vectors of the invention, the host cell of the invention or the pharmaceutical composition of the invention to a subject in need thereof. In one embodiment, the cancer involves cancer cells expressing CLDN18.2.

The invention also provides a use of the binding agent of the invention, the nucleic acid of the invention, the set of nucleic acids of the invention, the vector of the invention, the set of vectors of the invention, the host cell of the invention or the pharmaceutical composition of the invention for the preparation of a medicament. In one embodiment, the medicament is for treating or preventing of cancer. In one embodiment, the cancer involves cancer cells expressing CLDN18.2.

In one embodiment, said cancer is selected from the group consisting of gastric cancer, esophageal cancer, cancer of the gastroesophageal junction (GEJ), pancreatic cancer, lung cancer such as non-small cell lung cancer (NSCLC), breast cancer, ovarian cancer, colon cancer, rectal cancer, colorectal cancer, hepatic cancer, head-neck cancer, cancer of the gallbladder and the metastasis thereof, a Krukenberg tumor, peritoneal metastasis and/or lymph node metastasis.

The invention also provides a binding agent, a nucleic acid, a set of nucleic acids, a vector, a set of vectors, a host cell or a pharmaceutical composition as described herein for use in the methods of treatment described herein. In one embodiment, provided is a method of treating or preventing a disease such as cancer comprising administering the binding agent of the invention, the nucleic acid of the invention, the set of nucleic acids of the invention, the vector of the invention, the set of vectors of the invention, the host cell of the invention or the pharmaceutical composition of the invention to a subject having a disease such as a subject having cancer. Preferably, the disease involves cells such as diseased cells expressing CLDN18.2. Preferably, the disease is cancer and the cancer involves cancer cells expressing CLDN18.2.

According to the invention, CLDN18.2 preferably has the amino acid sequence according to SEQ ID NO: 1.

In some embodiments, the first polypeptide chain does not comprise a VL(CLDN18.2). In some embodiments, the third polypeptide chain does not comprise a VH(CLDN18.2).

In some embodiments, the binding domain(s) of the binding agent with specificity for CLDN18.2 are in the format of a Fab fragment. In some embodiments, the binding domain of the binding agent of the invention with specificity for CD3 is in the format of an scFv moiety.

In some embodiments, the binding agent of the invention does not bind to CLDN18.1. Preferably, the binding agent does not bind to CLDN18.1 of human, mouse or cynomolgus. In some embodiments, the binding agent of the invention does not bind to CLDN9, such as human CLDN9.

In some embodiments, the binding agent of the invention binds to CLDN18.2 of more than one species such as CLDN18.2 of human, mouse and cynomolgus.

In some embodiments, treating a patient with the binding agent described herein results in prolonged survival of said patient. In some embodiments, the binding agent described herein exhibits one or more immune effector functions. In some embodiments, said one or more immune effector functions are selected from the group consisting of complement dependent cytotoxicity (CDC), antibody-dependent cell mediated cytotoxicity (ADCC), antibody-dependent cell-mediated phagocytosis (ADCP), induction of apoptosis, and inhibition of proliferation. The binding agents described herein preferably are able to redirect T cells to attack cancer cells and, thus, act through redirected T cell cytotoxicity (RTCC). In some embodiments, the binding agent is not capable, or not substantially capable, of inducing ADCC. In some embodiments, the binding agent is not capable, or not substantially capable, of inducing CDC. In some embodiments, the binding agent is not capable, or not substantially capable, of inducing ADCP. In some embodiments, the binding agent is capable of reducing, preferably significantly reducing, growth and/or volume of a tumor of a subject such as a patient.

The invention also provides methods of producing the binding agent of the invention. In one embodiment, a method of producing the binding agent of the invention comprises transfecting a host cell with a nucleic acid of the invention, a set of nucleic acids of the invention, a vector of the invention or a set of vectors of the invention. In one embodiment, the host cell expresses a nucleic acid encoding the binding agent of the invention. In one embodiment, the host cell co-expresses a nucleic acid encoding the first polypeptide chain of the binding agent of the invention and a nucleic acid encoding the second polypeptide chain of the binding agent of the invention. In one embodiment, the host cell further expresses a nucleic acid encoding the third polypeptide chain of the binding agent of the invention. In one embodiment, the host cell further expresses a nucleic acid encoding the fourth polypeptide chain of the binding agent of the invention. In one embodiment, said nucleic acid(s) are contained in a vector or in a set of vectors. In one embodiment, the host cell expresses all polypeptide chains of the binding agent of the invention. In one embodiment, the host cell after transfection produces the binding agent of the invention, preferably when grown under appropriate conditions for binding agent production such as those described herein or known in the art. In one embodiment, the binding agent of the invention can be obtained from the host cell.

Thus, in one embodiment, a method of producing the binding agent of the invention comprises the steps of transfecting a host cell with a nucleic acid encoding the first polypeptide chain of the binding agent of the invention, a nucleic acid encoding the second polypeptide chain of the binding agent of the invention, a nucleic acid encoding the third polypeptide chain of the binding agent of the invention, and optionally a nucleic acid encoding the fourth polypeptide chain of the binding agent of the invention, expressing said nucleic acids in the host cell and obtaining the binding agent of the invention. In one embodiment, the host cell is a mammalian cell, preferably selected from the group consisting of CHO cells, BHK cells, HeLa cells, COS cells, HEK293 cells, HEK293 T cells and the like. In one embodiment, the host cell is a bacterial cell, a yeast cell, a fungal cell, a plant cell or an insect cell. In one embodiment, the binding agent is produced in vitro. In one embodiment, the binding agent is produced in vivo, e.g., in a subject to be treated such as a subject having a disease, in particular a disease associated with cells expressing CLDN18.2, e.g. cancer. In one embodiment, the first and/or the second polypeptide chain of the binding agent of the invention are produced, e.g., in a host cell, and the third polypeptide chain is produced, e.g., in another host cell. In one embodiment, all polypeptide chains of the binding agent of the invention are produced in the same host cell.

In one embodiment, the polypeptide chains of the binding agent of the invention are linked to one another, e.g., covalently linked. In one embodiment, the polypeptide chains of the binding agent are produced as one polypeptide comprising all polypeptide chains of the binding agent. In one embodiment, at least two polypeptide chains of the binding agent are linked together and are produced as one polypeptide. In one embodiment, the first and the second polypeptide chains are linked together and are produced as one polypeptide and the third polypeptide chain is produced as a separate polypeptide. In one embodiment, the third and first polypeptide chains are linked together and are produced as one polypeptide and the second polypeptide chain is produced as a separate polypeptide. In one embodiment, the second and third polypeptide chains are linked together and are produced as one polypeptide and the first polypeptide chain is produced as a separate polypeptide, or is linked to the fourth polypeptide chain and both are produced together as one polypeptide. Preferably, the polypeptide chains of the binding agent of the invention are produced separately, i.e., as separate polypeptides, e.g., in the same or in different cells and interact upon or after production to form the binding agent, e.g., within a cell or not within a cell. Preferably, the polypeptide chains are produced as separate polypeptides, i.e., the first polypeptide chain is produced as one polypeptide, the second polypeptide chain is produced as one polypeptide, the third polypeptide chain is produced as one polypeptide, and optionally the fourth polypeptide chain is produced as one polypeptide, and the polypeptide chains of the invention interact to form the binding agent of the invention. In one embodiment, administering the binding agent of the invention comprises administering the first, second, third, and optionally fourth, polypeptide chain formulated in a carrier such as a lipid nanoparticle, a liposome, a lipoplex etc. In one embodiment, the first and second polypeptide chains are administered together, e.g., formulated in the same or in different carriers, and the third polypeptide chain is administered, e.g., formulated separately, e.g., in a carrier. In one embodiment, the fourth polypeptide chain is further administered, e.g., formulated separately, e.g., in a carrier. In one embodiment, the third and the fourth polypeptide chains are administered together, e.g., formulated in the same or in different carriers. In one embodiment, all peptide chains of the binding agent of the invention are formulated together in the same carrier. In one embodiment, each polypeptide chain of the binding agent of the invention is formulated in a separate carrier, wherein the carriers may be the same or different.

Other features and advantages of the instant invention will be apparent from the following detailed description and claims.

BRIEF DESCRIPTION OF THE DRAWINGS

FIG. 23 depicts the EC50 for binding of anti-CLDN18.2 x anti-CD3 bispecific antibodies having murine and humanized (variant H1L1) CLDN18.2 ABD to HEK293 cells transiently transfected to express human, cynomolgus, and mouse CLDN18.2.

FIGS. 24A, 24B, 24C, and 24D depicts the binding of anti-CLDN18.2 x anti-CD3 bispecific antibodies having murine and humanized (variant H1L1) CLDN18.2 ABD to HEK293 cells transiently transfected to express A) human CLDN18.1, B) cynomolgus CLDN18.1, C) mouse CLDN18.1, and D) human CLDN9. The data show that none of anti-CLDN18.2 x anti-CD3 bispecific antibodies demonstrated off-target binding.

FIGS. 33A and 33B depicts induction of A) TNFα and B) IL2 secretion by anti-CLDN18.2 x anti-CD3 bispecific antibodies in the presence of KatoIII cells (having 30k CLDN18.2 binding sites) and effector cells at an E:T ratio of 10:1.

DETAILED DESCRIPTION OF THE INVENTION

Figure 1A:
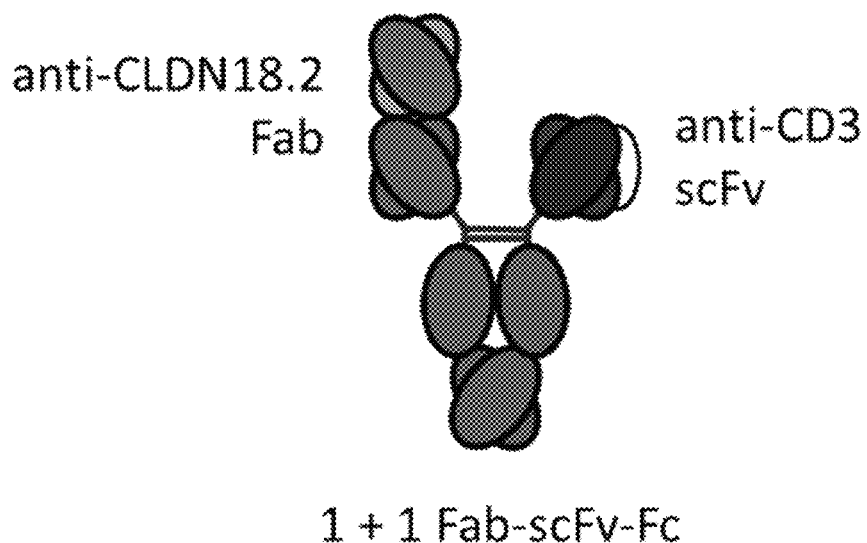
FIG. 1A depicts the "Fab-scFv" format which comprises a VH recombinantly fused to one side of a heterodimeric Fc (the first polypeptide chain described herein), a single-chain Fv ("scFv") recombinantly fused to the other side of the heterodimeric Fc (the second polypeptide chain described herein), and a light chain (LC; the third polypeptide chain described herein) transfected separately so that a Fab domain is formed with the VH of the first polypeptide chain.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments, such other member, integer or step or group of members, integers or steps may be excluded, i.e. the subject-matter consists in the inclusion of a stated member, integer or step or group of members, integers or steps. It is, however, contemplated as a specific embodiment of the present disclosure that the term "comprising" encompasses the possibility of no further members being present, i.e., for the purpose of this embodiment, "comprising" is to be understood as having the meaning of "consisting of" or "consisting essentially of".

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

The term "about" means approximately or nearly, and in the context of a numerical value or range set forth herein in one embodiment, means±20%, ±10%, ±5%, or ±3% of the numerical value or range recited or claimed.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention relates to bispecific binding agents, wherein the binding agents bind their target molecules either monovalently through a single antigen binding domain or bivalently through two antigen binding domains each independently binding to the antigen.

The first target molecule of the binding agents described herein is CLDN18.2.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop, termed EC1 or ECL1, consists on average of 53 amino acids, and the second extracellular loop, termed EC2 or ECL2, consists of around 24 amino acids. Cell surface proteins of the claudin family, such as CLDN18.2, are expressed in tumors of various origins, and are particularly suited as target structures in connection with antibody-mediated cancer immunotherapy due to their selective expression (no expression in a toxicity relevant normal tissue) and localization to the plasma membrane.

CLDN18.2 has been identified as differentially expressed in tumor tissues, with the only normal tissues expressing CLDN18.2 being stomach. CLDN18.2 is selectively expressed in normal tissues in differentiated epithelial cells of the gastric mucosa. CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, cancer of the gastroesophageal junction (GEJ), pancreatic cancer, lung cancer such as non-small cell lung cancer (NSCLC), ovarian cancer, colon cancer, rectal cancer, colorectal cancer, hepatic cancer, head-neck cancer, and cancers of the gallbladder, and metastases thereof, in particular gastric cancer metastasis such as Krukenberg tumors, peritoneal metastasis, and lymph node metastasis. The term "claudin 18" or "CLDN18" relates to claudin 18 and includes any variants, including claudin 18 splice variant 1 (claudin 18.1 (CLDN18.1)) and claudin 18 splice variant 2 (claudin 18.2 (CLDN18.2)).

The term "claudin 18.2" or "CLDN18.2" preferably relates to human CLDN18.2, and, in particular, to a protein comprising, preferably consisting of the amino acid sequence according to SEQ ID NO: 1 of the sequence listing or a variant of said amino acid sequence. The first extracellular loop of CLDN18.2 preferably comprises amino acids 27 to 81, more preferably amino acids 29 to 78 of the amino acid sequence shown in SEQ ID NO: 1. The second extracellular loop of CLDN18.2 preferably comprises amino acids 140 to 180 or 144 to 167 of the amino acid sequence shown in SEQ ID NO: 1. Said first and second extracellular loops preferably form the extracellular portion of CLDN18.2.

The second target molecule of the binding agents described herein is CD3 (cluster of differentiation 3). The CD3 complex denotes an antigen that is expressed on mature human T-cells, thymocytes and a subset of natural killer cells as part of the multimolecular T-cell receptor (TCR) complex. The T-cell co-receptor is a protein complex and is composed of four distinct chains. In mammals, the complex contains a CD3γ chain, a CD3δ chain, and two CD3ε chains. These chains associate with a molecule known as the T-cell receptor (TCR) and the ξ-chain to generate an activation signal in T lymphocytes. The TCR, ξ-chain, and CD3 molecules together comprise the TCR complex.

The human CD3 ε is indicated in GenBank Accession No. NM_000733. The human CD3 γ is indicated in GenBank Accession No. NM_000073. The human CD3 δ is indicated in GenBank Accession No. NM_000732. CD3 is responsible for the signal transduction of the TCR. As described by Lin and Weiss, Journal of Cell Science 114, 243-244 (2001), activation of the TCR complex by binding of MHC-presented specific antigen epitopes results in the phosphorylation of immunoreceptor tyrosine-based activation motifs (ITAMs) by Src family kinases, triggering recruitment of further kinases which results in T-cell activation including $Ca^{2+}$ release. Clustering of CD3 on T cells, e.g. by immobilized anti-CD3-antibodies, leads to T-cell activation similar to the engagement of the T-cell receptor, but independent from its clone typical specificity.

As used herein, "CD3" includes human CD3 and denotes an antigen that is expressed on human T cells as part of the multimolecular T-cell receptor complex. With respect to CD3, the binding agent of the invention preferably recognizes the epsilon-chain of CD3. In some embodiments, it recognizes an epitope that corresponds to the first 27 N-terminal amino acids of CD3 epsilon or functional fragments of this 27 amino acid stretch.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any post translationally modified variants and conformation variants.

According to the invention, the term "CLDN18.2 positive cancer" or similar terms mean a cancer involving cancer cells expressing CLDN18.2, preferably on the surface of said cancer cells.

"Cell surface" is used in accordance with its normal meaning in the art, and thus includes the outside of the cell which is accessible to binding by proteins and other molecules.

CLDN18.2 is expressed on the surface of cells if it is located at the surface of said cells and is accessible to binding by CLDN18.2-specific antibodies added to the cells.

CD3 is expressed on the surface of cells if it is located at the surface of said cells and is accessible to binding by CD3-specific antibodies added to the cells.

The term "extracellular portion" in the context of the present invention refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

The terms "part" or "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope or peptide is preferably immunologically equivalent to the epitope or peptide it is derived from. A part or fragment of an amino acid sequence preferably comprises a sequence of at least 4, in particular at least 6, at least 8, at least 12, at least 15, at least 20, at least 30, at least 50, or at least 100 consecutive amino acids of the protein sequence.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence.

By "variant" of an amino acid sequence or similar expressions herein is meant an amino acid sequence that differs from a parent amino acid sequence by virtue of at least one amino acid modification. The parent amino acid sequence may be a naturally occurring or wild type (WT) amino acid sequence, or may be a modified version of a wild type amino acid sequence. Preferably, the variant amino acid sequence has at least one amino acid modification compared to the parent amino acid sequence, e.g., from 1 to about 20 amino acid modifications, and preferably from 1 to about 10 or from 1 to about 5 amino acid modifications compared to the parent.

By "wild type" or "WT" or "native" used with respect to an amino acid sequence herein is meant an amino acid sequence that is found in nature, including allelic variations. A wild type amino acid sequence, peptide or protein has an amino acid sequence that has not been intentionally modified.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all mutants, splice variants, posttranslationally modified variants, conformations, isoforms, allelic variants, species variants, and species homologs, in particular those which are naturally occurring. The term "variant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

In the context of the present invention, conservative substitutions may be defined by substitutions within the classes of amino acids reflected in the following table:

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Preferably the degree of similarity, preferably identity between a given amino acid sequence and an amino acid sequence which is a variant of said given amino acid sequence will be at least about 60%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, in some embodiments, continuous amino acids. In some embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences. "Sequence identity" between two nucleic acid sequences indicates the percentage of nucleotides that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing the sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.). In some embodiments, percent identity of two sequences is determined using the BLASTN or BLASTP algorithm, as available on the United States National Center for Biotechnology Information (NCBI) website (e.g., at blast.ncbi.nlm.nih.gov/Blast.cgi?PAGE_TYPE=BlastSearch&BLAST_SPEC=blast2seq&LINK_LO C=align2seq). In some embodiments, the algorithm parameters used for BLASTN algorithm on the NCBI website include: (i) Expect Threshold set to 10; (ii) Word Size set to 28; (iii) Max matches in a query range set to 0; (iv) Match/Mismatch Scores set to 1, −2; (v) Gap Costs set to Linear; and (vi) the filter for low complexity regions being used. In some embodiments, the algorithm parameters used for BLASTP algorithm on the NCBI website include: (i) Expect Threshold set to 10; (ii) Word Size set to 3; (iii) Max matches in a query range set to 0; (iv) Matrix set to BLOSUM62; (v) Gap Costs set to Existence: 11 Extension: 1; and (vi) conditional compositional score matrix adjustment.

Percentage identity is obtained by determining the number of identical positions at which the sequences to be compared correspond, dividing this number by the number of positions compared (e.g., the number of positions in the reference sequence) and multiplying this result by 100.

In some embodiments, the degree of similarity or identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments, continuous nucleotides. In some embodiments, the degree of similarity or identity is given for the entire length of the reference sequence.

Homologous amino acid sequences exhibit according to the disclosure at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one embodiment, a fragment or variant of an amino acid sequence (peptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent. With respect to antigen binding domains comprising functional VH and VL variants, one particular function is to retain binding of said binding domain. The term "functional fragment" or "functional variant", as used herein, in particular refers to a variant molecule or sequence that comprises an amino acid sequence that is altered by one or more amino acids compared to the amino acid sequence of the parent molecule or sequence and that is still capable of fulfilling one or more, or all, of the functions of the parent molecule or sequence, e.g., forming a binding domain with specificity for a particular antigen. For example, a binding domain comprising functional VH and VL variants or functional CDR variant sequences has the same or similar binding characteristics compared to the parent molecule. In one embodiment, the modifications in the amino acid sequence of the parent molecule or sequence do not significantly affect or alter the characteristics of the molecule or sequence. In different embodiments, characteristics of a molecule comprising the functional fragment or functional variant, e.g. binding characteristics such as binding strength of a binding domain, may be reduced but still significantly present, e.g., binding characteristics such as binding strength of the binding domain comprising the functional variant may be at least 50%, at least 60%, at least 70%, at least 80%, or at least 90% of the parent molecule or sequence. For example, a functional variant may comprise 1, 2, 3, 4, 5, or more amino acid insertions, amino acid additions, amino acid substitutions and/or amino acid deletions compared to the parent molecule. However, in other embodiments, characteristics of the molecule comprising the functional variant or functional fragment, e.g., binding characteristics of a binding domain comprising the functional fragment or functional variant, may be enhanced compared to the parent molecule. In some embodiments, a "functional variant" is a "functional fragment", e.g., an amino acid sequence that is shortened at the N-terminal and/or C-terminal end compared to the parent molecule but retains or retains essentially one or more, or all, of the functions of the parent molecule, as described above, and in particular is functional equivalent to the parent molecule.

The term "functional variant" of an amino acid sequence includes "functional" fragments of said amino acid sequence.

Characteristics of functional variants, e.g., binding characteristics, can be analysed by known methods, e.g., using an ELISA-assay as described herein for binding agents competing with one another.

An amino acid sequence (peptide, protein or polypeptide, e.g., VH, VL, CH1, CH2 or CH3) "derived from" a designated amino acid sequence (peptide, protein or polypeptide, e.g., VH, VL, CH1, CH2 or CH3) refers to the origin of the first amino acid sequence. Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof, preferably functional variants thereof as described herein, including functional fragments. For example, it will be understood by one of ordinary skill in the art that the amino acid sequences suitable for use herein may be altered such that they vary in sequence, including amino acid insertions, amino acid deletions, amino acid additions and/or amino acid substitutions, from the naturally occurring or native sequences from which they were derived, while retaining or essentially retaining the desirable activity of the native sequences. For example, the amino acid sequences of the VH, VL, CH1, CH2 and/or CH3 domains on the peptide chains of the binding agent of the invention are derived from amino acid sequences of VH, VL, CH1, CH2 and/or CH3 domains of immunoglobulins but may be altered compared to the domains from which they are derived. For example, according to the invention, a VH or VL derived from an immunoglobulin comprises an amino acid sequence that can be identical to the amino acid sequence of the respective VH or VL it is derived from, or it can differ in one or more amino acid positions compared to the sequence of the respective parent VH or VL. For example, a VH domain of a binding agent of the invention may comprise an amino acid sequence comprising one or more amino acid insertions, amino acid additions, amino acid deletions and/or amino acid substitutions compared to the amino acid sequence of the VH domain it is derived from. For example, a VL domain of a binding agent of the invention may comprise an amino acid sequence comprising one or more amino acid insertions, amino acid additions, amino acid deletions and/or amino acid substitutions compared to the amino acid sequence of the VL domain it is derived from. Preferably, a VH or VL having an amino acid sequence that is a functional variant of the amino acid sequence of the parent VH or VL provides the same or essentially the same functions as the amino acid sequence of the parent VH or VL, e.g., in terms of binding specificity, binding strength etc. However, as one of ordinary skill in the art will be aware, in some embodiments, it may also be preferable to provide a functional variant of an amino acid sequence, e.g., of a VH or VL, which has altered characteristics compared to the amino acid sequence of the parent molecule. The same considerations apply to amino acid sequences of, e.g., CDRs, and to other amino acid sequences, e.g., those of CH1, CH2, CH3 and/or CL domains.

When a bispecific binding agent is described to comprise a VH "derived from" an immunoglobulin and a VL "derived from" the same or a different immunoglobulin, the term "derived from" indicates that the bispecific binding agent was generated by recombining, by any known method, said VH and VL from said immunoglobulin(s) into the resulting bispecific binding agent. In this context, "recombining" is not intended to be limited by any particular method of recombining and thus includes all of the methods for producing bispecific binding agents described herein below or known in the art, including for example recombining at nucleic acid level and/or through co-expression of different molecules in the same cells.

The term "bispecific antibody" or "bsAb" refers to a biding agent having two different antigen-binding domains defined by different amino acid sequences. In some embodiments, said different antigen-binding domains bind different epitopes on the same antigen. However, in preferred embodiments, said different antigen-binding domains bind different target antigens. A bispecific binding agent can be of any format, including any of the bispecific formats described herein. A binding agent can bind each of the different antigens or different epitopes with one, two, or more binding domains, i.e., bind each of the different antigens or different epitopes monovalently, divalently (or bivalently), trivalently, tetravalently and even with valency of higher order.

According to the invention, CLDN18.2 is not substantially expressed in a cell if the level of expression is lower compared to expression in stomach cells or stomach tissue. Preferably, the level of expression is less than 10%, preferably less than 5%, 3%, 2%, 1%, 0.5%, 0.1% or 0.05% of the expression in stomach cells or stomach tissue or even lower. Preferably, CLDN18.2 is not substantially expressed in a cell if the level of expression exceeds the level of expression in non-cancerous tissue other than stomach by no more than 2-fold, preferably 1.5-fold, and preferably does not exceed the level of expression in said non-cancerous tissue. Preferably, CLDN18.2 is not substantially expressed in a cell if the level of expression is below the detection limit and/or if the level of expression is too low to allow binding by CLDN18.2-specific antibodies added to the cell.

According to the invention, CLDN18.2 is expressed in a cell if the level of expression exceeds the level of expression in non-cancerous tissue other than stomach preferably by more than 2-fold, preferably 10-fold, 100-fold, 1000-fold, or 10000-fold. Preferably, CLDN18.2 is expressed in a cell if the level of expression is above the detection limit and/or if the level of expression is high enough to allow binding by CLDN18.2-specific antibodies added to the cell. Preferably, CLDN18.2 expressed in a cell is expressed or exposed on the surface of said cell.

According to the invention, the term "disease" refers to any pathological state, including cancer, in particular those forms of cancer described herein. Any reference herein to cancer or particular forms of cancer also includes cancer metastasis thereof. In a preferred embodiment, a disease to be treated according to the present teaching involves cells expressing CLDN18.2.

"Diseases associated with cells expressing CLDN18.2" or similar expressions mean according to the invention that CLDN18.2 is expressed in cells of a diseased tissue or organ. In one embodiment, expression of CLDN18.2 in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases associated with cells expressing CLDN18.2 include cancer diseases. According to the invention, cancer diseases preferably are those wherein the cancer cells express CLDN18.2.

As used herein, a "cancer disease" or "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease. Preferably, a "cancer disease" is characterized by cells expressing CLDN18.2 and a cancer cell expresses CLDN18.2. A cell expressing CLDN18.2 preferably is a cancer cell, preferably of the cancers described herein.

The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, rectal cancer, colorectal cancer, stomach cancer, intestine cancer, head and neck cancer, gastrointestinal cancer, lymph node cancer, esophagus cancer, cancer of the gastroesophageal junction (GEJ), colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis. One particular form of metastasis which is treatable using the therapy or methods of treatment of the invention is metastasis originating from gastric cancer as primary site. In preferred embodiments, such gastric cancer metastasis is Krukenberg tumors, peritoneal metastasis and/or lymph node metastasis.

Krukenberg tumor is an uncommon metastatic tumor of the ovary accounting for 1% to 2% of all ovarian tumors. Prognosis of Krukenberg tumor is still very poor and there is no established treatment for Krukenberg tumors. Krukenberg tumor is a metastatic signet ring cell adenocarcinoma of the ovary. Stomach is the primary site in most Krukenberg tumor cases (70%). Carcinomas of colon, appendix, and breast (mainly invasive lobular carcinoma) are the next most common primary sites. Rare cases of Krukenberg tumor originating from carcinomas of the gallbladder, biliary tract, pancreas, small intestine, ampulla of Vater, cervix, and urinary bladder/urachus have been reported.

By "treat" is meant to administer a compound or composition or a combination of compounds or compositions to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for cancer would be a candidate for therapy to prevent cancer.

By "being at risk" is meant a subject that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means according to the invention a subject for treatment, in particular a diseased subject, including human beings, nonhuman primates or another animals, in particular mammals such as cows, horses, pigs, sheeps, goats, dogs, cats or rodents such as mice and rats. In a particularly preferred embodiment, a patient is a human being.

"Target cell" shall mean any undesirable cell such as a cancer cell. In preferred embodiments, the target cell expresses CLDN18.2.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present disclosure, the term "immunologically equivalent" is preferably used with respect to the immunological effects or properties of antigens or antigen variants used for immunization. For example, an amino acid sequence is immunologically equivalent to a reference amino acid sequence if said amino acid sequence when exposed to the immune system of a subject induces an immune reaction having a specificity of reacting with the reference amino acid sequence, in particular stimulation, priming and/or expansion of T cells. Thus, a molecule which is immunologically equivalent to an antigen exhibits the same or essentially the same properties and/or exerts the same or essentially the same effects regarding the stimulation, priming and/or expansion of T cells as the antigen to which the T cells are targeted.

"Activation" or "stimulation", as used herein, refers to the state of an immune effector cell such as T cell that has been sufficiently stimulated to induce detectable cellular proliferation. Activation can also be associated with initiation of signaling pathways, induced cytokine production, and detectable effector functions. The term "activated immune effector cells" refers to, among other things, immune effector cells that are undergoing cell division.

The term "priming" refers to a process wherein an immune effector cell such as a T cell has its first contact with its specific antigen and causes differentiation into effector cells such as effector T cells.

The term "clonal expansion" or "expansion" refers to a process wherein a specific entity is multiplied. In the context of the present disclosure, the term is preferably used in the context of an immunological response in which immune effector cells are stimulated by an antigen, proliferate, and the specific immune effector cell recognizing said antigen is amplified. Preferably, clonal expansion leads to differentiation of the immune effector cells.

The term "antigen" relates to a molecule such as a protein or peptide comprising an epitope against which an agent is directed and/or is to be directed, preferably to induce an immune response. An antigen or a procession product thereof such as a T-cell epitope is in one embodiment, bound by a T- or B-cell receptor, or by an immunoglobulin molecule such as an antibody. Accordingly, an antigen or a procession product thereof may react specifically with antibodies or T lymphocytes (T cells). In a preferred embodiment, an antigen is a tumor-associated antigen, such as CLDN18.2, i.e., a constituent of cancer cells which may be derived from the cytoplasm, the cell surface and the cell nucleus, in particular those antigens which are produced, preferably in large quantity, intracellular or as surface antigens on cancer cells.

In the context of the present invention, the term "tumor-associated antigen" or "cancer-associated antigen" preferably relates to proteins that are under normal conditions specifically expressed in a limited number of tissues and/or organs or in specific developmental stages and are expressed or aberrantly expressed in one or more tumor or cancer tissues. In the context of the present invention, the tumor-associated antigen is preferably associated with the cell surface of a cancer cell and is preferably not or only rarely expressed in normal tissues.

The term "epitope" refers to an antigenic determinant in a molecule, e.g., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "binding agent", as used herein, refers to any agent capable of binding to desired antigens. In certain embodiments, of the invention, the binding agent is an antibody, antibody fragment, or construct thereof. The binding agent may also comprise synthetic, modified or non-naturally occurring moieties, in particular non-peptide moieties. Such moieties may, for example, link desired antigen-binding functionalities or regions such as antibodies or antibody fragments. In one embodiment, the binding agent is a synthetic construct comprising antigen-binding CDRs or variable regions.

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the VL (variable light chain) domain, CL (constant light chain) domain, the VH (variable heavy chain) and the CH (constant heavy chain) domains CH1, CH2, CH3, and CH4. There are five types of mammalian immunoglobulin heavy chains, i.e., $\alpha$, $\delta$, $\epsilon$, $\gamma$, and $\mu$ which account for the different classes of immunoglobulins, i.e., IgA, IgD, IgE, IgG, and IgM. Immunoglobulin classes are also referred to as "isotypes" (for instance IgG1, IgG2, IgG3, IgG4, IgD, IgA, IgE, or IgM) referring to the immunoglobulin class that is encoded by heavy chain constant region genes. When a particular isotype, e.g. IgG1, is mentioned herein, the term is not limited to a specific isotype sequence, e.g. a particular IgG1 sequence, but is used to indicate that the antibody is closer in sequence to that isotype, e.g. IgG1, than to other isotypes. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The term "antibody" refers to an immunoglobulin comprising at least two heavy (H) chains and two light (L) chains inter-connected by disulfide bonds, or an antigen binding portion thereof. The term "antibody" includes monoclonal antibodies, recombinant antibodies, human antibodies, humanized antibodies and chimeric antibodies. Each heavy chain is comprised of a heavy chain variable region (abbreviated herein as VH) and a heavy chain constant region (amino acid residues 118-447 of human IgG1 according to EU numbering) comprising CH1, CH2 and CH3 domains, wherein CH1 is typically connected to CH2-CH3 by a peptide linker (also called "hinge"). Each light chain is comprised of a light chain variable region (abbreviated herein as VL) and a light chain constant region (abbreviated herein as CL). The term "region" and the term "domain" are used interchangeably herein. The VH and VL domains can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (see also Chothia and Lesk, J. Mol. Biol. 196, 901-917 (1987)). Unless otherwise stated or contradicted by context, CDR sequences herein are identified according to the Kabat numbering system and reference to amino acid positions in the constant regions in the present invention is according to the EU-numbering (Edelman et al., (1969) Proc. Natl. Acad. Sci. USA 63(1):78-85; Kabat et al., Sequences of Proteins of Immunological Interest, 5th Edit. 1991 NIH Publication No. 91-3242). The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "amino acid corresponding to position . . . " as used herein refers to an amino acid position number in a human IgG1 heavy chain. Corresponding amino acid positions in other immunoglobulins may be found by alignment with human IgG1. Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present invention.

The term "IgG Fc ligand" as used herein refers to a molecule, preferably a polypeptide, that binds to the Fc region of an IgG immunoglobulin to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., (2002) Immunol. Rev. 190:123-136). Particular IgG Fc ligands are FcRn and Fc gamma receptors. An "Fc ligand" as used herein can be from any organism such as mouse, human and cynomolgus. "Fc gamma receptor", "FcγR" or "FcgammaR" refers to any member of the family of proteins that bind the IgG Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., (2002) Immunol. Lett. 82:57-65). An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2).

"FcRn" or "neonatal Fc Receptor" as used herein relates to a protein that binds the IgG Fc region and is encoded at least in part by an FcRn gene. The FcRn may be from any organism, including but not limited to humans, mice, rats, rabbits, and monkeys. The functional FcRn protein comprises two polypeptides, often referred to as the heavy chain (encoded by the FcRn gene) and light chain (beta-2-microglobulin). Unless specified otherwise, "FcRn" or "FcRn protein" refers to the complex of FcRn heavy chain with beta-2-microglobulin. An "FcRn variant" as used herein is one that increases binding to the FcRn receptor and may also increase serum half-life.

"Fc" or "Fc region" or "Fc domain" as used herein refers to a polypeptide comprising the CH2 and CH3 domains of an IgG molecule and optionally a peptide linker such as the hinge. The CH2-CH3 domains of human IgG1 comprise amino acid positions 231-447, and the hinge comprises 216-230, according to EU numbering. Thus, with reference to IgG, the term "Fc domain" as used herein includes amino acid positions 231-447 (CH2-CH3) and 216-447 (hinge-CH2-CH3) according to EU numbering, and functional variants thereof including functional fragments thereof. An "Fc fragment" may contain fewer amino acids, e.g., an N-terminal or C-terminal truncation variant, but still retains the ability to form a dimer with another Fc domain or Fc fragment, as can be detected using standard methods, e.g., based on size (e.g. non-denaturing chromatography, size exclusion chromatography, etc.), and thus is a functional variant. According to the present invention, an IgG Fc domain preferably is a human IgG Fc domain including the Fc domain from human IgG1, IgG2 or IgG4.

The terms "hinge", "hinge region", "antibody hinge region" or "hinge domain" as used herein refer to the peptide linker comprising the amino acids between CH1 and CH2 of an immunoglobulin, e.g., IgG. Structurally, in naturally occurring IgG, e.g., IgG1, molecules, the CH1 ends at amino acid position 215 according to EU numbering, and the CH2 begins at amino acid position 231 according to EU numbering. Thus, for IgG, the hinge includes amino acid positions 216 to 230 according to EU numbering.

A "variant Fc domain" contains amino acid modifications as compared to a parental Fc domain. Thus, a "variant IgG1 Fc domain", e.g., variant human IgG1 Fc domain, contains amino acid modifications (e.g., amino acid substitutions and/or deletions) in positions corresponding to positions of an IgG1 Fc domain, e.g., human IgG1 Fc domain, and preferably is a functional variant of the parental Fc domain. Such variant IgG Fc domains retain at least about 80%, 85%, 90%, 95%, 96%, 97%, 98% or 99% identity to the corresponding parental human IgG Fc domain. Optionally, the variant Fc domains can have 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental Fc domain. Optionally, the variant Fc domains can have up to 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental Fc domain. Preferably, a variant Fc domain retains the ability to form a dimer with another Fc domain as measured using techniques as described herein or known in the art, such as non-denaturing gel electrophoresis.

Fc Modifications

The binding agents described herein comprise at least three different polypeptide chains, wherein two polypeptide chains, e.g., the first polypeptide chain and the second polypeptide chain, comprise CH2-CH3 regions, preferably derived from IgG such as IgG1, in particular human IgG1. Preferably said first and second polypeptide chains comprising CH2-CH3 regions are able to interact, e.g., dimerize thereby forming a heterodimer comprising said first and second polypeptide chain of a binding agent described herein. Preferably, the CH2-CH3 regions of the binding agents of the invention are derived from IgG1, more preferably human IgG1, even though CH2 and CH3 derived from other serotypes can be used as described herein. Moreover, as discussed herein, the binding agents of the invention will self-assemble, e.g., within a producing host cell. For example, it is envisaged that the CH2 on the first polypeptide chain interacts with the CH2 on the second polypeptide chain and/or the CH3 on the first polypeptide chain interacts with the CH3 on the second polypeptide chain, thereby forming an Fc fragment. These Fc fragments may comprise one or more amino acid modifications or "Fc modifications" as discussed herein with respect to human IgG1 to promote interaction between the CH2 on the first and second polypeptide chains and/or CH3 on the first and second polypeptide chains, and/or allow for ease of purification of heteromultimers, such as heterodimers, containing first and second polypeptide chains interacting with one another over homomultimers only containing one type of polypeptide chain, and/or confer further beneficial functionalities as discussed herein. Amino acid modifications discussed herein may also be contained in CH1 domains, e.g., within the first and/or second polypeptide chains of a binding agent of the invention. In addition, peptide linkers such as peptide linkers within scFv moieties or peptide linkers connecting further domains of a binding agent, e.g., CH1 and scFv, or CH2 and scFv, or CH1 and CH2, may comprise one or more amino acid modifications as described herein. For example, a peptide linker connecting a CH2-CH3 region to another region or domain, such as VH(CD3), VL(CD3) or CH1, can have a serine at the amino acid position which corresponds to position 220 according to EU numbering in a naturally occurring IgG1 (where normally a cysteine can be found). Using a peptide linker comprising a serine at said position corresponding to position 220 of human IgG1 reduces disulfide formation between the two chains comprising CH2-CH3 regions.

Thus, formation of the binding agents of the present invention is based on the use of different monomers (e.g., first and second polypeptide chains described herein) comprising CH1, CH2 and/or CH3 containing amino acid substitutions such as those that "skew" formation of heterodimers formed by said monomers over homodimers described herein, preferably coupled with "pI modifications" that allow for simple purification of the heterodimers away from the homodimers, and optionally in combination with "ablation modifications" and additional Fc modifications discussed herein. A skilled person will understand that any of the amino acid modifications discussed herein with respect to CH1, CH2 and/or CH3 domains and peptide linkers, e.g., hinge variants, can be combined with further amino acid modifications discussed herein or known in the art. For example, any of the skew and pI modifications can independently be combined with ablation, and other Fc modifications. An Fc modification according to the present invention can be an amino acid insertion, addition, deletion, or substitution.

The Fc modifications discussed herein are defined according to the amino acid modifications that compose them. For example, N434S is an Fc modification with a substitution of serine at position 434 for asparagine relative to parental human IgG1 Fc polypeptide and according to EU numbering. The identity of the parental amino acid may be unspecified, in which case the aforementioned variant is referred to as 434S, i.e., the CH2-CH3 region comprising said Fc modification comprises a serine in an amino acid position that corresponds to position 434 in human IgG1 according to EU numbering.

pI Modifications pI modifications increase the isoelectric point (pI) difference between monomers what allows the isoelectric purification of homo- and heteromultimeric proteins. In general, a pI modification either increases the pI of the polypeptide chain (basic change) or decreases the pI of the polypeptide chain (acidic change).

As discussed herein, a pI difference of at least 0.1, e.g., 0.2, 0.3, 0.4 or 0.5, between two polypeptide chains can allow separation by ion exchange chromatography or isoelectric focusing, or other methods sensitive to isoelectric point known in the art. Therefore, inclusion of pI modifications that alter the pI of each of the polypeptide chains interacting with one another, e.g., first and second polypeptide chains described herein, such that each of said polypeptide chains has a different pI and the heteromultimer formed by said polypeptide chains also has a distinct pI facilitates isoelectric purification of binding agents comprising said heteromultimer. These substitutions also aid in the determination and monitoring of any contaminating unwanted homo- or heteromultimer formation.

pI modifications can be contained within one or both chains of a heteromultimer comprising heavy chain constant regions, e.g., first and second polypeptide chains of a binding agent of the invention, and within CH1, CH2 and/or CH3 and/or within peptide linkers such as linkers connecting the VH and VL domains of an scFv moiety. For example, pI variants can be contained in the first polypeptide chain and/or in the second polypeptide chain of a binding agent of the invention to decrease or prevent homomultimer formation. Typically, when contained in both the first and second polypeptide chain, pI variants will be used such that the pI of one polypeptide chain is increased while the pI of the second polypeptide chain is decreased. This can be done, e.g., by replacing a neutral amino acid residue by a positively or negatively charged amino acid residue, or vice versa, or by changing a charged amino acid residue from positive to negative charge or vice versa, as discussed herein. Accordingly, in certain embodiments, of the present invention, a sufficient change in pI in at least one of the polypeptide chains of a binding agent described herein is provided such that heteromultimers, e.g., of the first and second polypeptide chains, can be purified away from homomultimers. In certain embodiments, a pI difference of as little as 0.1, 0.2, 0.3, 0.4 or 0.5 or greater in pH units is used in the present invention. The amount of pI modifications to be included on one or more polypeptide chains of a binding agent of the invention to get good separation will depend in part on the starting pI of the polypeptide chains, the pI of the CH regions, Fv scaffold regions etc. as will be understood by a person skilled in the art. The change in pI can be calculated by any method known in the art, e.g., on the basis of the CH regions, e.g., using the method described by Sillero and Maldonado (Sillero, Maldonado, (2006) Comput. Biol. Med. 36(2):157-166). Alternatively, the pI of each polypeptide chain can be compared. In addition, heteromultimers can be separated according to their size.

In certain embodiments, pI modifications, skew modifications, additional Fc modifications or ablation modifications etc. are not included in the variable regions of a binding agent of the invention.

In certain embodiments, pI modifications are derived from different IgG isotypes such that the pI of the respective polypeptide chain is changed without introducing immunogenicity (cf., U.S. 2014/0370013). Preferably, pI modifications are derived from human IgG isotypes so as to decrease the risk of introducing immunogenicity. The modifications discussed herein are described in relation to human IgG1, but all IgG isotypes can be altered this way, as well as isotype hybrids. In the case where the heavy chain constant domain is from IgG2-4, R133E and R133Q can also be used.

IgG1 is a common isotype for therapeutic antibodies for a variety of reasons, including high effector function. However, the CH region of IgG1 has a higher pI than that of IgG2. By introducing IgG2 derived residues at particular positions into the IgG1 backbone, the pI of the resulting monomer is lowered or increased and, additionally, serum half-life may be increased. For example, human IgG1 has a glycine (pI approximately 5.97) at position 137 according to EU numbering, and human IgG2 has a glutamic acid (pI approximately 3.22) at the corresponding position; substituting the glutamic acid residue for a glycine residue will affect the pI of the resulting polypeptide. Lowering the pI of an antibody constant region may also increase serum half-life in vivo (see U.S. Ser. No. 13/194,904; Ghetie and Ward, 1997, Immunol Today. 18(12): 592-598). Also, variable regions with lower pI may add to longer serum half-lifes (see Igawa et al., (2010) PEDS 23(5): 385-392).

In a preferred combination of pI modifications, one polypeptide chain (e.g., the first polypeptide chain of a binding agent of the invention, e.g. comprising VH(CLDN18.2), CH1, CH2 and CH3) comprises an aspartic acid residue at position 208, a glutamic acid residue at position 295, an aspartic acid residue at position 384, a glutamic acid residue at position 418 and an aspartic acid residue at position 421 (i.e., N208D/Q295E/N384D/Q418E/N421D with respect to human IgG1) according to EU numbering and another polypeptide chain (e.g., the second polypeptide chain of said binding agent, e.g. comprising VH(CD3) and VL(CD3), CH2 and CH3, and optionally VH(CLDN18.2) and CH1) comprises a positively charged peptide linker connecting VH(CD3) and VL(CD3) ("scFv linker"), such as a polypeptide linker comprising or consisting of the amino acid sequence (GKPGS)$_4$ or a functional variant thereof.

In polypeptide chains that do not comprise a CH1 and, thus, do not include an amino acid position that corresponds to position 208 according to EU numbering, the following negative pI modifications can be used: a glutamic acid residue at position 295, an aspartic acid residue at position 384, a glutamic acid residue at position 418 and an aspartic acid residue at position 421 (human IgG1: Q295E/N384D/Q418E/N421D) according to EU numbering.

In some embodiments, one polypeptide chain, e.g., the first polypeptide chain, contains a set of variants as discussed herein and the polypeptide chain interacting therewith, e.g., the second polypeptide chain, comprises a charged scFv linker, such as a positively charged scFv linker selected from the group consisting of SEQ ID NO: 2, 3, 4, 5, 6, 7, 8, 9, 10, 11 and 12 or a functional variant thereof, or a negatively charged scFv linker selected from the group consisting of SEQ ID NO: 13, 14, 15, 16, 17, 18, 19 and 20 or a functional variant thereof.

Skew Modifications

"Skew modifications" are steric modifications that facilitate interaction of the polypeptide chains comprising such modifications. One strategy making use of steric modifications is referred to in the art as "knobs and holes", referring to amino acid engineering, wherein a protuberance is introduced on a first heavy-chain polypeptide, typically in the Fc region (CH2-CH3), and a corresponding cavity in a second heavy-chain polypeptide, typically in the Fc region (CH2-CH3), such that the protuberance can be positioned in the cavity at the interface of these two heavy chains to promote heterodimer formation and hinder homodimer formation (see U.S. Ser. No. 61/596,846, Ridgway et al., (1996) Protein Engineering 9(7):617; Atwell et al., (1997) J. Mol. Biol. 270:26; U.S. Pat. No. 8,216,805). "Protuberances" are constructed by replacing small amino-acid side-chains from the interface of the first heavy-chain polypeptide with larger side chains. Compensatory "cavities" of identical or similar size to the protuberances are created in the interface of the second heavy-chain polypeptide by replacing large amino-acid side-chains with smaller ones (U.S. Pat. No. 5,731, 168). "Knobs and holes" modifications can be combined with disulfide bonds to skew formation to heteromultimerisation, e.g., heterodimerization of said first and second heavy-chain polypeptides (see Merchant et al., (1998) Nature Biotech. 16:677).

Useful skew modifications include without limitation the following pairs of double modifications, wherein one part of each pair of double modifications will be present in one polypeptide chain (e.g., the first polypeptide chain described herein) of the binding agent of the invention and the second part will be present in another polypeptide chain (e.g., the second polypeptide chain described herein) of the binding agent of the invention: S364K/E357Q: L368D/K370S; L368D/K370S: S364K; L368D/K370S: S364K/E357Q; L368E/K370S: S364K; T411E/K360E/Q362E: D401K; L368D/K370S: S364K/E357L; K370S: S364K/E357Q; T366S/L368A/Y407V: T366W and T366S/L368A/Y407V/ Y349C: T366W/S354C according to EU numbering and with respect to human IgG1. Preferably, L368D/K370S: S364K/E357Q is used in the binding agent of the invention.

Skew modifications described herein may also have an effect on pI (cf., Gunasekaran et al., (2010) J. Biol. Chem. 285(25):19637), and thus on purification, and, therefore, could also be considered pI variants.

Ablation Modifications

By "ablation" herein is meant a decrease or removal of activity. "Ablating FcγR binding" means that an Fc region comprising one or more ablation modifications has more than 50% loss in FcγR binding activity as compared to an Fc region not containing the specific modifications. Preferably, the Fc region comprising the one or more ablation modifications has more than 70%, 80%, 90%, 95%, 98% or even more loss of FcγR binding activity. Preferably, the FcγR binding activity of an Fc region comprising the one or more ablation modifications as compared to an Fc region not containing the specific modifications is below the level of detectable binding in a Biacore, SPR or BLI assay.

As is known, the Fc domain of human IgG1 has the highest binding to Fcγ receptors, and thus ablation modifications can be used when the constant domains of a binding agent are derived from IgG1. Alternatively, or in addition to ablation modifications, mutations at the glycosylation position 297 (generally to A or S) can significantly ablate binding to FcγRIIIa, for example. Human IgG2 and IgG4 have naturally lower binding to Fcγ receptors (Parren et al., 1992, J. Clin Invest. 90: 1537-1546; Bruhns et al., 2009, Blood 113: 3716-3725), and thus CH1, CH2 and CH3 domains derived from IgG2 or IgG4 can be used with or without ablation modifications in binding agents of the invention. Amino acid modifications that ablate FcγR binding have, e.g., been described in Dall'Acqua W F et al., J Immunol. 177(2):1129-1138 (2006) and Hezareh M, J Virol.; 75(24): 12161-12168 (2001).

Thus, the Fc portion of a binding agent of the invention may comprise one or more "FcγR ablation modifications" or "Fc knock out (FcKO or KO) modifications". In certain embodiments, it is desirable to reduce or remove binding of the Fc domain to one or more or all of the Fcγ receptors (e.g. FcγRI, FcγRIIa, FcγRIIb, FcγRIIIa, etc). In some embodiments, it is desirable to ablate FcγRIIIa binding of binding agents that bind CD3 monovalently such as the binding agents of the present invention to eliminate or significantly reduce ADCC activity. Thus, in the binding agents of the invention, one or more of the polypeptide chains, e.g., the first polypeptide chain and the second polypeptide chain, of a binding agent of the invention comprise one or more FcγR ablation variants. In preferred embodiments, the one or more ablation variants are selected from the group consisting of G236R, S239G, S239K, S239Q, S239R, V266D, S267K, S267R, H268K, E269R, 299R, 299K, K322A, A327G, A327L, A327N, A327Q, L328E, L328R, P329A, P329H, P329K, A330L, A330S/P331S, I332K, I332R, V266D/ A327Q, V266D/P329K, S267R/A327Q, S267R/P329K, G236R/L328R, E233P/L234V/L235A/G236_/S267K, E233P/L234V/L235A/G236_/S239K/A327G, E233P/ L234V/L235A/G236del, S239K/S267K, 267K/P329K, E233P/L234V/L235A/G236del/S239K, E233P/L234V/ L235A/G236del/S267K, E233P/L234V/L235A/G236del/ S239K/A327G, E233P/L234V/L235A/G236del/S267K/ A327G and E233P/L234V/L235A/G236del according to EU numbering and with respect to human IgG1, wherein "del" represents an amino acid deletion at the indicated position. Preferably, the modifications E233P/L234V/ L235A/G236_/S267K according to EU numbering and with respect to human IgG1 are used in both the first and the second polypeptide chain of the binding agent of the invention. It should be noted that the ablation modifications disclosed herein ablate FcγR binding but generally not FcRn binding. However, techniques for reducing or increasing the binding to FcRn in order to reduce or increase serum half-life of the binding agent are known and can be used (see, e.g., Dall'Acqua et al. 2006, J. Biol. Chem., 281: 23514-24; Hinton et al. 2006, J. Immunol., 176:346-56; and Zalevsky et al. 2010 Nat. Biotechnol., 28:157-9).

For example, in the binding agent of the invention, the first polypeptide chain comprises an amino acid sequence according to SEQ ID NO: 28 and the second polypeptide chain comprises an amino acid sequence according to SEQ ID NO: 30, wherein the first and second polypeptide chains comprise the L368D/K370S: S364K/E357Q set of skew modifications, the first polypeptide chain further comprises the N208D/Q295E/N384D/Q418E/N421D set of pI modifications, and both the first and second polypeptide chain further comprises the E233P/L234V/L235A/G236del/ S267K set of ablation modifications, e.g. wherein the first polypeptide chain comprises VH(CLDN18.2) and CH1 and the second polypeptide chain comprises scFv(CD3), and optionally VH(CLDN18.2) and CH1. Of course, further modifications may be included into the amino acid sequences of a respective binding agent; e.g., a binding agent may comprise additional amino acid modifications such as substitutions in addition to the modifications discussed above.

Additional Fc Modifications

In addition to other modifications described herein, such as pI, skew and ablation modifications, a number of useful modifications that alter binding of one or more FcγR receptors, altered binding to FcRn receptors, etc. can be used.

Accordingly, there is a number of useful amino acid substitutions that can be made to alter binding of the binding agents of the invention to one or more FcγR receptors. Substitutions that result in increased binding as well as decreased binding can be useful. For example, it is known that increased binding to FcγRIIIa results in increased ADCC. Similarly, decreased binding to FcγRIIb can be beneficial as well. Amino acid substitutions that can be used in the present invention include those listed in U.S. Ser. Nos. 11/124,620, 11/174,287, 11/396,495, 11/538,406, all of which are incorporated herein by reference in their entirety.

Particular useful amino acid substitutions that can be incorporated into the binding agents of the invention include but are not limited to 236A, 239D, 239E, 332E, 332D, 239D/ 332E, 267D, 267E, 328F, 267E/328F, 236A/332E, 239D/ 332E/330Y, 239D/332E/330L, 243A, 243L, 264A, 264V and 299T.

In addition, there are additional modifications that are useful to increase binding to FcRn and increase serum half-life, as disclosed in U.S. Ser. No. 12/341,769, hereby incorporated by reference in its entirety, including but not limited to 434S, 434A, 428L, 308F, 259I, 428L/434S, 259I/ 308F, 436I/428L, 436I/434S, 436V/434S, 436V/428L and 259I/308F/428L according to EU numbering.

In addition, a CH3 on one or both polypeptide chains, preferably on both polypeptide chains, forming an Fc heterodimer may contain the modifications M428L/N434S resulting in longer serum half-life.

As will be appreciated by those skilled in the art, the modifications discussed herein can be independently combined with other modifications. In one embodiment, one polypeptide chain of a binding agent of the invention (e.g., the first polypeptide chain) comprises N208D, Q295E, N384D, Q418E and N481D according to EU numbering, and another polypeptide chain of the binding agent (e.g., the second polypeptide chain) comprises a positively charged scFv linker as described herein. Preferably, the first polypeptide chain of the binding agent further comprises K370S and L368D, and the second polypeptide chain of the binding agent further comprises E357Q and S364K, according to EU numbering. In addition, in a preferred embodiment, both the first and second polypeptide chains further comprise E233P, L234V, L235A, G236del and S267K according to EU numbering. Most preferably, the first polypeptide chain of a binding agent of the invention comprises N208D, E233P, L234V, L235A, G236del, S267K, Q295E, L368D, K370S, N384D, Q418E and N481D, and the second polypeptide chain of the binding agent comprises E233P, L234V, L235A, G236del, S267K, E357Q and S364K and, optionally, C220S to remove the cysteine that typically pairs with a light chain.

The term "monoclonal binding agent" as used herein includes a "monoclonal antibody" and refers to a preparation of binding agent molecules of single molecular composition. A monoclonal binding agent composition displays a single binding specificity and affinity for a particular epitope. Accordingly, the term "human monoclonal antibody" refers to binding agents displaying a single binding specificity, which have variable and constant regions derived from human germline immunoglobulin sequences. The human monoclonal binding agents may be generated by a hybridoma, which includes a B cell, obtained from a transgenic or transchromosomal non-human animal, such as a transgenic mouse, having a genome comprising a human heavy chain transgene and a light chain transgene, fused to an immortalized cell.

The term "recombinant binding agent" as used herein includes a "recombinant antibody" and includes all binding agents that are prepared, expressed, created or isolated by recombinant means, such as (a) binding agents isolated from an animal (e.g., a mouse) that is transgenic or transchromosomal with respect to the immunoglobulin genes or a hybridoma prepared therefrom, (b) binding agents isolated from a host cell transformed to express the binding agent, e.g., from a transfectoma, (c) binding agents isolated from a recombinant, combinatorial antibody library, and (d) binding agents prepared, expressed, created or isolated by any other means that involve splicing of immunoglobulin gene sequences to other DNA sequences.

The term "human binding agent" as used herein includes a "human antibody" and is intended to include binding agents having variable and constant regions derived from human germline immunoglobulin sequences. Human binding agents may include amino acid residues not encoded by human germline immunoglobulin sequences (e.g., mutations introduced by random or site-specific mutagenesis in vitro or by somatic mutation in vivo).

The term "humanized binding agent" as used herein includes a "humanized antibody" and refers to a molecule having an antigen binding site that is substantially derived from an immunoglobulin from a non-human species, wherein the remaining immunoglobulin structure of the molecule is based upon the structure and/or sequence of a human immunoglobulin. This can be achieved, e.g., by grafting of the six non-human antibody complementarity-determining regions (CDRs), which together form the antigen binding site, onto a homologous human acceptor framework region (FR) (see WO92/22653 and EP0629240). The antigen binding site may either comprise complete variable domains fused onto constant domains or only the complementarity determining regions (CDR) grafted onto appropriate framework regions in the variable domains. In order to fully reconstitute the binding affinity and specificity of the parental binding agent, the substitution of framework residues from the parental binding agent (i.e. the non-human binding agent, e.g., a murine antibody) into the human framework regions (back-mutations) may be required. Structural homology modeling may help to identify the amino acid residues in the framework regions that are important for the binding properties of the binding agent. Antigen binding sites may be wild-type or modified by one or more amino acid substitutions, e.g., modified to resemble human immunoglobulins more closely. Some forms of humanized binding agents preserve all CDR sequences (for example a humanized mouse antibody which contains all six CDRs from the mouse antibody). Other forms have one or more CDRs which are altered with respect to the original binding agent, e.g., antibody. Thus, a humanized binding agent may comprise non-human CDR sequences, primarily human framework regions optionally comprising one or more amino acid back-mutations to the non-human amino acid sequence, and fully human constant regions.

The term "chimeric binding agent" as used herein includes a "chimeric antibody" and refers to those binding agents wherein one portion of each of the amino acid sequences of heavy and light chains is homologous to corresponding sequences in binding agents, e.g., antibodies, derived from a particular species or belonging to a particular class, while the remaining segment of the chain is homologous to corresponding sequences in another. Typically, the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the binding agents are injected than would the constant region from a non-human source. However, the definition is not limited to this particular example.

Binding agents or fragments thereof, e.g., variable and/or constant regions, may be derived from different species, including but not limited to mouse, rat, rabbit, guinea pig and human.

Immunoglobulins described herein include IgA such as IgA1 or IgA2, IgG1 (including allotypes with polymorphisms at amino acid position 356 (D or E) and 358 (L or M) according to EU numbering), IgG2, IgG3, IgG4, IgE, IgM, and IgD antibodies. In various embodiments, the immunoglobulin is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ). Amino acid sequences described herein with respect to IgG1 allotype 356D/358M also include allotype 356E/358L.

The term "IgG subclass modification" or "isotype modification" means an amino acid modification that converts one amino acid of one IgG isotype to the corresponding amino acid in a different, aligned IgG isotype. For example, because IgG1 comprises a tyrosine and IgG2 a phenylalanine at amino acid position 296 according to EU numbering, a F296Y substitution in IgG2 is considered an IgG subclass modification.

As used herein, a "heterologous binding agent" includes a "heterologous antibody" and is defined in relation to a transgenic organism producing such a binding agent. This term refers to a binding agent having an amino acid sequence or an encoding nucleic acid sequence corresponding to that found in an organism not consisting of the transgenic organism, and being generally derived from a species other than the transgenic organism.

As used herein, a "heterohybrid binding agent" includes a "heterohybrid antibody" and refers to a binding agent having light and heavy chains of different organismal origins. For example, an antibody having a human heavy chain associated with a murine light chain is a heterohybrid antibody.

The binding agents including antibodies described herein are preferably isolated. "Isolated" as used herein, is intended to refer to a binding agent which is substantially free of other agents having different antigenic specificities (e.g., an isolated binding agent that specifically binds to CLDN18.2 and CD3 is substantially free of binding agents that specifically bind antigens other than CLDN18.2 and CD3). An isolated binding agent that specifically binds to an epitope, isoform or variant of human CLDN18.2 may, however, have cross-reactivity to other related antigens, e.g., from other species (e.g., CLDN18.2 species homologs). Moreover, an isolated binding agent may be substantially free of other cellular material and/or chemicals.

The terms "antigen-binding portion" of a binding agent such as an antibody (or simply "binding portion") or "antigen-binding fragment" of a binding agent such as an antibody (or simply "binding fragment") or similar terms refer to one or more fragments of a binding agent that retain the ability to specifically bind to an antigen. It has been shown that the antigen-binding function of an antibody can be performed by fragments of a full-length antibody. Examples of binding fragments encompassed within the term "antigen-binding portion" of a binding agent such as an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fab' fragments, derived from a F(ab')$_2$ fragment and containing a free sulfhydryl group that may be alkylated or utilized in conjugation with an enzyme, toxin or other protein of interest, wherein the Fab' may contain a small portion of Fc; (iv) Fd fragments consisting of the VH and CH domains; (v) Fv fragments consisting of the VL and VH domains of a single arm of an antibody, (vi) dAb fragments (Ward et al., (1989) Nature 341: 544-546), which consist of a VH domain; (vii) isolated complementarity determining regions (CDR), and (viii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH domains pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of a binding agent such as an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A single-chain variable fragment (scFv) is a fusion protein of the variable regions of the heavy (VH) and light chains (VL) of immunoglobulins, connected with a short linker peptide of usually ten to about 30 amino acids such as an scFv linker, e.g., as represented by SEQ ID NO: 2-20. The linker is usually rich in glycine for flexibility, as well as serine or threonine for solubility, and can either connect the N-terminus of the VH with the C-terminus of the VL, or vice versa. Divalent (or bivalent) single-chain variable fragments (di-scFvs, bi-scFvs) can be engineered by linking two scFvs. This can be done by producing a single peptide chain with two VH and two VL domains, yielding tandem scFvs. The invention also includes multispecific molecules comprising more than one scFvs binding domain. One common flexible linking peptide is $(G_4S)_x$, wherein x may be 2, 3, 4, 5 or 6. Preferably, a linker connecting the VH and VL domain of an scFv comprises, preferably consists of, the amino acid sequence $(GKPGS)_X$ or a functional variant thereof, wherein x may be 2, 3, 4, 5, or 6. Optionally, the association of the VH and VL can be stabilized by one or more intermolecular disulfide bonds.

Another possibility is the creation of scFvs with linker peptides that are too short for the two variable regions to fold together (about five amino acids), forcing scFvs to dimerize. This type is known as diabodies. Still shorter linkers (one or two amino acids) lead to the formation of trimers, so-called triabodies or tribodies. Tetrabodies have also been produced. They exhibit an even higher affinity to their targets than diabodies.

The term "specificity" as used herein is intended to have the following meaning unless contradicted by context. Two binding agents have the "same specificity" if they bind to the same antigen and the same epitope.

As used herein, the term "binding domain" or "antigen-binding domain" refers to the site, e.g. of a binding agent such as an antibody, that binds to an antigen and includes the antigen-binding portion of a binding agent. The binding domain may be comprised of heavy chain and light chain variable domains (VH and VL), each of which includes four conserved framework regions (FR) and three CDRs. The CDRs vary in sequence and determine the specificity to a particular antigen. The VH and VL domains together may form the site that specifically binds a particular antigen. A "binding domain with specificity" for an antigen is specific for said antigen if a binding agent comprising said binding domain binds to said antigen through said binding domain in standard assays, e.g., with a $K_D$ of about $10^{-7}$ M or less, while it does not bind significantly, in particular does not bind detectably, through said binding domain to antigens different from the indicated antigen the binding domain is specific for in standard assays. Of course, if the binding agent comprises more than one binding domain with different specificities, it will bind to the more than one antigen with specificity, as described herein. Binding of a binding agent to an antigen can be determined, e.g., using Bio-Layer Interferometry (BLI), or, for instance, using surface plasmon resonance (SPR) technology in a BIAcore 3000 instrument using the antigen as the ligand and the binding agent as the analyte.

Fab (fragment antigen binding) antibody fragments are immunoreactive polypeptides comprising monovalent antigen-binding domains of an antibody composed of a polypeptide consisting of a heavy chain variable region (VH) and heavy chain constant region 1 (CH1) portion and a polypeptide consisting of a light chain variable region (VL) and a light chain constant region (in which the CL and CH1 portions are bound together, for example by a disulfide bond between Cys residues). Preferably in the Fab fragments described herein the CH1 and the CL are of human origin. In one embodiment, the CL is a kappa-type CL. In one embodiment, the CH1 is derived from IgG1, preferably from human IgG1.

All antibodies and derivatives of antibodies such as antibody fragments as described herein for the purposes of the invention are encompassed by the term "antibody". The term "antibody derivatives" refers to any modified form of an antibody, e.g., a conjugate of the antibody and another agent or antibody, or an antibody fragment. Furthermore, the antibodies and derivatives of antibodies as described herein are useful for producing binding agents of the invention.

Naturally occurring antibodies are generally monospecific, i.e. they bind to a single antigen. The present invention provides binding agents binding to a cytotoxic cell such as a T cell (by engaging the CD3 receptor) and a target cell such as a cancer cell (by engaging CLDN18.2). The binding agents of the present invention bind to at least two different types of antigen and are at least bispecific or multispecific such as trispecific, tetraspecific and so on.

A binding agent of the present invention may be at least bivalent. In one embodiment, a binding agent of the present invention is at least trivalent. As used herein, "valent", "valence", "valencies", or other grammatical variations thereof, mean the number of antigen binding sites or binding domains in a binding agent. Antigen binding sites binding to the same antigen may recognize different epitopes or preferably the same epitope. Trivalent bispecific antibodies and tetravalent bispecific antibodies are known in the art. A binding agent of the present invention may also have valencies higher than 4.

A binding agent described herein is preferably an artificial protein (including protein complexes) that may be composed of fragments of at least two different antibodies (said fragments of at least two different antibodies forming at least two different binding domains) and consequently binds to at least two different types of antigen. A binding agent according to the invention is engineered to simultaneously bind to an immune cell, such as an immune effector cell, in particular a T cell such as a cytotoxic cell (e.g. by binding to CD3) and a target cell like a cancer cell (by binding to the tumor-associated antigen CLDN18.2) to be destroyed.

Several types of bivalent and trivalent antibodies have been developed and all types are within the scope of the present invention. Bispecific full-length antibodies may be obtained by covalently linking two monoclonal antibodies or by conventional hybrid-hybridoma techniques. Covalent linking of two monoclonal antibodies is described in Anderson, Blood 80 (1992), 2826-34. Another example of a bispecific antibody fragment is a diabody (Kipriyanov, Int. J. Cancer 77 (1998), 763-772), which is a small bivalent and bispecific antibody fragment. Diabodies comprise a heavy chain variable domain (VH) connected to a light chain variable domain (VL) on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites.

In bispecific molecules comprising two Fab fragments, each of the individual Fab fragments may be arranged in a single chain, preferably, VL-CL-CH-VH, and the individual variable and constant domains may be connected with a peptide linker such as a peptide linker discussed herein. In general, the individual single chains and Fab fragments may be connected via disulfide bonds, adhesive domains, chemically linked and/or peptide linker. The bispecific molecule may also comprise more than two Fab fragments, in particular, the molecule may be a Fab3, Fab4, or a multimeric Fab complex with specificity for 2, 3, 4, or more different antigens. The invention also includes chemically linked Fabs.

Triplebodies or single-chain triple antibodies (sctbs) are composed of three distinct scFv regions joined by linker sequences. Also, the natural in vivo heterodimerization of the heavy chain (CH1) and light chain (CL) may be used to form a scaffold on which multiple scFvs can be added. For example, a scFv specific to one antigen can be linked to a CH1, which is also linked to a scFv specific to another antigen and this chain can interact with another chain containing an scFv specific to either antigen linked to a CL (scFv3-CH1/CL). Another example of a trivalent construction involves the use of a Fab fragment specific to one epitope C-terminally linked to two scFvs specific to another epitope, one on each chain (Fab-scFv2). Yet another example of a trivalent construction involves the use of two Fab fragments specific to one antigen or epitope, wherein one of the Fab fragments is C-terminally linked to one scFv specific to another antigen or epitope (Fab2-scFv). Yet another example of a trivalent (or tetravalent) molecule includes a variety of formats which contain additional binding entities attached to N- or C-termini of antibodies. For example, one format consists of an intact antibody molecule specific to one antigen with a single chain Fab (scFab) linked to the C-terminal end of the molecule (IgG-scFab). The dock-and-lock (DNL) approach has also been used to generate trivalent antibodies (DNL-F(ab)3) (Chang, C.-H. et al. In: Bispecific Antibodies. Kontermann R. E. (ed.), Springer Heidelberg Dordrecht London New York, pp. 199-216 (2011)). Each of the foregoing antibodies is within the scope of the present invention.

Tetravalent antibodies have also been constructed and all types are within the scope of the present invention. Examples of tetravalent antibodies include, but are not limited to, scFv2-Fc, F(ab')2-scFv2, scFv2-H/L, and scFv-dhlx-scFv molecules. Bispecific scFv2-Fc constructs have an Fc domain with two scFvs specific to one molecule linked to the N-termini of the Fc chains and another two scFvs specific to another molecule linked to the C-termini of the Fc chain. Bispecific F(ab')2-scFv2 constructs include scFv fragments linked to the C-terminal end of an F(ab')2 fragment. scFv2-H/L constructs have scFvs specific to one molecule linked to the heavy chains while scFvs specific to another molecule are linked to the light chains. Finally, scFv-dhlx-scFv constructs contain one type of scFv linked to a helical dimerization domain followed by another type of scFv. Two chains of this type can dimerize, generating a tetravalent antibody.

The binding agent of the invention may be in the format of an antibody molecule or of an antibody-like molecule or of a protein scaffold with antibody-like properties or of a cyclic peptide with at least two binding specificities. Thus, the binding agent may comprise one or more antibodies as described herein or functional fragments thereof.

In one embodiment, the binding agent of the invention comprises the heavy chain (Fd fragment) and light chain (L) of a Fab fragment which are able to interact and upon which additional binding functions or domains can be incorporated. Such additional binding domains may independently be selected from the group consisting of binding domains comprising two antibody variable regions such as scFv binding domains, i.e. VH-VL or VL-VH, and binding domains comprising one antibody variable region such as VH binding domains and VHH binding domains.

In one embodiment, the binding agent of the invention is in the format of a Fab-scFv construct, i.e. a construct comprising a Fab fragment (comprising VH and CH1 domains on one polypeptide chain and corresponding VL und CL domains on another polypeptide chain, wherein an antigen binding domain is formed by interaction of said polypeptide chains) and an scFv moiety (comprising VH and VL domains connected to one another by a polypeptide linker on the same polypeptide chain, wherein the VH and VL interact to form an antigen binding domain). In one embodiment, the binding agent of the invention is a trimer composed of three polypeptide chains, wherein the first polypeptide chain comprises a VH derived from an immunoglobulin, e.g., an immunoglobulin with a first specificity, the second polypeptide comprises an scFv moiety comprising a VH derived from an immunoglobulin, e.g., an immunoglobulin with a second specificity, and a VL derived from an immunoglobulin, e.g., an immunoglobulin with a second specificity, and the third polypeptide chain comprises a VL derived from an immunoglobulin, e.g., an immunoglobulin with a first specificity. In one embodiment, the first polypeptide chain further comprises a CH1 derived from an immunoglobulin and the third polypeptide chain further comprises a CL derived from an immunoglobulin. In one embodiment, the first and second polypeptide chains further comprise CH2 and CH3 (CH2-CH3) domains derived from an immunoglobulin, e.g., C-terminal to the Fab fragment and scFv moiety, respectively. Thus, in one embodiment, the binding agent of the invention comprises a first polypeptide chain comprising VH-CH1 connected to CH2-CH3, a second polypeptide chain comprising an scFv moiety (VH-VL or VL-VH) connected to CH2-CH3, and a third polypeptide chain comprising VL-CL. In some embodiments, the first polypeptide chain interacts with the second polypeptide chain. In some embodiments, the first polypeptide chain interacts with the third polypeptide chain. In one embodiment, the first polypeptide chain and second polypeptide chain interact and the first polypeptide chain further interacts with the third polypeptide chain. In one embodiment, the CH2 on the first polypeptide chain interacts with the CH2 on the second polypeptide chain and/or the CH3 on the first polypeptide chain interacts with the CH3 on the second polypeptide chain. In some embodiments, the VH on the first polypeptide chain interacts with the VL on the third polypeptide chain to form a binding domain and/or the CH1 on the first polypeptide chain interacts with the CL on the third polypeptide chain. In some embodiments, a disulfide bridge is formed between a cysteine residue in the CL and a cysteine residue in the CH1. One or both polypeptide chains comprising CH2-CH3 may comprise one or more amino acid modifications, e.g., Fc modifications, described herein, such as pI, skew, additional Fc and ablation modifications, e.g., to promote polypeptide chain interaction. According to the invention, the VH and VL of the scFv moiety are preferably connected by a peptide linker ("scFv linker"). In some embodiments, the CH1 on the first polypeptide chain is connected to the CH2 on the same polypeptide chain by a peptide linker. In some embodiments, the scFv is connected to the CH2 by a peptide linker.

In one embodiment, the binding agent of the invention is in the format of a Fab2-scFv construct, i.e. a construct comprising two Fab fragments (each comprising VH and CH1 domains on one polypeptide chain and corresponding VL und CL domains on another polypeptide chain, wherein an antigen binding domain is formed by interaction of each of said set of polypeptide chains) and an scFv moiety (comprising VH and VL domains connected to one another by a polypeptide linker on the same polypeptide chain, wherein the VH and VL interact to form an antigen binding domain). In one embodiment, the binding agent of the invention is a tetramer composed of four polypeptide chains, wherein the first polypeptide chain comprises a VH derived from an immunoglobulin, e.g., an immunoglobulin with a first specificity, the second polypeptide comprises a VH derived from an immunoglobulin, e.g., an immunoglobulin with a first specificity, and an scFv moiety comprising a VH derived from an immunoglobulin, e.g., an immunoglobulin with a second specificity, and a VL derived from an immunoglobulin, e.g., an immunoglobulin with a second specificity, the third polypeptide chain comprises a VL derived from an immunoglobulin, e.g., an immunoglobulin with a first specificity, and the fourth polypeptide chain is identical to the third polypeptide chain. In one embodiment, the first and second polypeptide chains further comprise a CH1 derived from an immunoglobulin, e.g., C-terminal to the VH derived from an immunoglobulin with a first specificity, and the third and fourth polypeptide chains further comprise a CL derived from an immunoglobulin. In one embodiment, the first and second polypeptide chains further comprise CH2 and CH3 (CH2-CH3) domains derived from an immunoglobulin, e.g., C-terminal to the Fab fragment and scFv moiety, respectively. Thus, in one embodiment, the binding agent of the invention comprises a first polypeptide chain comprising VH-CH1 connected to CH2-CH3, a second polypeptide chain comprising VH-CH1 connected to an scFv moiety (VH-VL or VL-VH) connected to CH2-CH3, and third and fourth polypeptide chains each comprising VL-CL. In some embodiments, the first polypeptide chain interacts with the second polypeptide chain. In some embodiments, the first polypeptide chain interacts with the third polypeptide chain. In some embodiments, the second polypeptide chain interacts with the fourth polypeptide chain. In one embodiment, the first and second polypeptide chains interact, the first polypeptide chain further interacts with the third polypeptide chain, and the second polypeptide chain further interacts with the fourth polypeptide chain. In one embodiment, the CH2 on the first polypeptide chain interacts with the CH2 on the second polypeptide chain and/or the CH3 on the first polypeptide chain interacts with the CH3 on the second polypeptide chain. In some embodiments, the VH on the first polypeptide chain interacts with the VL on the third polypeptide chain to form a binding domain and/or the CH1 on the first polypeptide chain interacts with the CL on the third polypeptide chain. In some embodiments, the VH on the second polypeptide chain (which is not part of the scFv moiety) interacts with the VL on the fourth polypeptide chain to form a binding domain and/or the CH1 on the second polypeptide chain interacts with the CL on the fourth polypeptide chain. In some embodiments, a disulfide bridge is formed between a cysteine residue in the CL and a cysteine residue in the CH1. One or both polypeptide chains comprising CH2-CH3 may comprise one or more amino acid modifications, e.g., Fc modifications, described herein, such as pI, skew, additional Fc and ablation modifications, e.g., to promote polypeptide chain interaction. According to the invention, the VH and VL of the scFv moiety are preferably connected by a peptide linker ("scFv linker"). In some embodiments, the CH1 on the first and/or second polypeptide chain is connected to the CH2 on the same polypeptide chain by a peptide linker. In some embodiments, the scFv is connected to the CH2 by a peptide linker.

In a preferred embodiment, of the bivalent binding agents of the invention (in the Fab-scFv format), the VH on the first polypeptide chain and the VL on the third polypeptide chain interact to form a binding domain with specificity for CLDN18.2 and the VH and VL of the scFv on the second polypeptide chain interact to form a binding domain with specificity for CD3. However, in some embodiments, the binding domain formed by the VH on the first polypeptide chain and the VL on the third polypeptide chain has specificity for CD3 and the binding domain formed by the VH and VL of the scFv on the second polypeptide chain has specificity for CLDN18.2. In another preferred embodiment, of the trivalent binding agents of the invention (in the Fab2-scFv format), the additional VH on the second polypeptide chain that is not part of the scFv and the VL on the fourth polypeptide chain preferably interact to form a binding domain with specificity for CLDN18.2. However, also binding agents, wherein the binding domains formed by the scFv on the second polypeptide chain and by the VH and VL on the first and third polypeptide chains have specificity for CLDN18.2 and wherein the binding domain formed by the VH on the second polypeptide chain which is not part of the scFv and by the VL on the fourth polypeptide chain has specificity for CD3 are within the scope of the present application.

The term "linker" refers to any means that serves to join two distinct functional units (e.g. domains or regions on a polypeptide chain). Types of linkers include, but are not limited to, chemical linkers, peptide and polypeptide linkers. The sequences of the peptide and polypeptide linkers are not limited. Peptide linkers are preferably non-immunogenic and flexible, such as those comprising serine and glycine sequences. Depending on the particular construct, the linkers may be long or short.

In preferred embodiments, the scFv linker, i.e., the linker connecting VH and VL that form the scFv moiety, preferably comprises, and preferably consists of, a flexible peptide linker as described herein, preferably the amino acid sequence (GKPGS)$_x$ or a functional variant thereof, wherein x is 2, 3, 4, 5 or 6. In an even more preferred embodiment, the scFv linker comprises, and preferably consists of, the amino acid sequence (GKPGS)$_4$ (SEQ ID NO: 11) or a functional variant thereof. Preferably, the scFv moiety is connected to the CH2 on the second polypeptide chain by a peptide linker comprising an amino acid sequence selected from the group consisting of EPKSCDKTHTCPPCP (SEQ ID NO: 27), EPKSSDKTHTCPPCP (SEQ ID NO: 22), and (G$_4$S)$_2$KTHTCPPC (SEQ ID NO: 23) or a functional variant thereof. Other useful linkers include those having an amino acid sequence according to SEQ ID NO: 24 and 25.

According to the invention, a linker connecting an scFv and a CH1, preferably at the C-terminus of the CH1, preferably comprises, preferably consists of, the amino acid sequence (G$_4$S)$_x$ or a functional variant thereof, wherein x is 2, 3, 4, 5 or 6, preferably (G$_4$S)$_2$ (SEQ ID NO: 26) or a functional variant thereof. According to the invention, a linker connecting CH2 and scFv, preferably at the N-terminus of CH2, preferably comprises, and preferably consists of, an amino acid sequence selected from the group consisting of EPKSCDKTHTCPPCP (SEQ ID NO: 27), EPKSSDKTHTCPPCP (SEQ ID NO: 22) and (G$_4$S)$_2$KTHTCPPC (SEQ ID NO: 23) or a variant thereof. According to the invention, a linker connecting CH1 and CH2 preferably comprises, and preferably consists of, the amino acid sequence EPKSCDKTHTCPPCP or a functional variant thereof. According to the invention, CH1 and scFv, e.g., on the second polypeptide chain, are connected by a peptide linker preferably comprising, preferably consisting of, the amino acid sequence (G$_4$S)$_2$ (SEQ ID NO: 26) or a functional variant thereof. However, other linkers can be used as known in the art.

In one embodiment, the binding agent of the invention comprises a first, a second and a third polypeptide chain, wherein
i) the first polypeptide chain comprises from N-terminus to C-terminus the following domains: VH(CLDN18.2)-CH1-CH2-CH3,
ii) the second polypeptide chain comprises from N-terminus to C-terminus the following domains: VH(CD3)-VL(CD3)-CH2-CH3 or VL(CD3)-VH(CD3)-CH2-CH3, and
iii) the third polypeptide chain comprises from N-terminus to C-terminus the following domains: VL(CLDN18.2)-CL,
preferably wherein VH(CLDN18.2) and VL(CLDN18.2) interact to form a binding domain with specificity for CLDN18.2, VH(CD3) and VL(CD3) interact to form a binding domain with specificity for CD3, and the domains on the polypeptide chains preferably are connected to one another by peptide linkers as described herein.

In another embodiment, the binding agent of the invention comprises a first, a second, a third and a fourth polypeptide chain, wherein
i) the first polypeptide chain comprises from N-terminus to C-terminus the following domains: VH(CLDN18.2)-CH1-CH2-CH3,
ii) the second polypeptide chain comprises from N-terminus to C-terminus the following domains: VH(CLDN18.2)-CH1-VH(CD3)-VL(CD3)-CH2-CH3 or VH(CLDN18.2)-CH1-VL(CD3)-VH(CD3)-CH2-CH3,
iii) the third polypeptide chain comprises from N-terminus to C-terminus the following domains: VL(CLDN18.2)-CL, and
iv) the fourth polypeptide chain is identical to the third polypeptide chain,
preferably wherein VH(CLDN18.2) on the first polypeptide chain and VL(CLDN18.2) on the third polypeptide chain interact to form a binding domain with specificity for CLDN18.2, VH(CLDN18.2) on the second polypeptide chain and VL(CLDN18.2) on the fourth polypeptide chain interact to form a binding domain with specificity for CLDN18.2, VH(CD3) and VL(CD3) interact to form a binding domain with specificity for CD3, and the domains on the polypeptide chains preferably are connected to one another by peptide linkers as described herein.

In one embodiment, the binding agent of the invention comprises: a) a first polypeptide chain comprising a VH(CLDN18.2), and CH1, CH2 and CH3 comprising an aspartic acid residue at position 208, a proline residue at position 233, a valine residue at position 234, an alanine residue at position 235, a deletion at position 236, a lysine residue at position 267, a glutamic acid residue at position 295, an aspartic acid residue at position 368, a serine residue at position 370, an aspartic acid residue at position 384, a glutamic acid residue at position 418 and an aspartic acid residue at position 421 according to EU numbering; b) a second polypeptide chain comprising VH(CD3) and VL(CD3) connected to one another through a charged scFv linker with the amino acid sequence (GKPGS)$_4$ (SEQ ID NO: 11) and CH2 and CH3 comprising a proline residue at position 233, a valine residue at position 234, an alanine residue at position 235, a deletion at position 236, a lysine residue at position 267, a glutamine residue at position 357 and a lysine residue at position 364 according to EU numbering; and c) a third polypeptide chain comprising VL(CLDN18.2) and CL. In one embodiment, the second polypeptide chain further comprises a VH(CLDN18.2) and a CH1 as described herein, and the binding agent further comprises a fourth polypeptide chain identical to the third polypeptide chain.

Other embodiments include Fab2-scFv formats that comprise: a) a first polypeptide chain comprising a VH(CLDN18.2) and a CH1 and CH2 and CH3 that comprises the skew modifications L368D/K370S, the pI modifications N208D/Q295E/N384D/Q418E/N421D, the ablation modifications E233P/L234V/L235A/G236del/S267K, the additional Fc modifications M428L/N434S; b) a second polypeptide chain comprising VH(CD3) and VL(CD3) and CH2 and CH3 that comprises the skew modifications S364K/E357Q, the ablation modifications E233P/L234V/L235A/G236del/S267K, the additional Fc modifications M428L/N434S and a VH(CLDN18.2), and; c) a third polypeptide chain comprising VL(CLDN18.2) and CL; and d) a fourth polypeptide chain identical to the third polypeptide chain.

In one embodiment, the binding agent of the invention comprises a first, a second and a third polypeptide chain, wherein
i) the first polypeptide chain comprises from N-terminus to C-terminus: VH(CLDN18.2)-CH1-linker-CH2-CH3,
ii) the second polypeptide chain comprises from N-terminus to C-terminus: VH(CD3)-linker-VL(CD3)-linker-CH2-CH3 or VL(CD3)-linker-VH(CD3)-linker-CH2-CH3, and
iii) the third polypeptide chain comprises from N-terminus to C-terminus: VL(CLDN18.2)-CL,
preferably wherein VH(CLDN18.2) and VL(CLDN18.2) interact to form a binding domain with specificity for CLDN18.2, and VH(CD3) and VL(CD3) interact to form a binding domain with specificity for CD3.

In one embodiment, the binding agent of the invention comprises a first, a second and a third polypeptide chain, wherein i) the first polypeptide chain comprises from N-terminus to C-terminus: VH(CLDN18.2)-CH1-linker1-CH2-CH3, ii) the second polypeptide chain comprises from N-terminus to C-terminus: VH(CD3)-linker3-VL(CD3)-linker4-CH2-CH3 or VL(CD3)-linker3-VH(CD3)-linker4-CH2-CH3, and iii) the third polypeptide chain comprises from N-terminus to C-terminus: VL(CLDN18.2)-CL, wherein linker1 comprises the amino acid sequence EPKSCDKTHTCPPCP or a functional variant thereof, linker3 comprises the amino acid sequence $(GKPGS)_X$ or a functional variant thereof, wherein x is 2, 3, 4, 5 or 6, preferably wherein x is 4, and linker4 comprises an amino acid sequence selected from the group consisting of EPKSCDKTHTCPPCP, EPKSSDKTHTCPPCP and $(G_4S)_2$KTHTCPPCP or a functional variant thereof, and preferably wherein VH(CLDN18.2) and VL(CLDN18.2) interact to form a binding domain with specificity for CLDN18.2 and VH(CD3) and VL(CD3) interact to form a binding domain with specificity for CD3.

In one embodiment, the binding agent of the invention comprises a first, a second, a third and a fourth polypeptide chain, wherein i) the first polypeptide chain comprises from N-terminus to C-terminus: VH(CLDN18.2)-CH1-linker-CH2-CH3, ii) the second polypeptide chain comprises from N-terminus to C-terminus: VH(CLDN18.2)-CH1-linker-VH(CD3)-linker-VL(CD3)-linker-CH2-CH3 or VH(CLDN18.2)-CH1-linker-VL(CD3)-linker-VH(CD3)-linker-CH2-CH3, iii) the third polypeptide chain comprises from N-terminus to C-terminus the following domains: VL(CLDN18.2)-CL, and iv) the fourth polypeptide chain is identical to the third polypeptide chain, preferably wherein VH(CLDN18.2) on the first polypeptide chain and VL(CLDN18.2) on the third polypeptide chain interact to form a binding domain with specificity for CLDN18.2, VH(CLDN18.2) on the second polypeptide chain and VL(CLDN18.2) on the fourth polypeptide chain interact to form a binding domain with specificity for CLDN18.2, and VH(CD3) and VL(CD3) interact to form a binding domain with specificity for CD3.

In one embodiment, the binding agent of the invention comprises a first, a second, a third and a fourth polypeptide chain, wherein i) the first polypeptide chain comprises from N-terminus to C-terminus: VH(CLDN18.2)-CH1-linker1-CH2-CH3, ii) the second polypeptide chain comprises from N-terminus to C-terminus: VH(CLDN18.2)-CH1-linker2-VH(CD3)-linker3-VL(CD3)-linker4-CH2-CH3 or VH(CLDN18.2)-CH1-linker2-VL(CD3)-linker3-VH(CD3)-linker4-CH2-CH3, iii) the third polypeptide chain comprises from N-terminus to C-terminus: VL(CLDN18.2)-CL, and iv) the fourth polypeptide chain is identical to the third polypeptide chain, wherein linker1 comprises the amino acid sequence EPKSCDKTHTCPPCP or a functional variant thereof, linker2 comprises the amino acid sequence $(G_4S)_x$ or a functional variant thereof, wherein x is 2, 3, 4, 5 or 6, preferably wherein x is 2, linker3 comprises the amino acid sequence $(GKPGS)_X$ or a functional variant thereof, wherein x is 2, 3, 4, 5 or 6, preferably wherein x is 4, and linker4 comprises an amino acid sequence selected from the group consisting of EPKSCDKTHTCPPCP, EPKSSDKTHTCPPCP and $(G_4S)_2$KTHTCPPCP or a functional variant thereof, and preferably wherein VH(CLDN18.2) on the first polypeptide chain and VL(CLDN18.2) on the third polypeptide chain interact to form a binding domain with specificity for CLDN18.2, VH(CLDN18.2) on the second polypeptide chain and VL(CLDN18.2) on the fourth polypeptide chain interact to form a binding domain with specificity for CLDN18.2, and VH(CD3) and VL(CD3) interact to form a binding domain with specificity for CD3.

Binding agents described herein, and/or first, second and third (and optionally fourth) polypeptide chains of said binding agents described herein, may also comprise an amino acid sequence for facilitating secretion of the binding agent or polypeptide chain, such as a N-terminal secretion signal, and/or one or more epitope tags facilitating binding, purification or detection of the molecule. Preferably, the secretion signal is a signal sequence (e.g. the amino acid sequence MGWSCIILFLVATATGVHS) that allows a sufficient passage through the secretory pathway and/or secretion of the binding agent or the polypeptide chains thereof into the extracellular environment.

Preferably, the secretion signal sequence is cleavable and is removed from the mature binding agent or polypeptide chain. The secretion signal sequence preferably is chosen with respect to the cell or organism wherein the binding agent or polypeptide chain is produced in.

The amino acid sequence of an epitope tag may be introduced to any position within the amino acid sequence of the binding agent or polypeptide chain, and may take the shape of a loop within the encoded protein structure, or it may be N-terminally or C-terminally fused to the binding agent or polypeptide chain. Preferably, the epitope tag is C-terminally fused to the binding agent or polypeptide chain. The epitope tag may contain a cleavage site that allows a removal of the tag from the binding agent or polypeptide chain. Said epitope tag can be any kind of epitope tag that is functional under native and/or denaturing conditions, preferable a histidine tag, most preferable a tag comprising six histidines.

The binding agent of the invention may contain, in addition to said first, second and optionally third binding domains one or more further binding domains which serve e.g. to enhance selectivity for tumor cells. This can be achieved e.g. by providing binding domains that bind to other antigens expressed on tumor cells.

The term "posttranslational modification" or similar terms refer to modifications of a protein, such as covalent and enzymatic modifications, that occur following protein biosynthesis. As is commonly known in the art, binding agents such as antibodies that are expressed in cells are often modified after translation. For example, posttranslational modifications of binding agents such as antibodies can occur on the amino acid side chains or at the N- or C-termini of heavy or light chains, e.g., of the first and/or the second polypeptide chain described herein. Examples of posttranslational modifications that may occur in binding agents described herein include, without limitation, cleavage of lysine at the C-terminus of a heavy chain, e.g., of the first and/or second polypeptide chain, e.g., by a carboxypeptidase; modification of glutamine or glutamic acid at the N-terminus of a heavy chain, e.g., of the first and/or second polypeptide chain, to pyroglutamic acid by pyroglutamylation; modification of glutamine or glutamic acid at the N-terminus of a light chain, e.g., of the third and/or fourth polypeptide chain, to pyroglutamic acid by pyroglutamylation; glycosylation; oxidation; deamidation; and glycation. It is known that such posttranslational modifications occur in various binding agents (Liu et al., 2008, J. Pharmacol. Sci. 97(7):2426-2447). Posttranslational modifications due to pyroglutamylation at the N-terminus and deletion of lysine at the C-terminus commonly do not have any influence on the activity of binding agents (Lyubarskaya et al., 2006, Analyt. Biochem. 348(1):24-39).

Thus, in one embodiment, a binding agent described herein may comprise one or more posttranslational modifications. In one embodiment, the one or more posttranslational modifications comprise pyroglutamylation at the N-terminus of one or more polypeptide chains of the binding agent. In one embodiment, the one or more posttranslational modifications comprise pyroglutamylation at the N-terminus of one or more VH(CLDN18.2). In one embodiment, the one or more posttranslational modifications comprise pyroglutamylation at the N-terminus of VH(CD3). In one embodiment, the one or more posttranslational modifications comprise deletion of lysine at the C-terminus of the first polypeptide chain. In one embodiment, the one or more posttranslational modifications comprise deletion of lysine at the C-terminus of the second polypeptide chain.

In the context of the present invention, the binding agents generated are preferably capable of eliciting one or more immune effector functions as described herein. Preferably, said immune effector functions are directed against cells carrying the cancer-associated antigen CLDN18.2 on their surface.

The term "immune effector functions" in the context of the present invention includes any functions mediated by components of the immune system that result e.g. in the inhibition of cancer growth and/or inhibition of cancer development, including inhibition of cancer dissemination and metastasis. Preferably, immune effector functions result in killing of cancer cells. Immune effector functions comprise complement dependent cytotoxicity (CDC), antibody-dependent cell-mediated cytotoxicity (ADCC), antibody-dependent cell-mediated phagocytosis (ADCP), induction of apoptosis in the cells carrying the cancer-associated antigen, cytolysis of the cells carrying the cancer-associated antigen, and/or inhibition of proliferation of the cells carrying the cancer-associated antigen. The binding agents described herein preferably are able to recruit and redirect T cells such as CD4 and/or CD8 T cells, in particular CD107a+ T cells, to disease-associated cells such as cancer cells and, thus, act through redirected T cell cytotoxicity (RTCC), i.e., the T cells upon redirection preferably kill the disease-associated cells, e.g., cancer cells. CD107a expression is known to be associated with cytolytic potential of CD4 and CD8 T cells. Preferably, said CD107a+ T cells are capable to degranulate, i.e., they are capable to release cytotoxic molecules such as perforines, granzymes, etc., and may also release cytokines such as one or more of Tumor Necrosis Factor α (TNFα), interleukine-2 (IL2), Interferon γ (IFNγ) etc., thereby causing death of target cells, e.g., cancer cells the T cells are redirected to by the binding agents of the present invention. Binding agents may also exert an effect simply by binding to cancer-associated antigens on the surface of a cancer cell. For example, binding agents may block the function of the cancer-associated antigen or induce apoptosis just by binding to the cancer-associated antigen on the surface of a cancer cell.

The term "immune effector cell" or "effector cell" in the context of the present invention relates to a cell which exerts effector functions during an immune reaction. For example, immune effector cells comprise T cells (cytotoxic T cells, helper T cells, tumor infiltrating T cells), B cells, natural killer cells, neutrophils, macrophages, and dendritic cells. The terms "T cell" and "T lymphocyte" are used interchangeably herein and include T helper cells (CD4+ T cells) and cytotoxic T cells (CTLs, CD8+ T cells) which comprise cytolytic T cells. The term "MHC-dependent T cell" or similar terms relate to a T cell which recognizes an antigen when presented in the context of MHC and preferably exerts effector functions of T cells, e.g., killing of target cells expressing an antigen.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 glycoprotein on their surface. Helper T cells usually become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and cancer cells, and are also implicated in transplant rejection. These cells are also known as CD8+ T cells since they express the CD8 glycoprotein on their surface. These cells usually recognize their targets by binding to antigen associated with MHC class I, which is present on the surface of nearly every cell of the body.

All T cells have a T cell receptor (TCR) existing as a complex of several proteins. The TCR of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell. In the majority of T cells, the actual T cell receptor is composed of two separate peptide chains, which are produced from the independent T cell receptor alpha and beta (TCRα and TCRβ) genes and are called α- and β-TCR chains. A much less common (2% of total T cells) group of T cells, the γδ T cells (gamma delta T cells) possess a distinct T cell receptor (TCR) on their surface, which is made up of one γ-chain and one δ-chain.

All T cells originate from hematopoietic stem cells in the bone marrow. Hematopoietic progenitors derived from hematopoietic stem cells populate the thymus and expand by cell division to generate a large population of immature thymocytes. The earliest thymocytes express neither CD4 nor CD8, and are therefore classed as double-negative (CD4-CD8-) cells. As they progress through their development they become double-positive thymocytes (CD4+CD8+), and finally mature to single-positive (CD4+CD8- or CD4-CD8+) thymocytes that are then released from the thymus to peripheral tissues.

As used herein, the term "NK cell" or "Natural Killer cell" refers to a subset of peripheral blood lymphocytes defined by the expression of CD56 or CD16 and the absence of the T cell receptor.

MHC molecules in humans are normally referred to as HLA (human leukocyte antigen) molecules. There are two principal classes of MHC molecules: class I and class II. MHC class I antigens are found on nearly all nucleated cells of the body. The primary function of this class of MHC molecules is to display (or present) peptide fragments of intracellular proteins to CTLs. Based on this display, CTLs will attack those displaying MHC-bound peptides, including disease-associated peptides (antigens) such as cancer antigens. CD8-positive T cells are usually cytotoxic (therefore named cytotoxic T cells =CTL), recognize peptides of 9 to 10 amino acids which are intracellularly processed from proteins of any subcellular localization and which are presented on the cellular surface by MHC class I molecules. Thus, the surface expression of MHC class I molecules plays a crucial role in determining the susceptibility of target cells to CTLs.

The binding agents described herein may be conjugated to a therapeutic moiety or agent, such as a cytotoxin, a drug (e.g., an immunosuppressant) or a radioisotope. A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Suitable therapeutic agents for forming conjugates include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Binding agents also can be conjugated to a radioisotope, e.g., iodine-131, yttrium-90 or indium-111, to generate cytotoxic radiopharmaceuticals.

Techniques for conjugating such therapeutic moiety to binding agents are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies'84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

The term "binding" according to the invention preferably relates to a specific binding.

According to the present invention, an agent such as an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 μg/ml or higher. Preferably, an agent has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

A binding agent such as an antibody is specific for a predetermined target if it is capable of binding to said predetermined target while it is not capable of binding to other targets, i.e. has no significant affinity for other targets and does not significantly bind to other targets in standard assays. According to the invention, a binding agent is specific for CLDN18.2 if it is capable of binding to CLDN18.2 but is not (substantially) capable of binding to other targets. Preferably, a binding agent is specific for CLDN18.2 if the affinity for and the binding to such other targets does not significantly exceed the affinity for or binding to CLDN18.2-unrelated proteins such as bovine serum albumin (BSA), casein, human serum albumin (HSA) or non-claudin transmembrane proteins such as MHC molecules or transferrin receptor or any other specified polypeptide. Preferably, a binding agent is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of a binding agent to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

The term "$k_d$" (sec$^{-1}$), as used herein, refers to the dissociation rate constant of a particular antibody-antigen interaction. Said value is also referred to as the $k_{off}$ value.

The term "$K_D$" (M), as used herein, refers to the dissociation equilibrium constant of a particular antibody-antigen interaction.

Binding of a binding agent to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular interaction between binding agent and antigen can vary if measured under different conditions, e.g., salt concentration, pH. Thus, measurements of affinity and other antigen-binding parameters, e.g., $K_D$, $IC_{50}$, are preferably made with standardized solutions of binding agent and antigen, and a standardized buffer.

The term "competes" refers to the competition between two binding agents such as antibodies for binding to a target antigen. If two binding agents do not block each other for binding to a target antigen, such binding agents are non-competing and this is an indication that said binding agents do not bind to the same part, i.e. epitope of the target antigen. It is well known to a person skilled in the art how to test for competition of binding agents for binding to a target antigen. An example of such a method is a so-called cross-competition assay, which may e.g. be performed as an ELISA or by flow-cytometry.

For example an ELISA-based assay may be performed by coating ELISA plate wells with each of the binding agents; adding the competing binding agent and His-tagged extracellular domain of the antigen/target and incubate; detecting whether the added binding agent inhibited binding of the His-tagged protein to the coated binding agent may be performed by adding biotinylated anti-His antibody, followed by Streptavidin-poly-HRP, and further developing the reaction with ABTS and measuring the absorbance at 405 nm. For example a flow-cytometry assay may be performed by incubating cells expressing the antigen/target with an excess of unlabeled binding agent, incubating the cells with a sub-optimal concentration of biotin-labeled antibody, followed by incubation with fluorescently labeled streptavidin and analyzing by flow cytometry.

Two binding agents such as antibodies have the "same specificity" if they bind to the same antigen and to the same epitope. Such binding agents would compete for binding in a competition binding assay. In one embodiment, binding agents binding to the same epitope are considered to bind to the same amino acids on the target molecule. That antibodies bind to the same epitope on a target antigen may be determined by standard alanine scanning experiments or antibody-antigen crystallization experiments known to a person skilled in the art.

The ability of binding agents to compete for binding to an antigen indicates that these binding agents may bind to the same epitope region of the antigen or when binding to another epitope sterically hinder the binding of binding agents to that particular epitope region. Competing binding agents can be readily identified based on their ability to compete with one or more binding agents in standard binding assays such as Surface Plasmon Resonance analysis, ELISA assays or flow cytometry (see WO 2013/173223). For example, the competition between binding agents can be detected by a cross-blocking assay. For example, a competitive ELISA assay may be performed by coating target antigen on the wells of a microtiter plate and adding antigen-binding agent and candidate competing test binding agent. The amount of the antigen-binding agent bound to the antigen in the well indirectly correlates with the binding ability of the candidate competing test binding agent that competes therewith for binding, e.g., to the same epitope. Specifically, the larger the affinity of the candidate competing test binding agent is for the same epitope, the smaller the amount of the antigen-binding agent bound to the antigen-coated well. The amount of the antigen-binding agent bound to the well can be measured by labelling the binding agent with detectable or measurable labelling substances. As described in WO 2013/173223 and as known in the art, Surface Plasmon Resonance analysis, e.g., using a Biacore instrument, can be used to identify overlapping versus different epitope regions recognized by binding agents. Alternatively, competition may be determined using biolayer interferometry.

A binding agent competing for binding to an antigen with another binding agent, e.g., a binding agent comprising heavy and light chain variable regions as described herein, or a binding agent having the specificity for an antigen of another binding agent, e.g., a binding agent comprising heavy and light chain variable regions as described herein, such as an antibody, may be a binding agent comprising variants of said heavy and/or light chain variable regions as described herein, e.g. modifications in the CDRs and/or a certain degree of identity as described herein.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

In one embodiment, a binding agent of the invention has the ability of binding to CLDN18.2, i.e. the ability of binding to, and preferably binds to, an epitope present in CLDN18.2, preferably an epitope located within the extracellular domains of CLDN18.2, in particular the first extracellular loop, preferably amino acid positions 29 to 78 of CLDN18.2. In particular embodiments, an agent having the ability of binding to CLDN18.2 binds to an epitope on CLDN18.2 which is not present on CLDN18.1.

An agent having the ability of binding to CLDN18.2 preferably binds to CLDN18.2, preferably of human, mouse and/or cynomolgus, but not to CLDN18.1, preferably of human, mouse and/or cynomolgus. Preferably, an agent binding to CLDN18.2 does not bind to CLDN9, preferably of human, mouse and/or cynomolgus. Preferably, an agent having the ability of binding to CLDN18.2 is specific for CLDN18.2. Preferably, an agent having the ability of binding to CLDN18.2 binds to CLDN18.2 expressed on the cell surface. In particular preferred embodiments, an agent having the ability of binding to CLDN18.2 binds to native epitopes of CLDN18.2 present on the surface of living cells.

The term "fragment" refers, in particular, to one or more of the complementarity-determining regions (CDRs), preferably at least the CDR3 variable region, of the heavy chain variable region (VH) and/or of the light chain variable region (VL). In one embodiment, said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment, a binding domain comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of binding agents made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable regions or protein labels.

In one embodiment, a binding domain comprising one or more CDRs, a set of CDRs or a combination of sets of CDRs as described herein comprises said CDRs in a human antibody framework.

The exact identification of the CDR regions depends on the calculation method used for determining involved amino acid residues. For example, according to Kabat et al. (supra), variable regions generally encompass amino acid residues 24-34 (CDR1), 50-56 (CDR2) and 89-97 (CDR3) in the VL and around about 31-35 (CDR1), 50-65 (CDR2), and 95-102 (CDR3) in the VH; variable regions may also encompass those residues forming a hypervariable loop (e.g. residues 26-32 (CDR1), 50-52 (CDR2) and 91-96 (CDR3) in the VL and 26-32 (CDR1), 53-55 (CDR2) and 96-101 (CDR3) in the VH (Chothia and Lesk (1987) J. Mol. Biol. 196:901-917)).

A person skilled in the art will understand that the exact identification of the CDR positions within the sequences disclosed herein may be slightly different depending on the numbering system used as shown in the following Table 1 (see Lafranc et al., Dev. Comp. Immunol. 27(1):55-77 (2003):

TABLE 1

|  | Kabat + Chothia | IMGT | Kabat | AbM | Chothia | Contact |
| --- | --- | --- | --- | --- | --- | --- |
| VH: CDR1 | 26-35 | 27-38 | 31-35 | 26-35 | 26-32 | 30-35 |
| VH: CDR2 | 50-65 | 56-65 | 50-65 | 50-58 | 52-56 | 47-58 |
| VH: CDR3 | 95-102 | 105-117 | 95-102 | 95-102 | 95-102 | 93-101 |
| VL: CDR1 | 24-34 | 27-38 | 24-34 | 24-34 | 24-34 | 30-36 |
| VL: CDR2 | 50-56 | 56-65 | 50-56 | 50-56 | 50-56 | 46-55 |
| VL: CDR3 | 89-97 | 105-117 | 89-97 | 89-97 | 89-97 | 89-96 |

Thus, the CDR sequences disclosed herein also comprise variants thereof derived according to different numbering systems. Accordingly, the disclosure of each VH is a disclosure of the CDRs (e.g., CDR1, CDR2 and CDR3) derivable therefrom and the disclosure of each VL is a disclosure of the CDRs (e.g., CDR1, CDR2 and CDR3) derivable therefrom.

Throughout the present specification, the Kabat numbering system is used when referring to residues in variable regions (approximately, residues 1-107 of the light chain and residues 1-113 of the heavy chain) of binding domains with specificity for CD3 or CLDN18.2, and the EU numbering system for CH1 and CH2-CH3 (optionally including the hinge) regions, as described herein.

In a preferred embodiment, a binding domain with specificity for CLDN18.2 of a binding agent of the invention comprises a VH comprising complementarity determining regions CDR1, CDR2 and/or CDR3 identified within an amino acid sequence selected from the group consisting of SEQ ID NO: 38, 39 and 40. More preferably, a binding domain with specificity for CLDN18.2 of a binding agent of the invention comprises a VH comprising complementarity determining regions CDR1, CDR2 and/or CDR3 identified within the amino acid sequence represented by SEQ ID NO: 39.

In a preferred embodiment, a binding domain with specificity for CLDN18.2 of a binding agent of the invention comprises a VL comprising complementarity determining regions CDR1, CDR2 and/or CDR3 identified in within an amino acid sequence selected from the group consisting of SEQ ID NO: 41 and 42. More preferably, a binding domain with specificity for CLDN18.2 of a binding agent of the invention comprises a VL comprising complementarity determining regions CDR1, CDR2 and/or CDR3 identified within the amino acid sequence represented by SEQ ID NO: 42.

In a preferred embodiment, a binding domain with specificity for CLDN18.2 of a binding agent of the invention comprises the following set of CDRs:
the VH comprises a CDR3 comprising the sequence set forth in SEQ ID NO: 34 or a functional variant thereof, and
the VL comprises a CDR3 comprising the sequence set forth in SEQ ID NO: 37 or a functional variant thereof.

In one embodiment, the VH further comprises a CDR1 comprising the sequence set forth in SEQ ID NO: 32 or a functional variant thereof and/or a CDR2 comprising the sequence set forth in SEQ ID NO: 33 or a functional variant thereof, and/or the VL further comprises a CDR1 comprising the sequence set forth in SEQ ID NO: 35 or a functional variant thereof, and/or a CDR2 comprising the sequence set forth in SEQ ID NO: 36 or a functional variant thereof.

In a preferred embodiment, a binding domain with specificity for CLDN18.2 of a binding agent of the invention comprises the following set of CDRs:
the VH comprises a CDR1 comprising the sequence set forth in SEQ ID NO: 32 or a functional variant thereof, a CDR2 comprising the sequence set forth in SEQ ID NO: 33 or a functional variant thereof and a CDR3 comprising the sequence set forth in SEQ ID NO: 34 or a functional variant thereof and the VL comprises a CDR1 comprising the sequence set forth in SEQ ID NO: 35 or a functional variant thereof, a CDR2 comprising the sequence set forth in SEQ ID NO: 36 or a functional variant thereof and a CDR3 comprising the sequence set forth in SEQ ID NO: 37 or a functional variant thereof. Preferably, the VH comprises CDR1, 2 and 3 of SEQ ID NOs: 32, 33 and 34, and the VL comprises CDR1, 2 and 3 of SEQ ID NOs: 35, 36 and 37.

In one embodiment, said heavy and light chain variable regions comprise said complementarity determining regions interspersed within framework regions. In one embodiment, each variable region comprises three complementarity determining regions (CDR1, 2, and 3) and four framework regions (FR1, 2, 3, and 4). In one embodiment, said complementarity determining regions and said framework regions are arranged from amino-terminus to carboxy-terminus in the following order: FR1, CDR1, FR2, CDR2, FR3, CDR3, FR4.

In a preferred embodiment, a binding domain with specificity for CLDN18.2 of a binding agent of the invention comprises a VH(CLDN18.2) comprising an amino acid sequence selected from the group consisting of SEQ ID NOs: 38, 39, 40 or a functional variant thereof, preferably the amino acid sequences represented by SEQ ID NO: 39 or a functional variant thereof.

In a preferred embodiment, a binding domain with specificity for CLDN18.2 of a binding agent of the invention comprises VL(CLDN18.2) comprising an amino acid sequence selected from the group consisting of SEQ ID NOs: 41, 42 or a functional variant thereof, preferably the amino acid sequences represented by SEQ ID NO: 42 or a functional variant thereof.

In one embodiment, a binding domain with specificity for CLDN18.2 of a binding agent of the invention comprises the following combination of VH(CLDN18.2) and VL(CLDN18.2):
the VH(CLDN18.2) comprises an amino acid sequence represented by SEQ ID NO: 38 or a functional variant thereof and the VL(CLDN18.2) comprises an amino acid sequence represented by SEQ ID NO: 41 or a functional variant thereof.

In one embodiment, a binding domain with specificity for CLDN18.2 of a binding agent of the invention comprises the following combination of VH(CLDN18.2) and VL(CLDN18.2):
the VH(CLDN18.2) comprises an amino acid sequence represented by SEQ ID NO: 40 or a functional variant thereof and the VL(CLDN18.2) comprises an amino acid sequence represented by SEQ ID NO: 42 or a functional variant thereof.

In a particularly preferred embodiment, a binding domain with specificity for CLDN18.2 of a binding agent of the invention comprises the following combination of VH(CLDN18.2) and VL(CLDN18.2): the VH(CLDN18.2) comprises an amino acid sequence represented by SEQ ID NO: 39 or a functional variant thereof and the VL(CLDN18.2) comprises an amino acid sequence represented by SEQ ID NO: 42 or a functional variant thereof.

In a preferred embodiment, the framework regions of VH and VL domains present within a binding agent of the invention may comprise amino acid changes but retain at least 80%, 85% or 90% identity to a human germline sequence.

In further embodiments, a binding domain with specificity for CLDN18.2 of a binding agent of the invention comprises heavy and light chain variable regions of an antibody which (i) competes for CLDN18.2 binding with an antibody comprising heavy and light chain variable regions as described above and/or (ii) has the specificity for CLDN18.2 of an antibody comprising heavy and light chain variable regions as described above.

In one embodiment, a binding domain with specificity for CLDN18.2 of a binding agent of the invention has the format of a Fab molecule as described herein. In this embodiment, the VH(CLDN18.2) is part of one polypeptide chain such as the first polypeptide chain and the VL(CLDN18.2) is part of another polypeptide chain such as the third polypeptide chain of a binding agent of the invention. In one embodiment, a VH(CLDN18.2) is part of the first and the second polypeptide chains as described herein and a VL(CLDN18.2) is part of the third polypeptide chain and the fourth polypeptide chain identical to the third polypeptide chain of a binding agent of the invention.

It is to be understood that the binding domains binding to CLDN18.2 of a binding agent of the invention in the Fab2-scFv format may be identical or essentially identical or different and thus may bind to identical or essentially identical epitopes or different epitopes of CLDN18.2. Thus, both binding domains binding to CLDN18.2 of a binding agent of the invention in the Fab2-scFv format may correspond or correspond essentially to one of the binding domains binding to CLDN18.2 described herein or they may be independently selected from the binding domains binding to CLDN18.2 described herein.

In general, any CD3 binding domain or fragments thereof known in the art can be used in the binding agents of the invention, such as a CD3 binding domain of an anti-CD3 antibody. Anti-CD3 antibodies which are useful for providing binding agents according to the invention include but are not limited to UCHT1-HS (humanized mAb), UCHT1-MM (murine mAb), CLB-T3, TR66, 145-2C11.

UCHT1 is a monoclonal IgG1 anti-CD3 antibody which detects CD3 in human and primate sample types. CLB-T3 is a mouse monoclonal anti-CD3 antibody which is directed against the CD3 antigen and reacts with 80-90% human peripheral T lymphocytes and medullary thymocytes. TR66 is a mouse IgG1 monoclonal anti-CD3 antibody which recognizes the epsilon-chain of human CD3. 145-2C11 is an armenian hamster monoclonal anti-mouse CD3 antibody.

Preferably, the VH and VL domains of the binding domain with specificity for CD3 are derived from antibodies/antibody molecules and antibody-like molecules which are capable of specifically recognizing human CD3 in the context of other TCR subunits as present on activated primary human T cells expressing the TCR in its native configuration. The VH and VL domains derived from an antibody specific for the CD3-epsilon chain are most preferred and said (parental) antibodies should be capable of specifically binding epitopes reflecting the native or near-native structure or a conformational epitope of human CD3 presented in the context of the TCR complex. In one embodiment, of the invention, the VH and VL domains of the binding domain with specificity for CD3 are derived from a CD3-specific antibody selected from the group consisting of UCHT1-HS, UCHT1-MM, CLB-T3 and TR66.

In a preferred embodiment, a binding domain with specificity for CD3 of a binding agent of the invention comprises a VH comprising CDR1, CDR2 and/or CDR3 identified within an amino acid sequence selected from the group consisting of SEQ ID NO: 54, 58, 61, 64, 67 and 70.

In a preferred embodiment, a binding domain with specificity for CD3 of a binding agent of the invention comprises a VH comprising a set of CDR1, CDR2 and CDR3 selected from the following embodiments (i) to (vi):
(i) CDR1: SEQ ID NO: 43 or a functional variant thereof, CDR2: SEQ ID NO: 44 or a functional variant thereof, CDR3: SEQ ID NO: 45 or a functional variant thereof,
(ii) CDR1: SEQ ID NO: 43 or a functional variant thereof, CDR2: SEQ ID NO: 50 or a functional variant thereof, CDR3: SEQ ID NO: 45 or a functional variant thereof, (iii) CDR1: SEQ ID NO: 43 or a functional variant thereof, CDR2: SEQ ID NO: 44 or a functional variant thereof, CDR3: SEQ ID NO: 51 or a functional variant thereof, (iv) CDR1: SEQ ID NO: 43 or a functional variant thereof, CDR2: SEQ ID NO: 44 or a functional variant thereof, CDR3: SEQ ID NO: 52 or a functional variant thereof, (v) CDR1: SEQ ID NO: 43 or a functional variant thereof, CDR2: SEQ ID NO: 44 or a functional variant thereof, CDR3: SEQ ID NO: 53 or a functional variant thereof, and (vi) CDR1: SEQ ID NO: 49 or a functional variant thereof, CDR2: SEQ ID NO: 44 or a functional variant thereof, CDR3: SEQ ID NO: 45 or a functional variant thereof.

In a preferred embodiment, a binding domain with specificity for CD3 of a binding agent of the invention comprises a VL comprising CDR1, CDR2 and/or CDR3 identified within an amino acid sequence according to SEQ ID NO: 55.

In a preferred embodiment, a binding domain with specificity for CD3 of a binding agent of the invention comprises a VL comprising the following set of CDR1, CDR2 and CDR3: CDR1: SEQ ID NO: 46 or a functional variant thereof, CDR2: SEQ ID NO: 47 or a functional variant thereof, CDR3: SEQ ID NO: 48 or a functional variant thereof.

In a preferred embodiment, a binding domain with specificity for CD3 of a binding agent of the invention comprises a combination of VH and VL each comprising a set of CDR1, CDR2 and CDR3 selected from the following embodiments (i) to (vi):

(i) VH: CDR1: SEQ ID NO: 43 or a functional variant thereof, CDR2: SEQ ID NO: 44 or a functional variant thereof, CDR3: SEQ ID NO: 45 or a functional variant thereof, VL: CDR1: SEQ ID NO: 46 or a functional variant thereof, CDR2: SEQ ID NO: 47 or a functional variant thereof, CDR3: SEQ ID NO: 48 or a functional variant thereof, (ii) VH: CDR1: SEQ ID NO: 43 or a functional variant thereof, CDR2: SEQ ID NO: 50 or a functional variant thereof, CDR3: SEQ ID NO: 45 or a functional variant thereof, VL: CDR1: SEQ ID NO: 46 or a functional variant thereof, CDR2: SEQ ID NO: 47 or a functional variant thereof, CDR3: SEQ ID NO: 48 or a functional variant thereof, (iii) VH: CDR1: SEQ ID NO: 43 or a functional variant thereof, CDR2: SEQ ID NO: 44 or a functional variant thereof, CDR3: SEQ ID NO: 51 or a functional variant thereof, VL: CDR1: SEQ ID NO: 46 or a functional variant thereof, CDR2: SEQ ID NO: 47 or a functional variant thereof, CDR3: SEQ ID NO: 48 or a functional variant thereof, (iv) VH: CDR1: SEQ ID NO: 43 or a functional variant thereof, CDR2: SEQ ID NO: 44 or a functional variant thereof, CDR3: SEQ ID NO: 52 or a functional variant thereof, VL: CDR1: SEQ ID NO: 46 or a functional variant thereof, CDR2: SEQ ID NO: 47 or a functional variant thereof, CDR3: SEQ ID NO: 48 or a functional variant thereof, (v) VH: CDR1: SEQ ID NO: 43 or a functional variant thereof, CDR2: SEQ ID NO: 44 or a functional variant thereof, CDR3: SEQ ID NO: 53 or a functional variant thereof, VL: CDR1: SEQ ID NO: 46 or a functional variant thereof, CDR2: SEQ ID NO: 47 or a functional variant thereof, CDR3: SEQ ID NO: 48 or a functional variant thereof, and (v) VH: CDR1: SEQ ID NO: 49 or a functional variant thereof, CDR2: SEQ ID NO: 44 or a functional variant thereof, CDR3: SEQ ID NO: 45 or a functional variant thereof, VL: CDR1: SEQ ID NO: 46 or a functional variant thereof, CDR2: SEQ ID NO: 47 or a functional variant thereof, CDR3: SEQ ID NO: 48 or a functional variant thereof.

In a preferred embodiment, a binding domain with specificity for CD3 comprises a VH and a VL selected from the following embodiments (i) to (vi):

(i) the VH comprises or consists of an amino acid sequence according to SEQ ID NO: 54 or a functional variant thereof and the VL comprises or consists of an amino acid sequence according to SEQ ID NO: 55 or a functional variant thereof, (ii) the VH comprises or consists of an amino acid sequence according to SEQ ID NO: 58 or a functional variant thereof and the VL comprises or consists of an amino acid sequence according to SEQ ID NO: 55 or a functional variant thereof, (iii) the VH comprises or consists of an amino acid sequence according to SEQ ID NO: 61 or a functional variant thereof and the VL comprises or consists of an amino acid sequence according to SEQ ID NO: 55 or a functional variant thereof, (iv) the VH comprises or consists of an amino acid sequence according to SEQ ID NO: 64 or a functional variant thereof and the VL comprises or consists of an amino acid sequence according to SEQ ID NO: 55 or a functional variant thereof, (v) the VH comprises or consists of an amino acid sequence according to SEQ ID NO: 67 or a functional variant thereof and the VL comprises or consists of an amino acid sequence according to SEQ ID NO: 55 or a functional variant thereof, and (v) the VH comprises or consists of an amino acid sequence according to SEQ ID NO: 70 or a functional variant thereof and the VL comprises or consists of an amino acid sequence according to SEQ ID NO: 55 or a functional variant thereof.

In one embodiment, the binding domain with specificity for CD3 comprises or consists of an amino acid sequence selected from the group consisting of SEQ ID NO: 56, 57, 59, 60, 62, 63, 65, 66, 68, 69, 71 and 72 or a functional variant thereof. Of course, the scFv linkers comprised in said sequences can be replaced by any other scFv linker such as an scFv linker selected from the group consisting of SEQ ID NO: 2-20 or a functional variant thereof.

In a preferred embodiment, a binding domain with specificity for CD3 of a binding agent of the invention comprises a heavy chain variable region (VH) comprising the amino acid sequence selected from the group consisting of SEQ ID NO: 54, 58 and 61 or a functional variant thereof.

In a preferred embodiment, a binding domain with specificity for CD3 of a binding agent of the invention comprises a VL comprising the amino acid sequence set forth in SEQ ID NO: 55 or a functional variant thereof.

In a preferred embodiment, a binding domain with specificity for CD3 of a binding agent of the invention comprises a VH and a VL selected from the following embodiments (i) to (iii): (i) the VH comprises or consists of an amino acid sequence according to SEQ ID NO: 54 or a functional variant thereof and the VL comprises or consists of an amino acid sequence according to SEQ ID NO: 55 or a functional variant thereof, (ii) the VH comprises or consists of an amino acid sequence according to SEQ ID NO: 58 or a functional variant thereof and the VL comprises or consists of an amino acid sequence according to SEQ ID NO: 55 or a functional variant thereof, and (iii) the VH comprises or consists of an amino acid sequence according to SEQ ID NO: 61 or a functional variant thereof and the VL comprises or consists of an amino acid sequence according to SEQ ID NO: 55 or a functional variant thereof.

In some embodiments, a binding agent comprising a binding domain with specificity for CD3 binds with high affinity to CD3, i.e., is a strong CD3-binder (e.g., binding agents comprising SEQ ID NO: 56 or 57; or SEQ ID NO: 54, or CDR1, 2 and 3 identified therein, and 55, or CDR1, 2 and 3 identified therein). In some embodiments, a binding agent comprising a binding domain with specificity for CD3 binds with medium affinity to CD3, i.e., is a medium CD3-binder. In some embodiments, a binding agent comprising a binding domain with specificity for CD3 binds with low affinity to CD3, i.e., is a low CD3-binder. In some embodiments, higher binding affinity to CD3 enhances RTCC. In one embodiment, bivalent binding to CLDN18.2 enhances RTCC compared to monovalent binding.

In certain embodiments, one or more polypeptide chains of a binding agent of the invention comprise a CH1, as described herein. In a preferred embodiment, the first polypeptide chain of a binding agent of the invention comprises a CH1. In another preferred embodiment, the first and the second polypeptide chains of a binding agent of the invention comprise a CH1. Preferably, the CH1 of the first and/or second polypeptide chain of a binding agent of the invention is derived from IgG, preferably IgG1, more preferably human IgG1. In certain embodiments, one or more polypeptide chains of a binding agent of the invention comprise CH2 and CH3 domains. In a preferred embodiment, the first and/or the second polypeptide chain of a binding agent of the invention comprise CH2 and CH3 domains. Preferably, the CH2 and CH3 domains of the first and/or second polypeptide chain of a binding agent of the invention are derived from IgG, preferably IgG1, more preferably human IgG1. In a preferred embodiment, the first polypeptide chain of a binding agent of the invention comprising VH(CLDN18.2) comprises a CH1, a CH2 and a CH3, and the second polypeptide chain of a binding agent of the invention comprising VH(CD3) and VL(CD3) comprises a CH2 and a CH3, wherein said domains are preferably derived from IgG, such as IgG1, e.g., human IgG1. In another preferred embodiment, the first polypeptide chain of a binding agent of the invention comprising VH(CLDN18.2) comprises a CH1, a CH2 and a CH3, and the second polypeptide chain of a binding agent of the invention comprising VH(CLDN18.2), VH(CD3) and VL(CD3) comprises a CH1, a CH2 and a CH3, wherein said domains are preferably derived from IgG, such as IgG1, e.g., human IgG1.

In certain embodiments, a polypeptide chain of a binding agent of the invention such as the third, and optionally the fourth, polypeptide chain comprising VL(CLDN18.2) comprises a CL such as a CL derived from Igκ or Igλ, preferably Igκ, more preferably human Igκ.

In a preferred embodiment, the first polypeptide chain of a binding agent of the invention comprises an amino acid sequence represented by SEQ ID NO: 28 or a functional variant thereof. In a preferred embodiment, the second polypeptide chain of a binding agent of the invention comprises an amino acid sequence represented by SEQ ID NO: 29 or 30 or a functional variant thereof. In a preferred embodiment, the third, and optionally fourth, polypeptide chain of a binding agent comprises an amino acid sequence represented by SEQ ID NO: 31 or a functional variant thereof.

In a preferred embodiment, a binding agent of the invention comprises first, second, third, and optionally fourth, polypeptide chains comprising amino acid sequences selected from the following embodiments:

(i) the first polypeptide chain comprises SEQ ID NO: 28 or a functional variant thereof, the second polypeptide chain comprises SEQ ID NO: 29 or a functional variant thereof, and the third polypeptide chain comprises SEQ ID NO: 31 or a functional variant thereof, or (ii) the first polypeptide chain comprises SEQ ID NO: 28 or a functional variant thereof, the second polypeptide chain comprises SEQ ID NO: 30 or a functional variant thereof, and the third polypeptide chain comprises SEQ ID NO: 31 or a functional variant thereof, wherein the fourth polypeptide chain, if present, is identical to the third polypeptide chain.

In a preferred embodiment, a binding agent of the invention comprises at least one binding domain with specificity for CLDN18.2 and at least one binding domain with specificity for CD3. In a preferred embodiment, the first polypeptide chain of a binding agent of the invention comprises or consists of the amino acid sequence set forth in SEQ ID NO: 73 or a functional variant thereof. In a preferred embodiment, the second polypeptide chain of a binding agent of the invention comprises or consists of the amino acid sequence set forth in SEQ ID NO: 75 or a functional variant thereof. In a preferred embodiment, the third polypeptide chain of a binding agent of the invention comprises or consists of the amino acid sequence set forth in SEQ ID NO: 78 or a functional variant thereof. In a preferred embodiment, a binding agent of the invention comprising at least one binding domain with specificity for CLDN18.2 and at least one binding domain with specificity for CD3 comprises a set of first, second and third polypeptide chains of SEQ ID NOs: 73, 75 and 78 or a functional variant thereof.

In another preferred embodiment, a binding of the invention comprises at least two binding domains with specificity for CLN18.2 and at least one binding domain with specificity for CD3. In a preferred embodiment, the first polypeptide chain of a binding agent of the invention comprises or consists of the amino acid sequence set forth in SEQ ID NO: 73 or a functional variant thereof. In a preferred embodiment, the second polypeptide chain of a binding agent of the invention comprises or consists of an amino acid sequence selected from the group consisting of SEQ ID NO: 74, 76 and 77 or a functional variant thereof. In a preferred embodiment, the third polypeptide chain of a binding agent of the invention comprises or consists of the amino acid sequence set forth in SEQ ID NO: 78 or a functional variant thereof. In a preferred embodiment, a binding agent of the invention comprising at least two binding domains binding to CLDN18.2 and at least one binding domain with specificity for CD3 comprises a set of first, second, third and fourth polypeptide chains selected from the group consisting of SEQ ID NOs: (i) 73, 74 and 78; (ii) 73, 76 and 78; (iii) 73, 77 and 78 or a functional variant thereof, wherein the fourth binding domain is identical to the third binding domain.

It is to be understood that the binding agents described herein may be delivered to a patient by administering a nucleic acid such as RNA encoding the agent and/or by administering a host cell comprising a nucleic acid such as RNA encoding the agent. If the binding agent comprises more than one polypeptide chain, the different polypeptide chains may be encoded on the same nucleic acid or on different nucleic acids, e.g., a set of nucleic acids. Thus, a nucleic acid to be administered may be a mixture of different nucleic acid molecules such as a set of nucleic acids. A nucleic acid or set of nucleic acids encoding a binding agent, e.g., when administered to a subject such as a patient, may be present in naked form or in a suitable delivery vehicle such as in the form of liposomes or nanoparticles or viral particles, or within a host cell. The nucleic acid or set of nucleic acids provided can produce the agent over extended time periods in a sustained manner mitigating the instability at least partially observed for therapeutic antibodies. Nucleic acids or sets of nucleic acids to be delivered to a patient can be produced by recombinant means. If a nucleic acid or set of nucleic acids is administered to a patient without being present within a host cell, it is preferably taken up by cells of the patient for expression of the binding agent encoded by the nucleic acid. If a nucleic acid or set of nucleic acids is administered to a patient while being present within a host cell, it is preferably expressed by the host cell within the patient so as to produce the binding agent encoded by the nucleic acid(s).

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature.

For example, a peptide or nucleic acid that is present in an organism (including viruses) and can be isolated from a source in nature and which has not been intentionally modified by man in the laboratory is naturally occurring.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

Nucleic acids or sets of nucleic acids may be comprised in a vector. Sets of nucleic acids may also be comprised in sets of vectors such that each nucleic acid of the set of nucleic acids is comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably is entirely or substantially composed of ribonucleotide residues. "Ribonucleotide" relates to a nucleotide with a hydroxyl group at the 2'-position of a 3-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment, of the invention, the RNA is obtained by in vitro transcription or chemical synthesis. The in vitro transcription methodology is known to the skilled person. For example, there is a variety of in vitro transcription kits commercially available.

In one embodiment, of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. Alphaviral RNA may act as mRNA, as is known in the art. In one embodiment, the self-replicating RNA is a viral gene expression vector. In one embodiment, the virus is Semliki forest virus. In one embodiment, the self-replicating RNA contains one or more transgenes at least one of said transgenes encoding the binding agent described herein. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment, of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity and/or immunogenicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5'-triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment, the poly-A sequence has a length of approximately 120 adenosine residues. In addition, incorporation of two or more 3'-non translated regions (UTR) into the 3'-non translated region of an RNA molecule can result in an enhancement in translation efficiency. In one particular embodiment, the 3'-UTR is derived from the human β-globin gene.

Preferably, RNA if delivered to, i.e. transfected into, a cell, in particular a cell present in vivo, expresses the protein, peptide or antigen it encodes.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

According to the invention, the term "RNA encoding" means that RNA, if present in the appropriate environment, preferably within a cell, can be expressed to produce a protein or peptide it encodes.

Some aspects of the invention rely on the adoptive transfer of host cells which are transfected in vitro with a nucleic acid such as RNA encoding a binding agent described herein and transferred to recipients such as patients, preferably after ex vivo expansion from low precursor frequencies to clinically relevant cell numbers. The host cells used for treatment according to the invention may be autologous, allogeneic, or syngeneic to a treated recipient.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding to a target or to sustain effector functions. Preferably, a sequence which is a variant with respect to a specific sequence, when it replaces the specific sequence in an antibody retains binding of said antibody to CLDN18.2 and/or CD3 and preferably functions of said antibody as described herein. Furthermore, preferably, a sequence which is a variant with respect to a specific sequence, when it replaces the specific sequence in a binding agent retains binding of said binding agent to CLDN18.2 and/or CD3 and preferably functions of said binding agent as described herein, e.g. cytotoxic T-cell mediated lysis.

For example, the sequences shown in the sequence listing can be modified so as to remove one or more, preferably all free cysteine residues, in particular by replacing the cysteine residues by amino acids other than cysteine, preferably serine, alanine, threonine, glycine, tyrosine, tryptophan, leucine or methionine.

It will be appreciated by those skilled in the art that in particular the sequences of the CDR, hypervariable and variable regions can be modified without losing the ability to bind CLDN18.2 and/or CD3. For example, CDR regions will be either identical or highly homologous to the regions specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions specifically disclosed herein. In one embodiment, the variable region sequences only deviate in the framework sequences from the variable region sequences specifically disclosed herein.

The binding agents of the invention can be produced either intracellularly (e.g. in the cytosol, in the periplasma or in inclusion bodies) and then isolated from the host cells and optionally further purified; or they can be produced extracellularly (e.g. in the medium in which the host cells are cultured) and then isolated from the culture medium and optionally further purified. Methods and reagents used for the recombinant production of polypeptides, such as specific suitable expression vectors, transformation or transfection methods, selection markers, methods of induction of protein expression, culture conditions, and the like, are known in the art. Similarly, protein isolation and purification techniques are well known to the skilled person.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cells include cells from species of *Trichoderma, Neurospora*, and *Aspergillus*. Suitable yeast cells include cells from species of *Saccharomyces* (for example *Saccharomyces cerevisiae*), *Schizosaccharomyces* (for example *Schizosaccharomyces pombe*), *Pichia* (for example *Pichia pastoris* and *Pichia methanolica*), and *Hansenula*. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T-cell receptor (TCR).

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

Antibody-Dependent Cell-Mediated Cytotoxicity

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Antibody-Dependent Cell-Mediated Phagocytosis

ADCP is one mechanism of action of many antibody therapies. It is defined as a highly regulated process by which antibodies eliminate bound targets via connecting their Fc domain to specific receptors on phagocytic cells, and eliciting phagocytosis. ADCP can be mediated by monocytes, macrophages, neutrophils, and dendritic cells, through FcγRIIa, FcγRI, and FcγRIIIa, of which FcγRIIa (CD32a) on macrophages represent the predominant pathway.

ADCP preferably occurs when non-specific phagocytic cells that express FcγRs recognize antibody that is bond to target cells such as diseased cells including tumor cells and subsequently cause phagocytosis of the target cells such as the diseased cells including tumor cells. ADCP also provides for stimulation of downstream adaptive immune responses by facilitating antigen presentation or by stimulating the secretion of inflammatory mediators. ADCP may be improved in vivo by simultaneous treatment with immunomodulatory agents. The Fc receptor-dependent function of ADCP provides mechanisms for clearance of virus and virus-infected cells, as well as for stimulation of downstream adaptive immune responses by facilitating antigen presentation, or by stimulating the secretion of inflammatory mediators.

Complement-Dependent Cytotoxicity

CDC is yet another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1 q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

Binding agents and antibodies described herein can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal binding agents such as monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known. Other preferred animal systems for preparing hybridomas that secrete monoclonal binding agents such as monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human binding agents such as human antibodies can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human binding agents such as human antibodies in such transgenic mice can be performed as described in detail for CD20 in WO2004 035607.

Yet another strategy for generating monoclonal binding agents such as monoclonal antibodies is to directly isolate genes encoding antibodies from lymphocytes producing binding agents of defined specificity e.g. see Babcock et al., 1996; A novel strategy for generating monoclonal binding agents such as monoclonal antibodies from single, isolated lymphocytes producing binding agents of defined specificities. For details of recombinant binding agent engineering see also Welschof and Kraus, Recombinant antibodies for cancer therapy ISBN-O-89603-918-8 and Benny K. C. Lo Antibody Engineering ISBN 1-58829-092-1.

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses. The immune response can be monitored over the course of the immunization protocol with plasma and serum samples being obtained by tail vein or retroorbital bleeds. Mice with sufficient titers of immunoglobulin can be used for fusions. Mice can be boosted intraperitoneally or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Binding agents such as antibodies also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned binding agent, e.g., antibody, genes can be expressed in other expression systems, including prokaryotic cells, such as microorganisms, e.g. *E. coli*. Furthermore, the binding agents, e.g., antibodies, can be produced in transgenic non-human animals, such as in milk from sheep and rabbits or in eggs from hens, or in transgenic plants (see, e.g., Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839).

Chimerization

Non-labeled murine antibodies are highly immunogenic in man when repetitively applied leading to reduction of the therapeutic effect. The main immunogenicity is mediated by the heavy chain constant regions. The immunogenicity of binding agents derived from murine antibodies in man can be reduced or completely avoided if respective binding agents are chimerized or humanized. Chimeric binding agents are binding agents, the different portions of which are derived from different animal species, such as those having a variable region derived from a murine antibody and a human immunoglobulin constant region. Chimerization of binding agents is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment, chimeric binding agents are generated by joining human kappa-light chain constant region to murine light chain variable region. In an also preferred embodiment, chimeric binding agents can be generated by joining human lambda-light chain constant region to murine light chain variable region. The preferred heavy chain constant regions for generation of chimeric binding agents are IgG1, IgG3 and IgG4. Other preferred heavy chain constant regions for generation of chimeric binding agents are IgG2, IgA, IgD and IgM.

Humanization

Binding agents such as antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant binding agents, e.g., antibodies, that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

The ability of antibodies and other binding agents to bind an antigen can be determined using standard binding assays (e.g., ELISA, Western Blot, immunofluorescence and flow cytometric analysis).

To purify binding agents such as antibodies, selected producer cell lines can be grown in two-liter spinner-flasks for recombinant antibody purification. Alternatively, binding agents such as antibodies can be produced in dialysis based bioreactors. Supernatants can be filtered and, if necessary, concentrated before affinity chromatography with protein L-sepharose. Eluted binding agents can be checked by gel electrophoresis and high performance liquid chromatography to ensure purity. The buffer solution can be exchanged into PBS, and the concentration can be determined by OD280 using the respective extinction coefficient. The recombinant binding agents can be aliquoted and stored at −65 to −85° C.

In order to demonstrate binding of monoclonal binding agents such as monoclonal antibodies to living cells expressing antigen, flow cytometry can be used. Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at 4° C. for 30 min. After washing, the fluorescence-labeled detection reagent (such as fluorescence conjugated anti IgG antibody, anti Fab antibody or Protein-L) can bind to antigen-bound monoclonal binding agent under the same conditions as the primary binding agent staining. The samples can be analyzed by flow cytometry with a FACS instrument using light and side scatter properties to gate on single, living cells. In order to distinguish antigen-specific monoclonal binding agents from non-specific binders in a single measurement, the method of co-transfection can be employed. Cells transiently transfected with plasmids encoding antigen and a fluorescent marker can be stained as described above. Transfected cells can be detected in a different fluorescence channel than binding agent-stained cells. As the majority of transfected cells express both transgenes, antigen-specific monoclonal binding agents bind preferentially to fluorescence marker expressing cells, whereas non-specific binding agents bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate binding of monoclonal binding agents such as monoclonal antibodies to living cells expressing antigen, immunofluorescence microscopy analysis can be used. For example, cell lines expressing either spontaneously or after transfection antigen and negative controls lacking antigen expression are grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal binding agents against the antigen for 30 min. at 25° C. After washing, cells can be reacted with an Alexa555-labeled anti-mouse IgG secondary antibody (Molecular Probes) under the same conditions. Cells can then be examined by fluorescence microscopy.

Cell extracts from cells expressing antigen and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal binding agents to be tested. IgG binding can be detected using anti-mouse IgG peroxidase and developed with ECL substrate.

Binding agents such as antibodies can be further tested for reactivity with antigen by immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection antigen. For immunostaining, binding agents reactive to antigen can be incubated followed by horseradish-peroxidase conjugated goat anti-mouse or goat anti-rabbit antibodies (DAKO) according to the vendors instructions.

Preclinical Studies

Binding agents described herein also can be tested in an in vivo model (e.g. in immunodeficient mice carrying xenografted tumors inoculated with cell lines expressing CLDN18.2) to determine their efficacy in controlling growth of CLDN18.2-expressing tumor cells.

In vivo studies after xenografting CLDN18.2-expressing tumor cells into immunocompromised mice or other animals can be performed using binding agents described herein. Binding agents and optionally effector cells such as PBMCs can be administered to tumor free mice followed by injection of tumor cells to measure the effects of the binding agents to prevent formation of tumors or tumor-related symptoms. Binding agents and optionally effector cells such as PBMCs can be administered to tumor-bearing mice to determine the therapeutic efficacy of respective binding agents to reduce tumor growth, metastasis or tumor related symptoms. Application of binding agents and optionally effector cells can be combined with application of other substances as cystostatic drugs, growth factor inhibitors, cell cycle blockers, angiogenesis inhibitors or antibodies to determine increased efficacy and potential toxicity of combinations. To analyze toxic side effects mediated by binding agents animals can be inoculated with binding agents as described herein or control reagents and thoroughly investigated for symptoms possibly related to CLDN18.2-binding agent therapy.

Mapping of epitopes recognized by binding agents can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by ISBN-089603-375-9 and in "Epitope Mapping: A Practical Approach" Practical Approach Series, 248 by Olwyn M. R. Westwood, Frank C. Hay.

The compounds and agents described herein may be administered in the form of any suitable pharmaceutical composition.

The pharmaceutical compositions of the invention are preferably sterile and contain an effective amount of the binding agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application.

According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or non-aqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by an altered expression pattern of CLDN18.2.

For example, in one embodiment, agents described herein can be used to treat a patient with a cancer disease, e.g., a cancer disease such as described herein characterized by the presence of cancer cells expressing CLDN18.2.

The pharmaceutical compositions and methods of treatment described according to the invention may also be used for immunization or vaccination to prevent a disease described herein.

The pharmaceutical composition of the invention may be administered together with supplementing immunity-enhancing substances such as one or more adjuvants and may comprise one or more immunity-enhancing substances to further increase its effectiveness, preferably to achieve an additive effect of immunostimulation. The term "adjuvant" relates to compounds which prolong or enhance or accelerate an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFα, INF-γ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also suitable for use as adjuvants in the pharmaceutical composition of the present invention.

The agents and compositions provided herein may be used alone or in combination with conventional therapeutic regimens such as surgery, irradiation, chemotherapy and/or bone marrow transplantation (autologous, syngeneic, allogeneic or unrelated).

Treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment, of the present invention, a cancer treatment which utilizes immune- or vaccination-based mechanisms such as the methods and pharmaceutical compositions of the present invention may be effectively combined with various other drugs and/or methods targeting similar or other specific mechanisms. Among those are e.g. combinations with conventional tumor therapies, multi-epitope strategies, additional immunotherapy, and treatment approaches targeting angiogenesis or apoptosis (for review see, e.g., Andersen et al. 2008: Cancer treatment: the combination of vaccination with other therapies. Cancer Immunology Immunotherapy, 57(11): 1735-1743.) Sequential administration of different agents may inhibit cancer cell growth at different check points, while other agents may e.g. inhibit neo-angiogenesis, survival of malignant cells or metastases, potentially converting cancer into a chronic disease. The following list provides some non-limiting examples of anti-cancer drugs and therapies which can be used in combination with the present invention:

1. Chemotherapy

Chemotherapy is the standard of care for multiple types of cancer. The most common chemotherapy agents act by killing cells that divide rapidly, one of the main properties of cancer cells. Thus, a combination with conventional chemotherapeutic drugs such as e.g. alkylating agents, antimetabolites, anthracyclines, plant alkaloids, topoisomerase inhibitors, and other antitumour agents which either affect cell division or DNA synthesis may significantly improve the therapeutic effects of the present invention by clearing suppressor cells, reboot of the immune system, by rendering tumor cells more susceptible to immune mediated killing, or by additional activation of cells of the immune system. An additive anti-cancer action of chemotherapeutic and vaccination-based immunotherapeutic drugs has been demonstrated in multiple studies (see, e.g., Quoix et al. 2011: Therapeutic vaccination with TG4010 and first-line chemotherapy in advanced non-small-cell lung cancer: a controlled phase 2B trial. Lancet Oncol. 12(12): 1125-33.; see also Liseth et al. 2010: Combination of intensive chemotherapy and anticancer vaccines in the treatment of human malignancies: the hematological experience. J Biomed Biotechnol. 2010: 6920979; see also Hirooka et al 2009: A combination therapy of gemcitabine with immunotherapy for patients with inoperable locally advanced pancreatic cancer. Pancreas 38(3): e69-74). There are hundreds of chemotherapeutic drugs available which are basically suitable for combination therapies. Some (non-limiting) examples of chemotherapeutic drugs which can be combined with the present invention are carboplatin (Paraplatin), cisplatin (Platinol, Platinol-AQ), cyclophosphamide (Cytoxan, Neosar), docetaxel (Taxotere), doxorubicin (Adriamycin), erlotinib (Tarceva), etoposide (VePesid), gemcitabine (Gemzar), imatinib mesylate (Gleevec), irinotecan (Camptosar), methotrexate (Folex, Mexate, Amethopterin), paclitaxel (Taxol, Abraxane), sorafinib (Nexavar), sunitinib (Sutent), topotecan (Hycamtin), vincristine (Oncovin, Vincasar PFS), and vinblastine (Velban).

2. Surgery

Cancer surgery—an operation to remove the tumor—remains the foundation of cancer treatment. Surgery can be combined with other cancer treatments in order to delete any remaining tumor cells. Combining surgical methods with subsequent immunotherapeutic treatment is a promising approach which has been demonstrated countless times.

3. Radiation

Radiation therapy remains an important component of cancer treatment with approximately 50% of all cancer patients receiving radiation therapy during their course of illness. The main goal of radiation therapy is to deprive cancer cells of their multiplication (cell division) potential. The types of radiation used to treat cancer are photons radiation (x-rays and gamma rays) and particle radiations (electron, proton and neutron beams.) There are two ways to deliver the radiation to the location of the cancer. External beam radiation is delivered from outside the body by aiming high-energy rays (photons, protons or particle radiation) to the location of the tumor. Internal radiation or brachytherapy is delivered from inside the body by radioactive sources, sealed in catheters or seeds directly into the tumor site. Radiation therapy techniques which are applicable in combination with the present invention are e.g. fractionation (radiation therapy delivered in a fractionated regime, e.g. daily fractions of 1.5 to 3 Gy given over several weeks), 3D conformal radiotherapy (3DCRT; delivering radiation to the gross tumor volume), intensity modulated radiation therapy (IMRT; computer-controlled intensity modulation of multiple radiation beams), image guided radiotherapy (IGRT; a technique comprising pre-radiotherapy imaging which allows for correction), and stereotactic body radiation therapy (SRBT, delivers very high individual doses of radiation over only a few treatment fractions). For a radiation therapy review see Baskar et al. 2012: Cancer and radiation therapy: current advances and future directions. Int. J Med Sci. 9(3): 193-199.

4. Antibodies

Antibodies (preferably monoclonal antibodies) achieve their therapeutic effect against cancer cells through various mechanisms. They can have direct effects in producing apoptosis or programmed cell death. They can block components of signal transduction pathways such as e.g. growth factor receptors, effectively arresting proliferation of tumor cells. In cells that express monoclonal antibodies, they can bring about anti-idiotype antibody formation. Indirect effects include recruiting cells that have cytotoxicity, such as monocytes and macrophages. This type of antibody-mediated cell kill is called antibody-dependent cell mediated cytotoxicity (ADCC). Antibodies also bind complement, leading to direct cell toxicity, known as complement dependent cytotoxicity (CDC). Moreover, target cell-bound antibodies can be recognized by non-specific phagocytic cells causing phagocytosis of the target cell, known as antibody dependent cell-mediated phagocytosis (ADCP). Combining surgical methods with immunotherapeutic drugs or methods is a successful approach, as e.g. demonstrated in Gadri et al. 2009: Synergistic effect of dendritic cell vaccination and anti-CD20 antibody treatment in the therapy of murine lymphoma. J Immunother. 32(4): 333-40. The following list provides some non-limiting examples of anti-cancer antibodies and potential antibody targets (in brackets) which can be used in combination with the present invention: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Bavituximab (phosphatidylserine), Bectumomab (CD22), Belimumab (BAFF), Bevacizumab (VEGF-A), Bivatuzumab mertansine (CD44 v6), Blinatumomab (CD19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNTO888), Catumaxomab (EpCAM, CD3), Cetuximab (EGFR), Citatuzumab bogatox (EpCAM), Cixutumumab (IGF-1 receptor), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin $\alpha v\beta 3$), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-$\beta$), Galiximab (CD80), Ganitumab (IGF-I), Gemtuzumab ozogamicin (CD33), Gevokizumab (IL-1$\beta$), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Narnatumab (RON), Necitumumab (EGFR), Nimotuzumab (EGFR), Ofatumumab (CD20), Olaratumab (PDGF-R $\alpha$), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzumab (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL-6), Tabalumab (BAFF), Tacatuzumab tetraxetan (alpha-fetoprotein), Taplitumomab paptox (CD19), Tenatumomab (tenascin C), Teprotumumab (CD221), Tigatuzumab (TRAIL-R2), TNX-650 (IL-13), Tositumomab (CD20), Trastuzumab (HER2/neu), TRBS07 (GD2), Tucotuzumab celmoleukin (EpCAM), Ublituximab (MS4A1), Urelumab (4-1BB), Volociximab (integrin α5β1), Votumumab (tumor antigen CTAA16.88), Zalutumumab (EGFR), Zanolimumab (CD4).

5. Cytokines, Chemokines, Costimulatory Molecules, Fusion Proteins

Combined usage of the pharmaceutical compositions of the present invention with cytokines, chemokines, costimulatory molecules and/or fusion proteins thereof to evoke beneficial immune modulation or tumor inhibition effects is another embodiment, of the present invention. In order to increase the infiltration of immune cells into the tumor and facilitate the movement of antigen-presenting cells to tumor-draining lymph nodes, various chemokines with C, CC, CXC and CX3C structures might be used. Some of the most promising chemokines are e.g. CCR7 and its ligands CCL19 and CCL21, furthermore CCL2, CCL3, CCL5, and CCL16. Other examples are CXCR4, CXCR7 and CXCL12. Furthermore, costimulatory or regulatory molecules such as e.g. B7 ligands (B7.1 and B7.2) are useful. Also useful are other cytokines such as e.g. interleukins especially (e.g. IL-1 to IL17), interferons (e.g. IFNalpha1 to IFNalpha8, IFNalpha10, IFNalpha13, IFNalpha14, IFNalpha16, IFNalpha17, IFNalpha2l, IFNbetal, IFNW, IFNE1 and IFNK), hematopoietic factors, TGFs (e.g. TGF-α, TGF-β, and other members of the TGF family), finally members of the tumor necrosis factor family of receptors and their ligands as well as other stimulatory molecules, comprising but not limited to 4-1BB, 4-1BB-L, CD137, CD137L, CTLA-4GITR, GITRL, Fas, Fas-L, TNFR1, TRAIL-R1, TRAIL-R2, p75NGF-R, DR6, LT.beta.R, RANK, EDAR1, XEDAR, Fn114, Troy/Trade, TAJ, TNFRII, HVEM, CD27, CD30, CD40, 4-1BB, OX40, GITR, GITRL, TACI, BAFF-R, BCMA, RELT, and CD95 (Fas/APO-1), glucocorticoid-induced TNFR-related protein, TNF receptor-related apoptosis-mediating protein (TRAMP) and death receptor-6 (DR6). Especially CD40/CD40L and OX40/OX40L are important targets for combined immunotherapy because of their direct impact on T cell survival and proliferation. For a review see Lechner et al. 2011: Chemokines, costimulatory molecules and fusion proteins for the immunotherapy of solid tumors. Immunotherapy 3 (11), 1317-1340.

6. Bacterial Treatments

Researchers have been using anaerobic bacteria, such as *Clostridium novyi*, to consume the interior of oxygen-poor tumours. These should then die when they come in contact with the tumour's oxygenated sides, meaning they would be harmless to the rest of the body. Another strategy is to use anaerobic bacteria that have been transformed with an enzyme that can convert a non-toxic prodrug into a toxic drug. With the proliferation of the bacteria in the necrotic and hypoxic areas of the tumour, the enzyme is expressed solely in the tumour. Thus, a systemically applied prodrug is metabolised to the toxic drug only in the tumour. This has been demonstrated to be effective with the non-pathogenic anaerobe *Clostridium sporogenes*.

7. Kinase Inhibitors

Another large group of potential targets for complementary cancer therapy comprises kinase inhibitors, because the growth and survival of cancer cells is closely interlocked with the deregulation of kinase activity. To restore normal kinase activity and therefor reduce tumor growth a broad range of inhibitors is in use. The group of targeted kinases comprises receptor tyrosine kinases e.g. BCR-ABL, B-Raf, EGFR, HER-2/ErbB2, IGF-IR, PDGFR-α, PDGFR-β, c-Kit, Flt-4, Flt3-wildtype, FGFR1, FGFR3, FGFR4, CSF1R, c-Met, RON, c-Ret, ALK, cytoplasmic tyrosine kinases e.g. c-SRC, c-YES, Abl, JAK-2, serine/threonine kinases e.g. ATM, Aurora A & B, CDKs, mTOR, PKCi, PLKs, b-Raf, S6K, STK11/LKB1 and lipid kinases e.g. PI3K, SK1. Small molecule kinase inhibitors are e.g. PHA-739358, Nilotinib, Dasatinib, and PD166326, NSC 743411, Lapatinib (GW-572016), Canertinib (CI-1033), Semaxinib (SU5416), Vatalanib (PTK787/ZK222584), Sutent (SU11248), Sorafenib (BAY 43-9006) and Leflunomide (SU101). For more information see e.g. Zhang et al. 2009: Targeting cancer with small molecule kinase inhibitors. Nature Reviews Cancer 9, 28-39.

8. Toll-Like Receptors

The members of the Toll-like receptor (TLRs) family are an important link between innate and adaptive immunity and the effect of many adjuvants rely on the activation of TLRs. A large number of established vaccines against cancer incorporate ligands for TLRs for boosting vaccine responses. Besides TLR2, TLR3, TLR4 especially TLR7 and TLR8 have been examined for cancer therapy in passive immunotherapy approaches. The closely related TLR7 and TLR8 contribute to antitumor responses by affecting immune cells, tumor cells, and the tumor microenvironment and may be activated by nucleoside analogue structures. All TLRs have been used as stand-alone immunotherapeutics or cancer vaccine adjuvants and may be combined with the formulations and methods of the present invention. For more information see van Duin et al. 2005: Triggering TLR signaling in vaccination. Trends in Immunology, 27(1):49-55.

9. Angiogenesis Inhibitors

In addition to therapies which target immune modulatory receptors affected by tumor-mediated escape mechanisms and immune suppression there are therapies which target the tumor environment. Angiogenesis inhibitors prevent the extensive growth of blood vessels (angiogenesis) that tumors require to survive. The angiogenesis promoted by tumor cells to meet their increasing nutrient and oxygen demands for example can be blocked by targeting different molecules. Non-limiting examples of angiogenesis-mediating molecules or angiogenesis inhibitors which may be combined with the present invention are soluble VEGF (VEGF isoforms VEGF121 and VEGF165, receptors VEGFR1, VEGFR2 and receptor Neuropilin-2 (NRP-2), angiopoietin 2, TSP-1 and TSP-2, angiostatin and related molecules, endostatin, vasostatin, calreticulin, platelet factor-4, TIMP and CDAI, Meth-1 and Meth-2, IFN-α, -β and -γ, CXCL10, IL-4, -12 and -18, prothrombin (kringle domain-2), antithrombin III fragment, prolactin, VEGI, SPARC, osteopontin, maspin, canstatin, proliferin-related protein, restin and drugs like e.g. bevacizumab, itraconazole, carboxyamidotriazole, TNP-470, CM101, IFN-α, platelet factor-4, suramin, SU5416, thrombospondin, VEGFR antagonists, angiostatic steroids+heparin, cartilage-derived angiogenesis inhibitory factor, matrix metalloproteinase inhibitors, 2-methoxyestradiol, tecogalan, tetrathiomolybdate, thalidomide, thrombospondin, prolactin Vβ3 inhibitors, linomide, tasquinimod, for review see e.g. Schoenfeld and Dranoff 2011: Anti-angiogenesis immunotherapy. Hum Vaccin. (9):976-81.

10. Small Molecule Targeted Therapy Drugs

Small molecule targeted therapy drugs are generally inhibitors of enzymatic domains on mutated, overexpressed, or otherwise critical proteins within the cancer cell. Prominent and non-limiting examples are the tyrosine kinase inhibitors imatinib (Gleevec/Glivec) and gefitinib (Iressa).

The use of small molecules e.g. sunitinib malate and/or sorafenib tosylate targeting some kinases in combination with vaccines for cancer therapy is also described in previous patent application US2009004213.

11. Virus-Based Vaccines

There are a number of virus-based cancer vaccines available or under development which can be used in a combined therapeutic approach together with the formulations of the present invention. One advantage of the use of such viral vectors is their intrinsic ability to initiate immune responses, with inflammatory reactions occurring as a result of the viral infection creating the danger signal necessary for immune activation. An ideal viral vector should be safe and should not introduce an anti-vector immune response to allow for boosting antitumor specific responses. Recombinant viruses such as vaccinia viruses, herpes simplex viruses, adenoviruses, adeno-associated viruses, retroviruses and avipox viruses have been used in animal tumor models and based on their encouraging results, human clinical trials have been initiated. Especially important virus-based vaccines are virus-like particles (VLPs), small particles that contain certain proteins from the outer coat of a virus. Virus-like particles do not contain any genetic material from the virus and cannot cause an infection but they can be constructed to present tumor antigens on their coat. VLPs can be derived from various viruses such as e.g. the hepatitis B virus or other virus families including Parvoviridae (e.g. adeno-associated virus), Retroviridae (e.g. HIV), and Flaviviridae (e.g. Hepatitis C virus). For a general review see Sorensen and Thompsen 2007: Virus-based immunotherapy of cancer: what do we know and where are we going? APMIS 115 (11):1177-93; virus-like particles against cancer are reviewed in Buonaguro et al. 2011: Developments in virus-like particle-based vaccines for infectious diseases and cancer. Expert Rev Vaccines 10(11):1569-83; and in Guillén et al. 2010: Virus-like particles as vaccine antigens and adjuvants: application to chronic disease, cancer immunotherapy and infectious disease preventive strategies. Procedia in Vaccinology 2 (2), 128-133.

12. Multi-Epitope Strategies

The use of multi epitopes shows promising results for vaccination. Fast sequencing technologies combined with intelligent algorithm systems allow the exploitation of the tumor mutanome and may provide multi epitopes for individualized vaccines which can be combined with the present invention. For more information see 2007: Vaccination of metastatic colorectal cancer patients with matured dendritic cells loaded with multiple major histocompatibility complex class I peptides. J Immunother 30: 762-772; furthermore Castle et al. 2012: Exploiting the mutanome for tumor vaccination. Cancer Res 72 (5):1081-91.

13. Adoptive T-Cell Transfer

For example, a combination of a tumor antigen vaccination and T-cell transfer is described in: Rapoport et al. 2011: Combination immunotherapy using adoptive T-cell transfer and tumor antigen vaccination on the basis of hTERT and survivin after ASCT for myeloma. Blood 117(3):788-97.

14. Peptide-Based Target Therapies

Peptides can bind to cell surface receptors or affected extracellular matrix surrounding the tumor. Radionuclides which are attached to these peptides (e.g. RGDs) eventually kill the cancer cell if the nuclide decays in the vicinity of the cell. Especially oligo- or multimers of these binding motifs are of great interest, since this can lead to enhanced tumor specificity and avidity. For non-limiting examples see Yamada 2011: Peptide-based cancer vaccine therapy for prostate cancer, bladder cancer, and malignant glioma. Nihon Rinsho 69(9): 1657-61.

15. Other Therapies

There are numerous other cancer therapies which can be combined with the formulations and methods of the present invention in order to create synergistic effects. Non-limiting examples are treatments targeting apoptosis, hyperthermia, hormonal therapy, telomerase therapy, insulin potentiation therapy, gene therapy and photodynamic therapy.

The present invention is further illustrated by the following examples which are not be construed as limiting the scope of the invention.

EXAMPLES

Example 1: Generation of Binding Agents Comprising Binding Domains with Specificity for CLDN18.2 and CD3

We investigated the potential of using binding agents comprising binding domains with specificity for CLDN18.2 and CD3 (anti-CLDN18.2 x anti-CD3 bispecific antibodies, bsAbs) to redirect CD3+ effector T cells to destroy CLDN18.2-expressing cell lines. Several anti-CLDN18.2 x anti-CD3 bsAbs were generated using the antigen binding domain (ABD) from a murine anti-CLDN18.2 antibody (SEQ ID NOs: 38 and 41) (see WO 2007/059997). In addition, several sequences for anti-CD3 scFvs having different affinities for CD3 were used. The following Table 2 gives an overview over bsAbs carrying murine CLDN18.2 ABDs and CD3 ABDs.

TABLE 2

Overview over bsAbs carrying murine CLDN18.2 ABDs and CD3 ABDs

| bsAb | First chain, SEQ ID NO: | Second chain, SEQ ID NO: | Third chain*, SEQ ID NO: | Binding affinity to CD3 |
|---|---|---|---|---|
| XENP24645 | 79 | 80 | 81 | high (High) |
| XENP24646 | 79 | 82 | 81 | high/medium (HighInt#1) |
| XENP24647 | 79 | 83 | 81 | high (High) |
| XENP24648 | 79 | 84 | 81 | high/medium (HighInt#1) |
| XENP24649 | 79 | 85 | 81 | medium (Int) |

Figure 1B:
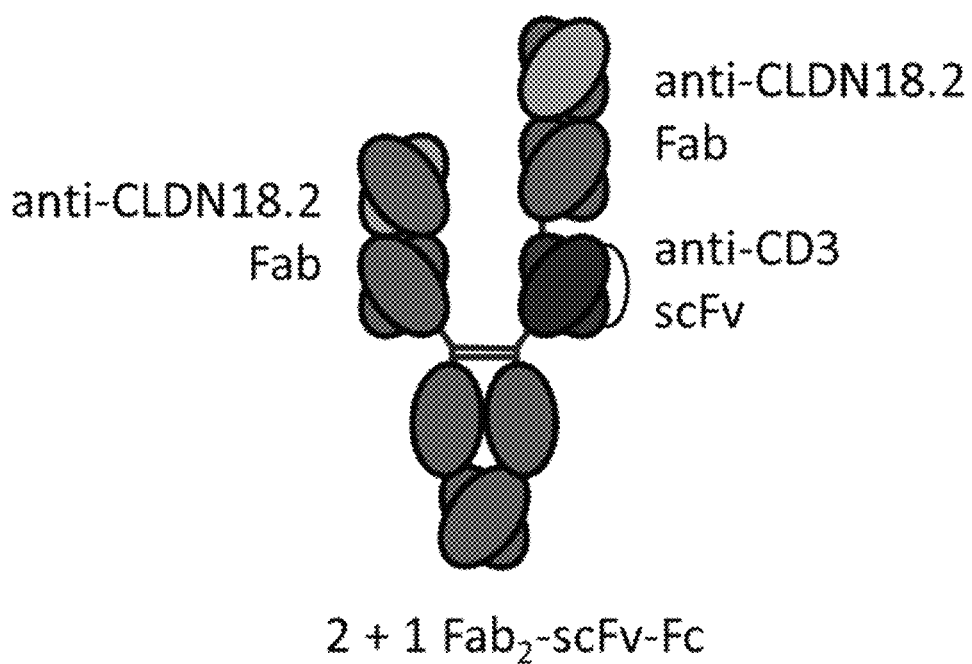
FIG. 1B depicts the "Fab2-scFv" format which comprises a VH recombinantly fused to one side of the heterodimeric Fc (the first polypeptide chain described herein), a VH recombinantly fused to an scFv fused to the other side of a heterodimeric Fc (the second polypeptide chain described herein), and a LC (third and fourth polypeptide chains described herein) transfected separately so that Fab domains are formed with the VH of the first polypeptide chain and the additional VH of the second polypeptide chain.

*bsAbs bivalently binding to CLDN18.2 comprise a fourth chain identical to the third chain Example 1A: Production of Anti-CLDN18.2 x Anti-CD3 bsAbs Schematic representations of anti-CLDN18.2 x anti-CD3 bsAbs are depicted in FIG. 1.

DNA encoding VH(CLDN18.2) and VL(CLDN18.2) was generated by gene synthesis and subcloned into a pTT5 expression vector containing appropriate fusion partners (e.g., constant regions or anti-CD3 scFv-Fc). DNA encoding anti-CD3 scFv-Fc heavy chains was generated by gene synthesis. DNA was transfected into HEK293E cells for expression. An anti-RSV x anti-CD3 bispecific antibody (SEQ ID NOs: 93, 94, 95) was also generated as a control.

Example 1B: Binding and Redirected T Cell Cytotoxicity on NUGC-4 and KP-4 Cell Lines by Anti-CLDN18.2 x Anti-CD3 bsAbs NUGC-4 is a gastric carcinoma cell line expressing high levels of CLDN18.2, and KP-4 is a pancreatic carcinoma cell line expressing very low levels of CLDN18.2 (comparable to a CLDN18.2-negative control cell line). Accordingly, we investigated binding and redirected T cell cytotoxicity (RTCC) on NUGC-4 and KP-4 cell lines mediated by anti-CLDN18.2 x anti-CD3 bsAbs as well as by an anti-RSV x anti-CD3 bsAb control.

Figure 2A:
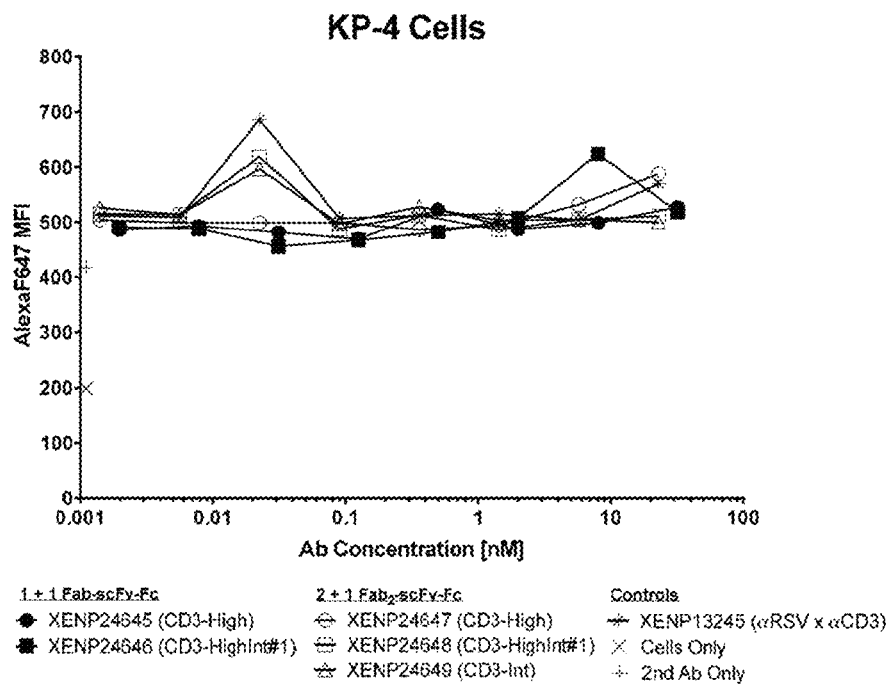
FIGS. 2A and 2B depicts binding of anti-CLDN18.2 x anti-CD3 bispecific antibodies having murine CLDN18.2 ABD to A) KP-4 cells and B) NUGC-4 cells, respectively. Controls included an anti-RSV x anti-CD3 bsAb, cells only, and secondary antibody only. The data show that the anti-CLDN18.2 x anti-CD3 bsAbs dose-dependently bound to NUGC-4 cells, with almost no binding to KP-4 cells at all concentrations tested. Notably, bsAbs of the "Fab2-scFv" format (i.e. XENP24647, XENP24648, and XENP24649) bound much more potently to NUGC-4 cells compared to bsAbs of the "Fab-scFv" format (i.e. XENP24645 and XENP24646), probably due to the extra avidity conveyed by the "Fab2-scFv" format.
Figure 2B:
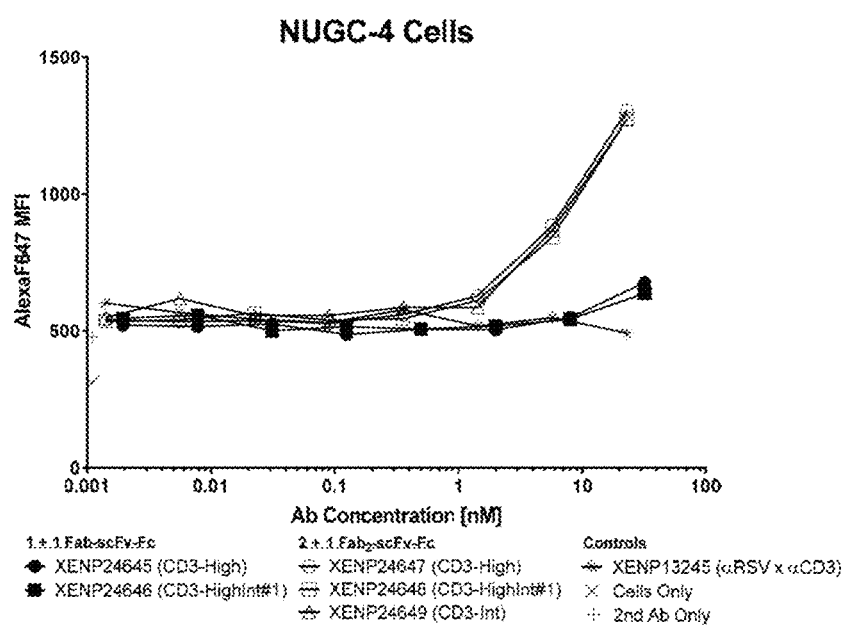

200,000 cells (either NUGC-4 or KP-4) were incubated with indicated concentrations of anti-CLDN18.2 x anti-CD3 bsAbs for an hour on ice. Samples were then washed and stained with Alexa Fluor® 647 AffiniPure F(ab')$_2$ Fragment Goat Anti-Human IgG, Fcγ Fragment Specific secondary antibody (Jackson ImmunoResearch, West Grove, Penn.) for an hour on ice. Samples were washed again and analyzed by flow cytometry. Data showing binding to KP-4 and NUGC-4 cells are depicted in FIG. 2.

Figure 3A:
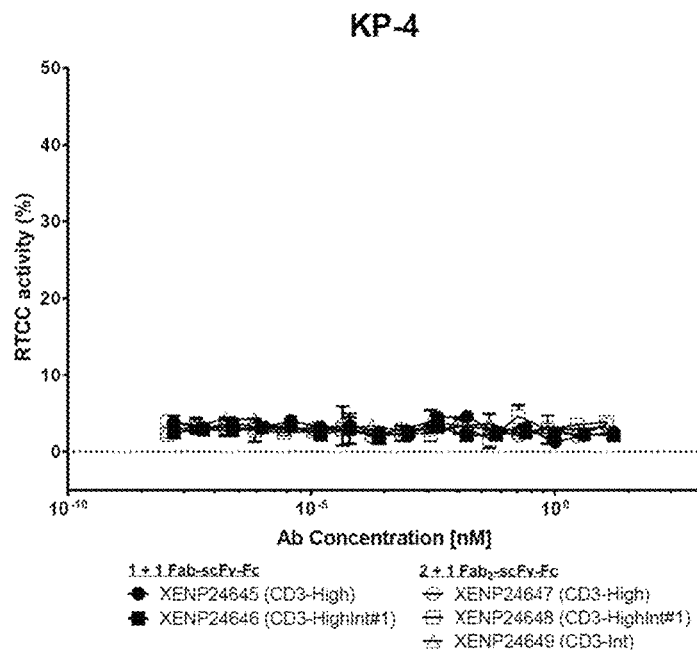
FIGS. 3A and 3B depicts induction of RTCC on A) KP-4 cells and B) NUGC-4 cells, respectively, by anti-CLDN18.2 x anti-CD3 bsAbs having murine CLDN18.2 ABD. The data show that the prototype anti-CLDN18.2 x anti-CD3 bsAbs dose dependently induced RTCC on NUGC-4, and no RTCC on KP-4 cells.
Figure 3B:
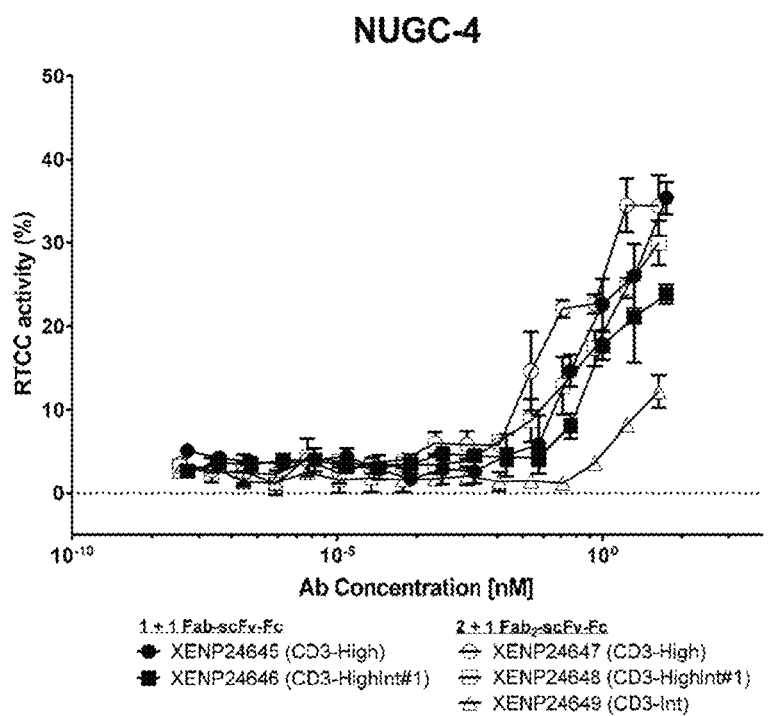

To investigate RTCC mediated by anti-CLDN18.2 x anti-CD3 bsAbs, NUGC-4 or KP-4 were incubated with human PBMCs (10:1 effector to target cell ratio) and indicated concentrations of anti-CLDN18.2 x anti-CD3 bsAbs for 24 hours at 37° C. RTCC was determined using CytoTox-ONE™ Homogeneous Membrane Integrity Assay (Promega, Madison, Wis.) to measure lactate dehydrogenase levels according to manufacturer's instructions and data was acquired on a Wallac Victor2 Microplate Reader (PerkinElmer, Waltham, Mass.), see FIG. 3.

Collectively, the data show that at all concentrations tested the anti-CLDN18.2 x anti-CD3 bsAbs dose-dependently bound to NUGC-4 cells, while almost no binding to KP-4 cells could be detected. Notably, bsAbs of the "Fab2-scFv" format (i.e. XENP24647, XENP24648, and XENP24649) bound much more potently to NUGC-4 cells than bsAbs of the "Fab-scFv" format (i.e. XENP24645 and XENP24646). This is probably due to the extra avidity conveyed by the "Fab2-scFv" format. Consistent with cell-binding, the data show that the anti-CLDN18.2 x anti-CD3 bsAbs dose-dependently induced RTCC on NUGC-4, while no RTCC was induced on KP-4 cells.

Figure 4A:
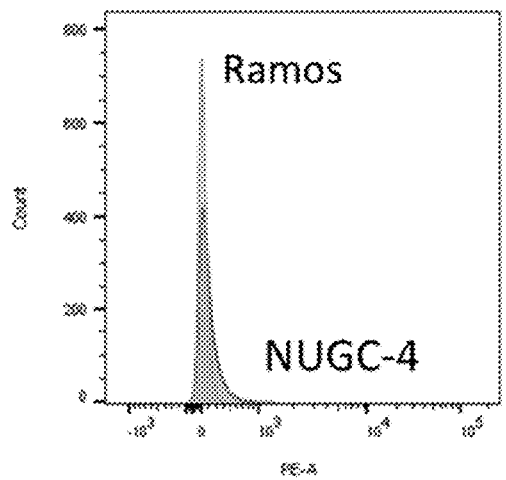
FIGS. 4A and 4B depicts the expression levels on A) NUGC-4 cells and B) SNU-601 cells, respectively, as determined by flow cytometry. The data indicate that SNU-601 expresses more CLDN18.2 than does NUGC-4.
Figure 4B:
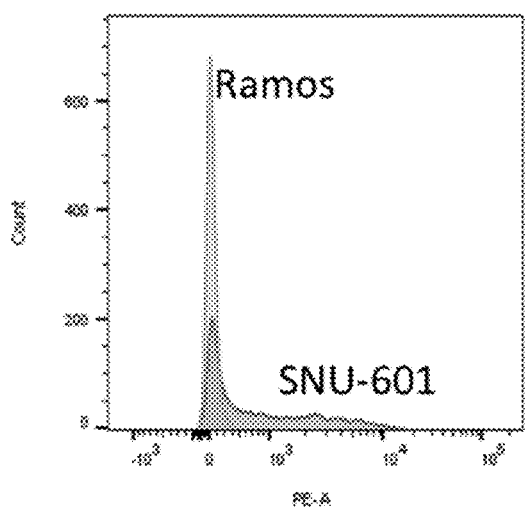

Example 1C: Further Characterization of Anti-CLDN18.2 x Anti-CD3 bsAbs Using NUGC-4 and SNU-601 Cells (a) Identification of SNU-601 as CLDN18.2-Expressing Cell Line In order to better characterize the anti-CLDN18.2 x anti-CD3 bsAbs of the invention, we sought to identify cell lines with higher CLDN18.2 expression levels compared to expression of NUGC-4. We investigated the binding of XENP24647 to various cell lines using flow cytometry as follows. 200,000 cells from various cell lines (and Ramos cells as negative control) were incubated with XENP24647 for an hour on ice, followed by staining with PE AffiniPure F(ab')$_2$ Fragment Goat Anti-Human IgG, Fc Fragment Specific secondary antibody (Jackson ImmunoResearch, West Grove, Penn.) for an hour on ice, and analyzed by flow cytometry. FIG. 4 shows the binding of XENP24647 to NUGC-4 and SNU-601. The data indicate that SNU-601 expresses higher CLDN18.2 levels compared to NUGC-4. Accordingly, we further characterized anti-CLDN18.2 x anti-CD3 bsAbs using NUGC-4 and SNU-601 cells.

(b) Binding of Anti-CLDN18.2 x Anti-CD3 bsAbs on NUGC-4 and SNU-601 Cells

Figure 5A:
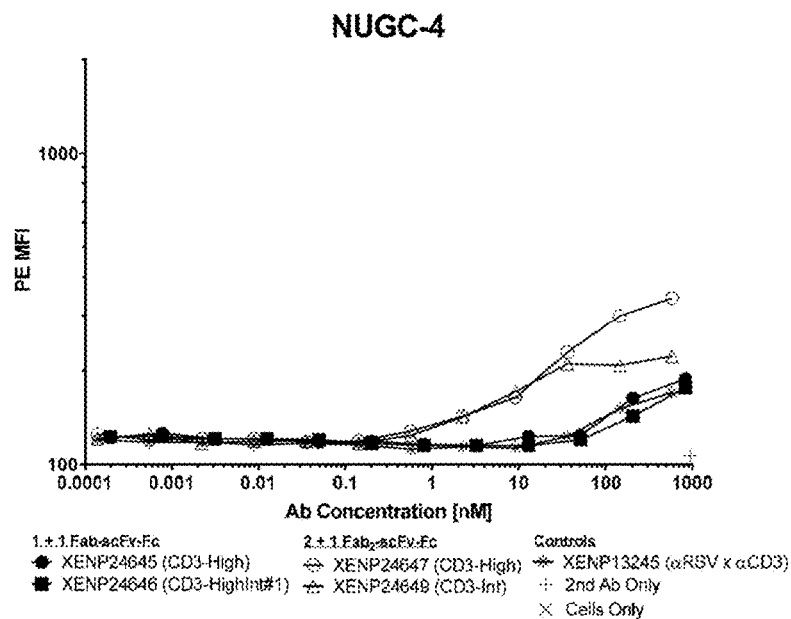
FIGS. 5A and 5B depicts binding of anti-CLDN18.2 x anti-CD3 bispecific antibodies having murine CLDN18.2 ABD to A) NUGC-4 cells and B) SNU-601 cells, respectively. Controls included an anti-RSV x anti-CD3 bispecific antibody, cells only, and secondary antibody only. The data show that each of the bispecific antibodies dose-dependently bound to both NUGC-4 and SNU-601, with higher maximal binding to SNU-601 cells than to NUGC-4, which is consistent with the respective CLDN18.2 expression levels on each cell line.
Figure 5B:
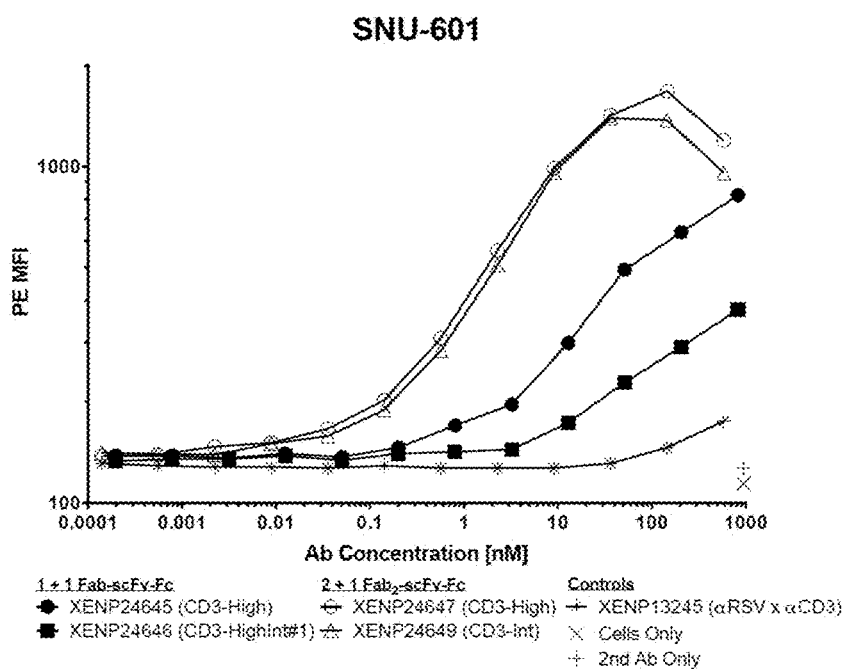
Figure 6A:
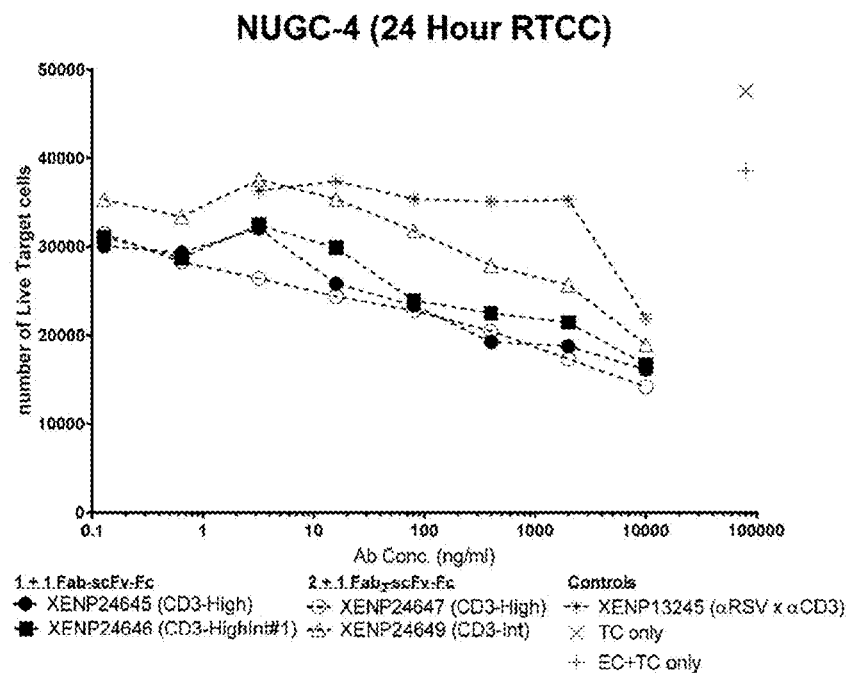
FIGS. 6A and 6B depicts induction of RTCC (as indicated by decrease in live target cells) on A) NUGC-4 and B) SNU-601 cells, respectively, after incubation for 24 hours with human PBMCs (20:1 effector to target cell ratio) and anti-CLDN18.2 x anti-CD3 bispecific antibodies having murine CLDN18.2 ABD. Controls included an anti-RSV x anti-CD3 bispecific antibody, target cells only, and target cells and effector cells only. The data show that the bispecific antibodies enhance killing of target cells (i.e. NUGC-4 and SNU-601 cells) as indicated by decrease in live cells.
Figure 6B:
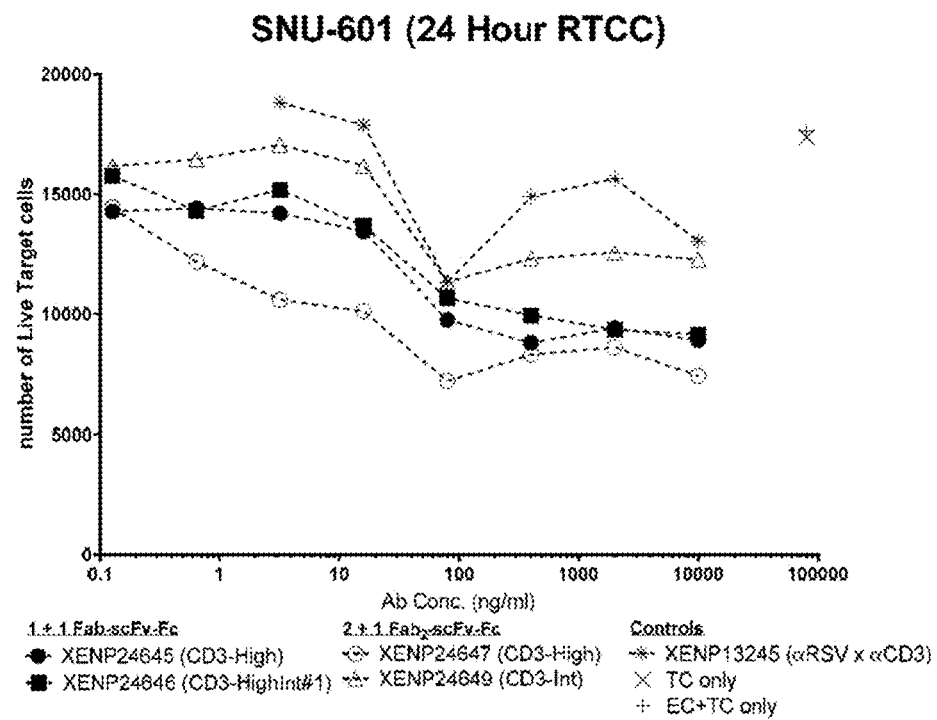
Figure 7A:
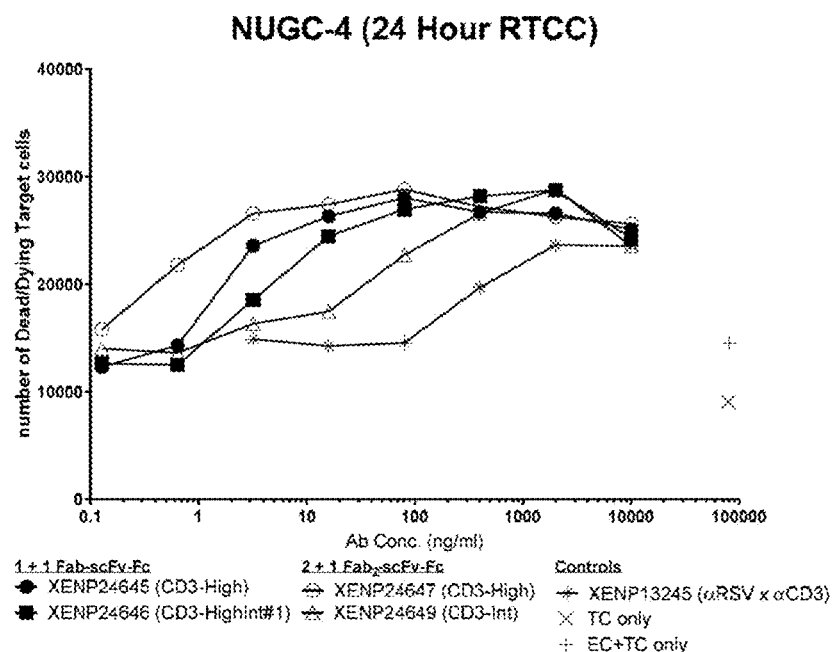
FIGS. 7A and 7B depicts induction of RTCC (as indicated by increase in dead target cells) on A) NUGC-4 and B) SNU-601 cells, respectively, after incubation for 24 hours with human PBMCs (20:1 effector to target cell ratio) and anti-CLDN18.2 x anti-CD3 bispecific antibodies having murine CLDN18.2 ABD. Controls included an anti-RSV x anti-CD3 bispecific antibody, target cells only, and target cells and effector cells only. The data show that the bispecific antibodies enhance killing of target cells (i.e. NUGC-4 and SNU-601 cells) as indicated by increase in dead/dying cells.
Figure 7B:
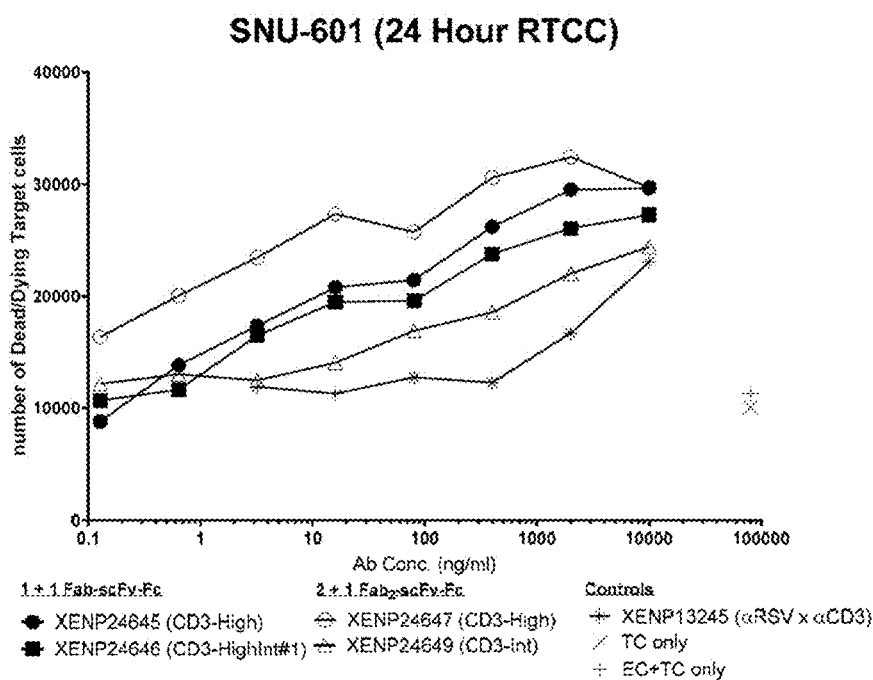
Figure 8A:
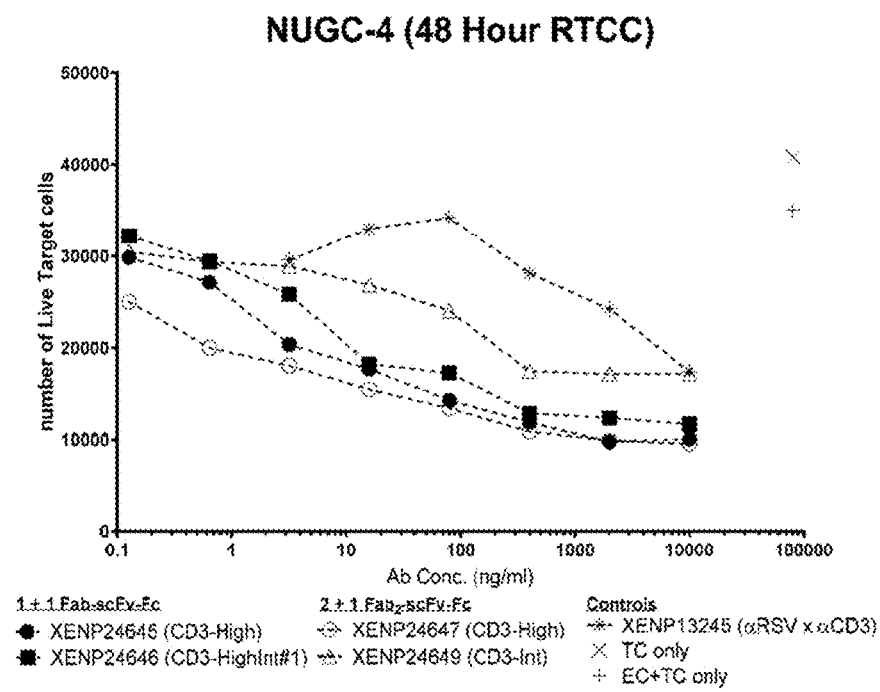
FIGS. 8A and 8B depicts induction of RTCC (as indicated by decrease in live target cells) on A) NUGC-4 and B) SNU-601 cells, respectively, after incubation for 48 hours with human PBMCs (20:1 effector to target cell ratio) and anti-CLDN18.2 x anti-CD3 bispecific antibodies having murine CLDN18.2 ABD. Controls included an anti-RSV x anti-CD3 bispecific antibody, target cells only, and target cells and effector cells only. The data show that the bispecific antibodies enhance killing of target cells (i.e. NUGC-4 and SNU-601 cells) as indicated by decrease in live cells.
Figure 8B:
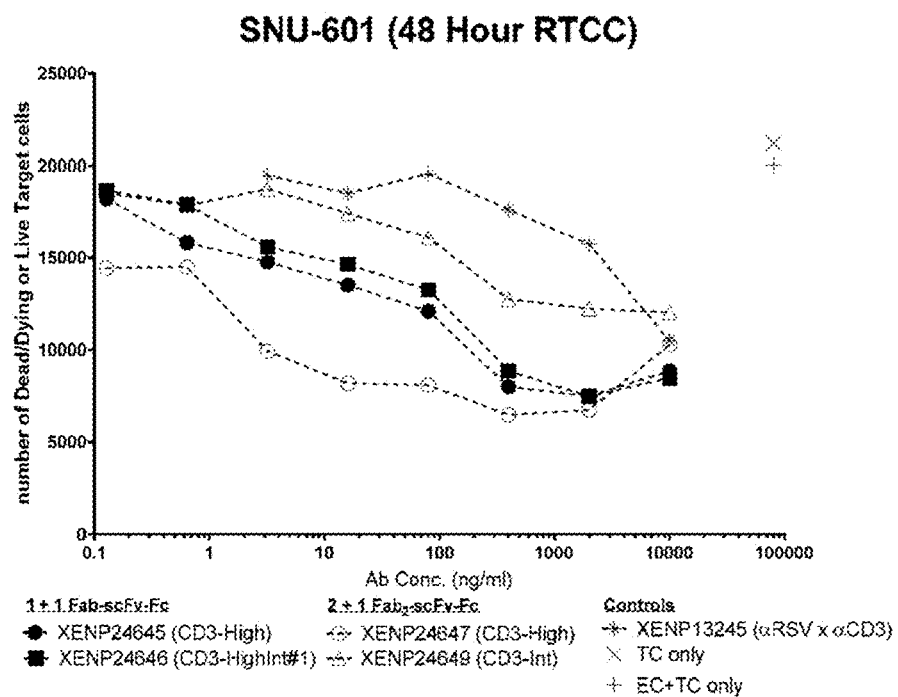
Figure 9A:
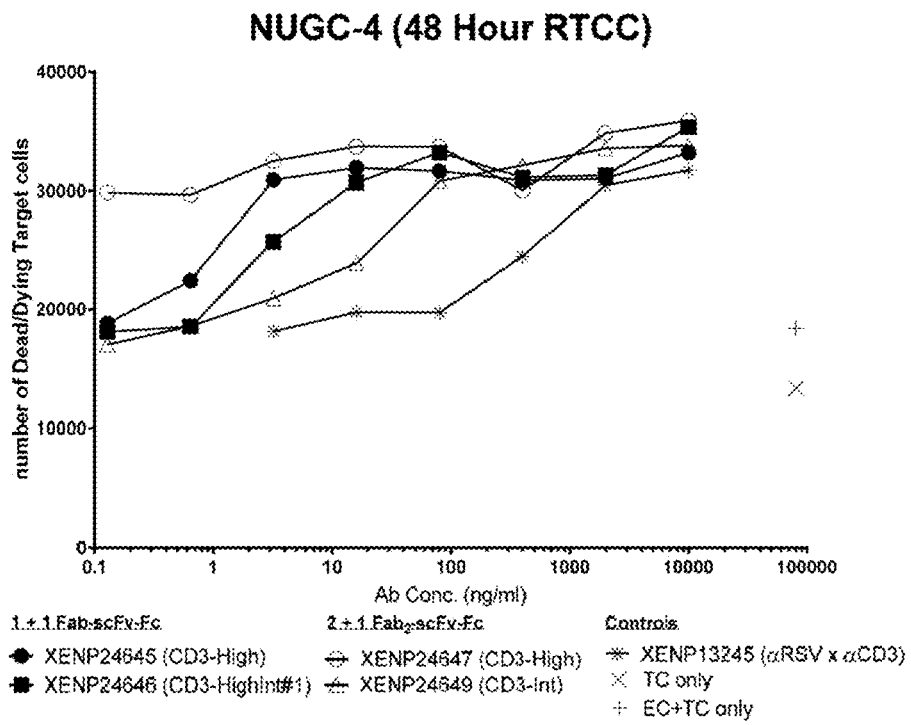
FIGS. 9A and 9B depicts induction of RTCC (as indicated by increase in dead target cells) on A) NUGC-4 and B) SNU-601 cells, respectively, after incubation for 48 hours with human PBMCs (20:1 effector to target cell ratio) and anti-CLDN18.2 x anti-CD3 bispecific antibodies having murine CLDN18.2 ABD. Controls included an anti-RSV x anti-CD3 bispecific antibody, target cells only, and target cells and effector cells only. The data show that the bispecific antibodies enhance killing of target cells (i.e. NUGC-4 and SNU-601 cells) as indicated by increase in dead/dying cells.
Figure 9B:
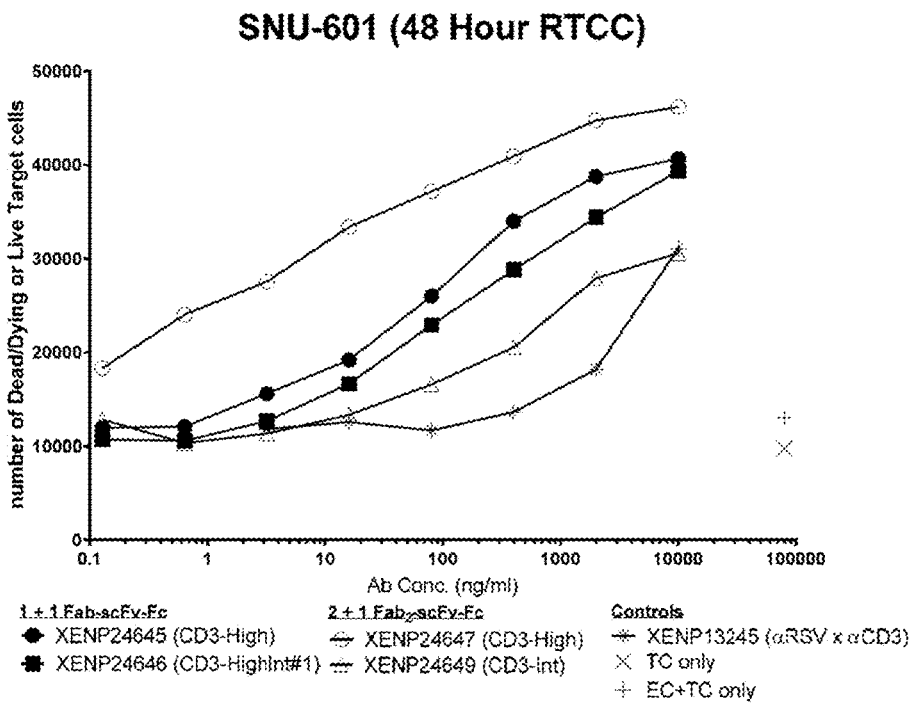
Figure 10A:
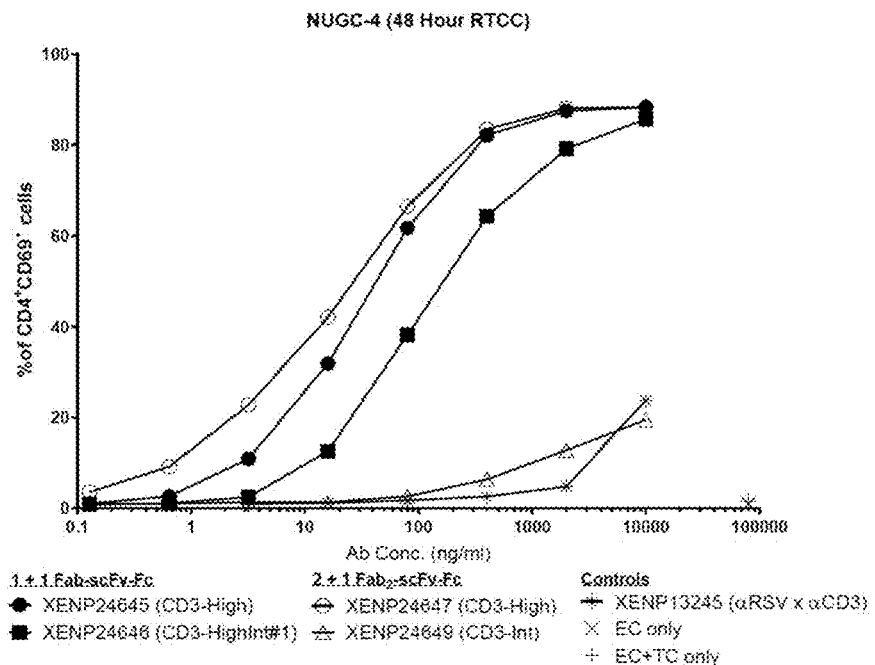
FIGS. 10A, 10B, and 10C depicts percentage of CD4+ T cells expressing A) CD69, B) CD25, and C) CD107a, respectively, following incubation of NUGC-4 cells for 48 hours with human PBMCs (20:1 effector to target cell ratio) and anti-CLDN18.2 x anti-CD3 bispecific antibodies having murine CLDN18.2 ABD. Controls included an anti-RSV x anti-CD3 bispecific antibody, target cells only, and target cells and effector cells only. The data shows a trend consistent with RTCC, i.e. for example, higher affinity CD3 binding and/or bivalent CLDN18.2 binding enhance T cell activation and degranulation.
Figure 10B:
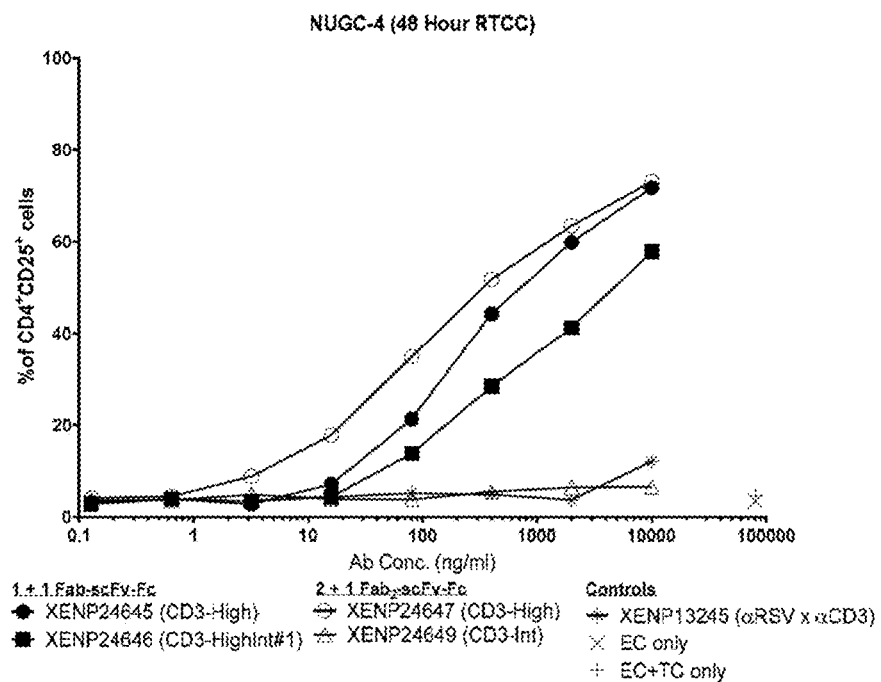
Figure 10C:
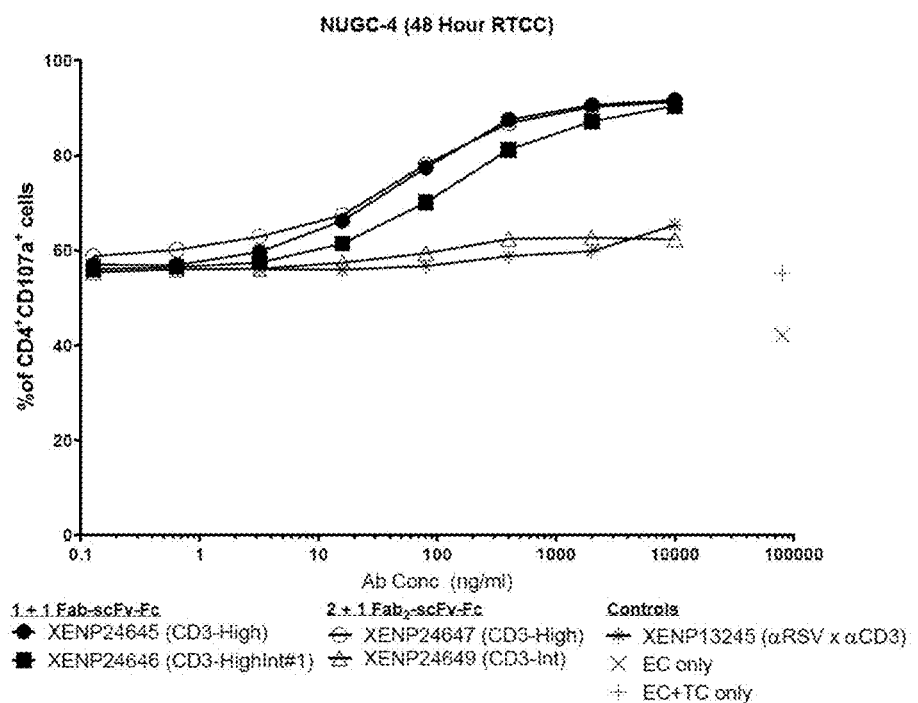
Figure 11A:
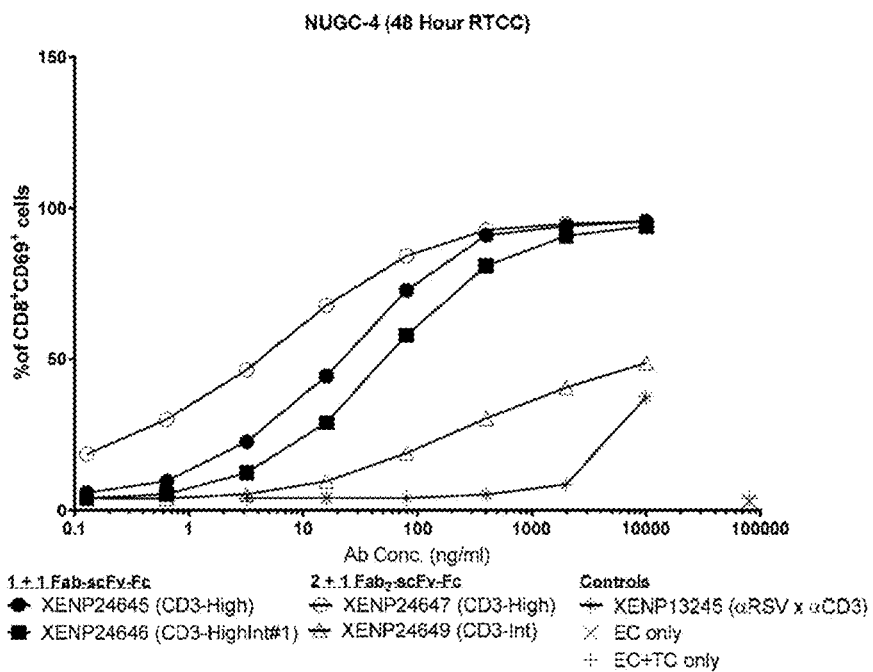
FIGS. 11A, 11B, and 11C depicts percentage of CD8+ T cells expressing A) CD69, B) CD25, and C) CD107a, respectively, following incubation of NUGC-4 cells for 48 hours with human PBMCs (20:1 effector to target cell ratio) and anti-CLDN18.2 x anti-CD3 bispecific antibodies having murine CLDN18.2 ABD. Controls included an anti-RSV x anti-CD3 bispecific antibody, target cells only, and target cells and effector cells only. The data shows a trend consistent with RTCC, i.e. for example, higher affinity CD3 binding and/or bivalent CLDN18.2 binding enhance T cell activation and degranulation.
Figure 11B:
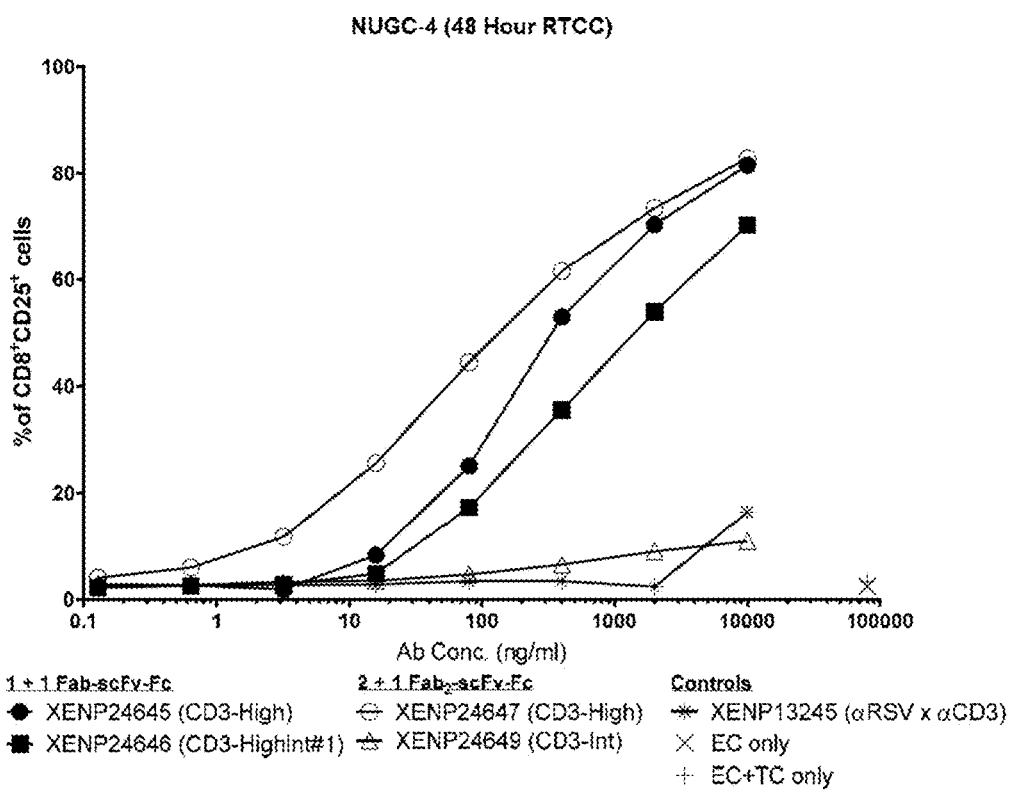
Figure 11C:
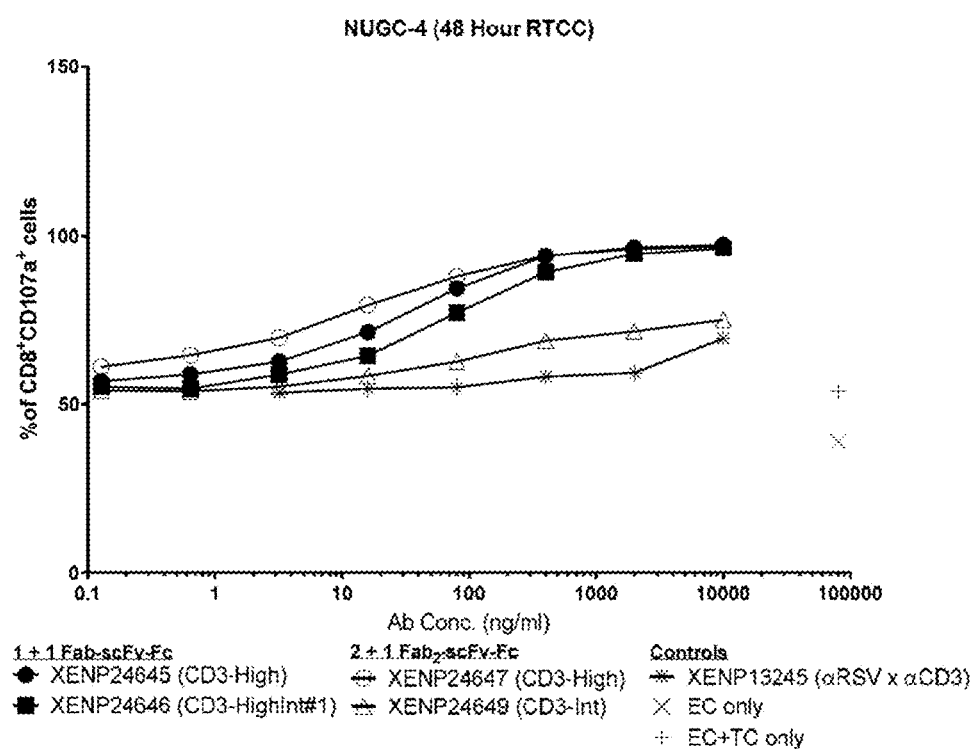
Figure 12A:
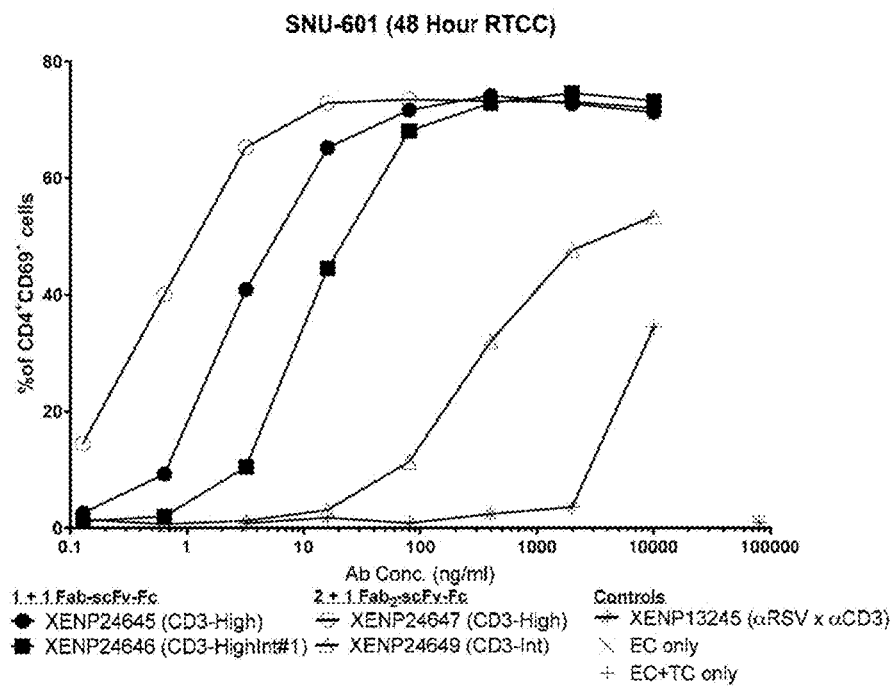
FIGS. 12A, 12B, and 12C depicts percentage of CD4+ T cells expressing A) CD69, B) CD25, and C) CD107a, respectively, following incubation of SNU-601 cells for 48 hours with human PBMCs (20:1 effector to target cell ratio) and anti-CLDN18.2 x anti-CD3 bispecific antibodies having murine CLDN18.2 ABD. Controls included an anti-RSV x anti-CD3 bispecific antibody, target cells only, and target cells and effector cells only. The data shows a trend consistent with RTCC, i.e. for example, higher affinity CD3 binding and/or bivalent CLDN18.2 binding enhance T cell activation and degranulation.
Figure 12B:
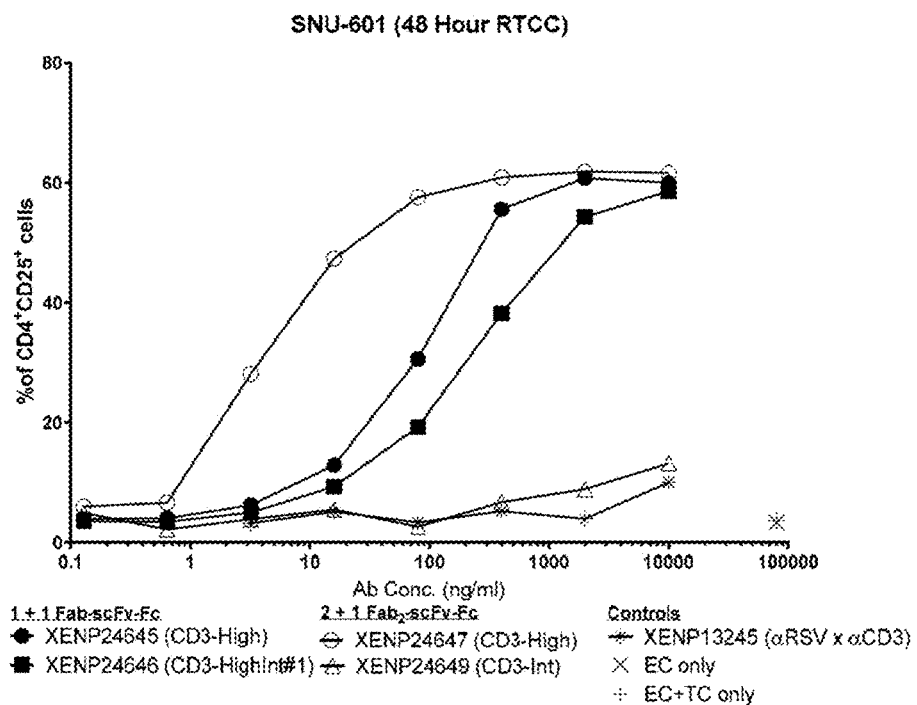
Figure 12C:
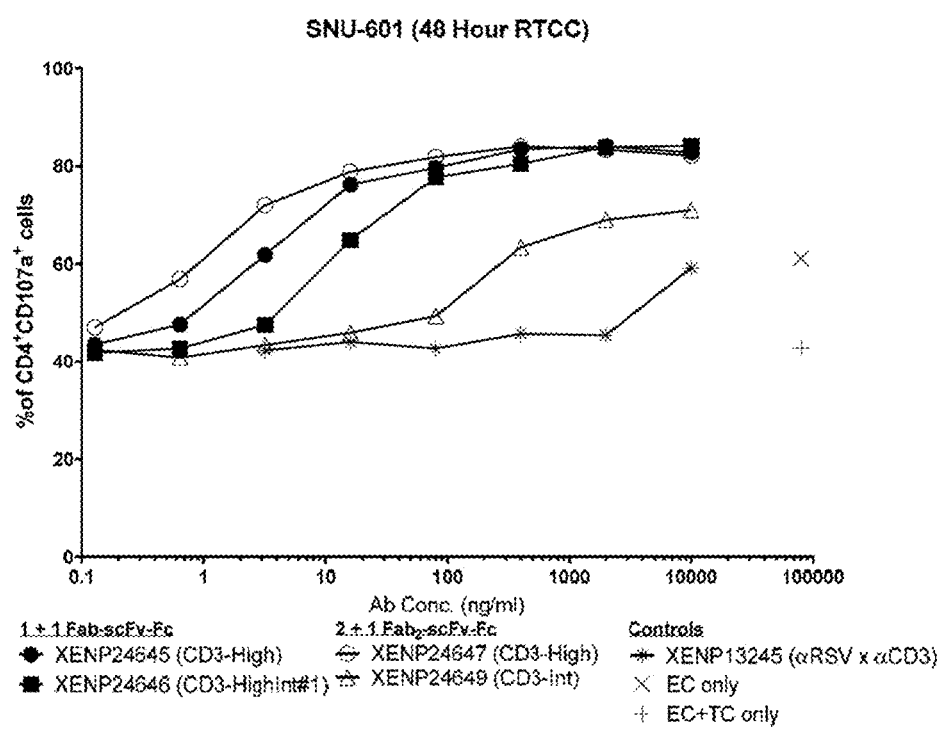
Figure 13A:
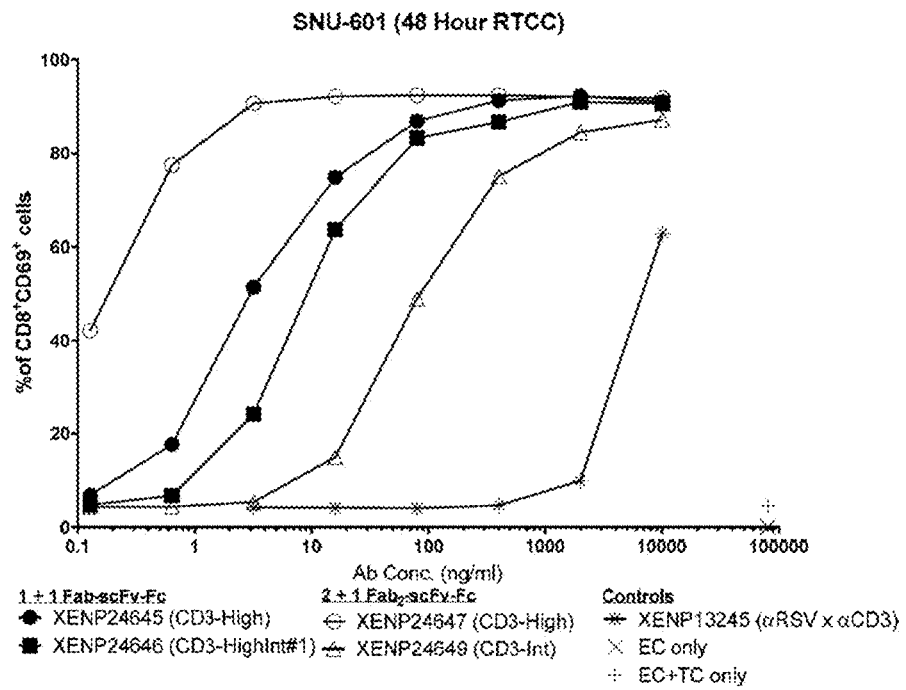
FIGS. 13A, 13B, and 13C depicts percentage of CD8+ T cells expressing A) CD69, B) CD25, and C) CD107a, respectively, following incubation of SNU-601 cells for 48 hours with human PBMCs (20:1 effector to target cell ratio) and anti-CLDN18.2 x anti-CD3 bispecific antibodies having murine CLDN18.2 ABD. Controls included an anti-RSV x anti-CD3 bispecific antibody, target cells only, and target cells and effector cells only. The data shows a trend consistent with RTCC, i.e. for example, higher affinity CD3 binding and/or bivalent CLDN18.2 binding enhance T cell activation and degranulation.
Figure 13B:
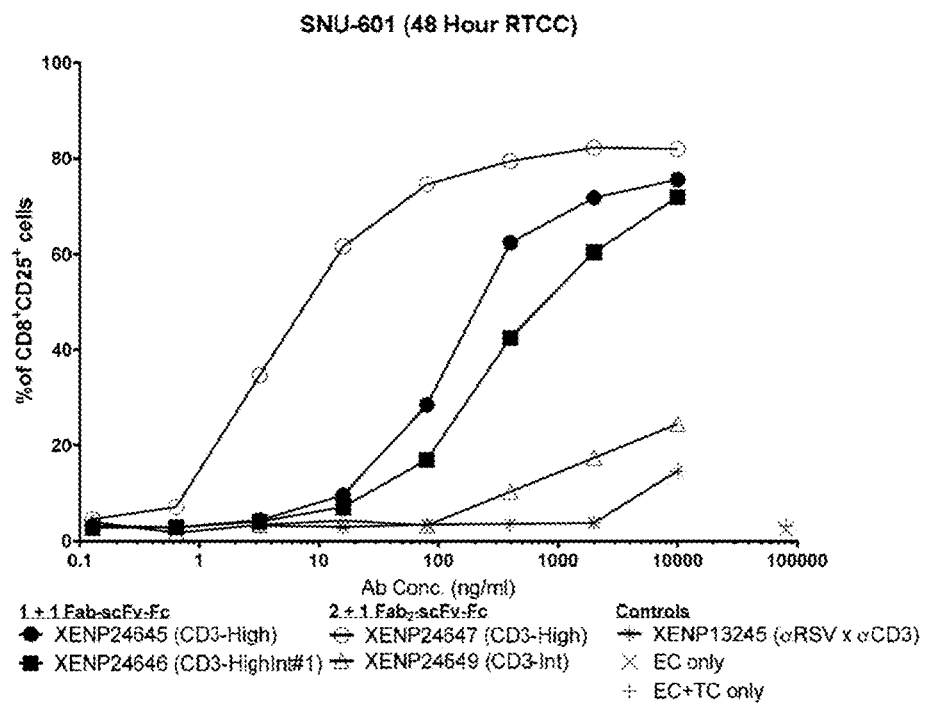
Figure 13C:
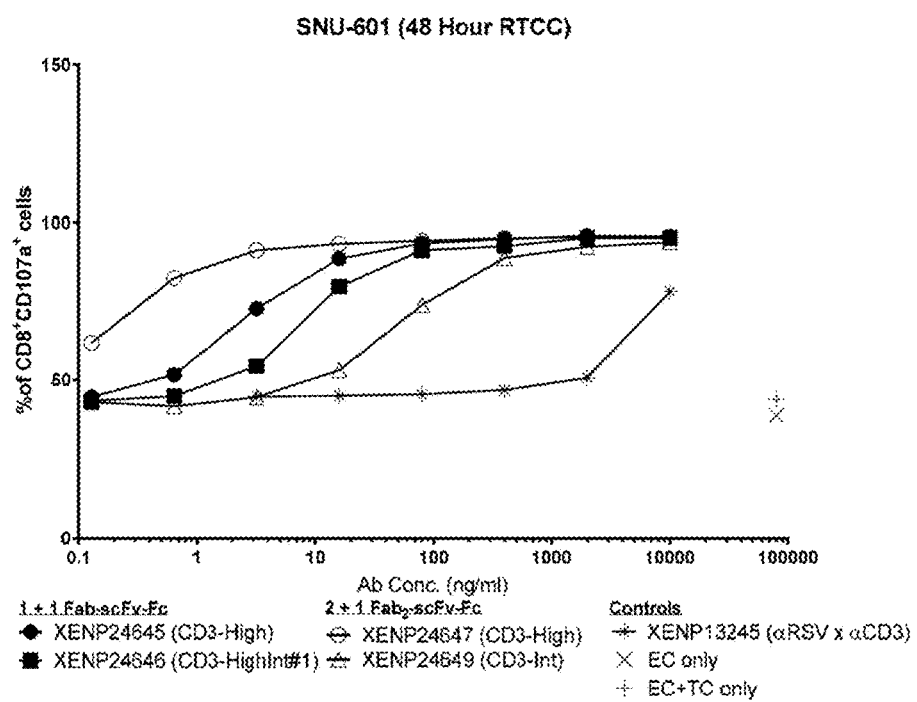

We investigated the binding of anti-CLDN18.2 x anti-CD3 bsAbs on NUGC-4 and SNU-601 cells. Experiments were conducted as described above. In particular, 200,000 cells from various cell lines (and Ramos cells as negative control) were incubated with indicated concentrations of indicated bsAbs for an hour on ice, followed by staining with PE AffiniPure F(ab')$_2$ Fragment Goat Anti-Human IgG, Fcγ Fragment Specific secondary antibody (Jackson ImmunoResearch, West Grove, Penn.) for an hour on ice, and analyzed by flow cytometry. PE MFI indicating binding by the bsAbs to NUGC-4 and SNU-601 are depicted in FIG. 5. Each of the bsAbs dose-dependently bound to both NUGC-4 and SNU-601, with higher maximal binding to SNU-601 cells than to NUGC-4, which is consistent with the respective CLDN18.2 expression levels on each cell line. Consistent with the findings of Example 1B, above, the data show that the bsAbs in the "Fab2-scFv" format bound cells more potently than bsAbs in the "Fab-scFv" format.

(c) Induction of Redirected T Cell Cytotoxicity on NUGC-4 and SNU-601 Cells by Anti-CLDN18.2 x Anti-CD3 bsAbs Next, we investigated RTCC mediated by anti-CLDN18.2 x anti-CD3 bsAbs on NUGC-4 and SNU-601. Experiments were conducted as described above. In particular, NUGC-4 or SNU-601 cells were incubated with human PBMCs (20:1 effector to target cell ratio) and indicated concentrations of the indicated bsAbs and anti-CD107a-BV421 for 24 hours or 48 hours at 37° C. As controls, target cells only or target cells and effector cells without bsAbs were used. After incubation, samples were stained with the following antibodies for 1 hour on ice: anti-CD69-PE, anti-CD25-APC, anti-CD4-APC-Fire750, and anti-CD8-BV605. Cells were then stained with BUV395 Annexin-V (BD Bioscience, San Jose, Calif.) and 7-AAD Viability Staining Solution (BioLegend, San Diego, Calif.). Finally, cells were analyzed by flow cytometry.

AnnexinV and 7AAD binding are indicators of the induction of apoptosis. Accordingly, live cells were AnnexinV-7AAD-, while dead cells were a sum of AnnexinV+, 7AAD+, and AnnexinV+7AAD+ cells. Data depicting numbers of dead/dying target cells and live target cells following incubation with effector cells and indicated bsAbs are shown in FIGS. 6-9. The data show that the bsAbs enhance killing of target cells (i.e. NUGC-4 and SNU-601 cells) as indicated by increase in dead/dying cells as well as decrease in living cells. Notably, the data show that binding domains with higher affinity for CD3 enhance RTCC (for example in comparing XENP24645 and XENP24646; and in comparing XENP24647 and XENP24649). Further, in the case of bsAbs having the same binding domain with specificity for CD3, bsAbs in the "Fab2-scFv" format enhance RTCC more potently than bsAbs in the "Fab-scFv" format (for example in comparing XENP24647 and XENP24645). Additionally, the enhanced RTCC by "Fab2-scFv" bsAbs over "Fab-scFv" bsAbs (e.g. XENP24645 (Fab-scFv format) and XENP24647 (Fab2-scFv format), having the same affinity for CD3) is more pronounced in SNU-601 which expresses higher levels of CLDN18.2, suggesting that the "Fab2-scFv" format provides selectivity for cell lines expressing higher levels of CLDN18.2. We also investigated the activation of T cells by the bsAbs of the invention. CD69 is an early activation marker, and CD25 is a late activation marker, both of which are upregulated following T cell activation via TCR signalling. CD107a is a functional marker for T cell degranulation and cytotoxic activity. Effector cells were gated to identify CD4+ and CD8+ T cells. T cells were then gated for CD69, CD25, and CD107a expression. Data depicting upregulation of the markers on CD4+ and CD8+ T cells are depicted in FIGS. 10-13. The data show a trend consistent with RTCC results. For example, higher affinity CD3 binding and/or bivalent CLDN18.2 binding enhance T cell activation and degranulation.

Example 2: Generation of Anti-CLDN18.2 x Anti-CD3 bsAbs Having Humanized CLDN18.2 Antigen Binding Domains bsAbs carrying humanized ABDs with specificity for CLDN18.2 were generated. The following Table 3 gives an overview over humanized bsAbs generated.

TABLE 3

Overview over bsAbs carrying humanized ABDs with specificity for CLDN18.2

| bsAb | First chain, SEQ ID NO: | Second chain, SEQ ID NO: | Third chain*, SEQ ID NO: | Binding affinity to CD3 |
|---|---|---|---|---|
| XENP29472 | 73 | 75 | 78 | high (High) |
| XENP29473 | 86 | 87 | 78 | high (High) |
| XENP29474 | 73 | 91 | 78 | high/medium (HighInt#1) |
| XENP29475 | 86 | 88 | 78 | high/medium (HighInt#1) |
| XENP29476 | 73 | 92 | 78 | high (High) |
| XENP29477 | 86 | 89 | 78 | high (High) |
| XENP29478 | 73 | 76 | 78 | high/medium (HighInt#1) |
| XENP29479 | 86 | 90 | 78 | high/medium (HighInt#1) |

*bsAbs bivalently binding to CLDN18.2 comprise a fourth chain identical to the third chain

Example 2A: Humanization of CLDN18.2 Antigen Binding Domains

We engineered anti-CLDN18.2 mAbs having humanized variable regions using string content optimization (see, e.g., WO 2005/056759 and U.S. Pat. No. 7,657,380) (VH: SEQ ID NOs: 39, 40, VL: SEQ ID NO: 42). Human germline identity was increased from 73.2% for the murine ABD (SEQ ID NO: 38, 41; "H0L0") to 86.6% (SEQ TD NOs: 40, 42; "H2L1") and 88.3% (SEQ TD NOs: 39, 42; "H1L1") respectively for the two variants. The variable regions from the humanized mAbs were used to generate additional anti-CLDN18.2 x anti-CD3 bsAbs in both the "Fab-scFv" and "Fab2-scFv" format, as described in Example 1A.

Example 2B3: Humanization of CLDN18.2 ABD Preserved Binding, RTCC, and T Cell Activation Next, we compared cell binding, induction of RTCC, and induction of T cell activation by anti-CLDN18.2 x anti-CD3 bsAbs having murine CLDN18.2 ABDs with bsAbs having humanized CLDN18.2 ABDs.

Figure 14A:
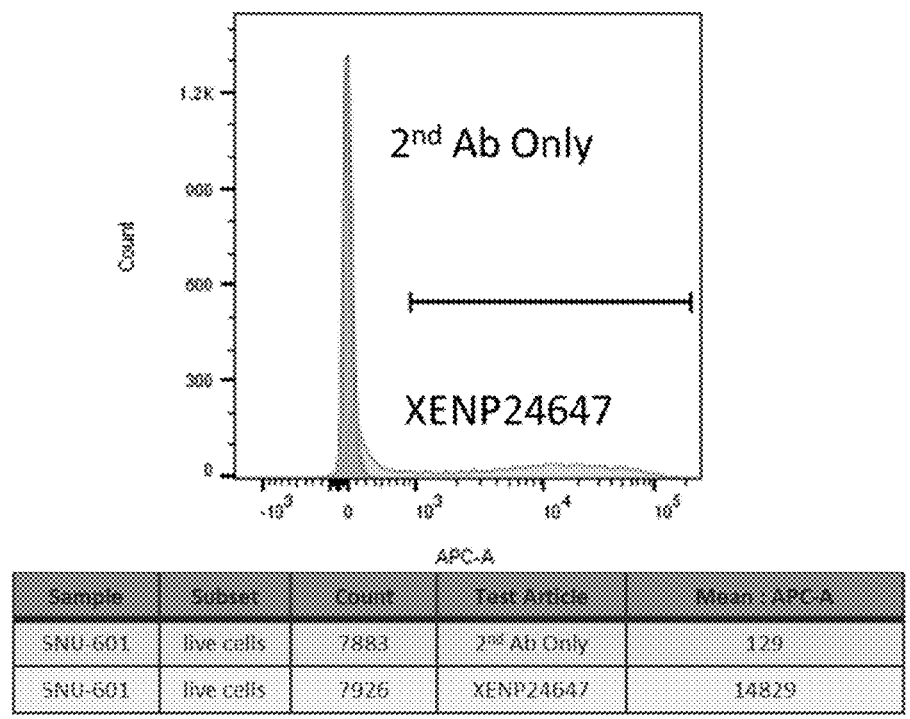
FIGS. 14A and 14B depicts the expression levels on A) SNU-601 cells and B) SNU-601(2E4) cells (enriched for CLDN18.2 expressing population) as determined by flow cytometry. The data show that the SNU-601(2E4) contains substantially higher population of CLDN18.2+ cells. Experiments in this section are performed using SNU-601 (2E4) cells.
Figure 14B:
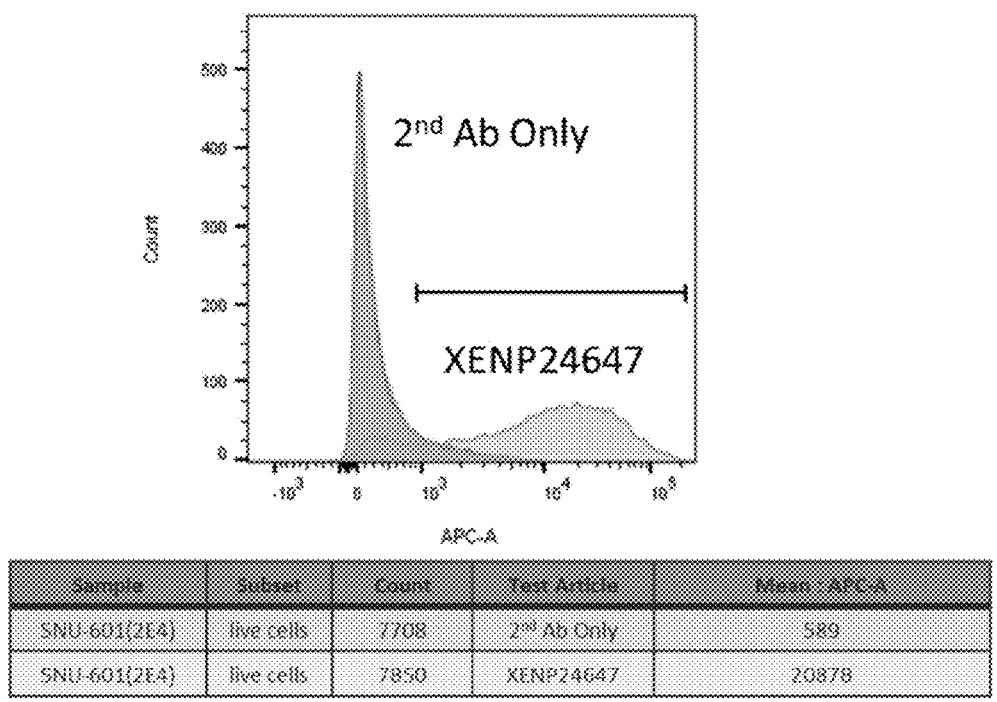

As observed in FIG. 4, although the SNU-601 cell line was characterized by higher levels of CLDN18.2 expression than the NUGC-4 cell line, the SNU-601 cell population was very heterogeneous for CLDN18.2 expression. Accordingly, using flow cytometry, we sorted SNU-601 cells based on CLDN18.2 expression and expanded CLDN18.2+ population for 4 days. The expanded CLDN18.2+ population (hereon referred to as enriched SNU-601 or SNU-601(2E4)) was re-assessed for CLDN18.2 expression as described in Example 1C and compared to non-enriched SNU-601 cells, see FIG. 14. The data show that the SNU-601(2E4) contains substantially higher population of CLDN18.2+ cells. Experiments in this section are performed using SNU-601 (2E4) cells.

Figure 15:
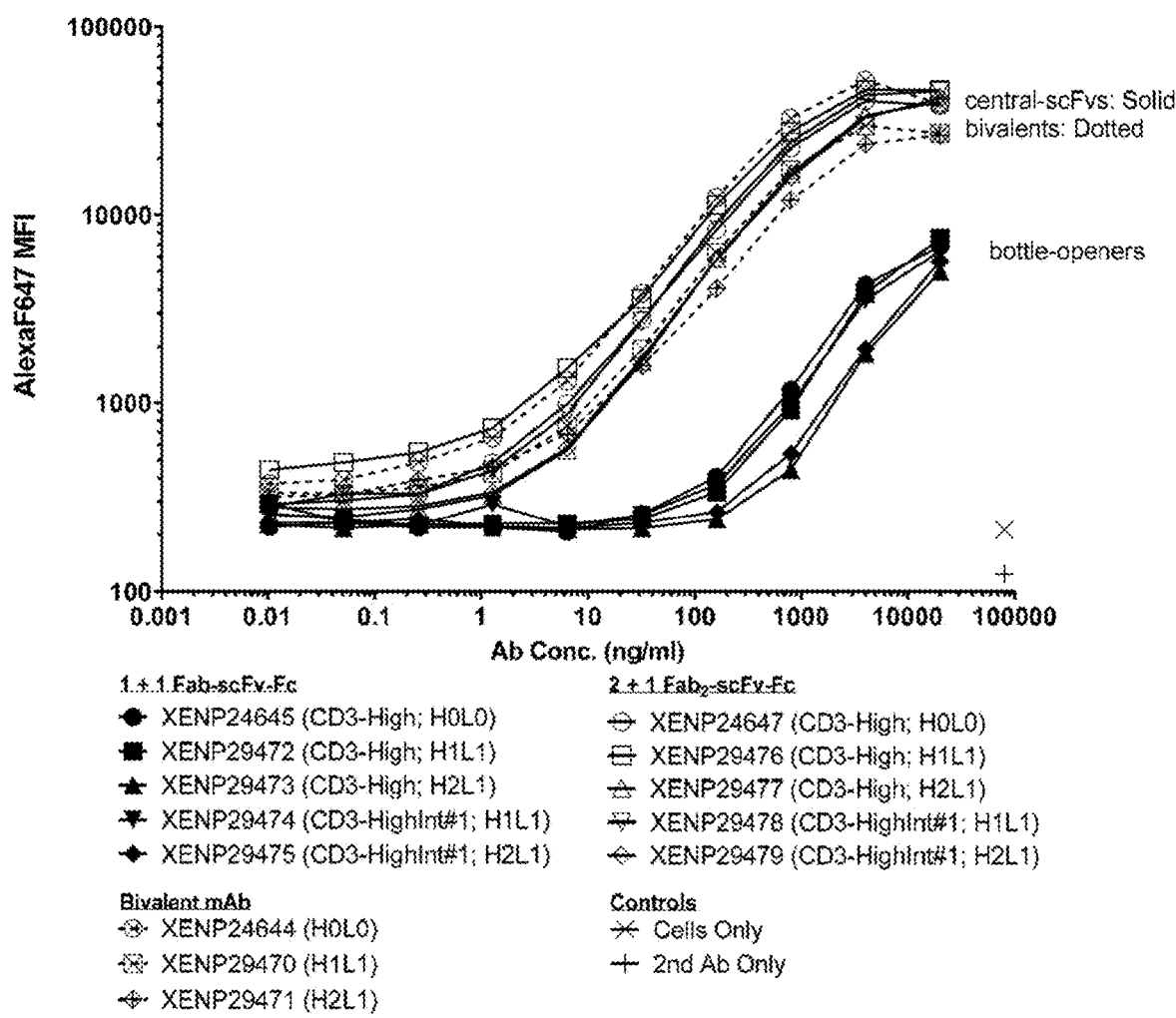
FIG. 15 depicts binding by anti-CLDN18.2 x anti-CD3 bispecific antibodies having humanized CLDN18.2 ABD to SNU-601(2E4) cells. Controls used were XENP24644 (H0L0 CLDN18.2; bivalent mAb), XENP29470 (H1L1 CLDN18.2; bivalent mAb), XENP29471 (H2L1 CLDN18.2; bivalent mAb), XENP24645 (Fab-scFv), XENP24647 (Fab2-scFv), cells only, and secondary antibody only. The data show that the bispecific antibodies having humanized CLDN18.2 ABDs had similar binding to SNU-601(2E4) cells as bispecific antibodies having murine CLDN18.2 ABDs indicating that humanization preserved the binding efficacy of the antibodies. Notably, bispecific antibodies in the "Fab2-scFv" format showed similar binding to bivalent anti-CLDN18.2 mAbs. Additionally, the data show that bispecific antibodies based on the H1L1 humanized variant (e.g. XENP29472, XENP29474, XENP29476, and XENP29478) better preserved binding than did bispecific antibodies based on the H2L1 humanized variant (e.g. XENP29473, XENP29475, XENP29477, and XENP29479).
Figure 16A:
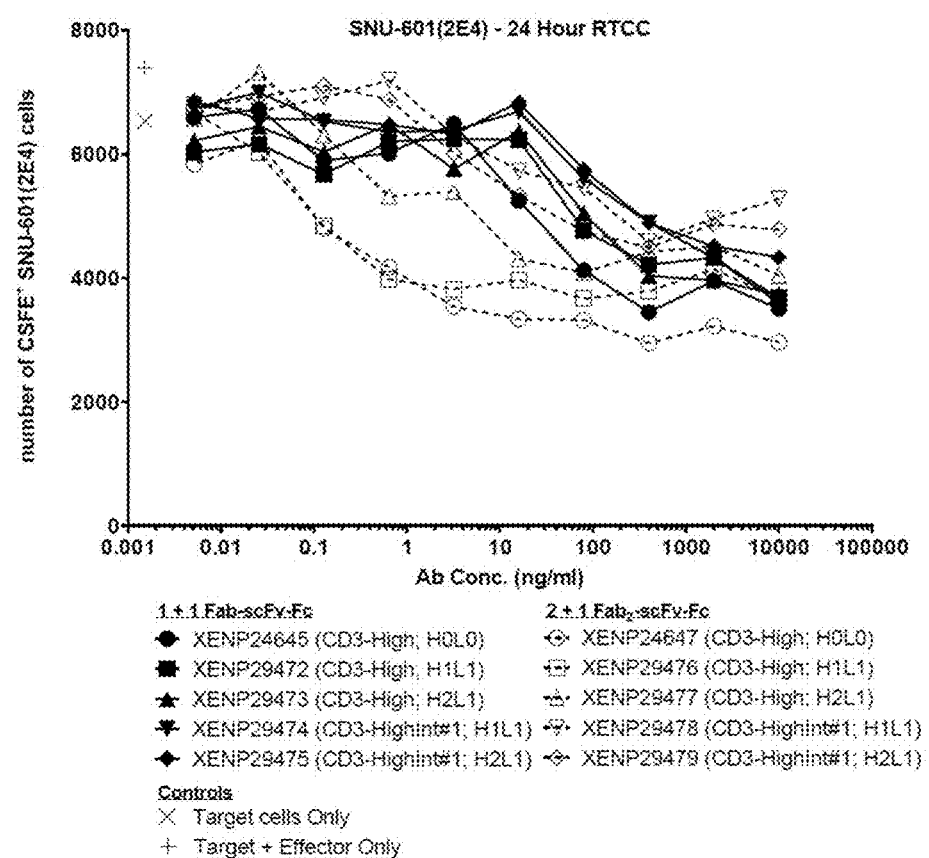
FIGS. 16A, 16B, and 16C depicts induction of RTCC on SNU-601(2E4) cells A) as indicated by decrease in number of CFSE+ SNU-601(2E4), B) as indicated by percentage of CFSE+ SNU-601(2E4) cells stained with Zombie Aqua, and C) as indicated by Zombie Aqua MFI on CFSE+ SNU-601 (2E4) cells after incubation of CFSE-labeled SNU-601(2E4) for 24 hours with human PBMCs (10:1 effector to target cell ratio) and anti-CLDN18.2 x anti-CD3 bispecific antibodies having humanized CLDN18.2 ABD to SNU-601(2E4) cells. Controls used were XENP24645 (Fab-scFv), XENP24647 (Fab2-scFv), cells only, and secondary antibody only. Consistent with the binding data, humanization preserved the induction of RTCC by the bsAbs having humanized CLDN18.2 ABDs.
Figure 16B:
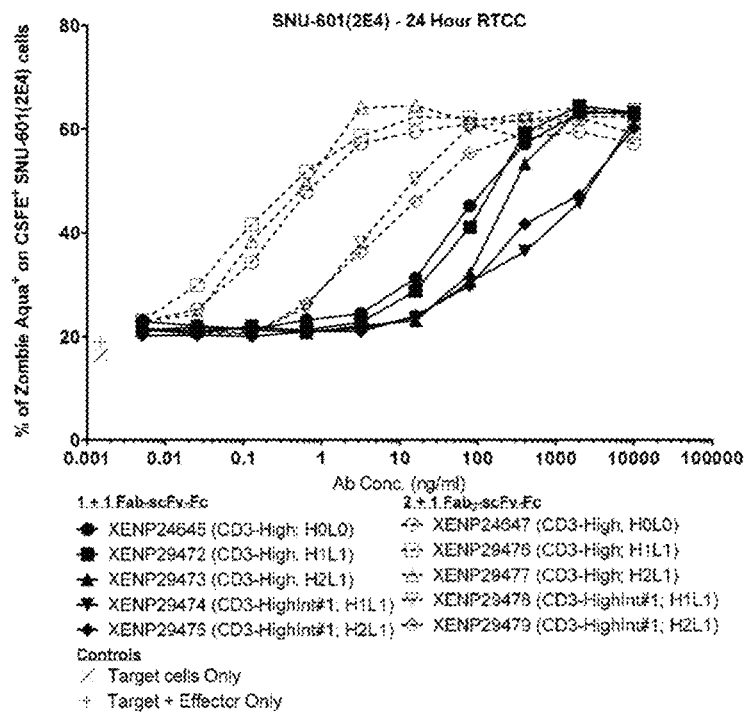
Figure 16C:
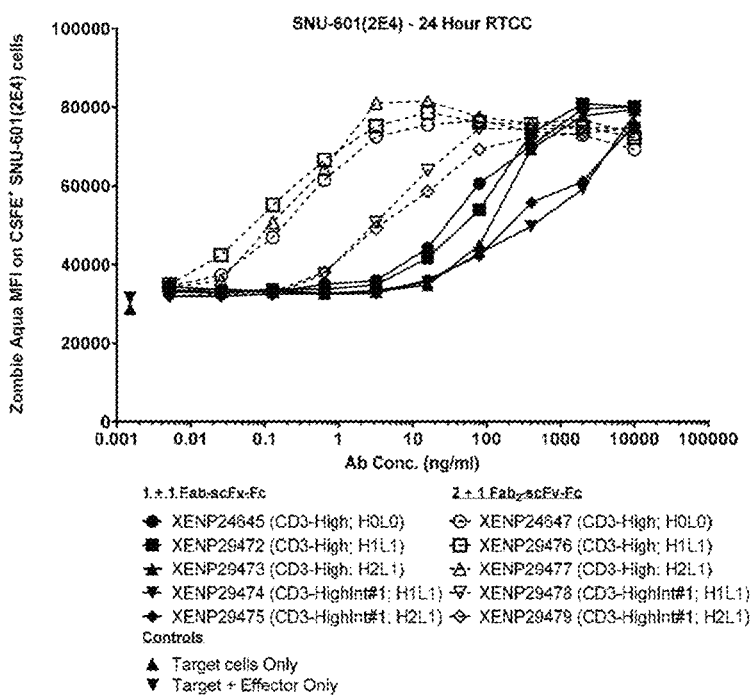
Figure 17A:
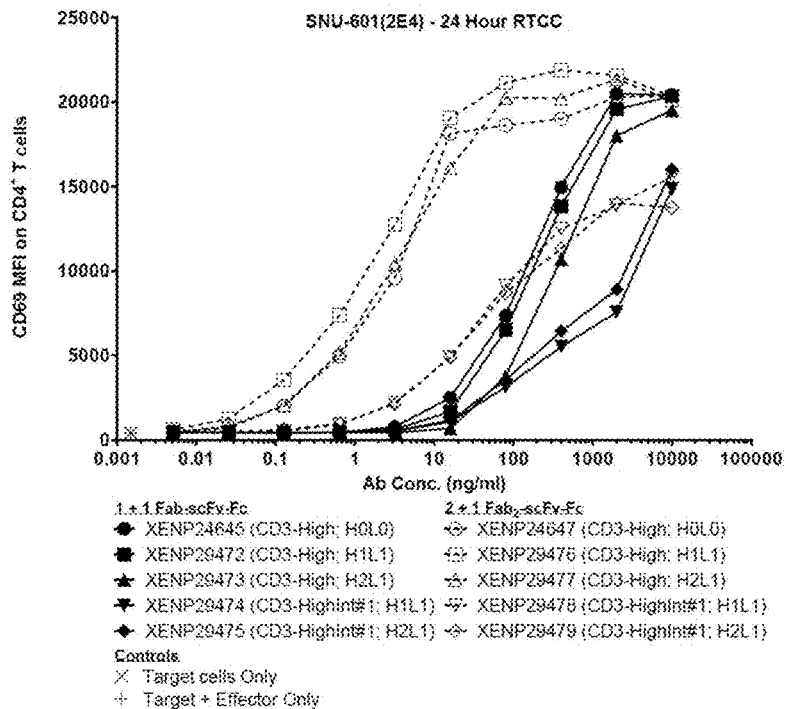
FIGS. 17A and 17B depicts activation CD4+ T cells as indicated by A) CD69 MFI on CD4+ T cells, and B) percentage of CD4+ T cells expressing CD69 after incubation of SNU-601(2E4) for 24 hours with human PBMCs (10:1 effector to target cell ratio) and anti-CLDN18.2 x anti-CD3 bispecific antibodies having humanized CLDN18.2 ABD. Controls used were XENP24645 (Fab-scFv-Fc), XENP24647 (Fab2-scFv), cells only, and secondary antibody only. Consistent with the binding data, humanization preserved T cell activation by the bsAbs having humanized CLDN18.2 ABDs.
Figure 17B:
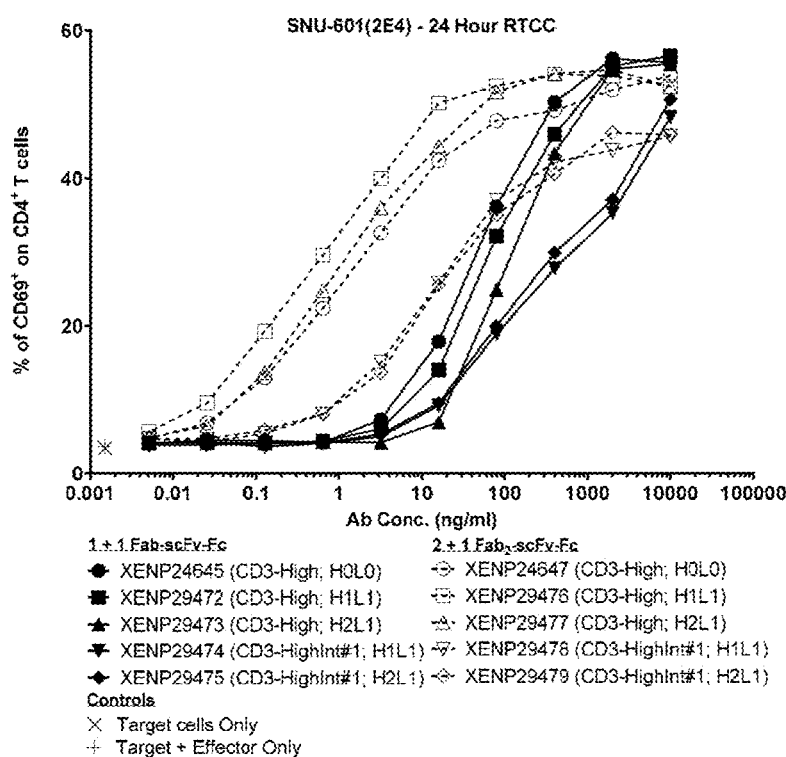
Figure 18A:
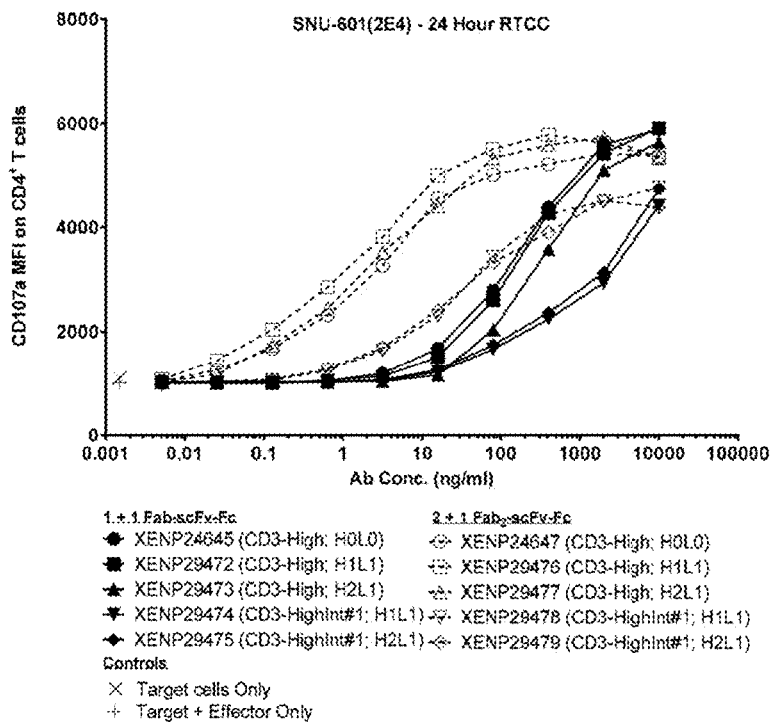
FIGS. 18A and 18B depicts degranulation of CD4+ T cells as indicated by A) CD107a MFI on CD4+ T cells, and B) percentage of CD4+ T cells expressing CD107a after incubation of SNU-601(2E4) for 24 hours with human PBMCs (10:1 effector to target cell ratio) and anti-CLDN18.2 x anti-CD3 bispecific antibodies having humanized CLDN18.2 ABD. Controls used were XENP24645 (Fab-scFv-Fc), XENP24647 (Fab2-scFv), cells only, and secondary antibody only.
Figure 18B:
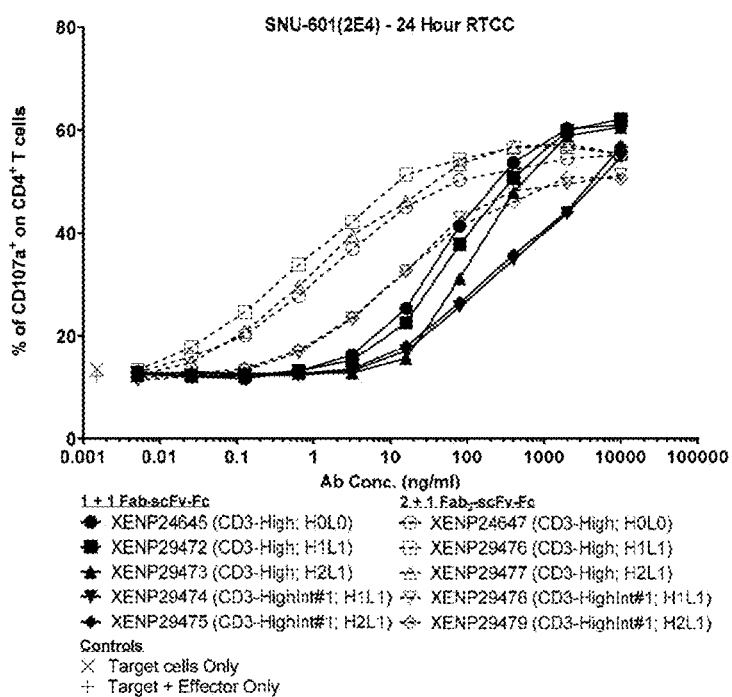
Figure 19A:
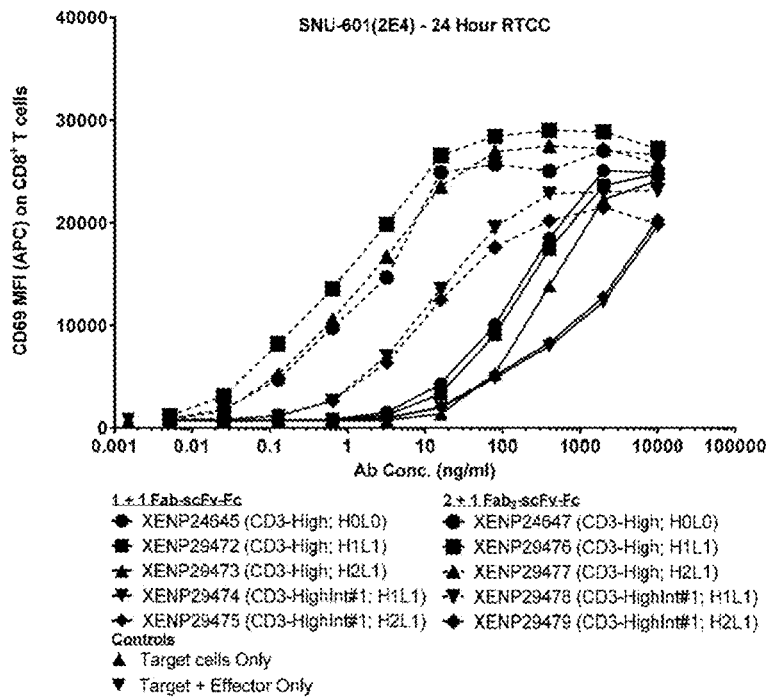
FIGS. 19A and 19B depicts activation CD8+ T cells as indicated by A) CD69 MFI on CD8+ T cells, and B) percentage of CD8+ T cells expressing CD69 after incubation of SNU-601(2E4) for 24 hours with human PBMCs (10:1 effector to target cell ratio) and anti-CLDN18.2 x anti-CD3 bispecific antibodies having humanized CLDN18.2 ABD. Controls used were XENP24645 (Fab-scFv-Fc), XENP24647 (Fab2-scFv), cells only, and secondary antibody only. Consistent with the binding data, humanization preserved T cell activation by the bsAbs having humanized CLDN18.2 ABDs.
Figure 19B:
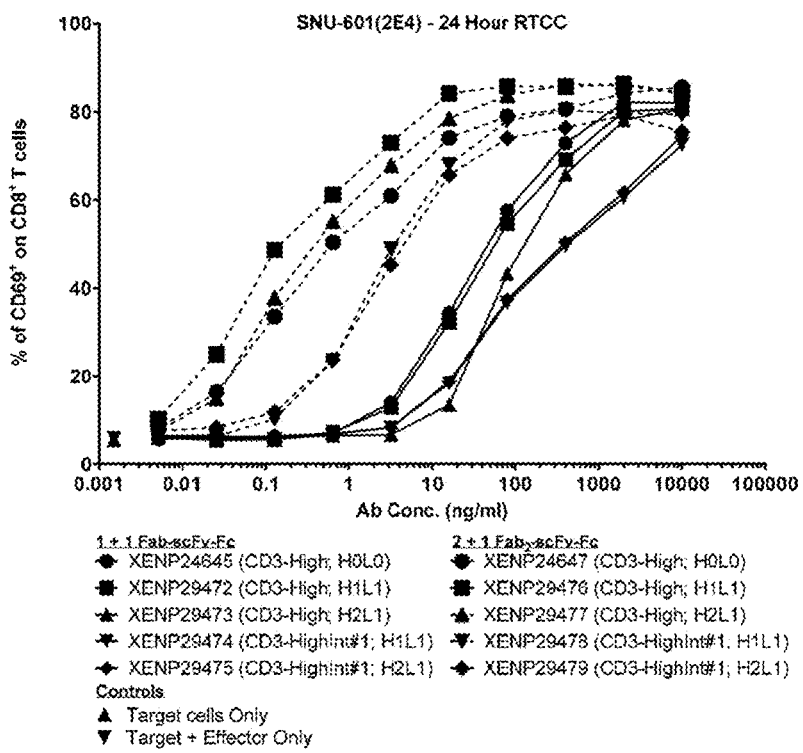
Figure 20A:
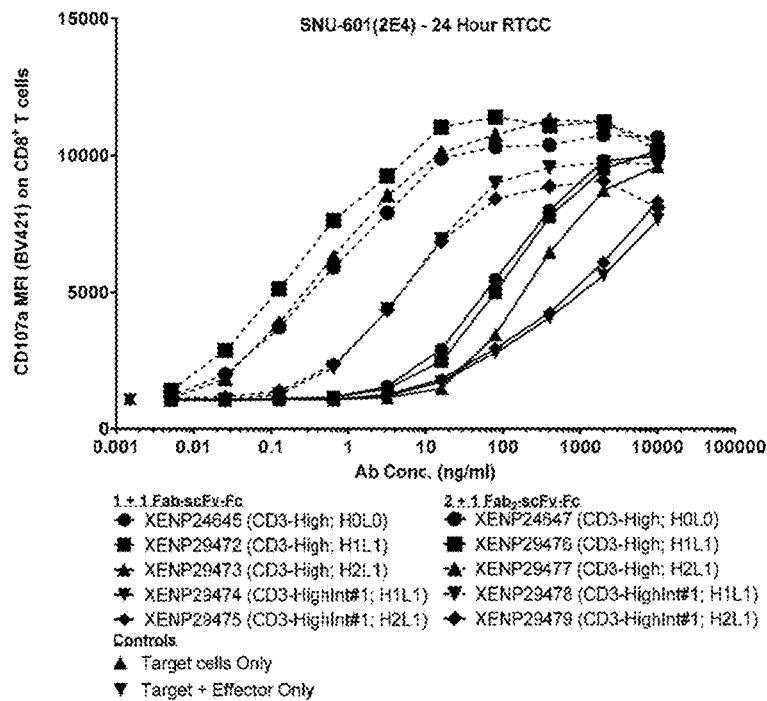
FIGS. 20A and 20B depicts degranulation of CD8+ T cells as indicated by A) CD107a MFI on CD8+ T cells, and B) percentage of CD8+ T cells expressing CD107a after incubation of SNU-601(2E4) for 24 hours with human PBMCs (10:1 effector to target cell ratio) and anti-CLDN18.2 x anti-CD3 bispecific antibodies having humanized CLDN18.2 ABD. Controls used were XENP24645 (Fab-scFv-Fc), XENP24647 (Fab2-scFv), cells only, and secondary antibody only.
Figure 20B:
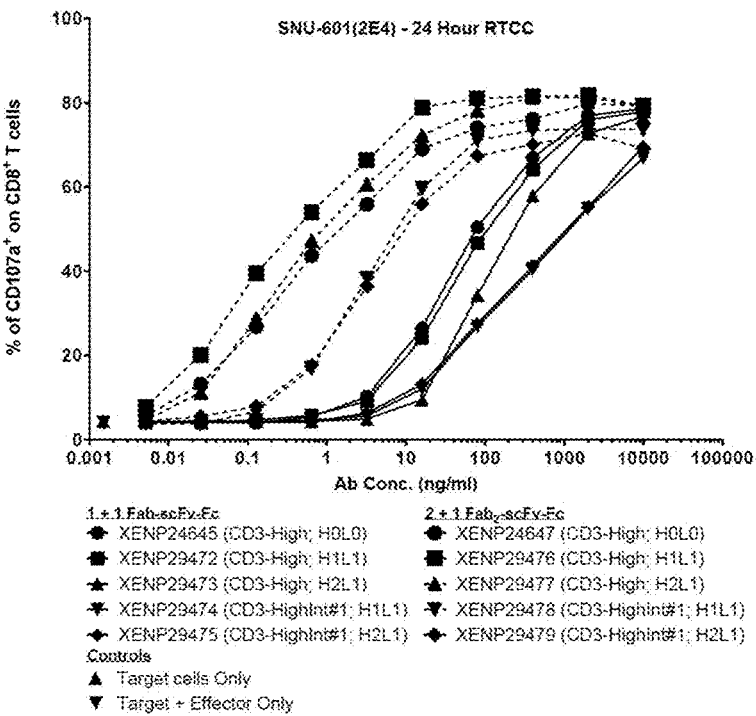

Binding by the bsAbs having humanized CLDN18.2 ABDs to SNU-601(2E4) cells were assessed as described in Example 1B. In particular, 200,000 SNU-601(2E4) cells were incubated with indicated concentrations of indicated bsAbs for an hour on ice. Samples were then stained with Alexa Fluor® 647 AffiniPure F(ab')₂ Fragment Goat Anti-Human IgG, Fc Fragment Specific secondary antibody (Jackson ImmunoResearch, West Grove, Penn.), and analyzed by flow cytometry. Control samples included bsAbs having murine CLDN18.2 ABDs, bivalent anti-CLDN18.2 mAbs, cells only, and secondary antibody only. AlexaF657 MFI indicating binding by the bsAbs are depicted in FIG. 15. The data show that the bsAbs having humanized CLDN18.2 ABDs had similar binding to SNU-601(2E4) cells as bsAbs having murine CLDN18.2 ABDs indicating that humanization preserved the binding efficacy of the bsAbs. Notably, bsAbs in the "Fab2-scFv" format showed similar binding compared to bivalent anti-CLDN18.2 mAbs. Additionally, the data show that bsAbs comprising humanized VH and VL according to SEQ ID NOs: 39 and 42 (H1L1) (e.g. XENP29472, XENP29474, XENP29476, and XENP29478) better preserved binding than did bsAbs comprising humanized VH and VL according to SEQ ID NOs: 40 and 42 (H2L1) (e.g. XENP29473, XENP29475, XENP29477, and XENP29479).

Figure 21A:
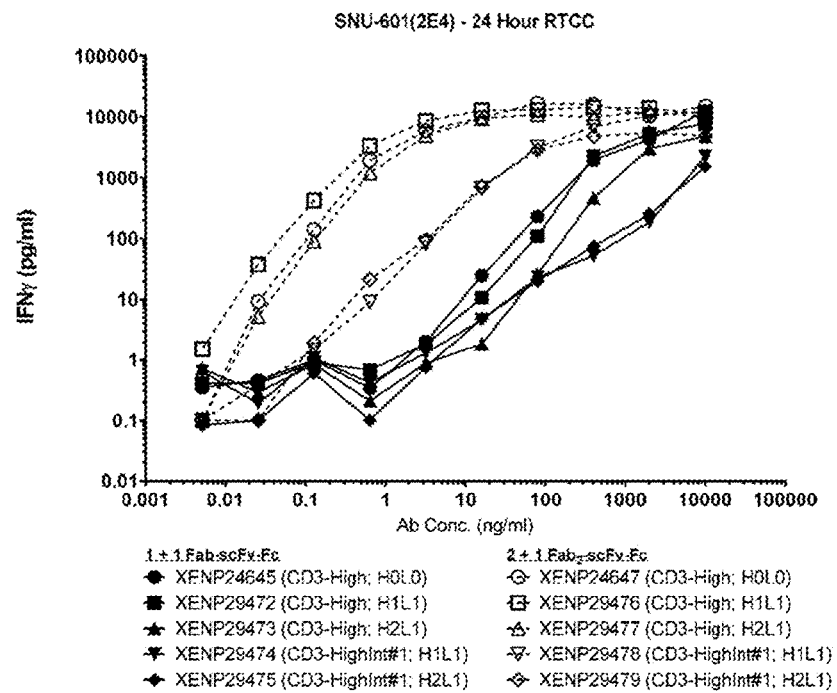
FIGS. 21A and 21B depicts A) IFNγ and B) TNFα secretion by T cells after incubation of SNU-601(2E4) for 24 hours with human PBMCs (10:1 effector to target cell ratio) and anti-CLDN18.2 x anti-CD3 bispecific antibodies having humanized CLDN18.2 ABD. Controls used were XENP24645 (Fab-scFv-Fc) and XENP24647 (Fab2-scFv). Consistent with the binding data, humanization preserved the induction of cytokine secretion by the bsAbs having humanized CLDN18.2 ABDs.
Figure 21B:
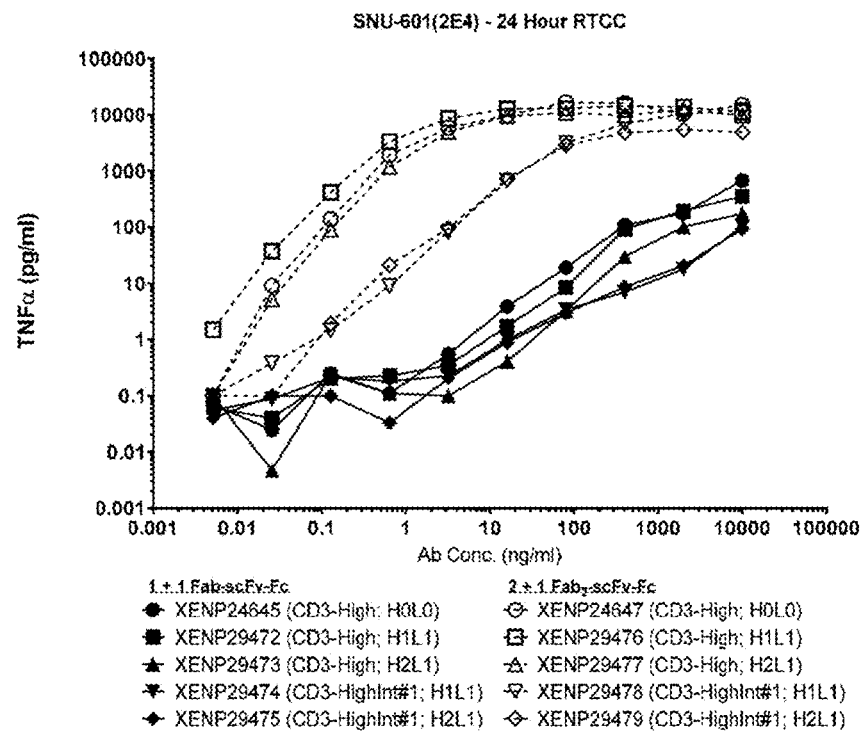

Next, we investigated induction of RTCC on SNU-601 (2E4) cells and T cell activation by the bsAbs having humanized CLDN18.2 ABDs. SNU-601(2E4) cells were labeled with CellTrace™ CFSE Cell Proliferation Kit (ThermoFisher Scientific, Waltham, Mass.). CFSE-labeled SNU-601(2E4) cells were incubated with human PBMCs (10:1 effector to target ratio) and anti-CD107a-BV421 for 24 hours at 37° C. After incubation, supernatant was collected for cytokine analysis by V-PLEX Proinflammatory Panel 1 Human Kit (according to manufacturer protocol; Meso Scale Discovery, Rockville, Md.) and cells were stained with Aqua Zombie stain for 15 minutes at room temperature. Cells were then washed and stained with anti-CD4-APC-Cy7, anti-CD8-perCP-Cy5.5, and anti-CD69-APC staining antibodies, and analyzed by flow cytometry. We used two different approaches for investigating induction of RTCC: a) decrease in the number of CSFE+ target cells (see FIG. 15A), and b) Zombie Aqua staining on CSFE+ target cells (see FIGS. 15B, C). We also investigated activation and degranulation of CD4+ and CD8+ T cells based on CD69 and CD107a expression (see FIGS. 16-20). Finally, we investigated the secretion of IFNγ and TNFα by T cells, see FIG. 21. Consistent with the binding data, humanization preserved the induction of RTCC and T cell activation and cytokine secretion by the bsAbs having humanized CLDN18.2 ABDs. Notably consistent with Example 1C, higher affinity CD3 binding and/or bivalent CLDN18.2 binding enhance potency of RTCC as well as T cell activation, degranulation, and cytokine secretion.

Example 3: Further Characterization of Anti-CLDN18.2 x Anti-CD3 bsAbs

The following Table 4 gives an overview over further bsAbs generated and tested.

TABLE 4

Overview over further bsAbs

| bsAb | First chain, SEQ ID NO: | Second chain, SEQ ID NO: | Third chain*, SEQ ID NO: |
|---|---|---|---|
| XENP31726 | 73 | 74 | 78 |
| XENP32461 | 73 | 77 | 78 |

*bsAbs bivalently binding to CLDN18.2 comprise a fourth chain identical to the third chain

Example 3A: Anti-CLDN18.2 x Anti-CD3 bsAbs are Cross-Reactive for Cynomolgus and Mouse CLDN18.2

Figure 22A:
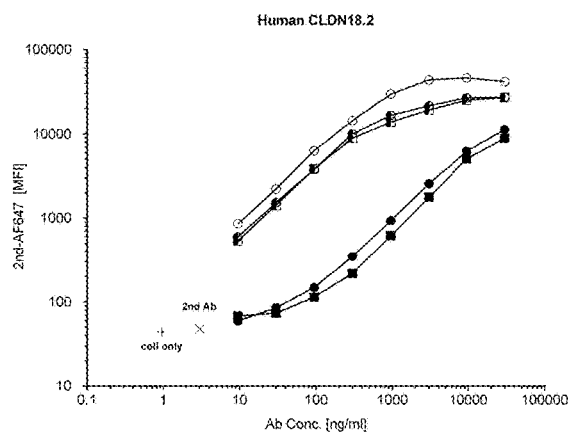
FIGS. 22A, 22B, and 22C depicts binding of anti-CLDN18.2 x anti-CD3 bispecific antibodies having murine and humanized (variant H1L1) CLDN18.2 ABD to HEK293 cells transiently transfected to express A) human, B) cynomolgus, and C) mouse CLDN18.2. The data show that the anti-CLDN18.2 x anti-CD3 bispecific antibodies dose-dependently bound the cells transfected with each of human, cynomolgus, and mouse CLDN18.2. Notably, bispecific antibodies of the "Fab2-scFv" format (i.e. XENP24647 and XENP29476) bound much more potently to the CLDN18.2 transfected cells compared to bispecific antibodies of the "Fab-scFv" format (i.e. XENP24645 and XENP29472), and with similar potency to the bivalent mAb format (i.e. XENP24644).
Figure 22B:
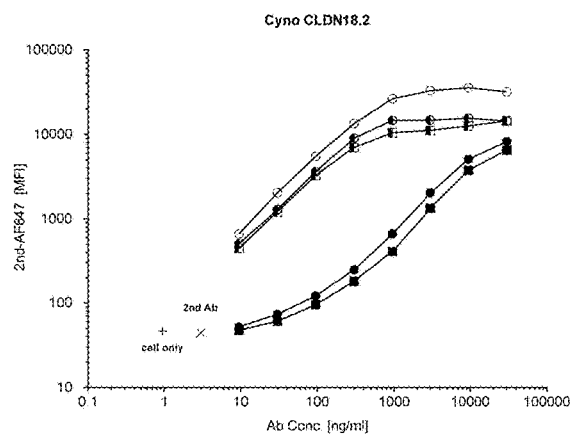
Figure 22C:
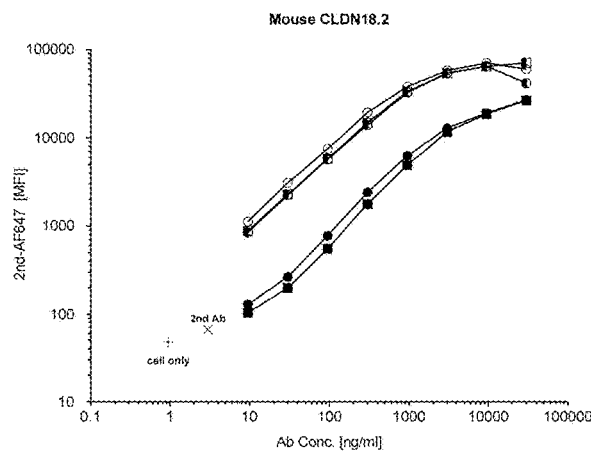

For ease of clinical development (e.g. by investigating the therapeutics in model animals), it is useful for the bsAbs to be cross-reactive for mouse and/or cynomolgus CLDN18.2. Therefore, the anti-CLDN18.2 x anti-CD3 bsAbs were investigated for their binding to human CLDN18.2, cynomolgus CLDN18.2, and murine CLDN18.2. HEK293 cells were transiently transfected to express human, cynomolgus, or mouse CLDN18.2. 48 hours post transfection, cells were mixed with indicated concentrations of the bsAbs and incubated for 1 hour at 4° C. Cells were washed and then stained with a secondary Ab for 1 hour at 4° C. After two more washes, cells were analyzed on an Attune flow cytometer. The data as depicted in FIGS. 22 and 23 show that the anti-CLDN18.2 x anti-CD3 bsAbs dose-dependently bound the cells transfected with each of human, cynomolgus, and mouse CLDN18.2. Notably, bsAbs of the "Fab2-scFv" format (i.e. XENP24647 and XENP29476) bound much more potently to the CLDN18.2 transfected cells compared to bsAbs of the "Fab-scFv" format (i.e. XENP24645 and XENP29472), and with similar potency to the bivalent mAb format (i.e. XENP24644).

Example 3B: Anti-CLDN18.2 x Anti-CD3 bsAbs do not Demonstrate Off-Target Reactivity To ascertain lack of off-target reactivity, binding of bsAbs of the invention to human, cynomolgus, and mouse CLDN18.1 and human CLDN9 was investigated as generally described above, except with HEK293 transiently transfected to express human, cynomolgus, or mouse CLDN18.1 or human CLDN9. The data as depicted in FIG. 24 show that the anti-CLDN18.2 x anti-CD3 bsAbs did not demonstrate any off-target reactivity.

Figure 25A:
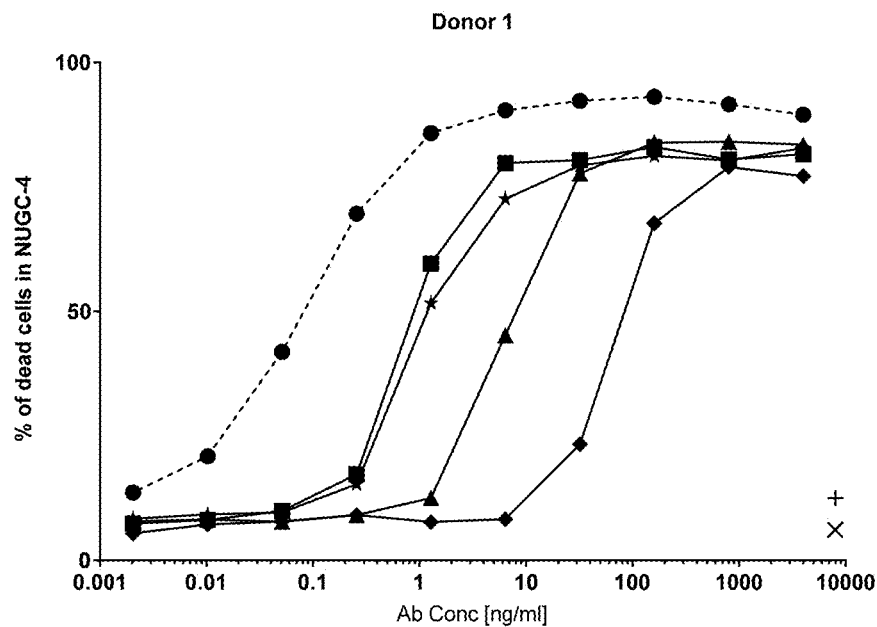
FIGS. 25A and 25B depicts induction of RTCC on NUGC-4 cells by bispecific antibodies and a comparator anti-CLDN18.2 x anti-CD3 bispecific antibody (AMG 910) using PBMCs from A) a first and B) a second donor. The data show that XENP32461 induced RTCC with similar potency as the comparator bispecific antibody, and XENP31726 induced RTCC with enhanced potency in comparison to the comparator bispecific antibody.
Figure 25B:
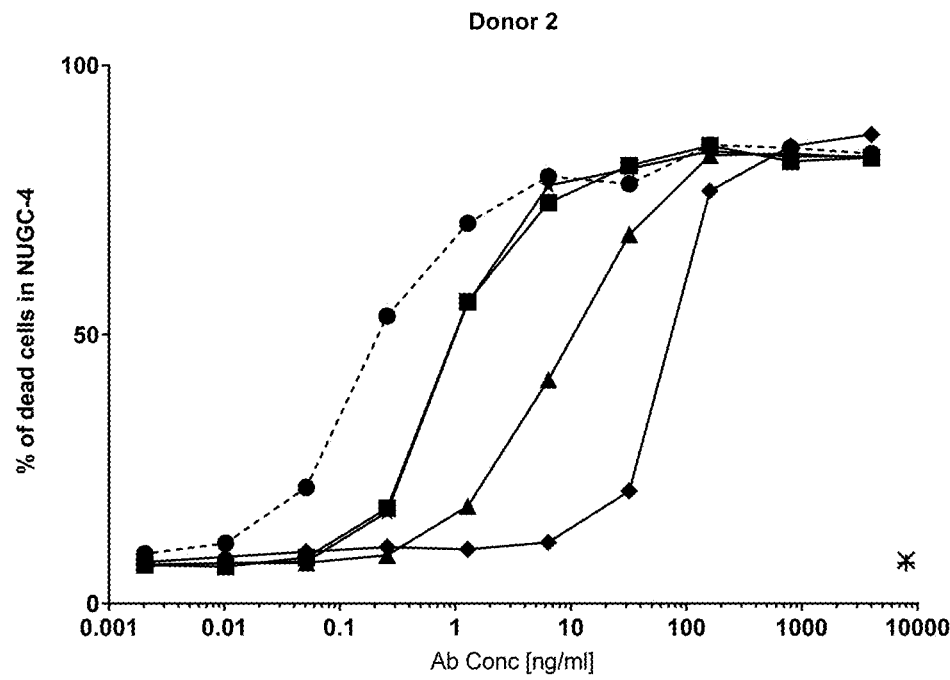
Figure 26A:
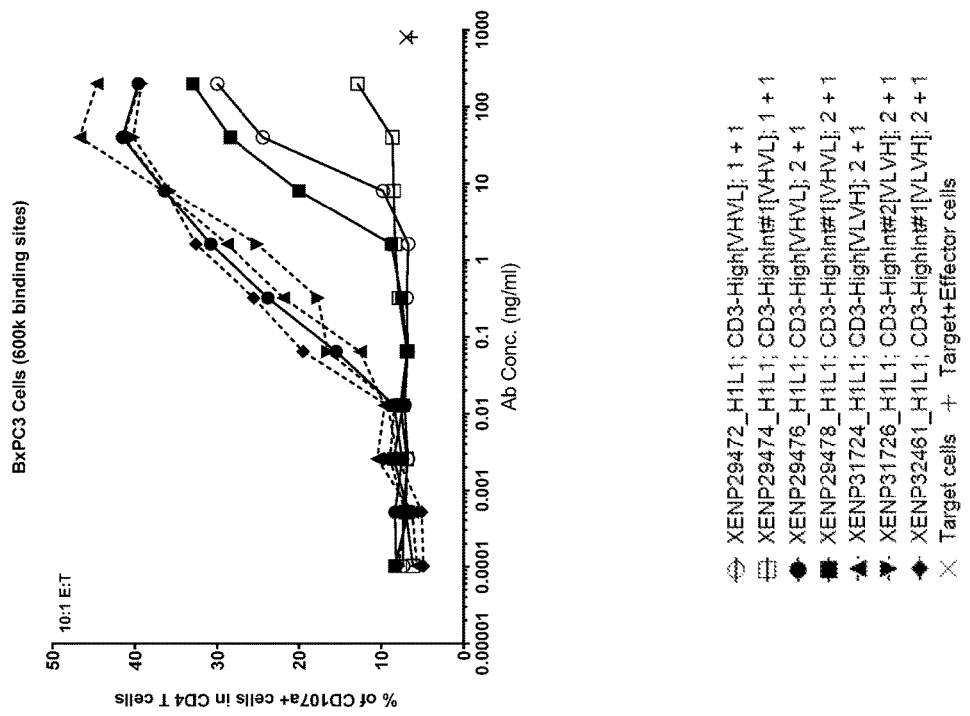
FIGS. 26A, 26B, and 26C depicts A) induction of RTCC, B) induction of CD4 T cell activation (as indicated by percentage of cells expressing CD107a), and C) induction of CD8 T cell activation (as indicated by percentage cells expressing CD107a) by anti-CLDN18.2 x anti-CD3 bispecific antibodies in the presence of BxPC3 cells (having 600k CLDN18.2 binding sites) and effector cells at an E:T ratio of 10:1.
Figure 26B:
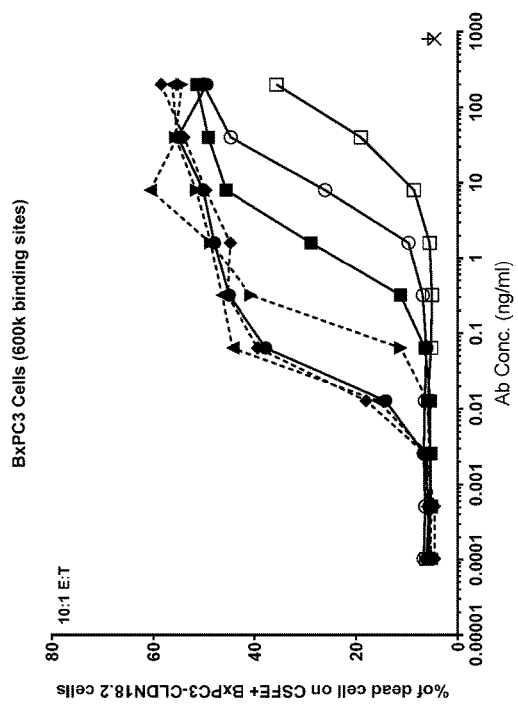
Figure 26C:
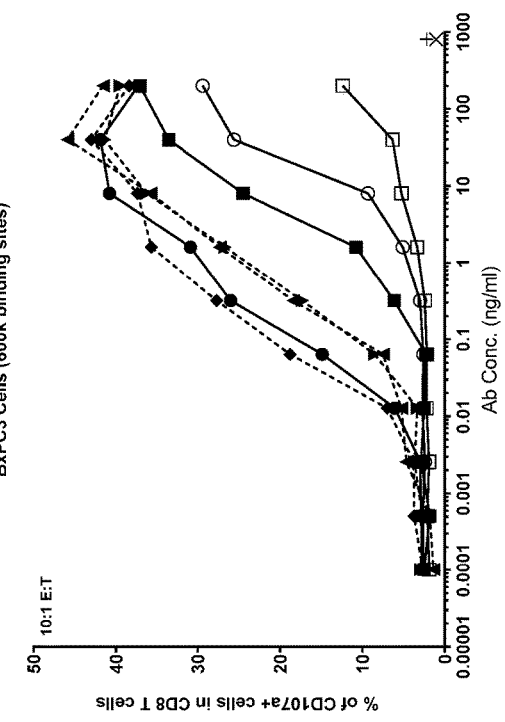
Figure 27A:
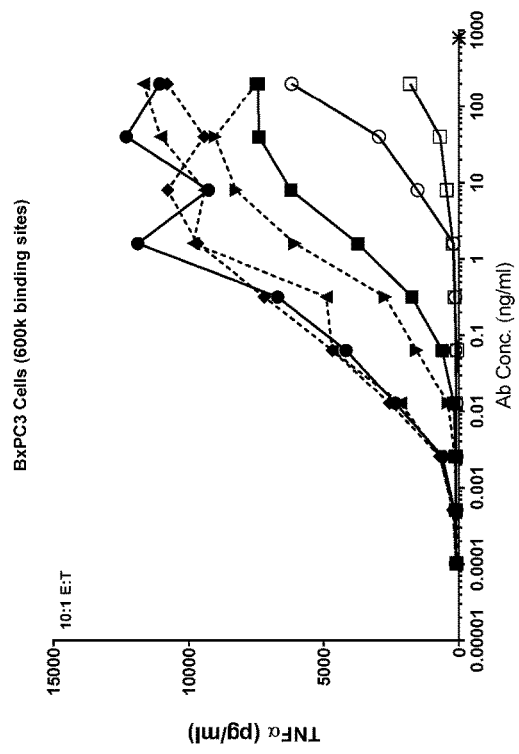
FIGS. 27A, 27B, and 27C depicts induction of A) IFNγ, B) TNFα, and C) IL2 secretion by anti-CLDN18.2 x anti-CD3 bispecific antibodies in the presence of BxPC3 cells (having 600k CLDN18.2 binding sites) and effector cells at an E:T ratio of 10:1.
Figure 27B:
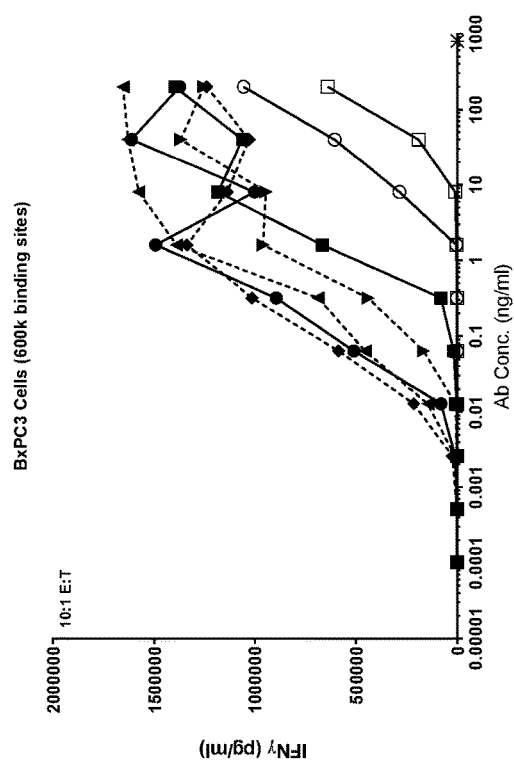
Figure 27C:
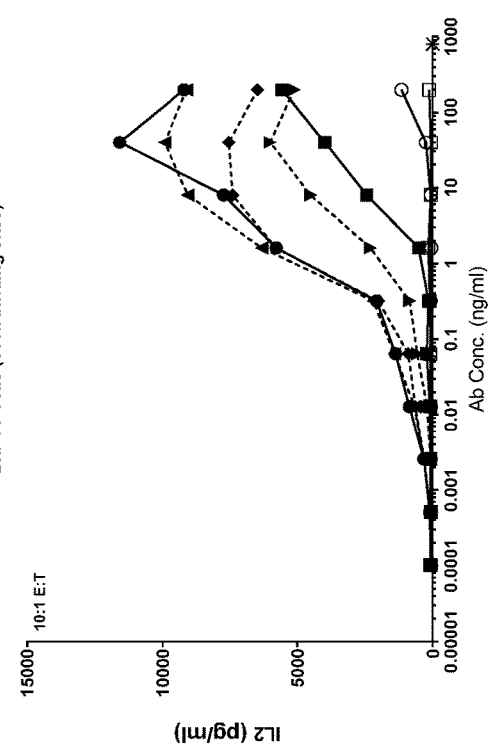
Figure 28A:
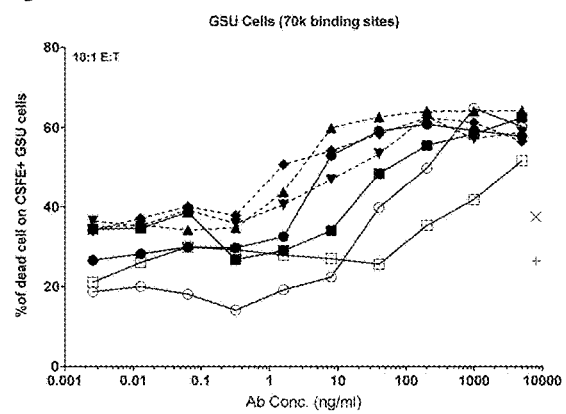
FIGS. 28A, 28B, and 28C depicts A) induction of RTCC, B) induction of CD4 T cell activation (as indicated by percentage of cells expressing CD107a), and C) induction of CD8 T cell activation (as indicated by percentage of cells expressing CD107a) by anti-CLDN18.2 x anti-CD3 bispecific antibodies in the presence of GSU cells (having 70k CLDN18.2 binding sites) and effector cells at an E:T ratio of 10:1.
Figure 28B:
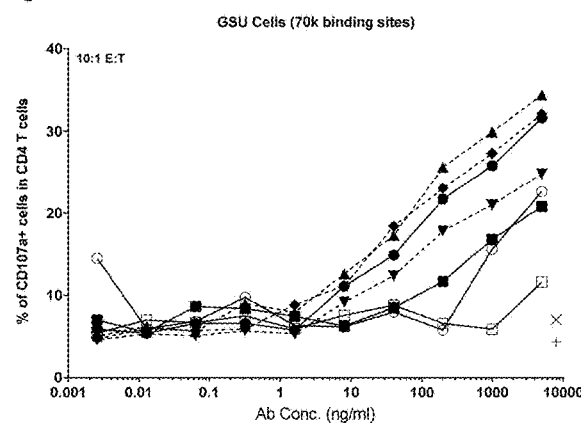
Figure 28C:
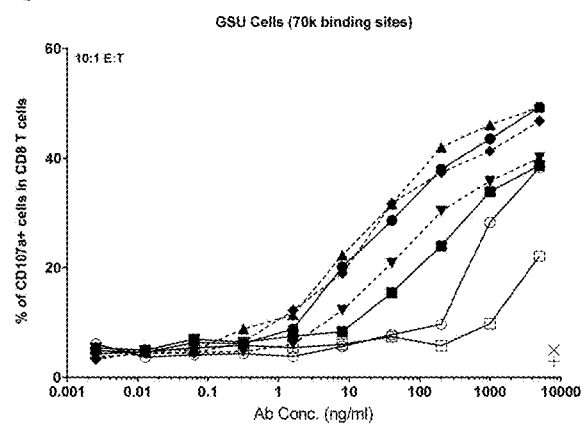
Figure 29B:
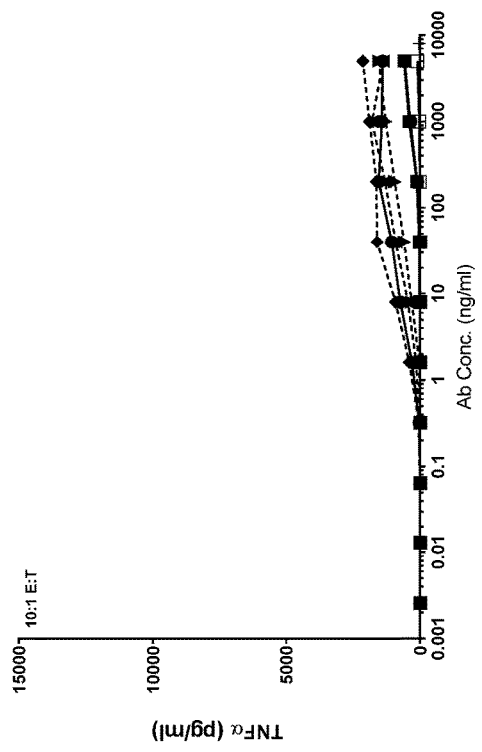
FIGS. 29A, 29B, and 29C depicts induction of A) IFNγ, B) TNFα, and C) IL2 secretion by anti-CLDN18.2 x anti-CD3 bispecific antibodies in the presence of GSU cells (having 70k CLDN18.2 binding sites) and effector cells at an E:T ratio of 10:1.
Figure 29A:
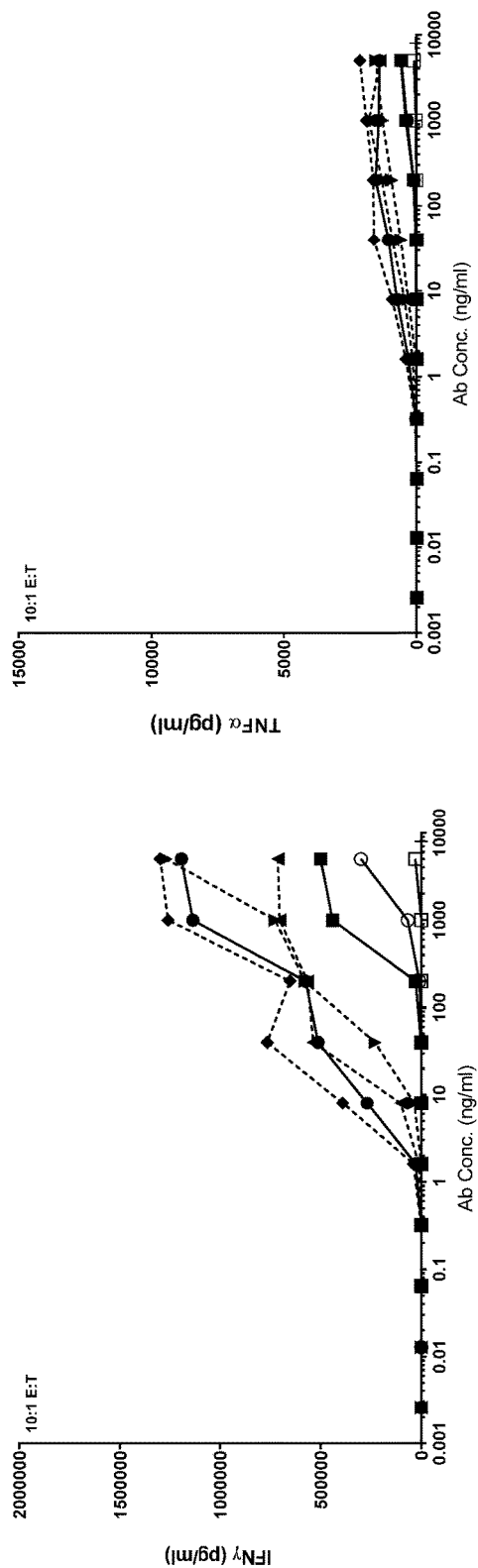
Figure 29C:
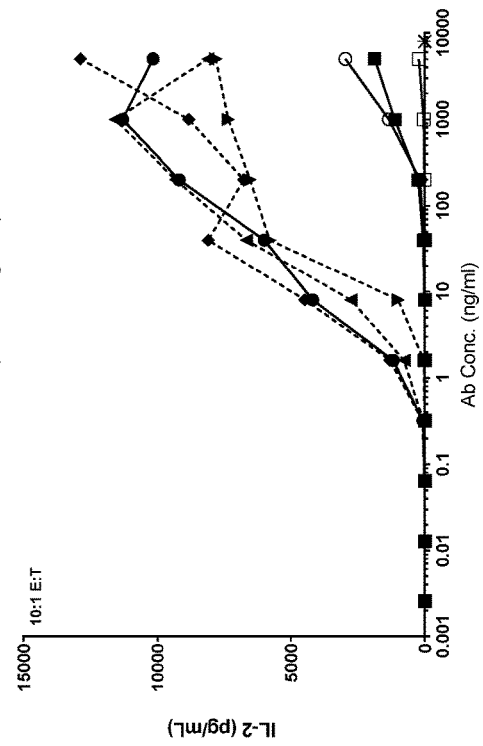
Figure 30A:
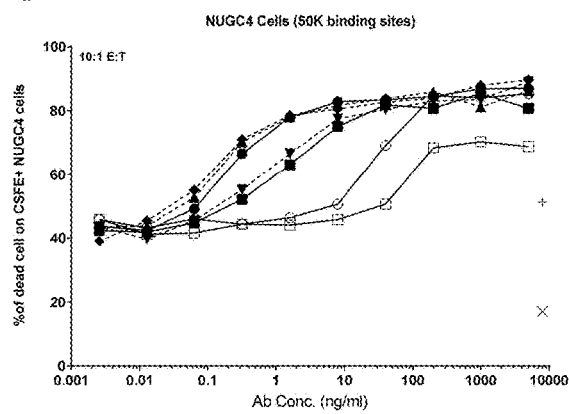
FIGS. 30A, 30B, and 30C depicts A) induction of RTCC, B) induction of CD4 T cell activation (as indicated by percentage of cells expressing CD107a), and C) induction of CD8 T cell activation (as indicated by percentage of cells expressing CD107a) by anti-CLDN18.2 x anti-CD3 bispecific antibodies in the presence of NUGC4 cells (having 50k CLDN18.2 binding sites) and effector cells at an E:T ratio of 10:1.
Figure 30B:
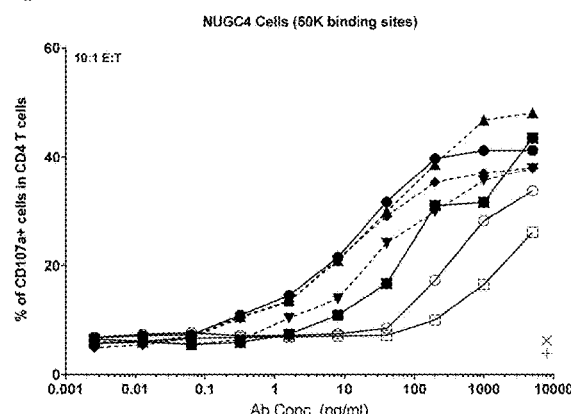
Figure 30C:
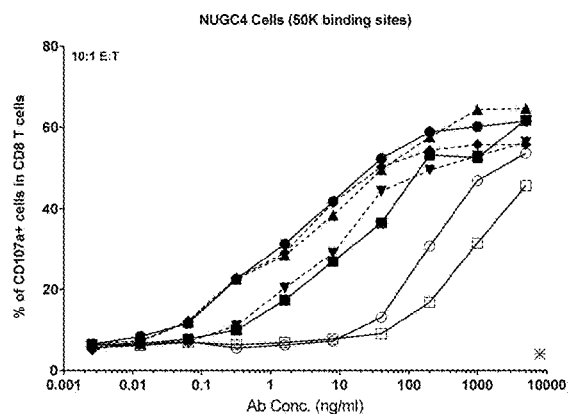
Figure 31A:
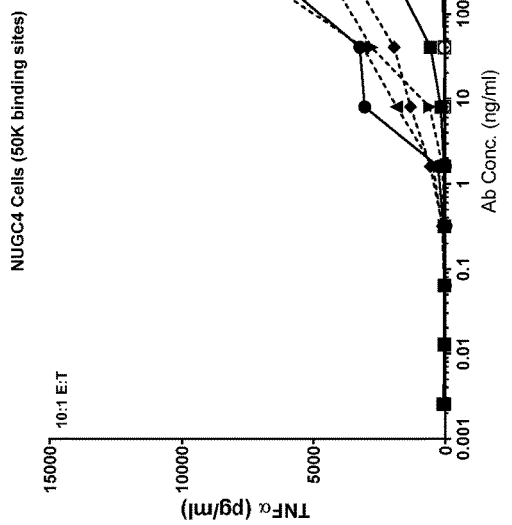
FIGS. 31A, 31B, and 31C depicts induction of A) IFNγ, B) TNFα, and C) IL2 secretion by anti-CLDN18.2 x anti-CD3 bispecific antibodies in the presence of NUGC4 cells (having 50k CLDN18.2 binding sites) and effector cells at an E:T ratio of 10:1.
Figure 31B:
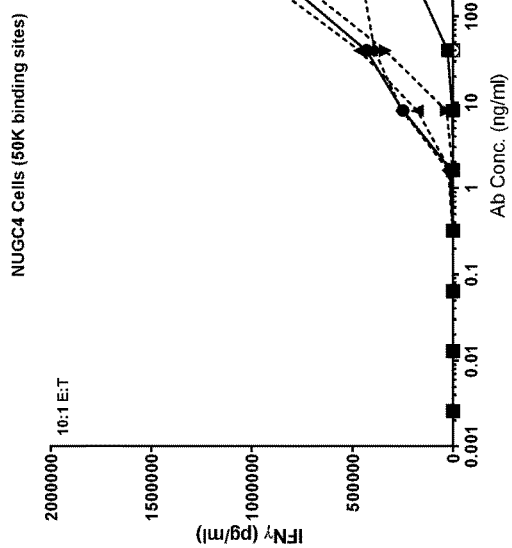
Figure 31C:
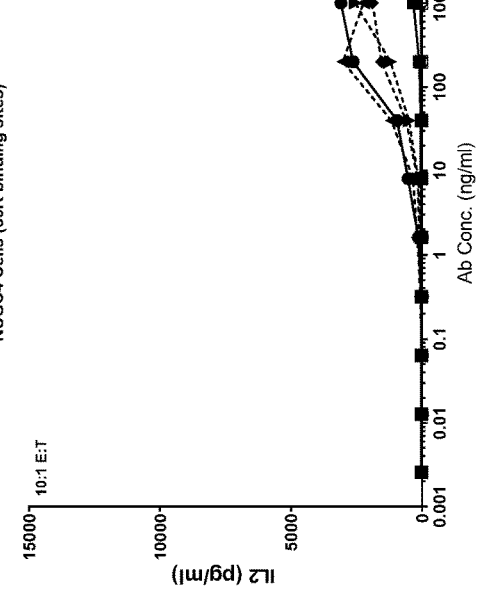
Figure 32A:
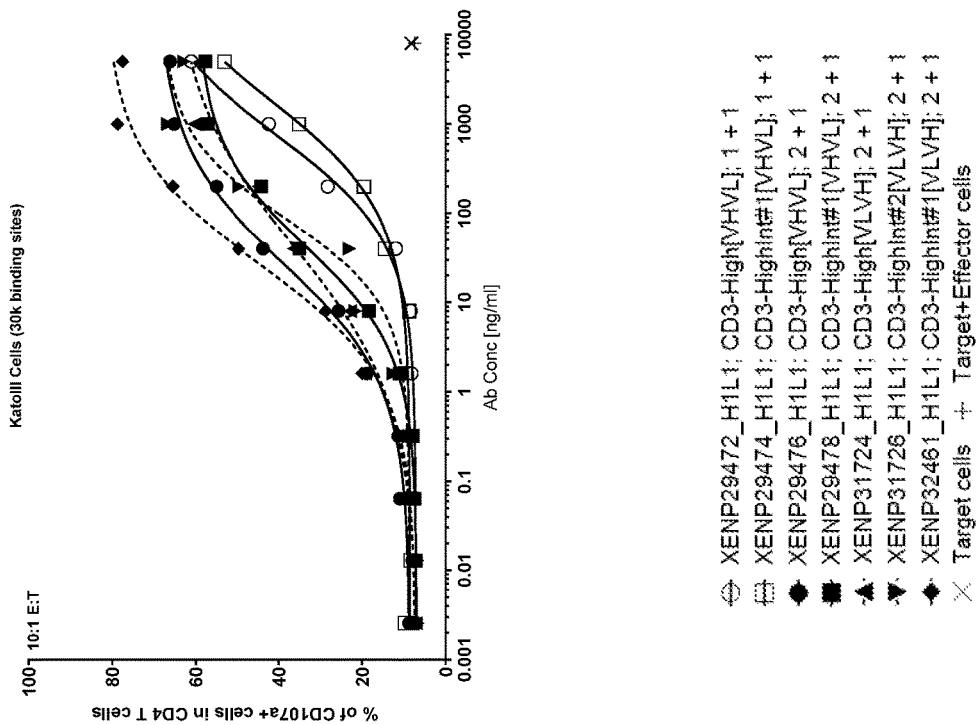
FIGS. 32A, 32B, and 32C depicts A) induction of RTCC, B) induction of CD4 T cell activation (as indicated by percentage of cells expressing CD107a), and C) induction of CD8 T cell activation (as indicated by percentage of cells expressing CD107a) by anti-CLDN18.2 x anti-CD3 bispecific antibodies in the presence of KatoIII cells (having 30k CLDN18.2 binding sites) and effector cells at an E:T ratio of 10:1.
Figure 32B:
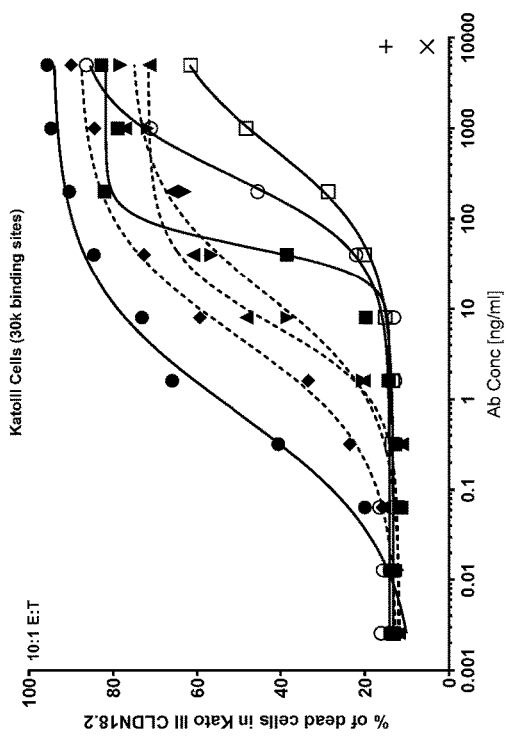
Figure 32C:
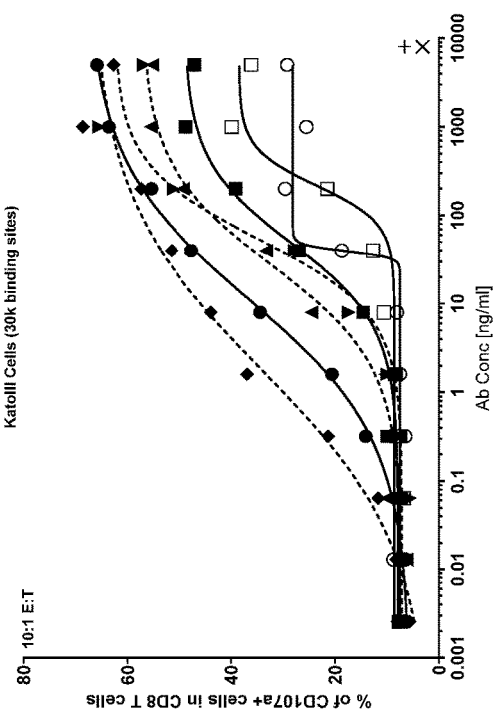

Example 3C: Anti-CLDN18.2 x Anti-CD3 bsAbs Demonstrate a Range of RTCC Potency To rank the potencies of anti-CLDN18.2 x anti-CD3 bsAbs, NUGC4 target cell killing by the bsAbs and a comparator bsAb (AMG 910; SEQ ID NO: 132 from WO 2020/025792) was investigated. NUGC4 target cells were labeled with CSFE and recovered overnight at 37° C. NUGC4 cells were then incubated with effector cells (different donor for each experiment) at an effector:target ratio of 10:1 and indicated concentrations of antibodies for 48 hours. Cells were stained to differentiate live/dead cells, stained with anti-CD4-APC-Fire750, anti-CD8-PerCP-Cy5.5, anti-CD107a-BV421, and anti-CD69-BV785 to differentiate T cell activation on various T cell populations, and analyzed on a Symphony flow cytometer. The data as depicted in FIG. 25 show that the bsAbs efficiently induce RTCC. The bsAbs can be ranked according to their RTCC potencies as follows: XENP31726 (most potent) >XENP32461>XENP29478>XENP29472 (least potent). Notably, XENP32461 induced RTCC with similar potency as the comparator bispecific antibody, and XENP31726 induced RTCC with enhanced potency in comparison to the comparator bispecific antibody.

Figure 34A:
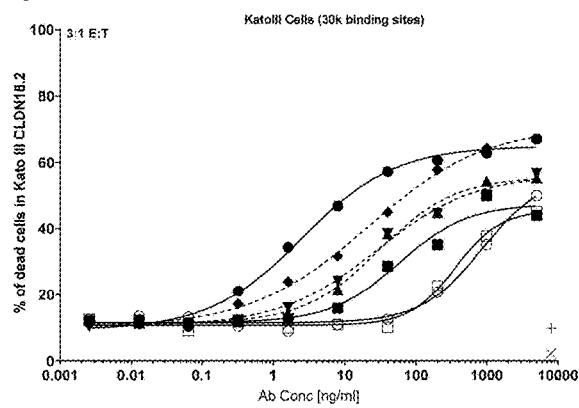
FIGS. 34A, 34B, and 34C depicts A) induction of RTCC, B) induction of CD8 T cell activation (as indicated by percentage of cells expressing CD107a), and C) induction of TNFα secretion by anti-CLDN18.2 x anti-CD3 bispecific antibodies in the presence of KatoIII cells (having 30k CLDN18.2 binding sites) and effector cells at an E:T ratio of 3:1.
Figure 34B:
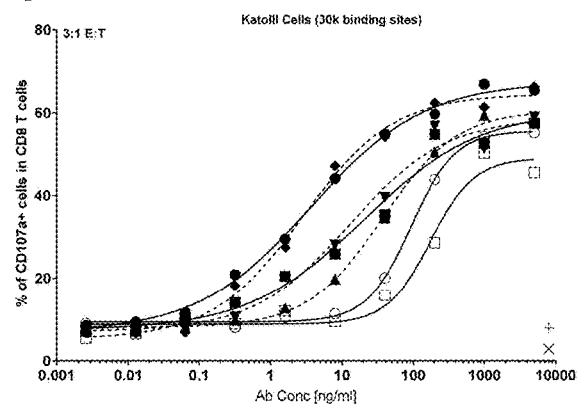
Figure 34C:
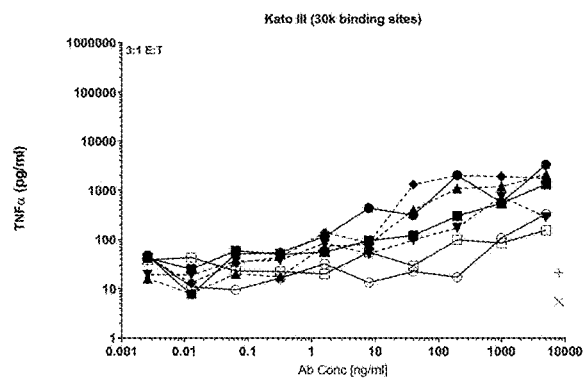
Figure 35A:
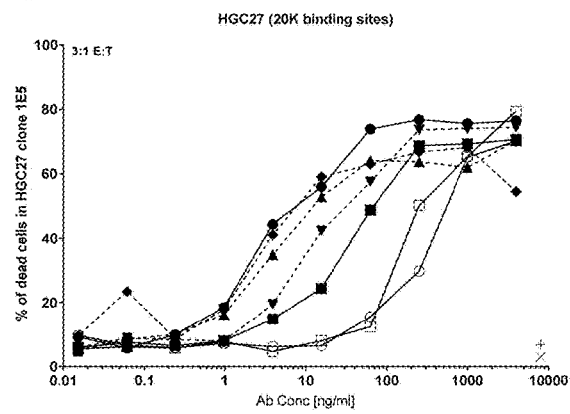
FIGS. 35A, 35B, and 35C depicts A) induction of RTCC, B) induction of CD4 T cell activation (as indicated by percentage of cells expressing CD107a), and C) induction of CD8 T cell activation (as indicated by percentage of cells expressing CD107a) by anti-CLDN18.2 x anti-CD3 bispecific antibodies in the presence of HGC27 cells (having 20k CLDN18.2 binding sites) and effector cells at an E:T ratio of 3:1.
Figure 35B:
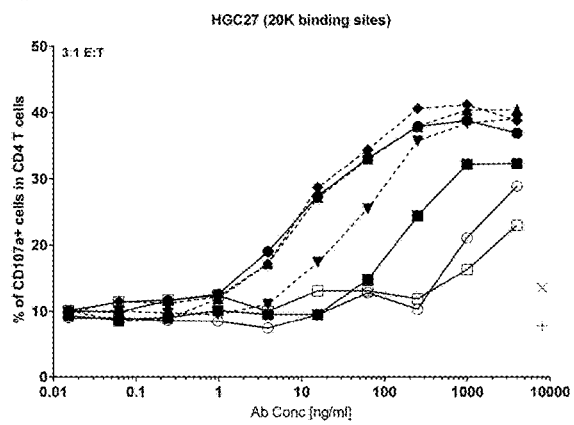
Figure 35C:
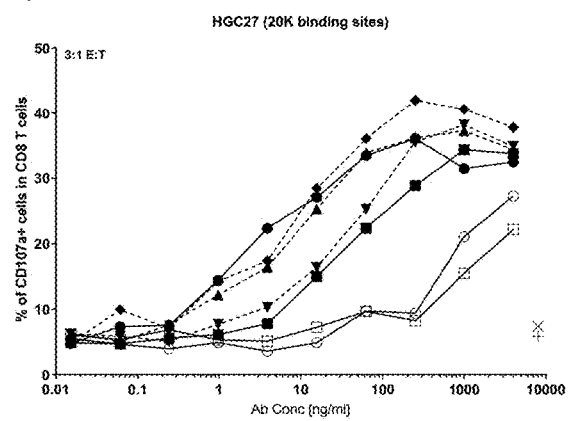
Figure 36A:
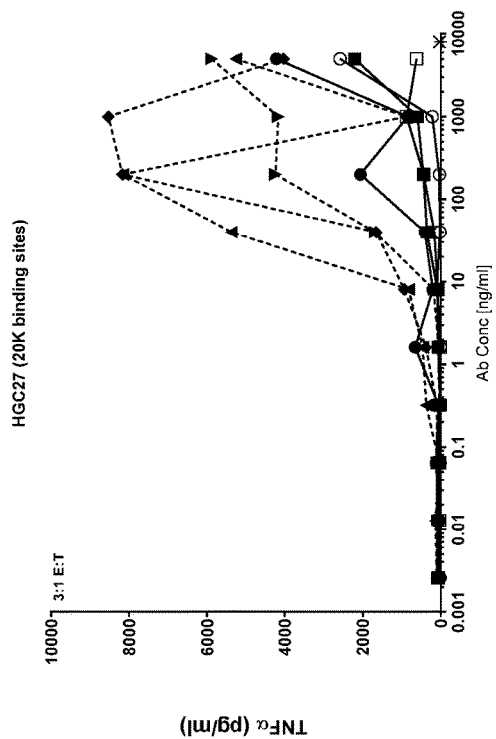
FIGS. 36A, 36B, and 36C depicts induction of A) IFNγ, B) TNFα, and C) IL2 secretion by anti-CLDN18.2 x anti-CD3 bispecific antibodies in the presence of HGC27 cells (having 20k CLDN18.2 binding sites) and effector cells at an E:T ratio of 3:1.
Figure 36B:
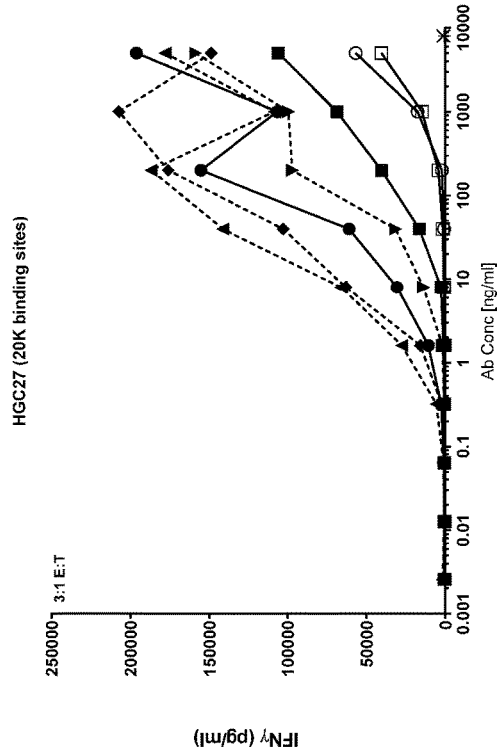
Figure 36C:
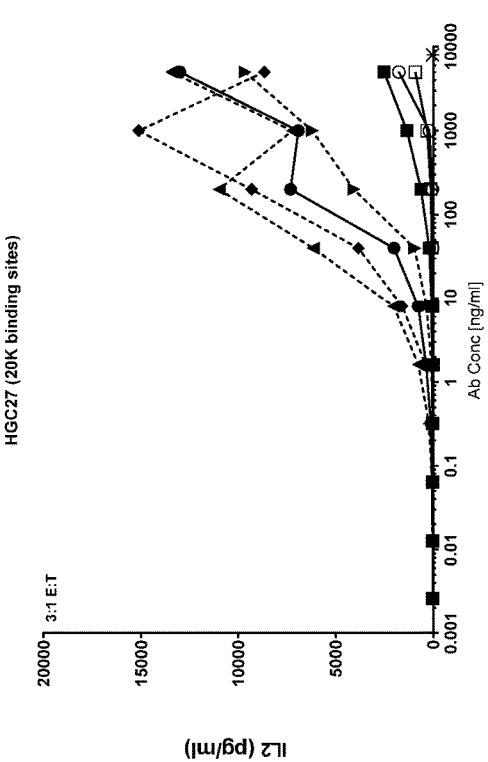

Example 3D: In Vitro Characterization of RTCC Induction on Cell Lines Expressing Various CLDN18.2 Antigen Densities The anti-CLDN18.2 x anti-CD3 bsAbs were investigated for cell killing activity on cells having different CLDN18.2 densities. In a first set of experiments, BxPc3 (600k CLDN18.2 binding sites), GSU (70k CLDN18.2 binding sites), NUGC4 (50k CLDN18.2 binding sites), and KatoIII (30k CLDN18.2 binding sites) target cells were labeled with CSFE and seeded at ~10K cells/well in 100 µl assay medium (RPMI1640/10% FBS) in a 96 well flat bottom culture plate to recover overnight at 37° C. Effector cells were isolated from human PBMCs and incubated with target cells at an effector:target ratio of 10:1 and indicated concentrations of bsAbs. After a 48 h incubation, cells were stained with Live/Dead fixable blue dead cell stain kit (1:1000) in PBS at room temperature for 30 minutes. Samples were then washed with 1x FACS buffer. Cells were stained with Anti-CD4-APC-Fire750, Anti-CD8-PerCP-Cy5.5, Anti-CD107a-BV421, and Anti-CD69-BV785, washed again with ice cold PBS and resuspended in 90 µl of FACS buffer. Data was acquired by FACS Fortessa in a fixed volume (60 µl). Data depicting induction of RTCC, T cell activation, and cytokine secretion are depicted in FIGS. 26-33. Consistent with the data in Example 3C, the data show that XENP31726 and XENP32461 (as well as additional bsAbs XENP31724 and XENP29476) induced RTCC more potently in comparison to XENP29478 and XENP29472 (as well as additional bsAbs XENP29474). In another set of experiments, activity at lower effector:target ratio of 3:1 was investigated. KatoIII (30k CLDN18.2 binding sites) and HGC27-4H2 (20k CLDN18.2 binding sites) target cells were labeled with CSFE and seeded in 100 µl assay medium (RPMI1640/10% FBS) in a 96 well flat bottom culture plate to recover overnight at 37° C. Effector cells were isolated from human PBMCs and incubated with target cells at an effector:target ratio of 3:1 and indicated concentrations of bsAbs. After 24 hours incubation, cells were stained with Live/Dead fixable blue dead cell stain kit (1:1000) in PBS at room temperature for 30 minutes. Samples were then washed with 1x FACS buffer. Cells were stained with Anti-CD4-APC-Fire750, Anti-CD8-PerCP-Cy5.5, Anti-CD107a-BV421, and Anti-CD69-BV785, washed again with ice cold PBS and resuspended in 90 µl of FACS buffer. Data was acquired by FACS Fortessa in a fixed volume (60 µl). Data depicting induction of RTCC, T cell activation, and cytokine secretion are depicted in FIGS. 34-36.

Figure 37A:
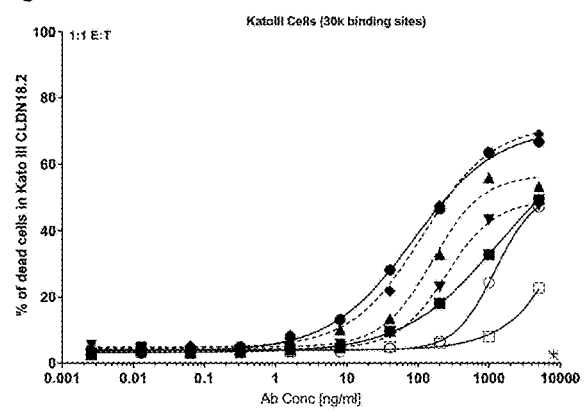
FIGS. 37A and 37B depicts A) induction of RTCC and B) induction of TNFα secretion by anti-CLDN18.2 x anti-CD3 bispecific antibodies in the presence of KatoIII cells (having 30k CLDN18.2 binding sites) and effector cells at an E:T ratio of 1:1.
Figure 37B:
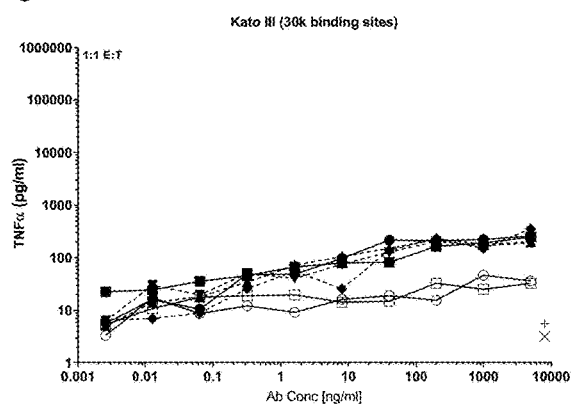

In a final experiment, activity at an even lower effector:target ratio of 1:1 was investigated as generally described above using KatoIII target cells. Data are depicted in FIG. 37. The data show that tested bsAbs efficiently induce RTCC and target cell killing on CLDN18.2 expressing cancer cells.

Example 4: Anti-Tumor Effect of ASP2138 (XENP31726) in NUGC-4_10cF7_5_3E10 Tumor-Bearing Human PBMC Engrafted NOG Mouse Model Effects of the anti-CLDN18.2 x anti-CD3 bsAb ASP2138 (XENP31726) on tumor growth in the NUGC-4 10cF7_5_3E10 tumor-bearing human peripheral blood mononuclear cell (PBMC) engrafted NOG mouse model was examined. Once-weekly intraperitoneal administration of ASP2138 for 14 days induced significant growth inhibition of NUGC-4 10cF7_5_3E10 tumors at 1, 3 and 10 mg/kg by 60%, 91% and 99%, respectively, without body weight loss. Additionally, 1 out of 10 mice in the 3 mg/kg group achieved complete tumor regression.

This study demonstrated that ASP2138 exhibits anti-tumor effect for human claudin18.2-expressing gastric cancer in the human PBMC engrafted NOG mouse model.

Example 4A: Material and Methods (a) Antibody

ASP2138 (Lot No. DSP20804; Astellas Pharma Inc., Tokyo, Japan) was dissolved in phosphate buffered saline (PBS) prior to administration.

(b) Cell Line

NUGC-4 10cF7_5_3E10, a subclone of gastric cancer cell line NUGC-4 expressing human claudin18.2 endogenously, was obtained from Ganymed Pharmaceuticals AG (Mainz, Germany) and cultured in RPMI 1640 medium supplemented with 10% heat inactivated fetal bovine serum and 1% glutamax at 37° C. in 5% $CO_2$.

(c) Animals

Six-week-old female NOG mice were purchased from In-Vivo Science Inc. (Tokyo, Japan). This study was approved by the Institutional Animal Care and Use Committee of Astellas Pharma Inc., Tsukuba Research Center, which is accredited by AAALAC International.

(d) Human PBMC Injection and Tumor Inoculation

Human PBMCs (Precision for Medicine, 93000-10M) were suspended in PBS at $2.5 \times 10^7$ cells/mL and intravenously injected of 7-week-old mice at $5 \times 10^6$ cells/200 µL/mouse. One week after human PBMC injection, NUGC-4 10cF7_5_3E10 cells were suspended in PBS at $1 \times 10^7$ cells/mL and subcutaneously inoculated into the flank of 8-week-old mice at $1 \times 10^6$ cells/100 µL/mouse and allowed to grow.

(e) Administration and Measurement

Eight days after the inoculation of NUGC-4 10cF7_5_3E10 cells, mice were allocated with similar mean tumor volumes between groups (n=10). Then, administration of ASP2138 was started. The first day of the administration was defined as day 0. Mice received intraperitoneal administration of PBS or ASP2138 (0.1, 1, 3 and 10 mg/kg) on day 0 and day 7. Tumor diameters and body weights were measured on day 0, 3, 7, 10 and 14 using a caliper and a balance, respectively. Tumor volume [$mm^3$] was determined with the formula:

(Length of tumor long axis[mm])×(Length of tumor short axis[mm])$^2$×0.5.

Percent inhibition of tumor growth (% Inh) was calculated using the following formula:

% Inh=100×(1−[mean tumor volume on day 14−mean tumor volume on day 0]in each group÷[mean tumor volume on day 14−mean tumor volume on day0]in PBS group).

(f) Statistical Analysis

Values are expressed as the means±standard errors of the mean (SEM) for tumor volume and body weight. Mean tumor volumes and body weights on day 14 in ASP2138-treated groups were compared with that in the PBS group using Dunnett's multiple comparison test. P<0.05 were considered statistically significant. GraphPad Prism (ver 8.0.2, GraphPad Software, San Diego, Calif., USA) and Microsoft Excel (ver 2002, Microsoft Corporation, Redmond, Wash., USA) were used for data processing.

Example 4B: Results and Conclusion

Figure 38A:
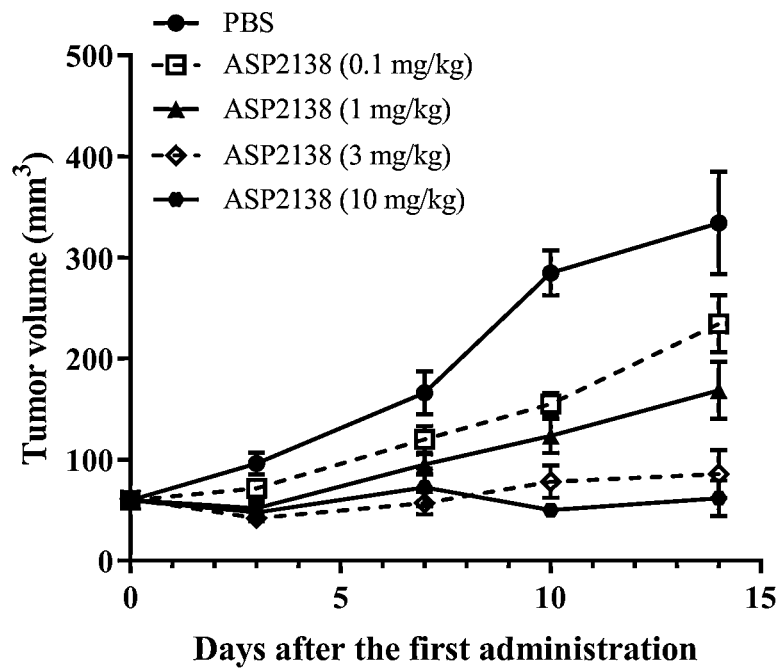
FIGS. 38A, 38B, and 38C depicts change in tumor volume and change in body weight in NUGC-4 10cF7_5_3E10 tumor-bearing human PBMC engrafted NOG mice dosed with ASP2138 (XENP31726). Human PBMCs were intravenously injected at $5 \times 10^6$ cells. One week after human PBMC injection, NUGC-4 10cF7_5_3E10 cells were subcutaneously inoculated into the flank of mice at $1 \times 10^6$ cells on day −8. NOG mice received once-weekly intraperitoneal administration of PBS or ASP2138 on day 0 and day 7. A) the tumor volumes and B) the body weights of each group were plotted at each time point as the mean±SEM (n=10). C) scatter plots indicate the individual tumor volume on day 14 and the mean±SEM were expressed as short horizontal lines and error bars. Statistical analysis was performed on the values on day 14. ns: not significant, **: p<0.01 compared with the value of the PBS group (Dunnett's multiple comparison test).
Figure 38B:
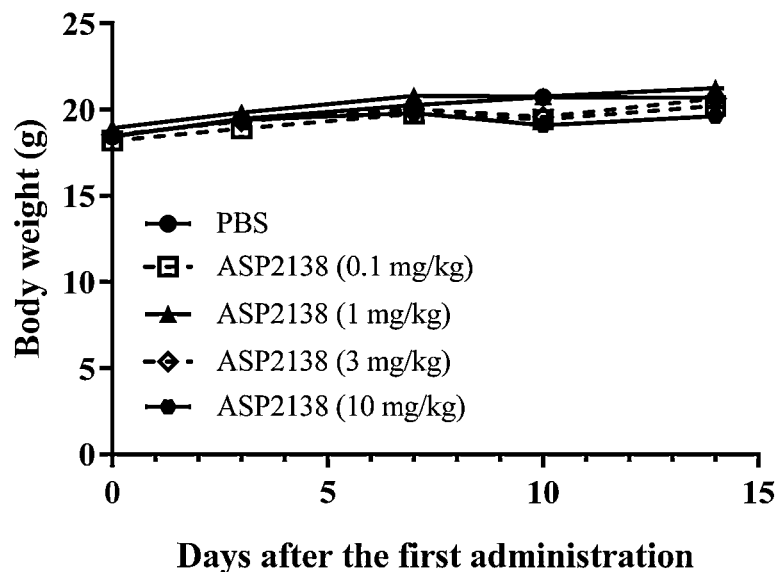
Figure 38C:
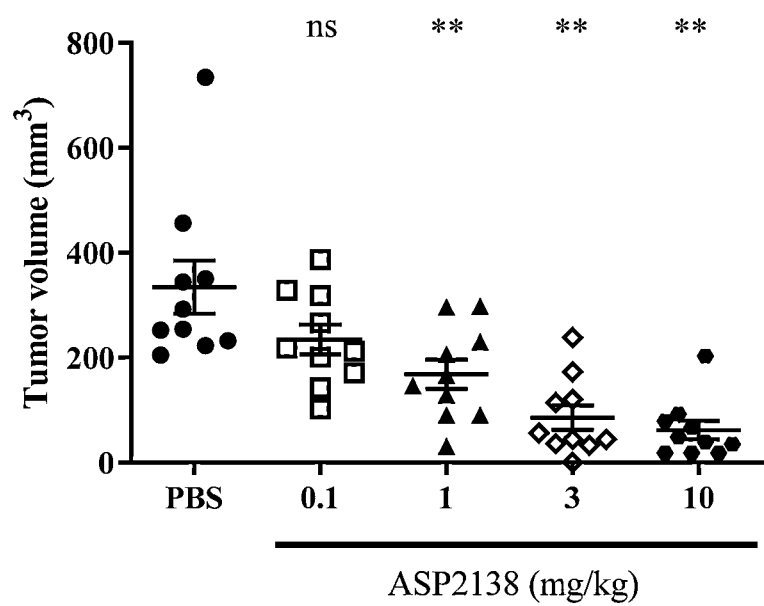

Once-weekly intraperitoneal administration of ASP2138 for 14 days induced significant growth inhibition of NUGC-4 10cF7_5_3E10 tumors at 1, 3 and 10 mg/kg by 60%, 91% and 99%, respectively, in the human PBMC engrafted NOG mouse model (FIG. 38). Additionally, 1 out of 10 mice in the 3 mg/kg group achieved complete tumor regression. Body weights of the mice treated with ASP2138 was not affected at any tested dose (FIG. 38).

This study demonstrated that ASP2138 exhibits anti-tumor effect for human gastric cancer in the human PBMC engrafted NOG mouse model. Excellent anti-tumor effects in vivo were shown for all tested bsAb concentrations.

The invention claimed is:

1. A bispecific binding agent comprising a first binding domain that binds to human CLDN18.2, a second binding domain that binds to human CLDN18.2, and a third binding domain that binds to human CD3,
wherein the bispecific binding agent comprises four polypeptide chains, wherein
(i) the first polypeptide chain comprises the amino acid sequence of SEQ ID NO: 73;
(ii) the second polypeptide chain comprises the amino acid sequence of SEQ ID NO: 74;
(iii) the third polypeptide chain comprises the amino acid sequence of SEQ ID NO: 78; and
(iv) the fourth polypeptide chain comprises the amino acid sequence of SEQ ID NO: 78.

2. The bispecific binding agent of claim 1, wherein the first polypeptide chain consists of the amino acid sequence of SEQ ID NO: 73.

3. The bispecific binding agent of claim 1, wherein the second polypeptide chain consists of the amino acid sequence of SEQ ID NO: 74.

4. The bispecific binding agent of claim 1, wherein the third polypeptide chain consists of the amino acid sequence of SEQ ID NO: 78.

5. The bispecific binding agent of claim 1, wherein the fourth polypeptide chain consists of the amino acid sequence of SEQ ID NO: 78.

6. A bispecific binding agent comprising a first binding domain that binds to human CLDN18.2, a second binding domain that binds to human CLDN18.2, and a third binding domain that binds to human CD3, wherein the bispecific binding agent comprises four polypeptide chains,
wherein the first polypeptide chain consists of the amino acid sequence of SEQ ID NO: 73;
wherein the second polypeptide chain consists of the amino acid sequence of SEQ ID NO: 74;
wherein the third polypeptide chain consists of the amino acid sequence of SEQ ID NO: 78; and
wherein the fourth polypeptide chain consists of the amino acid sequence of SEQ ID NO: 78.

7. One or more nucleic acid molecules encoding the bispecific binding agent of claim 1.

8. The one or more nucleic acid molecules of claim 7, wherein the one or more nucleic acid molecules is a set of nucleic acids.

9. A host cell comprising the one or more nucleic acid molecules of claim 7.

10. A vector comprising the one or more nucleic acid molecules of claim 7.

11. A host cell comprising the vector of claim 10.

12. One or more nucleic acid molecules comprising:
a) a first nucleic acid sequence encoding a first polypeptide chain comprising the amino acid sequence of SEQ ID NO: 73;
b) a second nucleic acid sequence encoding a second polypeptide chain comprising the amino acid sequence of SEQ ID NO: 74; and
c) a third nucleic acid sequence encoding a third polypeptide chain comprising the amino acid sequence of SEQ ID NO: 78.

13. A host cell comprising the one or more nucleic acid molecules of claim 12.

14. A set of vectors comprising:
i) a first vector comprising a nucleic acid encoding a first polypeptide chain comprising the amino acid sequence of SEQ ID NO: 73;
ii) a second vector comprising a nucleic acid encoding a second polypeptide chain comprising the amino acid sequence of SEQ ID NO: 74; and
iii) a third vector comprising a nucleic acid encoding a third polypeptide chain comprising the amino acid sequence of SEQ ID NO: 78.

15. A host cell comprising the vector set of claim 14.

16. A bispecific binding agent comprising a first binding domain that binds to human CLDN18.2, a second binding domain that binds to human CLDN18.2, and a third binding domain that binds to human CD3, wherein the bispecific binding agent comprises four polypeptide chains, wherein
(i) the first polypeptide chain is encoded by a first nucleic acid sequence encoding the amino acid sequence of SEQ ID NO: 73;
(ii) the second polypeptide chain is encoded by a second nucleic acid encoding the amino acid sequence of SEQ ID NO: 74;
(iii) the third polypeptide chain is encoded by a third nucleic acid encoding the amino acid sequence of SEQ ID NO: 78; and
(iv) the fourth polypeptide chain is encoded by the third nucleic acid encoding the amino acid sequence of SEQ ID NO: 78.

17. The bispecific binding agent of claim 16, wherein the first polypeptide chain comprises the amino acid sequence of SEQ ID NO: 73 or a C-terminal truncation variant thereof, wherein the C-terminal truncation variant of SEQ ID NO: 73 comprises deletion of lysine at position 447 of SEQ ID NO: 73.

18. The bispecific binding agent of claim 16, wherein the second polypeptide chain comprises the amino acid sequence of SEQ ID NO: 74 or a C-terminal truncation variant thereof, wherein the C-terminal truncation variant of SEQ ID NO: 74 comprises deletion of lysine at position 720 of SEQ ID NO: 74.

19. The bispecific binding agent of claim 16, wherein the third polypeptide chain comprises the amino acid sequence of SEQ ID NO: 78.

20. The bispecific binding agent of claim 16, wherein the fourth polypeptide chain comprises the amino acid sequence of SEQ ID NO: 78.

21. A bispecific binding agent comprising a first binding domain that binds to human CLDN18.2, a second binding domain that binds to human CLDN18.2, and a third binding domain that binds to human CD3, wherein the bispecific binding agent comprises four polypeptide chains,
i) wherein the first polypeptide chain comprises the amino acid sequence of SEQ ID NO: 73 or a C-terminal truncation variant thereof, wherein the C-terminal truncation variant of SEQ ID NO: 73 comprises deletion of lysine at position 447 of SEQ ID NO: 73;
ii) wherein the second polypeptide chain comprises the amino acid sequence of SEQ ID NO: 74 or a C-terminal truncation variant thereof, wherein the C-terminal truncation variant of SEQ ID NO: 74 comprises deletion of lysine at position 720 of SEQ ID NO: 74;
iii) wherein the third polypeptide chain comprises the amino acid sequence of SEQ ID NO: 78; and
iv) wherein the fourth polypeptide chain comprises the amino acid sequence of SEQ ID NO: 78.

22. A bispecific binding agent comprising a first binding domain that binds to human CLDN18.2, a second binding domain that binds to human CLDN18.2, and a third binding domain that binds to human CD3, wherein the bispecific binding agent comprises four polypeptide chains,
i) wherein the first polypeptide chain consists of the amino acid sequence of SEQ ID NO: 73 or a C-terminal truncation variant thereof, wherein the C-terminal truncation variant of SEQ ID NO: 73 comprises deletion of lysine at position 447 of SEQ ID NO: 73;
ii) wherein the second polypeptide chain consists of the amino acid sequence of SEQ ID NO: 74 or a C-terminal truncation variant thereof, wherein the C-terminal truncation variant of SEQ ID NO: 74 comprises deletion of lysine at position 720 of SEQ ID NO: 74;
iii) wherein the third polypeptide chain consists of the amino acid sequence of SEQ ID NO: 78; and
iv) wherein the fourth polypeptide chain consists of the amino acid sequence of SEQ ID NO: 78.

* * * * *

SEQUENCE LISTING

```
Sequence total quantity: 95
SEQ ID NO: 1            moltype = AA  length = 261
FEATURE                 Location/Qualifiers
source                  1..261
                        mol_type = protein
                        organism = Homo sapiens
SEQUENCE: 1
MAVTACQGLG FVVSLIGIAG IIAATCMDQW STQDLYNNPV TAVFNYQGLW RSCVRESSGF   60
TECRGYFTLL GLPAMLQAVR ALMIVGIVLG AIGLLVSIFA LKCIRIGSME DSAKANMTLT  120
SGIMFIVSGL CAIAGVSVFA NMLVTNFWMS TANMYTGMGG MVQTVQTRYT FGAALFVGWV  180
AGGLTLIGGV MMCIACRGLA PEETNYKAVS YHASGHSVAY KPGGFKASTG FGSNTKNKKI  240
YDGGARTEDE VQSYPSKHDY V                                            261

SEQ ID NO: 2            moltype = AA  length = 15
FEATURE                 Location/Qualifiers
REGION                  1..15
                        note = Peptide linker
```

```
source                  1..15
                        mol_type = protein
                        organism = synthetic construct
SEQUENCE: 2
GGGGSGGGGS GGGGS                                                            15

SEQ ID NO: 3            moltype = AA  length = 18
FEATURE                 Location/Qualifiers
REGION                  1..18
                        note = Peptide linker
source                  1..18
                        mol_type = protein
                        organism = synthetic construct
SEQUENCE: 3
GSTSGSGKPG SGEGSTKG                                                         18

SEQ ID NO: 4            moltype = AA  length = 14
FEATURE                 Location/Qualifiers
REGION                  1..14
                        note = Peptide linker
source                  1..14
                        mol_type = protein
                        organism = synthetic construct
SEQUENCE: 4
IRPRAIGGSK PRVA                                                             14

SEQ ID NO: 5            moltype = AA  length = 15
FEATURE                 Location/Qualifiers
REGION                  1..15
                        note = Peptide linker
source                  1..15
                        mol_type = protein
                        organism = synthetic construct
SEQUENCE: 5
GKGGSGKGGS GKGGS                                                            15

SEQ ID NO: 6            moltype = AA  length = 15
FEATURE                 Location/Qualifiers
REGION                  1..15
                        note = Peptide linker
source                  1..15
                        mol_type = protein
                        organism = synthetic construct
SEQUENCE: 6
GGKGSGGKGS GGKGS                                                            15

SEQ ID NO: 7            moltype = AA  length = 15
FEATURE                 Location/Qualifiers
REGION                  1..15
                        note = Peptide linker
source                  1..15
                        mol_type = protein
                        organism = synthetic construct
SEQUENCE: 7
GGGKSGGGKS GGGKS                                                            15

SEQ ID NO: 8            moltype = AA  length = 15
FEATURE                 Location/Qualifiers
REGION                  1..15
                        note = Peptide linker
source                  1..15
                        mol_type = protein
                        organism = synthetic construct
SEQUENCE: 8
GKGKSGKGKS GKGKS                                                            15

SEQ ID NO: 9            moltype = AA  length = 15
FEATURE                 Location/Qualifiers
REGION                  1..15
                        note = Peptide linker
source                  1..15
                        mol_type = protein
                        organism = synthetic construct
SEQUENCE: 9
GGGKSGGKGS GKGGS                                                            15
```

```
SEQ ID NO: 10              moltype = AA   length = 15
FEATURE                    Location/Qualifiers
REGION                     1..15
                           note = Peptide linker
source                     1..15
                           mol_type = protein
                           organism = synthetic construct
SEQUENCE: 10
GKPGSGKPGS GKPGS                                                         15

SEQ ID NO: 11              moltype = AA   length = 20
FEATURE                    Location/Qualifiers
REGION                     1..20
                           note = Peptide linker
source                     1..20
                           mol_type = protein
                           organism = synthetic construct
SEQUENCE: 11
GKPGSGKPGS GKPGSGKPGS                                                    20

SEQ ID NO: 12              moltype = AA   length = 20
FEATURE                    Location/Qualifiers
REGION                     1..20
                           note = Peptide linker
source                     1..20
                           mol_type = protein
                           organism = synthetic construct
SEQUENCE: 12
GKGKSGKGKS GKGKSGKGKS                                                    20

SEQ ID NO: 13              moltype = AA   length = 20
FEATURE                    Location/Qualifiers
REGION                     1..20
                           note = Peptide linker
source                     1..20
                           mol_type = protein
                           organism = synthetic construct
SEQUENCE: 13
GGGGSGGGGS GGGGSGGGGS                                                    20

SEQ ID NO: 14              moltype = AA   length = 14
FEATURE                    Location/Qualifiers
REGION                     1..14
                           note = Peptide linker
source                     1..14
                           mol_type = protein
                           organism = synthetic construct
SEQUENCE: 14
STAGDTHLGG EDFD                                                          14

SEQ ID NO: 15              moltype = AA   length = 15
FEATURE                    Location/Qualifiers
REGION                     1..15
                           note = Peptide linker
source                     1..15
                           mol_type = protein
                           organism = synthetic construct
SEQUENCE: 15
GEGGSGEGGS GEGGS                                                         15

SEQ ID NO: 16              moltype = AA   length = 15
FEATURE                    Location/Qualifiers
REGION                     1..15
                           note = Peptide linker
source                     1..15
                           mol_type = protein
                           organism = synthetic construct
SEQUENCE: 16
GGEGSGGEGS GGEGS                                                         15

SEQ ID NO: 17              moltype = AA   length = 15
FEATURE                    Location/Qualifiers
REGION                     1..15
                           note = Peptide linker
source                     1..15
                           mol_type = protein
                           organism = synthetic construct
```

```
SEQUENCE: 17
GGGESGGGES GGGES                                                15

SEQ ID NO: 18         moltype = AA  length = 15
FEATURE               Location/Qualifiers
REGION                1..15
                      note = Peptide linker
source                1..15
                      mol_type = protein
                      organism = synthetic construct
SEQUENCE: 18
GEGESGEGES GEGES                                                15

SEQ ID NO: 19         moltype = AA  length = 15
FEATURE               Location/Qualifiers
REGION                1..15
                      note = Peptide linker
source                1..15
                      mol_type = protein
                      organism = synthetic construct
SEQUENCE: 19
GGGESGGEGS GEGGS                                                15

SEQ ID NO: 20         moltype = AA  length = 20
FEATURE               Location/Qualifiers
REGION                1..20
                      note = Peptide linker
source                1..20
                      mol_type = protein
                      organism = synthetic construct
SEQUENCE: 20
GEGESGEGES GEGESGEGES                                           20

SEQ ID NO: 21         moltype = AA  length = 9
FEATURE               Location/Qualifiers
REGION                1..9
                      note = Peptide linker
source                1..9
                      mol_type = protein
                      organism = synthetic construct
SEQUENCE: 21
KTHTCPPCP                                                        9

SEQ ID NO: 22         moltype = AA  length = 15
FEATURE               Location/Qualifiers
REGION                1..15
                      note = Peptide linker
source                1..15
                      mol_type = protein
                      organism = synthetic construct
SEQUENCE: 22
EPKSSDKTHT CPPCP                                                15

SEQ ID NO: 23         moltype = AA  length = 19
FEATURE               Location/Qualifiers
REGION                1..19
                      note = Peptide linker
source                1..19
                      mol_type = protein
                      organism = synthetic construct
SEQUENCE: 23
GGGGSGGGGS KTHTCPPCP                                            19

SEQ ID NO: 24         moltype = AA  length = 19
FEATURE               Location/Qualifiers
REGION                1..19
                      note = Peptide linker
source                1..19
                      mol_type = protein
                      organism = synthetic construct
SEQUENCE: 24
GKPGSGKPGS KTHTCPPCP                                            19

SEQ ID NO: 25         moltype = AA  length = 14
FEATURE               Location/Qualifiers
REGION                1..14
                      note = Peptide linker
```

```
source                  1..14
                        mol_type = protein
                        organism = synthetic construct
SEQUENCE: 25
GKPGSKTHTC PPCP                                                       14

SEQ ID NO: 26           moltype = AA  length = 10
FEATURE                 Location/Qualifiers
REGION                  1..10
                        note = Peptide linker
source                  1..10
                        mol_type = protein
                        organism = synthetic construct
SEQUENCE: 26
GGGGSGGGGS                                                            10

SEQ ID NO: 27           moltype = AA  length = 15
FEATURE                 Location/Qualifiers
REGION                  1..15
                        note = Peptide linker
source                  1..15
                        mol_type = protein
                        organism = synthetic construct
SEQUENCE: 27
EPKSCDKTHT CPPCP                                                      15

SEQ ID NO: 28           moltype = AA  length = 329
FEATURE                 Location/Qualifiers
REGION                  1..329
                        note = Immunoglobulin-derived sequence
source                  1..329
                        mol_type = protein
                        organism = synthetic construct
SEQUENCE: 28
ASTKGPSVFP LAPSSKSTSG GTAALGCLVK DYFPEPVTVS WNSGALTSGV HTFPAVLQSS       60
GLYSLSSVVT VPSSSLGTQT YICNVNHKPS DTKVDKKVEP KSCDKTHTCP PCPAPPVAGP      120
SVFLFPPKPK DTLMISRTPE VTCVVVDVKH EDPEVKFNWY VDGVEVHNAK TKPREEEYNS      180
TYRVVSVLTV LHQDWLNGKE YKCKVSNKAL PAPIEKTISK AKGQPREPQV YTLPPSREEM      240
TKNQVSLTCD VSGFYPSDIA VEWESDGQPE NNYKTTPPVL DSDGSFFLYS KLTVDKSRWE      300
QGDVFSCSVM HEALHNHYTQ KSLSLSPGK                                       329

SEQ ID NO: 29           moltype = AA  length = 231
FEATURE                 Location/Qualifiers
REGION                  1..231
                        note = Immunoglobulin-derived sequence
source                  1..231
                        mol_type = protein
                        organism = synthetic construct
SEQUENCE: 29
EPKSSDKTHT CPPCPAPPVA GPSVFLFPPK PKDTLMISRT PEVTCVVVDV KHEDPEVKFN       60
WYVDGVEVHN AKTKPREEQY NSTYRVVSVL TVLHQDWLNG KEYKCKVSNK ALPAPIEKTI      120
SKAKGQPREP QVYTLPPSRE QMTKNQVKLT CLVKGFYPSD IAVEWESNGQ PENNYKTTPP      180
VLDSDGSFFL YSKLTVDKSR WQQGNVFSCS VMHEALHNHY TQKSLSLSPG K               231

SEQ ID NO: 30           moltype = AA  length = 216
FEATURE                 Location/Qualifiers
REGION                  1..216
                        note = Immunoglobulin-derived sequence
source                  1..216
                        mol_type = protein
                        organism = synthetic construct
SEQUENCE: 30
APPVAGPSVF LFPPKPKDTL MISRTPEVTC VVVDVKHEDP EVKFNWYVDG VEVHNAKTKP       60
REEQYNSTYR VVSVLTVLHQ DWLNGKEYKC KVSNKALPAP IEKTISKAKG QPREPQVYTL      120
PPSREQMTKN QVKLTCLVKG FYPSDIAVEW ESNGQPENNY KTTPPVLDSD GSFFLYSKLT      180
VDKSRWQQGN VFSCSVMHEA LHNHYTQKSL SLSPGK                               216

SEQ ID NO: 31           moltype = AA  length = 107
FEATURE                 Location/Qualifiers
REGION                  1..107
                        note = Immunoglobulin-derived sequence
source                  1..107
                        mol_type = protein
                        organism = synthetic construct
SEQUENCE: 31
RTVAAPSVFI FPPSDEQLKS GTASVVCLLN NFYPREAKVQ WKVDNALQSG NSQESVTEQD       60
SKDSTYSLSS TLTLSKADYE KHKVYACEVT HQGLSSPVTK SFNRGEC                   107
```

```
SEQ ID NO: 32           moltype = AA   length = 5
FEATURE                 Location/Qualifiers
REGION                  1..5
                        note = CDR sequence
source                  1..5
                        mol_type = protein
                        organism = synthetic construct
SEQUENCE: 32
SYWIN                                                                    5

SEQ ID NO: 33           moltype = AA   length = 17
FEATURE                 Location/Qualifiers
REGION                  1..17
                        note = CDR sequence
source                  1..17
                        mol_type = protein
                        organism = synthetic construct
SEQUENCE: 33
NIYPSDSYTN YNQKFQG                                                      17

SEQ ID NO: 34           moltype = AA   length = 9
FEATURE                 Location/Qualifiers
REGION                  1..9
                        note = CDR sequence
source                  1..9
                        mol_type = protein
                        organism = synthetic construct
SEQUENCE: 34
SWRGNSFDY                                                                9

SEQ ID NO: 35           moltype = AA   length = 17
FEATURE                 Location/Qualifiers
REGION                  1..17
                        note = CDR sequence
source                  1..17
                        mol_type = protein
                        organism = synthetic construct
SEQUENCE: 35
KSSQSLLNSG NQKNYLT                                                      17

SEQ ID NO: 36           moltype = AA   length = 7
FEATURE                 Location/Qualifiers
REGION                  1..7
                        note = CDR sequence
source                  1..7
                        mol_type = protein
                        organism = synthetic construct
SEQUENCE: 36
WASTRES                                                                  7

SEQ ID NO: 37           moltype = AA   length = 9
FEATURE                 Location/Qualifiers
REGION                  1..9
                        note = CDR sequence
source                  1..9
                        mol_type = protein
                        organism = synthetic construct
SEQUENCE: 37
QNDYSYPFT                                                                9

SEQ ID NO: 38           moltype = AA   length = 118
FEATURE                 Location/Qualifiers
REGION                  1..118
                        note = Immunoglobulin-derived sequence
source                  1..118
                        mol_type = protein
                        organism = synthetic construct
SEQUENCE: 38
QVQLQQPGAE LVRPGASVKL SCKASGYTFT SYWINWVKQR PGQGLEWIGN IYPSDSYTNY        60
NQKFKDKATL TVDKSSSTAY MQLSSPTSED SAVYYCTRSW RGNSFDYWGQ GTTLTVSS         118

SEQ ID NO: 39           moltype = AA   length = 118
FEATURE                 Location/Qualifiers
REGION                  1..118
                        note = Immunoglobulin-derived sequence
source                  1..118
                        mol_type = protein
                        organism = synthetic construct
```

```
SEQUENCE: 39
EVQLVQSGAE VKKPGESLRI SCKASGYTFT SYWINWVRQM PGKGLEWMGN IYPSDSYTNY      60
NQKFQGHVTI SVDKSISTAY LQWSSLKASD TAMYYCTRSW RGNSFDYWGQ GTLVTVSS       118

SEQ ID NO: 40            moltype = AA   length = 118
FEATURE                  Location/Qualifiers
REGION                   1..118
                         note = Immunoglobulin-derived sequence
source                   1..118
                         mol_type = protein
                         organism = synthetic construct
SEQUENCE: 40
QVQLVQSGAE VKKPGASVKV SCKASGYTFT SYWINWVRQA PGQGLEWMGN IYPSDSYTNY      60
NQKFQGRVTM TVDKSTSTAY MELSSLRSED TAVYYCTRSW RGNSFDYWGQ GTLVTVSS       118

SEQ ID NO: 41            moltype = AA   length = 113
FEATURE                  Location/Qualifiers
REGION                   1..113
                         note = Immunoglobulin-derived sequence
source                   1..113
                         mol_type = protein
                         organism = synthetic construct
SEQUENCE: 41
DIVMTQSPSS LTVTAGEKVT MSCKSSQSLL NSGNQKNYLT WYQQKPGQPP KLLIYWASTR      60
ESGVPDRFTG SGSGTDFTLT ISSVQAEDLA VYYCQNDYSY PFTFGSGTKL EIK            113

SEQ ID NO: 42            moltype = AA   length = 113
FEATURE                  Location/Qualifiers
REGION                   1..113
                         note = Immunoglobulin-derived sequence
source                   1..113
                         mol_type = protein
                         organism = synthetic construct
SEQUENCE: 42
DIVMTQSPDS LAVSLGERAT INCKSSQSLL NSGNQKNYLT WYQQKPGQPP KLLIYWASTR      60
ESGVPDRFTG SGSGTDFTLT ISSLQAEDVA VYYCQNDYSY PFTFGSGTKL EIK            113

SEQ ID NO: 43            moltype = AA   length = 5
FEATURE                  Location/Qualifiers
REGION                   1..5
                         note = CDR sequence
source                   1..5
                         mol_type = protein
                         organism = synthetic construct
SEQUENCE: 43
TYAMN                                                                  5

SEQ ID NO: 44            moltype = AA   length = 19
FEATURE                  Location/Qualifiers
REGION                   1..19
                         note = CDR sequence
source                   1..19
                         mol_type = protein
                         organism = synthetic construct
SEQUENCE: 44
RIRSKYNNYA TYYADSVKG                                                  19

SEQ ID NO: 45            moltype = AA   length = 14
FEATURE                  Location/Qualifiers
REGION                   1..14
                         note = CDR sequence
source                   1..14
                         mol_type = protein
                         organism = synthetic construct
SEQUENCE: 45
HGNFGDSYVS WFAY                                                       14

SEQ ID NO: 46            moltype = AA   length = 14
FEATURE                  Location/Qualifiers
REGION                   1..14
                         note = CDR sequence
source                   1..14
                         mol_type = protein
                         organism = synthetic construct
SEQUENCE: 46
GSSTGAVTTS NYAN                                                       14

SEQ ID NO: 47            moltype = AA   length = 7
FEATURE                  Location/Qualifiers
```

```
REGION                    1..7
                          note = CDR sequence
source                    1..7
                          mol_type = protein
                          organism = synthetic construct
SEQUENCE: 47
GTNKRAP                                                                        7

SEQ ID NO: 48             moltype = AA  length = 9
FEATURE                   Location/Qualifiers
REGION                    1..9
                          note = CDR sequence
source                    1..9
                          mol_type = protein
                          organism = synthetic construct
SEQUENCE: 48
ALWYSNHWV                                                                      9

SEQ ID NO: 49             moltype = AA  length = 5
FEATURE                   Location/Qualifiers
REGION                    1..5
                          note = CDR sequence
source                    1..5
                          mol_type = protein
                          organism = synthetic construct
SEQUENCE: 49
TYAMS                                                                          5

SEQ ID NO: 50             moltype = AA  length = 19
FEATURE                   Location/Qualifiers
REGION                    1..19
                          note = CDR sequence
source                    1..19
                          mol_type = protein
                          organism = synthetic construct
SEQUENCE: 50
RIRSKANNYA TYYADSVKG                                                          19

SEQ ID NO: 51             moltype = AA  length = 14
FEATURE                   Location/Qualifiers
REGION                    1..14
                          note = CDR sequence
source                    1..14
                          mol_type = protein
                          organism = synthetic construct
SEQUENCE: 51
HGNFGDEYVS WFAY                                                               14

SEQ ID NO: 52             moltype = AA  length = 14
FEATURE                   Location/Qualifiers
REGION                    1..14
                          note = CDR sequence
source                    1..14
                          mol_type = protein
                          organism = synthetic construct
SEQUENCE: 52
HGNFGDPYVS WFAY                                                               14

SEQ ID NO: 53             moltype = AA  length = 14
FEATURE                   Location/Qualifiers
REGION                    1..14
                          note = CDR sequence
source                    1..14
                          mol_type = protein
                          organism = synthetic construct
SEQUENCE: 53
HGNFGDSYVS WFDY                                                               14

SEQ ID NO: 54             moltype = AA  length = 125
FEATURE                   Location/Qualifiers
REGION                    1..125
                          note = Immunoglobulin-derived sequence
source                    1..125
                          mol_type = protein
                          organism = synthetic construct
SEQUENCE: 54
EVQLVESGGG LVQPGGSLRL SCAASGFTFS TYAMNWVRQA PGKGLEWVGR IRSKYNNYAT              60
YYADSVKGRF TISRDDSKNT LYLQMNSLRA EDTAVYYCVR HGNFGDSYVS WFAYWGQGTL             120
VTVSS                                                                        125
```

```
SEQ ID NO: 55          moltype = AA  length = 109
FEATURE                Location/Qualifiers
REGION                 1..109
                       note = Immunoglobulin-derived sequence
source                 1..109
                       mol_type = protein
                       organism = synthetic construct
SEQUENCE: 55
QAVVTQEPSL TVSPGGTVTL TCGSSTGAVT TSNYANWVQQ KPGKSPRGLI GGTNKRAPGV    60
PARFSGSLLG GKAALTISGA QPEDEADYYC ALWYSNHWVF GGGTKLTVL               109

SEQ ID NO: 56          moltype = AA  length = 254
FEATURE                Location/Qualifiers
REGION                 1..254
                       note = Immunoglobulin-derived sequence
source                 1..254
                       mol_type = protein
                       organism = synthetic construct
SEQUENCE: 56
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVL                                                    254

SEQ ID NO: 57          moltype = AA  length = 254
FEATURE                Location/Qualifiers
REGION                 1..254
                       note = Immunoglobulin-derived sequence
source                 1..254
                       mol_type = protein
                       organism = synthetic construct
SEQUENCE: 57
QAVVTQEPSL TVSPGGTVTL TCGSSTGAVT TSNYANWVQQ KPGKSPRGLI GGTNKRAPGV    60
PARFSGSLLG GKAALTISGA QPEDEADYYC ALWYSNHWVF GGGTKLTVLG KPGSGKPGSG   120
KPGSGKPGSE VQLVESGGGL VQPGGSLRLS CAASGFTFST YAMNWVRQAP GKGLEWVGRI   180
RSKYNNYATY YADSVKGRFT ISRDDSKNTL YLQMNSLRAE DTAVYYCVRH GNFGDSYVSW   240
FAYWGQGTLV TVSS                                                    254

SEQ ID NO: 58          moltype = AA  length = 125
FEATURE                Location/Qualifiers
REGION                 1..125
                       note = Immunoglobulin-derived sequence
source                 1..125
                       mol_type = protein
                       organism = synthetic construct
SEQUENCE: 58
EVQLVESGGG LVQPGGSLRL SCAASGFTFS TYAMNWVRQA PGKGLEWVGR IRSKANNYAT    60
YYADSVKGRF TISRDDSKNT LYLQMNSLRA EDTAVYYCVR HGNFGDSYVS WFAYWGQGTL   120
VTVSS                                                              125

SEQ ID NO: 59          moltype = AA  length = 254
FEATURE                Location/Qualifiers
REGION                 1..254
                       note = Immunoglobulin-derived sequence
source                 1..254
                       mol_type = protein
                       organism = synthetic construct
SEQUENCE: 59
EVQLVESGGG LVQPGGSLRL SCAASGFTFS TYAMNWVRQA PGKGLEWVGR IRSKANNYAT    60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVL                                                    254

SEQ ID NO: 60          moltype = AA  length = 254
FEATURE                Location/Qualifiers
REGION                 1..254
                       note = Immunoglobulin-derived sequence
source                 1..254
                       mol_type = protein
                       organism = synthetic construct
SEQUENCE: 60
QAVVTQEPSL TVSPGGTVTL TCGSSTGAVT TSNYANWVQQ KPGKSPRGLI GGTNKRAPGV    60
PARFSGSLLG GKAALTISGA QPEDEADYYC ALWYSNHWVF GGGTKLTVLG KPGSGKPGSG   120
KPGSGKPGSE VQLVESGGGL VQPGGSLRLS CAASGFTFST YAMNWVRQAP GKGLEWVGRI   180
RSKANNYATY YADSVKGRFT ISRDDSKNTL YLQMNSLRAE DTAVYYCVRH GNFGDSYVSW   240
FAYWGQGTLV TVSS                                                    254
```

```
SEQ ID NO: 61              moltype = AA   length = 125
FEATURE                    Location/Qualifiers
REGION                     1..125
                           note = Immunoglobulin-derived sequence
source                     1..125
                           mol_type = protein
                           organism = synthetic construct
SEQUENCE: 61
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDEYVS WFAYWGQGTL  120
VTVSS                                                              125

SEQ ID NO: 62              moltype = AA   length = 254
FEATURE                    Location/Qualifiers
REGION                     1..254
                           note = Immunoglobulin-derived sequence
source                     1..254
                           mol_type = protein
                           organism = synthetic construct
SEQUENCE: 62
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDEYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVL                                                    254

SEQ ID NO: 63              moltype = AA   length = 254
FEATURE                    Location/Qualifiers
REGION                     1..254
                           note = Immunoglobulin-derived sequence
source                     1..254
                           mol_type = protein
                           organism = synthetic construct
SEQUENCE: 63
QAVVTQEPSL TVSPGGTVTL TCGSSTGAVT TSNYANWVQQ KPGKSPRGLI GGTNKRAPGV   60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMNWVRQAP GKGLEWVGRI  180
RSKYNNYATY YADSVKGRFT ISRDDSKNTL YLQMNSLRAE DTAVYYCVRH GNFGDEYVSW  240
FAYWGQGTLV TVSS                                                    254

SEQ ID NO: 64              moltype = AA   length = 125
FEATURE                    Location/Qualifiers
REGION                     1..125
                           note = Immunoglobulin-derived sequence
source                     1..125
                           mol_type = protein
                           organism = synthetic construct
SEQUENCE: 64
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDPYVS WFAYWGQGTL  120
VTVSS                                                              125

SEQ ID NO: 65              moltype = AA   length = 254
FEATURE                    Location/Qualifiers
REGION                     1..254
                           note = Immunoglobulin-derived sequence
source                     1..254
                           mol_type = protein
                           organism = synthetic construct
SEQUENCE: 65
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDPYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVL                                                    254

SEQ ID NO: 66              moltype = AA   length = 254
FEATURE                    Location/Qualifiers
REGION                     1..254
                           note = Immunoglobulin-derived sequence
source                     1..254
                           mol_type = protein
                           organism = synthetic construct
SEQUENCE: 66
QAVVTQEPSL TVSPGGTVTL TCGSSTGAVT TSNYANWVQQ KPGKSPRGLI GGTNKRAPGV   60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMNWVRQAP GKGLEWVGRI  180
RSKYNNYATY YADSVKGRFT ISRDDSKNTL YLQMNSLRAE DTAVYYCVRH GNFGDPYVSW  240
```

```
FAYWGQGTLV TVSS                                                          254

SEQ ID NO: 67           moltype = AA  length = 125
FEATURE                 Location/Qualifiers
REGION                  1..125
                        note = Immunoglobulin-derived sequence
source                  1..125
                        mol_type = protein
                        organism = synthetic construct
SEQUENCE: 67
EVQLVESGGG LVQPGGSLRL SCAASGFTFS TYAMNWVRQA PGKGLEWVGR IRSKYNNYAT          60
YYADSVKGRF TISRDDSKNT LYLQMNSLRA EDTAVYYCVR HGNFGDSYVS WFDYWGQGTL         120
VTVSS                                                                    125

SEQ ID NO: 68           moltype = AA  length = 254
FEATURE                 Location/Qualifiers
REGION                  1..254
                        note = Immunoglobulin-derived sequence
source                  1..254
                        mol_type = protein
                        organism = synthetic construct
SEQUENCE: 68
EVQLVESGGG LVQPGGSLRL SCAASGFTFS TYAMNWVRQA PGKGLEWVGR IRSKYNNYAT          60
YYADSVKGRF TISRDDSKNT LYLQMNSLRA EDTAVYYCVR HGNFGDSYVS WFDYWGQGTL         120
VTVSSGKPGS GKPGSGKPGS GKPGSQAVVT QEPSLTVSPG GTVTLTCGSS TGAVTTSNYA         180
NWVQQKPGKS PRGLIGGTNK RAPGVPARFS GSLLGGKAAL TISGAQPEDE ADYYCALWYS         240
NHWVFGGGTK LTVL                                                          254

SEQ ID NO: 69           moltype = AA  length = 254
FEATURE                 Location/Qualifiers
REGION                  1..254
                        note = Immunoglobulin-derived sequence
source                  1..254
                        mol_type = protein
                        organism = synthetic construct
SEQUENCE: 69
QAVVTQEPSL TVSPGGTVTL TCGSSTGAVT TSNYANWVQQ KPGKSPRGLI GGTNKRAPGV          60
PARFSGSLLG GKAALTISGA QPEDEADYYC ALWYSNHWVF GGGTKLTVLG KPGSGKPGSG         120
KPGSGKPGSE VQLVESGGGL VQPGGSLRLS CAASGFTFST YAMNWVRQAP GKGLEWVGRI         180
RSKYNNYATY YADSVKGRFT ISRDDSKNTL YLQMNSLRAE DTAVYYCVRH GNFGDSYVSW         240
FDYWGQGTLV TVSS                                                          254

SEQ ID NO: 70           moltype = AA  length = 125
FEATURE                 Location/Qualifiers
REGION                  1..125
                        note = Immunoglobulin-derived sequence
source                  1..125
                        mol_type = protein
                        organism = synthetic construct
SEQUENCE: 70
EVQLVESGGG LVQPGGSLRL SCAASGFTFS TYAMSWVRQA PGKGLEWVGR IRSKYNNYAT          60
YYADSVKGRF TISRDDSKNT LYLQMNSLRA EDTAVYYCVR HGNFGDSYVS WFAYWGQGTL         120
VTVSS                                                                    125

SEQ ID NO: 71           moltype = AA  length = 254
FEATURE                 Location/Qualifiers
REGION                  1..254
                        note = Immunoglobulin-derived sequence
source                  1..254
                        mol_type = protein
                        organism = synthetic construct
SEQUENCE: 71
EVQLVESGGG LVQPGGSLRL SCAASGFTFS TYAMSWVRQA PGKGLEWVGR IRSKYNNYAT          60
YYADSVKGRF TISRDDSKNT LYLQMNSLRA EDTAVYYCVR HGNFGDSYVS WFAYWGQGTL         120
VTVSSGKPGS GKPGSGKPGS GKPGSQAVVT QEPSLTVSPG GTVTLTCGSS TGAVTTSNYA         180
NWVQQKPGKS PRGLIGGTNK RAPGVPARFS GSLLGGKAAL TISGAQPEDE ADYYCALWYS         240
NHWVFGGGTK LTVL                                                          254

SEQ ID NO: 72           moltype = AA  length = 254
FEATURE                 Location/Qualifiers
REGION                  1..254
                        note = Immunoglobulin-derived sequence
source                  1..254
                        mol_type = protein
                        organism = synthetic construct
SEQUENCE: 72
QAVVTQEPSL TVSPGGTVTL TCGSSTGAVT TSNYANWVQQ KPGKSPRGLI GGTNKRAPGV          60
PARFSGSLLG GKAALTISGA QPEDEADYYC ALWYSNHWVF GGGTKLTVLG KPGSGKPGSG         120
KPGSGKPGSE VQLVESGGGL VQPGGSLRLS CAASGFTFST YAMSWVRQAP GKGLEWVGRI         180
```

```
RSKYNNYATY YADSVKGRFT ISRDDSKNTL YLQMNSLRAE DTAVYYCVRH GNFGDSYVSW  240
FAYWGQGTLV TVSS                                                   254

SEQ ID NO: 73            moltype = AA  length = 447
FEATURE                  Location/Qualifiers
REGION                   1..447
                         note = Immunoglobulin-derived sequence
source                   1..447
                         mol_type = protein
                         organism = synthetic construct
SEQUENCE: 73
EVQLVQSGAE VKKPGESLRI SCKASGYTFT SYWINWVRQM PGKGLEWMGN IYPSDSYTNY   60
NQKFQGHVTI SVDKSISTAY LQWSSLKASD TAMYYCTRSW RGNSFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSDT KVDKKVEPKS CDKTHTCPPC PAPPVAGPSV  240
FLFPPKPKDT LMISRTPEVT CVVVDVKHED PEVKFNWYVD GVEVHNAKTK PREEEYNSTY  300
RVVSVLTVLH QDWLNGKEYK CKVSNKALPA PIEKTISKAK GQPREPQVYT LPPSREEMTK  360
NQVSLTCDVS GFYPSDIAVE WESDGQPENN YKTTPPVLDS DGSFFLYSKL TVDKSRWEQG  420
DVFSCSVMHE ALHNHYTQKS LSLSPGK                                     447

SEQ ID NO: 74            moltype = AA  length = 720
FEATURE                  Location/Qualifiers
REGION                   1..720
                         note = Immunoglobulin-derived sequence
source                   1..720
                         mol_type = protein
                         organism = synthetic construct
SEQUENCE: 74
EVQLVQSGAE VKKPGESLRI SCKASGYTFT SYWINWVRQM PGKGLEWMGN IYPSDSYTNY   60
NQKFQGHVTI SVDKSISTAY LQWSSLKASD TAMYYCTRSW RGNSFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CGGGGSGGGG SQAVVTQEPS  240
LTVSPGGTVT LTCGSSTGAV TTSNYANWVQ QKPGKSPRGL IGGTNKRAPG VPARFSGSLL  300
GGKAALTISG AQPEDEADYY CALWYSNHWV FGGGTKLTVL GKPGSGKPGS GKPGSGKPGS  360
EVQLVESGGG LVQPGGSLRL SCAASGFTFS TYAMNWVRQA PGKGLEWVGR IRSKANNYAT  420
YYADSVKGRF TISRDDSKNT LYLQMNSLRA EDTAVYYCVR HGNFGDSYVS WFAYWGQGTL  480
VTVSSGGGGS GGGGSKTHTC PPCPAPPVAG PSVFLFPPKP KDTLMISRTP EVTCVVVDVK  540
HEDPEVKFNW YVDGVEVHNA KTKPREEQYN STYRVVSVLT VLHQDWLNGK EYKCKVSNKA  600
LPAPIEKTIS KAKGQPREPQ VYTLPPSREQ MTKNQVKLTC LVKGFYPSDI AVEWESNGQP  660
ENNYKTTPPV LDSDGSFFLY SKLTVDKSRW QQGNVFSCSV MHEALHNHYT QKSLSLSPGK  720

SEQ ID NO: 75            moltype = AA  length = 485
FEATURE                  Location/Qualifiers
REGION                   1..485
                         note = Immunoglobulin-derived sequence
source                   1..485
                         mol_type = protein
                         organism = synthetic construct
SEQUENCE: 75
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 76            moltype = AA  length = 720
FEATURE                  Location/Qualifiers
REGION                   1..720
                         note = Immunoglobulin-derived sequence
source                   1..720
                         mol_type = protein
                         organism = synthetic construct
SEQUENCE: 76
EVQLVQSGAE VKKPGESLRI SCKASGYTFT SYWINWVRQM PGKGLEWMGN IYPSDSYTNY   60
NQKFQGHVTI SVDKSISTAY LQWSSLKASD TAMYYCTRSW RGNSFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CGGGGSGGGG SEVQLVESGG  240
GLVQPGGSLR LSCAASGFTF STYAMNWVRQ APGKGLEWVG RIRSKANNYA TYYADSVKGR  300
FTISRDDSKN TLYLQMNSLR AEDTAVYYCV RHGNFGDSYV SWFAYWGQGT LVTVSSGKPG  360
SGKPGSGKPG SGKPGSQAVV TQEPSLTVSP GGTVTLTCGS STGAVTTSNY ANWVQQKPGK  420
SPRGLIGGTN KRAPGVPARF SGSLLGGKAA LTISGAQPED EADYYCALWY SNHWVFGGGT  480
KLTVLGGGGS GGGGSKTHTC PPCPAPPVAG PSVFLFPPKP KDTLMISRTP EVTCVVVDVK  540
HEDPEVKFNW YVDGVEVHNA KTKPREEQYN STYRVVSVLT VLHQDWLNGK EYKCKVSNKA  600
LPAPIEKTIS KAKGQPREPQ VYTLPPSREQ MTKNQVKLTC LVKGFYPSDI AVEWESNGQP  660
ENNYKTTPPV LDSDGSFFLY SKLTVDKSRW QQGNVFSCSV MHEALHNHYT QKSLSLSPGK  720
```

```
SEQ ID NO: 77            moltype = AA   length = 716
FEATURE                  Location/Qualifiers
REGION                   1..716
                         note = Immunoglobulin-derived sequence
source                   1..716
                         mol_type = protein
                         organism = synthetic construct
SEQUENCE: 77
EVQLVQSGAE VKKPGESLRI SCKASGYTFT SYWINWVRQM PGKGLEWMGN IYPSDSYTNY    60
NQKFQGHVTI SVDKSISTAY LQWSSLKASD TAMYYCTRSW RGNSFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CGGGGSGGGG SQAVVTQEPS   240
LTVSPGGTVT LTCGSSTGAV TTSNYANWVQ QKPGKSPRGL IGGTNKRAPG VPARFSGSLL   300
GGKAALTISG AQPEDEADYY CALWYSNHWV FGGGTKLTVL GKPGSGKPGS GKPGSGKPGS   360
EVQLVESGGG LVQPGGSLRL SCAASGFTFS TYAMNWVRQA PGKGLEWVGR IRSKYNNYAT   420
YYADSVKGRF TISRDDSKNT LYLQMNSLRA EDTAVYYCVR HGNFGDEYVS WFAYWGQGTL   480
VTVSSEPKSS DKTHTCPPCP APPVAGPSVF LFPPKPKDTL MISRTPEVTC VVVDVKHEDP   540
EVKFNWYVDG VEVHNAKTKP REEQYNSTYR VVSVLTVLHQ DWLNGKEYKC KVSNKALPAP   600
IEKTISKAKG QPREPQVYTL PPSREQMTKN QVKLTCLVKG FYPSDIAVEW ESNGQPENNY   660
KTTPPVLDSD GSFFLYSKLT VDKSRWQQGN VFSCSVMHEA LHNHYTQKSL SLSPGK       716

SEQ ID NO: 78            moltype = AA   length = 220
FEATURE                  Location/Qualifiers
REGION                   1..220
                         note = Immunoglobulin-derived sequence
source                   1..220
                         mol_type = protein
                         organism = synthetic construct
SEQUENCE: 78
DIVMTQSPDS LAVSLGERAT INCKSSQSLL NSGNQKNYLT WYQQKPGQPP KLLIYWASTR    60
ESGVPDRFTG SGSGTDFTLT ISSLQAEDVA VYYCQNDYSY PFTFGSGTKL EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 79            moltype = AA   length = 447
FEATURE                  Location/Qualifiers
REGION                   1..447
                         note = Immunoglobulin-derived sequence
source                   1..447
                         mol_type = protein
                         organism = synthetic construct
SEQUENCE: 79
QVQLQQPGAE LVRPGASVKL SCKASGYTFT SYWINWVKQR PGQGLEWIGN IYPSDSYTNY    60
NQKFKDKATL TVDKSSSTAY MQLSSPTSED SAVYYCTRSW RGNSFDYWGQ GTTLTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSDT KVDKKVEPKS CDKTHTCPPC PAPPVAGPSV   240
FLFPPKPKDT LMISRTPEVT CVVVDVKHED PEVKFNWYVD GVEVHNAKTK PREEEYNSTY   300
RVVSVLTVLH QDWLNGKEYK CKVSNKALPA PIEKTISKAK GQPREPQVYT LPPSREEMTK   360
NQVSLTCDVS GFYPSDIAVE WESDGQPENN YKTTPPVLDS DGSFFLYSKL TVDKSRWEQG   420
DVFSCSVMHE ALHNHYTQKS LSLSPGK                                       447

SEQ ID NO: 80            moltype = AA   length = 485
FEATURE                  Location/Qualifiers
REGION                   1..485
                         note = Immunoglobulin-derived sequence
source                   1..485
                         mol_type = protein
                         organism = synthetic construct
SEQUENCE: 80
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                               485

SEQ ID NO: 81            moltype = AA   length = 220
FEATURE                  Location/Qualifiers
REGION                   1..220
                         note = Immunoglobulin-derived sequence
source                   1..220
                         mol_type = protein
                         organism = synthetic construct
```

```
SEQUENCE: 81
DIVMTQSPSS LTVTAGEKVT MSCKSSQSLL NSGNQKNYLT WYQQKPGQPP KLLIYWASTR    60
ESGVPDRFTG SGSGTDFTLT ISSVQAEDLA VYYCQNDYSY PFTFGSGTKL EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                          220

SEQ ID NO: 82          moltype = AA   length = 485
FEATURE                Location/Qualifiers
REGION                 1..485
                       note = Immunoglobulin-derived sequence
source                 1..485
                       mol_type = protein
                       organism = synthetic construct
SEQUENCE: 82
EVQLVESGGG LVQPGGSLRL SCAASGFTFS TYAMNWVRQA PGKGLEWVGR IRSKANNYAT    60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                               485

SEQ ID NO: 83          moltype = AA   length = 720
FEATURE                Location/Qualifiers
REGION                 1..720
                       note = Immunoglobulin-derived sequence
source                 1..720
                       mol_type = protein
                       organism = synthetic construct
SEQUENCE: 83
QVQLQQPGAE LVRPGASVKL SCKASGYTFT SYWINWVKQR PGQGLEWIGN IYPSDSYTNY    60
NQKFKDKATL TVDKSSSTAY MQLSSPTSED SAVYYCTRSW RGNSFDYWGQ GTTLTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CGGGGSGGGG SEVQLVESGG   240
GLVQPGGSLR LSCAASGFTF STYAMNWVRQ APGKGLEWVG RIRSKYNNYA TYYADSVKGR   300
FTISRDDSKN TLYLQMNSLR AEDTAVYYCV RHGNFGDSYV SWFAYWGQGT LVTVSSGKPG   360
SGKPGSGKPG SGKPGSQAVV TQEPSLTVSP GGTVTLTCGS STGAVTTSNY ANWVQQKPGK   420
SPRGLIGGTN KRAPGVPARF SGSLLGGKAA LTISGAQPED EADYYCALWY SNHWVFGGGT   480
KLTVLGGGGS GGGGSKTHTC PPCPAPPVAG PSVFLFPPKP KDTLMISRTP EVTCVVVDVK   540
HEDPEVKFNW YVDGVEVHNA KTKPREEQYN STYRVVSVLT VLHQDWLNGK EYKCKVSNKA   600
LPAPIEKTIS KAKGQPREPQ VYTLPPSREQ MTKNQVKLTC LVKGFYPSDI AVEWESNGQP   660
ENNYKTTPPV LDSDGSFFLY SKLTVDKSRW QQGNVFSCSV MHEALHNHYT QKSLSLSPGK   720

SEQ ID NO: 84          moltype = AA   length = 720
FEATURE                Location/Qualifiers
REGION                 1..720
                       note = Immunoglobulin-derived sequence
source                 1..720
                       mol_type = protein
                       organism = synthetic construct
SEQUENCE: 84
QVQLQQPGAE LVRPGASVKL SCKASGYTFT SYWINWVKQR PGQGLEWIGN IYPSDSYTNY    60
NQKFKDKATL TVDKSSSTAY MQLSSPTSED SAVYYCTRSW RGNSFDYWGQ GTTLTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CGKPGSGKPG SEVQLVESGG   240
GLVQPGGSLR LSCAASGFTF STYAMNWVRQ APGKGLEWVG RIRSKANNYA TYYADSVKGR   300
FTISRDDSKN TLYLQMNSLR AEDTAVYYCV RHGNFGDSYV SWFAYWGQGT LVTVSSGKPG   360
SGKPGSGKPG SGKPGSQAVV TQEPSLTVSP GGTVTLTCGS STGAVTTSNY ANWVQQKPGK   420
SPRGLIGGTN KRAPGVPARF SGSLLGGKAA LTISGAQPED EADYYCALWY SNHWVFGGGT   480
KLTVLGGGGS GGGGSKTHTC PPCPAPPVAG PSVFLFPPKP KDTLMISRTP EVTCVVVDVK   540
HEDPEVKFNW YVDGVEVHNA KTKPREEQYN STYRVVSVLT VLHQDWLNGK EYKCKVSNKA   600
LPAPIEKTIS KAKGQPREPQ VYTLPPSREQ MTKNQVKLTC LVKGFYPSDI AVEWESNGQP   660
ENNYKTTPPV LDSDGSFFLY SKLTVDKSRW QQGNVFSCSV MHEALHNHYT QKSLSLSPGK   720

SEQ ID NO: 85          moltype = AA   length = 720
FEATURE                Location/Qualifiers
REGION                 1..720
                       note = Immunoglobulin-derived sequence
source                 1..720
                       mol_type = protein
                       organism = synthetic construct
SEQUENCE: 85
QVQLQQPGAE LVRPGASVKL SCKASGYTFT SYWINWVKQR PGQGLEWIGN IYPSDSYTNY    60
NQKFKDKATL TVDKSSSTAY MQLSSPTSED SAVYYCTRSW RGNSFDYWGQ GTTLTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CGKPGSGKPG SEVQLVESGG   240
GLVQPGGSLR LSCAASGFTF STYAMNWVRQ APGKGLEWVG RIRSKYNNYA TYYADSVKGR   300
```

```
FTISRDDSKN TLYLQMNSLR AEDTAVYYCV RHGNFGDSYV SWFDYWGQGT LVTVSSGKPG    360
SGKPGSGKPG SGKPGSQAVV TQEPSLTVSP GGTVTLTCGS STGAVTTSNY ANWVQQKPGK    420
SPRGLIGGTN KRAPGVPARF SGSLLGGKAA LTISGAQPED EADYYCALWY SNHWVFGGGT    480
KLTVLGGGS GGGGSKTHTC PPCPAPPVAG PSVFLFPPKP KDTLMISRTP EVTCVVVDVK    540
HEDPEVKFNW YVDGVEVHNA KTKPREEQYN STYRVVSVLT VLHQDWLNGK EYKCKVSNKA    600
LPAPIEKTIS KAKGQPREPQ VYTLPPSREQ MTKNQVKLTC LVKGFYPSDI AVEWESNGQP    660
ENNYKTTPPV LDSDGSFFLY SKLTVDKSRW QQGNVFSCSV MHEALHNHYT QKSLSLSPGK    720

SEQ ID NO: 86          moltype = AA  length = 447
FEATURE                Location/Qualifiers
REGION                 1..447
                       note = Immunoglobulin-derived sequence
source                 1..447
                       mol_type = protein
                       organism = synthetic construct
SEQUENCE: 86
QVQLVQSGAE VKKPGASVKV SCKASGYTFT SYWINWVRQA PGQGLEWMGN IYPSDSYTNY     60
NQKFQGRVTM TVDKSTSTAY MELSSLRSED TAVYYCTRSW RGNSFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSDT KVDKKVEPKS CDKTHTCPPC PAPPVAGPSV    240
FLFPPKPKDT LMISRTPEVT CVVVDVKHED PEVKFNWYVD GVEVHNAKTK PREEEYNSTY    300
RVVSVLTVLH QDWLNGKEYK CKVSNKALPA PIEKTISKAK GQPREPQVYT LPPSREEMTK    360
NQVSLTCDVS GFYPSDIAVE WESDGQPENN YKTTPPVLDS DGSFFLYSKL TVDKSRWEQG    420
DVFSCSVMHE ALHNHYTQKS LSLSPGK                                       447

SEQ ID NO: 87          moltype = AA  length = 485
FEATURE                Location/Qualifiers
REGION                 1..485
                       note = Immunoglobulin-derived sequence
source                 1..485
                       mol_type = protein
                       organism = synthetic construct
SEQUENCE: 87
EVQLVESGGG LVQPGGSLRL SCAASGFTFS TYAMNWVRQA PGKGLEWVGR IRSKYNNYAT     60
YYADSVKGRF TISRDDSKNT LYLQMNSLRA EDTAVYYCVR HGNFGDSYVS WFAYWGQGTL    120
VTVSSGKPGS GKPGSGKPGS GKPGSQAVVT QEPSLTVSPG GTVTLTCGSS TGAVTTSNYA    180
NWVQQKPGKS PRGLIGGTNK RAPGVPARFS GSLLGGKAAL TISGAQPEDE ADYYCALWYS    240
NHWVFGGGTK LTVLEPKSSD KTHTCPPCPA PPVAGPSVFL FPPKPKDTLM ISRTPEVTCV    300
VVDVKHEDPE VKFNWYVDGV EVHNAKTKPR EEQYNSTYRV VSVLTVLHQD WLNGKEYKCK    360
VSNKALPAPI EKTISKAKGQ PREPQVYTLP PSREQMTKNQ VKLTCLVKGF YPSDIAVEWE    420
SNGQPENNYK TTPPVLDSDG SFFLYSKLTV DKSRWQQGNV FSCSVMHEAL HNHYTQKSLS    480
LSPGK                                                               485

SEQ ID NO: 88          moltype = AA  length = 485
FEATURE                Location/Qualifiers
REGION                 1..485
                       note = Immunoglobulin-derived sequence
source                 1..485
                       mol_type = protein
                       organism = synthetic construct
SEQUENCE: 88
EVQLVESGGG LVQPGGSLRL SCAASGFTFS TYAMNWVRQA PGKGLEWVGR IRSKANNYAT     60
YYADSVKGRF TISRDDSKNT LYLQMNSLRA EDTAVYYCVR HGNFGDSYVS WFAYWGQGTL    120
VTVSSGKPGS GKPGSGKPGS GKPGSQAVVT QEPSLTVSPG GTVTLTCGSS TGAVTTSNYA    180
NWVQQKPGKS PRGLIGGTNK RAPGVPARFS GSLLGGKAAL TISGAQPEDE ADYYCALWYS    240
NHWVFGGGTK LTVLEPKSSD KTHTCPPCPA PPVAGPSVFL FPPKPKDTLM ISRTPEVTCV    300
VVDVKHEDPE VKFNWYVDGV EVHNAKTKPR EEQYNSTYRV VSVLTVLHQD WLNGKEYKCK    360
VSNKALPAPI EKTISKAKGQ PREPQVYTLP PSREQMTKNQ VKLTCLVKGF YPSDIAVEWE    420
SNGQPENNYK TTPPVLDSDG SFFLYSKLTV DKSRWQQGNV FSCSVMHEAL HNHYTQKSLS    480
LSPGK                                                               485

SEQ ID NO: 89          moltype = AA  length = 720
FEATURE                Location/Qualifiers
REGION                 1..720
                       note = Immunoglobulin-derived sequence
source                 1..720
                       mol_type = protein
                       organism = synthetic construct
SEQUENCE: 89
QVQLVQSGAE VKKPGASVKV SCKASGYTFT SYWINWVRQA PGQGLEWMGN IYPSDSYTNY     60
NQKFQGRVTM TVDKSTSTAY MELSSLRSED TAVYYCTRSW RGNSFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CGGGGSGGGG SEVQLVESGG    240
GLVQPGGSLR LSCAASGFTF STYAMNWVRQ APGKGLEWVG RIRSKYNNYA TYYADSVKGR    300
FTISRDDSKN TLYLQMNSLR AEDTAVYYCV RHGNFGDSYV SWFAYWGQGT LVTVSSGKPG    360
SGKPGSGKPG SGKPGSQAVV TQEPSLTVSP GGTVTLTCGS STGAVTTSNY ANWVQQKPGK    420
SPRGLIGGTN KRAPGVPARF SGSLLGGKAA LTISGAQPED EADYYCALWY SNHWVFGGGT    480
KLTVLGGGGS GGGGSKTHTC PPCPAPPVAG PSVFLFPPKP KDTLMISRTP EVTCVVVDVK    540
HEDPEVKFNW YVDGVEVHNA KTKPREEQYN STYRVVSVLT VLHQDWLNGK EYKCKVSNKA    600
```

```
LPAPIEKTIS KAKGQPREPQ VYTLPPSREQ MTKNQVKLTC LVKGFYPSDI AVEWESNGQP    660
ENNYKTTPPV LDSDGSFFLY SKLTVDKSRW QQGNVFSCSV MHEALHNHYT QKSLSLSPGK    720

SEQ ID NO: 90              moltype = AA  length = 720
FEATURE                    Location/Qualifiers
REGION                     1..720
                           note = Immunoglobulin-derived sequence
source                     1..720
                           mol_type = protein
                           organism = synthetic construct
SEQUENCE: 90
QVQLVQSGAE VKKPGASVKV SCKASGYTFT SYWINWVRQA PGQGLEWMGN IYPSDSYTNY     60
NQKFQGRVTM TVDKSTSTAY MELSSLRSED TAVYYCTRSW RGNSFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CGGGGSGGGG SEVQLVESGG    240
GLVQPGGSLR LSCAASGFTF STYAMNWVRQ APGKGLEWVG RIRSKANNYA TYYADSVKGR    300
FTISRDDSKN TLYLQMNSLR AEDTAVYYCV RHGNFGDSYV SWFAYWGQGT LVTVSSGKPG    360
SGKPGSGKPG SGKPGSQAVV TQEPSLTVSP GGTVTLTCGS STGAVTTSNY ANWVQQKPGK    420
SPRGLIGGTN KRAPGVPARF SGSLLGGKAA LTISGAQPED EADYYCALWY SNHWVFGGGT    480
KLTVLGGGGS GGGGSKTHTC PPCPAPPVAG PSVFLFPPKP KDTLMISRTP EVTCVVVDVK    540
HEDPEVKFNW YVDGVEVHNA KTKPREEQYN STYRVVSVLT VLHQDWLNGK EYKCKVSNKA    600
LPAPIEKTIS KAKGQPREPQ VYTLPPSREQ MTKNQVKLTC LVKGFYPSDI AVEWESNGQP    660
ENNYKTTPPV LDSDGSFFLY SKLTVDKSRW QQGNVFSCSV MHEALHNHYT QKSLSLSPGK    720

SEQ ID NO: 91              moltype = AA  length = 485
FEATURE                    Location/Qualifiers
REGION                     1..485
                           note = Immunoglobulin-derived sequence
source                     1..485
                           mol_type = protein
                           organism = synthetic construct
SEQUENCE: 91
EVQLVESGGG LVQPGGSLRL SCAASGFTFS TYAMNWVRQA PGKGLEWVGR IRSKANNYAT     60
YYADSVKGRF TISRDDSKNT LYLQMNSLRA EDTAVYYCVR HGNFGDSYVS WFAYWGQGTL    120
VTVSSGKPGS GKPGSGKPGS GKPGSQAVVT QEPSLTVSPG GTVTLTCGSS TGAVTTSNYA    180
NWVQQKPGKS PRGLIGGTNK RAPGVPARFS GSLLGGKAAL TISGAQPEDE ADYYCALWYS    240
NHWVFGGGTK LTVLEPKSSD KTHTCPPCPA PPVAGPSVFL FPPKPKDTLM ISRTPEVTCV    300
VVDVKHEDPE VKFNWYVDGV EVHNAKTKPR EEQYNSTYRV VSVLTVLHQD WLNGKEYKCK    360
VSNKALPAPI EKTISKAKGQ PREPQVYTLP PSREQMTKNQ VKLTCLVKGF YPSDIAVEWE    420
SNGQPENNYK TTPPVLDSDG SFFLYSKLTV DKSRWQQGNV FSCSVMHEAL HNHYTQKSLS    480
LSPGK                                                                485

SEQ ID NO: 92              moltype = AA  length = 720
FEATURE                    Location/Qualifiers
REGION                     1..720
                           note = Immunoglobulin-derived sequence
source                     1..720
                           mol_type = protein
                           organism = synthetic construct
SEQUENCE: 92
EVQLVQSGAE VKKPGESLRI SCKASGYTFT SYWINWVRQM PGKGLEWMGN IYPSDSYTNY     60
NQKFQGHVTI SVDKSISTAY LQWSSLKASD TAMYYCTRSW RGNSFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CGGGGSGGGG SEVQLVESGG    240
GLVQPGGSLR LSCAASGFTF STYAMNWVRQ APGKGLEWVG RIRSKYNNYA TYYADSVKGR    300
FTISRDDSKN TLYLQMNSLR AEDTAVYYCV RHGNFGDSYV SWFAYWGQGT LVTVSSGKPG    360
SGKPGSGKPG SGKPGSQAVV TQEPSLTVSP GGTVTLTCGS STGAVTTSNY ANWVQQKPGK    420
SPRGLIGGTN KRAPGVPARF SGSLLGGKAA LTISGAQPED EADYYCALWY SNHWVFGGGT    480
KLTVLGGGGS GGGGSKTHTC PPCPAPPVAG PSVFLFPPKP KDTLMISRTP EVTCVVVDVK    540
HEDPEVKFNW YVDGVEVHNA KTKPREEQYN STYRVVSVLT VLHQDWLNGK EYKCKVSNKA    600
LPAPIEKTIS KAKGQPREPQ VYTLPPSREQ MTKNQVKLTC LVKGFYPSDI AVEWESNGQP    660
ENNYKTTPPV LDSDGSFFLY SKLTVDKSRW QQGNVFSCSV MHEALHNHYT QKSLSLSPGK    720

SEQ ID NO: 93              moltype = AA  length = 449
FEATURE                    Location/Qualifiers
REGION                     1..449
                           note = Immunoglobulin-derived sequence
source                     1..449
                           mol_type = protein
                           organism = synthetic construct
SEQUENCE: 93
QVTLRESGPA LVKPTQTLTL TCTFSGFSLS TAGMSVGWIR QPPGKALEWL ADIWWDDKKH     60
YNPSLKDRLT ISKDTSKNQV VLKVTNMDPA DTATYYCARD MIFNFYFDVW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS DTKVDKKVEP KSCDKTHTCP PCPAPPVAGP    240
SVFLFPPKPK DTLMISRTPE VTCVVVDVKH EDPEVKFNWY VDGVEVHNAK TKPREEEYNS    300
TYRVVSVLTV LHQDWLNGKE YKCKVSNKAL PAPIEKTISK AKGQPREPQV YTLPPSREEM    360
TKNQVSLTCD VSGFYPSDIA VEWESDGQPE NNYKTTPPVL DSDGSFFLYS KLTVDKSRWE    420
QGDVFSCSVM HEALHNHYTQ KSLSLSPGK                                      449
```

```
SEQ ID NO: 94           moltype = AA  length = 485
FEATURE                 Location/Qualifiers
REGION                  1..485
                        note = Immunoglobulin-derived sequence
source                  1..485
                        mol_type = protein
                        organism = synthetic construct
SEQUENCE: 94
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 95           moltype = AA  length = 213
FEATURE                 Location/Qualifiers
REGION                  1..213
                        note = Immunoglobulin-derived sequence
source                  1..213
                        mol_type = protein
                        organism = synthetic construct
SEQUENCE: 95
DIQMTQSPST LSASVGDRVT ITCSASSRVG YMHWYQQKPG KAPKLLIYDT SKLASGVPSR   60
FSGSGSGTEF TLTISSLQPD DFATYYCFQG SGYPFTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213
```